US007776791B2

(12) United States Patent
Fischer et al.

(10) Patent No.: US 7,776,791 B2
(45) Date of Patent: Aug. 17, 2010

(54) N-HETEROCYCLYL PHENYL-SUBSTITUTED CYCLIC KETOENOLS

(75) Inventors: Reiner Fischer, Monheim (DE); Astrid Ullmann, Köln (DE); Thomas Bretschneider, Lohmar (DE); Stefan Lehr, Liederbach (DE); Klaus Kunz, Düsseldorf (DE); Jörg Konze, Köln (DE); Olga Malsam, Rösrath (DE); Mark Wilhelm Drewes, Langenfeld (DE); Dieter Feucht, Eschborn (DE); Karl-Heinz Kuck, Langenfeld (DE); Ulrike Wachendorff-Neumann, Neuwied (DE); Wahed Ahmed Moradi, Köln (DE); Guido Bojack, Wiesbaden (DE); Thomas Auler, Leichlingen (DE); Martin Hills, Idstein (DE); Heinz Kehne, Hofheim (DE)

(73) Assignee: Bayer CropScience AG, Monheim (DE)

( * ) Notice: Subject to any disclaimer, the term of this patent is extended or adjusted under 35 U.S.C. 154(b) by 729 days.

(21) Appl. No.: 10/559,703

(22) PCT Filed: Jun. 7, 2004

(86) PCT No.: PCT/EP2004/006127

§ 371 (c)(1),
(2), (4) Date: Dec. 7, 2005

(87) PCT Pub. No.: WO2004/111042

PCT Pub. Date: Dec. 23, 2004

(65) Prior Publication Data

US 2006/0166829 A1    Jul. 27, 2006

(30) Foreign Application Priority Data

Jun. 12, 2003    (DE) ................................ 103 26 386

(51) Int. Cl.
*A01N 43/36* (2006.01)
*A01N 43/56* (2006.01)

(52) U.S. Cl. ........................ 504/282; 504/246; 504/281; 504/283; 504/284; 514/224.2; 514/299; 514/404; 514/405; 514/411; 514/413; 514/425; 544/47; 546/183; 548/359.1; 548/363.1; 548/366.4; 548/408; 548/544

(58) Field of Classification Search .............. 504/116.1, 504/282, 246; 548/357.5, 544, 359.1
See application file for complete search history.

(56) References Cited

U.S. PATENT DOCUMENTS

| 3,542,809 A | 11/1970 | Nakanishi | 260/332.2 |
|---|---|---|---|
| 3,644,409 A | 2/1972 | Felder et al | 260/247.2 |
| 4,021,224 A | 5/1977 | Pallos et al. | 71/88 |
| 4,104,043 A | 8/1978 | Durden, Jr. et al. | 71/107 |
| 4,137,070 A | 1/1979 | Pallos et al. | 71/100 |
| 4,175,135 A | 11/1979 | Haines | 424/311 |
| 4,186,130 A | 1/1980 | Teach | 548/215 |
| 4,209,423 A | 6/1980 | Hutchings et al. | 252/435 |
| 4,243,811 A | 1/1981 | Teach | 548/215 |
| 4,256,657 A | 3/1981 | Wheeler | 260/465 D |
| 4,256,658 A | 3/1981 | Wheeler | 260/465 D |
| 4,256,659 A | 3/1981 | Wheeler | 260/465 D |
| 4,257,858 A | 3/1981 | Wheeler | 204/158 R |
| 4,269,618 A | 5/1981 | Pallos et al. | 71/88 |
| 4,283,348 A | 8/1981 | Wheeler | 260/465 D |
| 4,303,669 A | 12/1981 | D'Silva | 424/282 |
| 4,338,122 A | 7/1982 | Wheeler | 71/122 |
| 4,351,666 A | 9/1982 | Koerwer | 71/106 |
| 4,409,153 A | 10/1983 | Hodakowski | 260/946 |
| 4,415,352 A | 11/1983 | Pallos et al. | 71/88 |
| 4,415,353 A | 11/1983 | Pallos et al. | 71/100 |
| 4,422,870 A | 12/1983 | Wheeler | 71/106 |
| 4,436,666 A | 3/1984 | Wheeler | 260/455 B |
| 4,526,723 A | 7/1985 | Wheeler et al. | 260/410.5 |
| 4,551,547 A | 11/1985 | Wheeler | 560/255 |
| 4,613,617 A | 9/1986 | Sousa | 514/521 |
| 4,623,727 A | 11/1986 | Hübele | 546/176 |
| 4,632,698 A | 12/1986 | Wheeler | 71/106 |
| 4,639,266 A | 1/1987 | Heubach et al. | 71/92 |
| 4,659,372 A | 4/1987 | Wheeler | 71/106 |

(Continued)

FOREIGN PATENT DOCUMENTS

CA    2199636    4/1996

(Continued)

OTHER PUBLICATIONS

Chem. Pharm. Bull., vol. 15, (month unavailable) 1967, pp. 1120-1122, Seikichi Suzuki et al, "Studies on Antiviral Agents. IV. Biological Activity of Tenuazonic Acid Derivatives".

(Continued)

*Primary Examiner*—Shelley A. Dodson
*Assistant Examiner*—Danielle Sullivan
(74) *Attorney, Agent, or Firm*—Richard E. L. Henderson

(57) ABSTRACT

The invention relates to novel N-heterocyclylphenyl-substituted cyclic ketoenols of the formula (I)

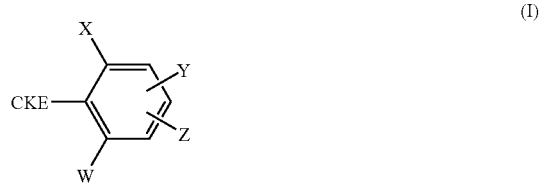

in which CKE, W, X, Y and Z are as defined in the disclosure,
to a plurality of processes and intermediates for their preparation and to their use as pesticides and/or herbicides and/or microbicides. The invention further relates to selective herbicidal compositions comprising firstly the N-heterocyclylphenyl-substituted cyclic ketoenols and secondly a compound which improves crop plant tolerance.

5 Claims, No Drawings

U.S. PATENT DOCUMENTS

| | | | |
|---|---|---|---|
| 4,708,735 A | 11/1987 | Pallos et al. | 71/118 |
| 4,758,264 A | 7/1988 | Hubele | 71/94 |
| 4,785,105 A | 11/1988 | Hubele | 546/178 |
| 4,785,106 A | 11/1988 | Hubele | 546/178 |
| 4,822,884 A | 4/1989 | Hubele | 546/177 |
| 4,851,033 A | 7/1989 | Hubele | 71/94 |
| 4,881,966 A | 11/1989 | Nyffeler et al. | 71/94 |
| 4,891,057 A | 1/1990 | Sohn et al. | 71/72 |
| 4,902,340 A | 2/1990 | Hubele | 71/94 |
| 4,925,868 A | 5/1990 | Terao et al. | 514/425 |
| 4,971,618 A | 11/1990 | Pallos et al. | 71/93 |
| 4,985,063 A | 1/1991 | Fischer et al. | 71/88 |
| 5,023,333 A | 6/1991 | Hubele | 546/175 |
| 5,045,107 A | 9/1991 | Hubele | 71/94 |
| 5,045,560 A | 9/1991 | Fischer et al. | 514/425 |
| 5,082,949 A | 1/1992 | Sohn et al. | 548/378 |
| 5,091,537 A | 2/1992 | Fischer et al. | 546/226 |
| 5,094,681 A | 3/1992 | Krämer et al. | 71/88 |
| 5,102,445 A | 4/1992 | Hubele | 71/94 |
| 5,116,836 A | 5/1992 | Fischer et al. | 514/224.2 |
| 5,142,065 A | 8/1992 | Fischer et al. | 548/533 |
| 5,186,737 A | 2/1993 | Fischer et al. | 504/283 |
| 5,207,817 A | 5/1993 | Krämer et al. | 504/299 |
| 5,258,527 A | 11/1993 | Krauskopf et al. | 548/543 |
| 5,262,383 A | 11/1993 | Fischer et al. | 504/195 |
| 5,314,863 A | 5/1994 | Löher et al. | 504/100 |
| 5,332,720 A | 7/1994 | Krüger et al. | 504/281 |
| 5,358,924 A | 10/1994 | Krüger et al. | 504/197 |
| 5,380,852 A | 1/1995 | Schütze et al. | 546/174 |
| 5,401,700 A | 3/1995 | Sohn et al. | 504/106 |
| 5,407,897 A | 4/1995 | Cary et al. | 504/108 |
| 5,462,913 A | 10/1995 | Fischer et al. | 504/138 |
| 5,474,974 A | 12/1995 | Krüger et al. | 504/236 |
| 5,494,890 A | 2/1996 | Cederbaum et al. | 504/281 |
| 5,504,057 A | 4/1996 | Fischer et al. | 504/283 |
| 5,506,193 A | 4/1996 | Cederbaum et al. | 504/282 |
| 5,516,750 A | 5/1996 | Willms et al. | 504/106 |
| 5,516,918 A | 5/1996 | Cary et al. | 549/23 |
| 5,567,671 A | 10/1996 | Fischer et al. | 504/283 |
| 5,589,469 A | 12/1996 | Fischer et al. | 514/91 |
| 5,602,078 A | 2/1997 | Fischer et al. | 504/283 |
| 5,610,122 A | 3/1997 | Fischer et al. | 504/251 |
| 5,616,536 A | 4/1997 | Fischer et al. | 504/225 |
| 5,622,917 A | 4/1997 | Fischer et al. | 504/283 |
| 5,661,110 A | 8/1997 | Krüger et al. | 504/281 |
| 5,677,449 A | 10/1997 | Fischer et al. | 544/165 |
| 5,696,050 A | 12/1997 | Cary et al. | |
| 5,700,758 A | 12/1997 | Rösch et al. | 504/106 |
| 5,703,008 A | 12/1997 | Rösch et al. | 504/106 |
| 5,719,310 A | 2/1998 | Fischer et al. | 560/83 |
| 5,739,079 A | 4/1998 | Holdgrün et al. | 504/103 |
| 5,739,389 A | 4/1998 | Krüger et al. | 562/489 |
| 5,780,394 A | 7/1998 | Krüger et al. | 504/281 |
| 5,808,135 A | 9/1998 | Fischer et al. | 560/129 |
| 5,830,825 A | 11/1998 | Fischer et al. | 504/130 |
| 5,830,826 A | 11/1998 | Fischer et al. | 504/195 |
| 5,847,211 A | 12/1998 | Fischer et al. | 564/123 |
| 5,922,732 A | 7/1999 | Urch et al. | 514/304 |
| 5,945,444 A | 8/1999 | Fischer et al. | 514/445 |
| 5,945,541 A | 8/1999 | Sohn et al. | 548/374.1 |
| 5,968,947 A | 10/1999 | Urch et al. | 514/299 |
| 5,977,029 A | 11/1999 | Fischer et al. | 504/292 |
| 5,981,567 A | 11/1999 | Fischer et al. | 514/409 |
| 5,994,274 A | 11/1999 | Fischer et al. | 504/282 |
| 6,051,723 A | 4/2000 | Fischer et al. | 549/420 |
| 6,071,937 A | 6/2000 | Bretschneider et al. | 514/336 |
| 6,093,726 A | 7/2000 | Urch et al. | 514/299 |
| 6,110,872 A | 8/2000 | Lieb et al. | 504/284 |
| 6,114,374 A | 9/2000 | Lieb et al. | 514/424 |
| 6,133,296 A | 10/2000 | Lieb et al. | 514/343 |
| 6,140,358 A | 10/2000 | Lieb et al. | 514/425 |
| 6,150,304 A | 11/2000 | Fischer et al. | 504/309 |
| 6,172,255 B1 | 1/2001 | Fischer et al. | 560/24 |
| 6,174,894 B1 | 1/2001 | Urch et al. | 514/299 |
| 6,177,442 B1 | 1/2001 | Urch et al. | 514/299 |
| 6,200,932 B1 | 3/2001 | Fischer et al. | 504/225 |
| 6,207,676 B1 | 3/2001 | Urch et al. | 514/304 |
| 6,235,680 B1 | 5/2001 | Ziemer et al. | 504/112 |
| 6,251,830 B1 | 6/2001 | Fischer et al. | 504/251 |
| 6,251,833 B1 | 6/2001 | Erdelen et al. | 504/348 |
| 6,255,342 B1 | 7/2001 | Lieb et al. | 514/533 |
| 6,271,180 B2 | 8/2001 | Lieb et al. | 504/292 |
| 6,288,102 B1 | 9/2001 | Hagemann et al. | 514/409 |
| 6,291,474 B1 | 9/2001 | Brightwell et al. | 514/299 |
| 6,316,486 B1 | 11/2001 | Lieb et al. | 514/411 |
| 6,358,887 B1 | 3/2002 | Fischer et al. | 504/284 |
| 6,359,151 B2 | 3/2002 | Lieb et al. | 549/265 |
| 6,380,246 B1 | 4/2002 | Lieb et al. | 514/462 |
| 6,388,123 B1 | 5/2002 | Lieb et al. | 560/76 |
| 6,391,912 B1 | 5/2002 | Hagemann et al. | 514/444 |
| 6,410,480 B1 | 6/2002 | Mühlebach et al. | 504/105 |
| 6,458,965 B1 | 10/2002 | Lieb et al. | |
| 6,469,196 B2 | 10/2002 | Fischer et al. | 560/105 |
| 6,472,419 B1 | 10/2002 | Fischer et al. | 514/425 |
| 6,479,489 B1 | 11/2002 | Fischer et al. | 514/235.5 |
| 6,482,947 B1 | 11/2002 | Holdgrün et al. | 544/239 |
| 6,486,343 B1 | 11/2002 | Lieb et al. | 560/39 |
| 6,504,036 B1 | 1/2003 | Lieb et al. | 549/265 |
| 6,511,940 B1 | 1/2003 | Ziemer et al. | 504/118 |
| 6,511,942 B1 | 1/2003 | Lieb et al. | 504/299 |
| 6,515,184 B1 | 2/2003 | Fischer et al. | 568/327 |
| 6,555,499 B1 | 4/2003 | Glock et al. | 504/130 |
| 6,555,567 B1 | 4/2003 | Fischer et al. | 514/409 |
| 6,569,810 B1 | 5/2003 | Fischer et al. | 504/290 |
| 6,573,275 B1 | 6/2003 | Urch et al. | 514/304 |
| 6,576,771 B1 | 6/2003 | Bretschneider et al. | 549/216 |
| 6,589,976 B1 | 7/2003 | Fischer et al. | 514/409 |
| 6,596,873 B1 | 7/2003 | Lieb et al. | 546/256 |
| 6,608,211 B1 | 8/2003 | Hagemann et al. | 548/410 |
| 6,630,594 B2 | 10/2003 | Hagemann et al. | 548/410 |
| 6,670,488 B1 | 12/2003 | Hagemann et al. | 549/424 |
| 6,693,092 B2 | 2/2004 | Lieb et al. | |
| 6,746,990 B2 | 6/2004 | Fischer et al. | 504/299 |
| 6,759,548 B2 | 7/2004 | Fischer et al. | 560/81 |
| 6,759,554 B2 | 7/2004 | Buchwald et al. | 564/192 |
| 6,774,133 B2 | 8/2004 | Fischer et al. | 514/278 |
| 6,806,264 B2 | 10/2004 | Lieb et al. | |
| 6,858,741 B2 | 2/2005 | Lieb et al. | 549/67 |
| 6,861,391 B1 | 3/2005 | Fischer et al. | 504/283 |
| 6,867,298 B2 | 3/2005 | Buchwald et al. | 540/489 |
| 6,894,005 B1 | 5/2005 | Maetzke et al. | 504/218 |
| 6,900,341 B2 | 5/2005 | Hagemann et al. | 549/424 |
| 6,933,261 B2 | 8/2005 | Lieb et al. | 504/298 |
| 6,939,888 B2 | 9/2005 | Fischer et al. | 514/409 |
| 6,962,894 B1 | 11/2005 | Glock | 504/238 |
| 2001/0004629 A1 | 6/2001 | Lieb et al. | 504/292 |
| 2002/0022575 A1 | 2/2002 | Fischer et al. | 504/221 |
| 2002/0061913 A1 | 5/2002 | Urch et al. | 514/366 |
| 2002/0072617 A1 | 6/2002 | Hagemann et al. | 548/541 |
| 2002/0161034 A1 | 10/2002 | Fischer et al. | 504/221 |
| 2003/0045432 A1 | 3/2003 | Fischer et al. | 504/221 |
| 2003/0144504 A1 | 7/2003 | Fischer et al. | 544/54 |
| 2003/0171219 A1 | 9/2003 | Lieb et al. | 504/221 |
| 2003/0171220 A1 | 9/2003 | Ziemer et al. | 504/271 |
| 2003/0216260 A1 | 11/2003 | Ruther et al. | 504/283 |
| 2003/0228984 A1 | 12/2003 | Hagemann et al. | 504/284 |
| 2004/0009999 A1 | 1/2004 | Fischer et al. | 514/278 |
| 2004/0019061 A1 | 1/2004 | Fischer et al. | 514/256 |
| 2004/0102327 A1 | 5/2004 | Hagemann et al. | 504/292 |
| 2005/0038021 A1 | 2/2005 | Lieb et al. | 514/227.5 |
| 2005/0090399 A1 | 4/2005 | Friedmann et al. | 504/282 |
| 2005/0164883 A1 | 7/2005 | Maetzke et al. | 504/131 |
| 2005/0164885 A1 | 7/2005 | Lieb et al. | 504/221 |
| 2005/0164886 A1 | 7/2005 | Glock | 504/282 |

| 2005/0187110 A1 | 8/2005 | Maetzke et al. ............ 504/221 |
| 2005/0215794 A1 | 9/2005 | Buchwald et al. ........... 546/108 |

FOREIGN PATENT DOCUMENTS

| CA | 2210286 | 7/1996 |
| CA | 2 492 096 | 1/2004 |
| CA | 2 497 074 | 3/2004 |
| DE | 101 39 465 | 2/2003 |
| EP | 346 620 A1 | 12/1989 |
| EP | 442 077 B1 | 11/1995 |
| GB | 2 266 888 A | 11/1993 |
| JP | 2000-53670 | 2/2000 |
| WO | 96/02539 | 2/1996 |
| WO | 99/43649 | 9/1999 |
| WO | 99/55673 | 11/1999 |
| WO | 01/09092 | 2/2001 |
| WO | 01/17351 A1 | 3/2001 |
| WO | 01/17973 | 3/2001 |
| WO | 03/028446 A2 | 4/2003 |

OTHER PUBLICATIONS

Liebigs Ann. Chem., (month unavailable) 1985, pp. 1095-1098, Roland Schmierer et al, "Cyclisierung von N-Acylalanin- and N-Acylglycinestem".

J. Chem. Soc. Perkin Trans. I (month unavailable) 1985, pp. 1567-1576, Alexander C. Campbell et al, "Synthesis of (E)- and (Z)-Pulvinones".

Arch Pharm 309, (month unavailable) 1976, pp. 558-564, Ali M. Chirazi et al, "Synthesen von Heterocyclen, 184, Zur Synthese von Kawalactonderivaten".

Chem. Ber., 91, (month unavailable) 1958, p. 2849, Karl-Heniz Boltze et al, "Rincischlüsse mit Malonsäure-dichloriden".

Monatsh, 95, (month unavailable) 1964 pp. 147-155, E. Ziegler et al, "Synthesen von Heterocyclen, 52. Mitt.".

H. Heterocycl. Chem., 10, Apr. 1973, pp. 223-224, Roger Ketcham et al, "Synthesis of Heterocycles. 174 (1.2) Substituted Thiazines and Bisthiazinyls from Dithiooxamide and Trichlorophenyl Malonates".

Tetrahedron, vol. 48, No. 36, (month unavailable) 1992, pp. 7519-7526, Jason Micklefield et al, "Alkylation and Acylation of 5-Penylsulphonyl- and 5-Cyanobutyrolactones".

J. Chem. Soc. (C), (month unavailable) 1967, pp. 405-409, R.L. Edwards et al, Constituents of the Higher Fungi. Part IV. Involutin, a Diphenylcyclopenteneone from Paxillus involutus (Oeder ex Fries).

Journal of Ecomonic Entomology, 66, (month unavailable) 1973, pp. 584-586, A.A. Sousa et al, "Esters of 3-Hydroxy-2-Arylindones, a New Class of Acaricide".

J. Org. Chem., vol. 44, No. 26, (month unavailable) 1979, pp. 4906-4912, Thomas N. Wheeler, "Novel Photochemical Synthesis of 2-Aryl-1,3-cyclohexanediones".

Chemical Reviews, 52, (month unavailable) 1953, pp. 237-416, Norman O.V. Sonntag, "The Reactions of Aliphatic Acid Chlorides".

Indian J. Chem., vol. 6, Jul. 1968, pp. 341-345, Bhabatosh Bhattacharya, "Isoquinoline Derivatives: Part XVIII-Formation of I-Alkyl-(or alkaryl or aryl)-3-methyl-7-chloro-(or 5-chloro)-isoquinolines".

Chem. Ind., (London) Nov. 9, 1968, p. 1568, H.R. Harrison et al, "Use of molecular sieves in the methyl esterification of carboxylic acids".

Schotten-Baumann, Organikum, VEB Deutscher Verlag der Wissenschaften, Berlin (month unavailable) 1977, p. 505, "Reaktionen von Carbonsäuren und Carbonsäurederivaten mit Basen".

Houben-Weyl, Methoden der Organischen Chemie [Methods of Organic Chemistry], vol. 8, (month unavailable) 1952, pp. 467-469, H. Henecka, "Isoanthraflavinsaure; Morpholchinon".

Ann. Chim., (Paris) [14], 5, (month unavailable) 1970, pp. 11-22, P.L. Compagnon et M. Miocque, "Addition Des Réactifs Nucléophiles Sur La Triple Liaison Nitrile, I.—Addition Des Hydrures, De L'eau, De L'hydrogéne Sulfuré Et De L'hydrogéne Sélenié".

Ann. Chim, (Paris) [14], 5, (month unavailable) 1970, pp. 23-38, P.L. Compagnon et M. Miocque, "Addition Des Réactifs Nucléophiles Sur La Triple Liaison Nitrile, II.—Addition Des Alcools, Des Composés Azotés, Des Organométalliques; Condensation De Plusieurs Molécules De Nitriles".

J. Chem. Soc., (month unavailable) 1961, pp. 4372-4379, L. Munday, "Amino-acids of the Cyclohexane Series. Part I.".

Can. J. Chem., vol. 53, (month unavailable) 1975, pp. 3339-3350, John T. Edwards et al, "Stereochemistry of the Bucherer-Bergs and Strecker Reactions of 4-tert-Butylcyclohexanone".

J. Am. Chem. Soc. vol. 123, No. 31, (month unavailable) 2001, pp. 7727-7729, Adis Klapars et al, "A General and Efficient Copper Catalyst for the Amidation of Aryl Halides and the N-Arylation of Nitrogen Heterocycles".

J. Chem. Soc., Chem. Commun., (month unavailable) 1987, pp. 1228-1230, Mark S. Chambers et al, "An Asymmetric Synthesis of Thiotetronic Acids using Chirality Transfer via an Allyl Xanthate-to-Dithiocarbonate Rearrangement, X-Ray Crystal Structure of (5R)-2,5-Dihydro-4-hydroxy-5-methyl-3-phenyl-5-prop1'-enyl-2-oxothiophene".

The Journal of Antibiotics, vol. XXXVI, No. 11, Nov. 1983, pp. 1589-1591, Kazuo Tsuzuki et al, "Syntheses and Biological Activties of Thiotetromycin Analogs".

Organic Preparations and Procedures Int. 7(4), (month unavailable) 1975, pp. 155-158, Susumu Nakanishi et al, "Synthesis of Chlorocarbonyl Ketenes".

Organikum, VEB Deutscher Verlag der Wissenschaften, Berlin, (month unavailable) 1977, pp. 517-518, "Reaktionven von Carbonsäuren and Carbonsäurderivaten mit Basen".

Tetrahedron Letters, vol. 27, No. 24, (month unavailable) 1986, pp. 2763-2766, Enrico Baciocchi et al, "Dimethyl Arylmalonates from Cerium(IV) Ammonium Nitrate Promoted Reactions of Dimethyl Malonate with Aromatic Compounds in Methanol".

Organikum VEB Deutscher Verlag der Wissenschaften, Berlin, (month unavailable) 1977, pp. 587-589, "Esterkondensation".

Organikum, 15th Edition, Berlin, (month unavailable) 1977, p. 499, "Reaktionen mit metallorganischen Verbindungen".

Organikum, 15th Edition, Berlin, (month unavailable) 1977, pp. 519-521, "Reaktionen vinyloger Elektronendonorverbindungen".

Liebios Ann. Chem. 585, (month unavailable) 1954, pp. 1-15, Von Heinz Dannenberg et al, "Versuche zur Synthese des Steranthrens" III. 3,4-Aceperinaphthan und 6,7-Aceperinaphthan.

Reaktionen der organischen Synthese [Reaction of organic synthesis], (month unavailable) 1978, C Ferris, p. 212 and 513-515, "Organische Reaktionen, nach Reaktionstypen geordnet".

Liebigs Ann. Chem., 443, (month unavailable) 1925, pp. 242-262, Otto Diels et al, "Über das aus Cyclopentadien und Azoester entstehende Endomethylen-piperidazin und seine Überführung in 1,3-Diamino-cyclopentan".

Chem. Ber. 98, (month unavailable) 1965, pp. 2551-2555, Rainer Askani, "Zur Reaktion von Cyclohexadien-(1.3) mit Azodicarbonsäure-diäthylester".

Synlett, 3, (month unavailable) 2002, pp. 423-426, S. Majumdar et al, "Catalytic Asymmetric and Stereoselective Synthesis of Vinylcyclopropanes".

Synlett, 3, (month unavailable) 2002, pp. 427-430, S.-K. Kang et al, "Copper-catalyzed N-Arylation of Aryl Iodides with Benzamides or Nitrogen Heterocycles in the Presence of Ethylenediamine".

Chem. Ind., 37, (month unavailable) 1985, pp. 730-732, Harry R. Ungerer, "Schiffsfarben—eine Spezialität der seenahen Lackindustrie".

Williams P D et al: "Nonpeptide oxytocin antagonists: analogs of L-371, 257 with improved potency" Bioorganic & Medicinal Chemistry Letters, Oxford, GB, Bd. 9, NR. 9, 3. Mai 1999 (May 3, 1999), Seiten 1311-1316, XP004163964.

Nannini G et al: "New Analgesic-Anti-Inflammatory Drugs 1-0X0-2-Substituted Isoindoline Derivatives" Arzneimittel Forschgung. Drug Research, Editio Cantor. Aulendorf, DE, Bd. 23, Nr. 8, 1973, Seiten 1090-1100, XP002953827.

Database Beilstein, Beilstein Institue for Organic Chemistry, Frankfurt-Main, DE; XP002296804 Database accession no. BRN 347923 Zusammenfassung & Borsche; Bahr Justus Liebigs Annalen Der Chemie., Bd. 402, 1913, Seite 108.

N-HETEROCYCLYL PHENYL-SUBSTITUTED CYCLIC KETOENOLS

The present patent application has been filed under 35 U.S.C. 371 as a national stage application of PCT/EP2004/006127, filed Jun. 7, 2004, which was published in German as International Patent Publication WO 2004/111042 on Dec. 23, 2004, and is entitled to the right of priority of German Patent Application 103 26 386.1, filed Jun. 12, 2003.

The present invention relates to novel N-heterocyclylphenyl-substitute cyclic ketoenols, to a plurality of processes for their preparation and to their use as pesticides and/or herbicides and/or microbicides.

Moreover, the invention relates to novel selective herbicidal active compound combinations comprising firstly the N-heterocyclylphenyl-substituted cyclic ketoenols and secondly at least one compound which improves crop plant tolerance, which combinations can be used with particularly good results for the selective control of weeds and crops of various useful plants.

Pharmaceutical properties of 3-acylpyrrolidine-2,4-diones have already been described (S. Suzuki et al. Chem. Pharm. Bull. 15 1120 (1967)). Furthermore, N-phenylpyrrolidine-2,4-diones were synthesized by R. Schmierer and H. Mildenberger (Liebigs Ann. Chem. 1985, 1095). A biological activity of these compounds has not been described.

EP-A-0 262 399 and GB-A-2 266 888 disclose compounds of a similar structure (3-arylpyrrolidine-2,4-diones), of which, however, no herbicidal, insecticidal or acaricidal action has been disclosed. Unsubstituted, bicyclic 3-arylpyrrolidine-2,4-dione derivatives (EP-A-355 599, EP-A-415 211 and JP-A-12-053670) and substituted monocyclic 3-arylpyrrolidine-2,4-dione derivatives (EP-A-377 893 and EP-A-442 077) having herbicidal, insecticidal or acaricidal action have been disclosed.

There have also been disclosed polycyclic 3-arylpyrrolidine-2,4-dione derivatives (EP-A-442 073) and 1H-arylpyrrolidinedione derivatives (EP-A-456 063, EP-A-521 334, EP-A-596 298, EP-A-613 884, EP-A-613 885, WO 95/01 358, WO 95/26 954, WO 95/20 572, EP-A-0 668 267, WO 96/25 395, WO 96/35 664, WO 97/01 535, WO 97/02 243, WO 97/36 868, WO 97/43275, WO 98/05638, WO 98/06721, WO 98/25928, WO 99/16748, WO 99/24437, WO 99/43649, WO 99/48869, WO 99/55673, WO 01/17972, WO 01/23354, WO 01/74770, WO 03/062244, DE-A-10 231 333 and DE-A-10 239 479).

It is known that certain substituted $\Delta^3$-dihydrofuran-2-one derivatives have herbicidal properties (cf. DE-A-4 014 420). The synthesis of the tetronic acid derivatives used as starting materials (such as, for example, 3-(2-methylphenyl)-4-hydroxy-5-(4-fluorophenyl)-$\Delta^3$-dihydrofuran-2-one) is also described in DE-A-4 014 420. Compounds of a similar structure are known from the publication Campbell et al., J. Chem. Soc., Perkin Trans. 1, 1985, (8) 1567-76, but no insecticidal and/or acaricidal activity is mentioned. 3-Aryl-$\Delta^3$-dihydrofuranone derivatives having herbicidal, acaricidal and insecticidal properties are also known from EP-A-528 156, EP-A-0 647 637, WO 95/26 345, WO 96/20 196, WO 96/25 395, WO 96/35 664, WO 97/01 535, WO 97/02 243, WO 97/36 868, WO 98/05638, WO 98/25928, WO 99/16748, WO 99/43649, WO 99/48869, WO 99/55673, WO 01/17972, WO 01/23354, WO 01/74770, WO 03/062244 and DE-A-10 239 479. 3-Aryl-$\Delta^3$-dihydrothiophenone derivatives are likewise known (WO 95/26 345, 96/25 395, WO 97/01 535, WO 97/02 243, WO 97/36 868, WO 98/05638, WO 98/25928, WO 99/16748, WO 99/43649, WO 99/48869, WO 99/55673, WO 01/17972, WO 01/23354, WO 01/74770 and WO 03/062244).

Certain phenylpyrone derivatives which are unsubstituted in the phenyl ring are already known (cf. A. M. Chirazi, T. Kappe and E. Ziegler, Arch. Pharm. 309, 558 (1976) and K.-H. Boltze and K. Heidenbluth, Chem. Ber. 91, 2849), but a possible use of these compounds as pesticides has not been mentioned. Phenylpyrone derivatives which are substituted in the phenyl ring and have herbicidal, acaricidal and insecticidal properties are described in EP-A-588 137, WO 96/25 395, WO 96/35 664, WO 97/01 535, WO 97/02 243, WO 97/16 436, WO 97/19 941, WO 97/36 868, WO 98/05638, WO 99/43649, WO 99/48869, WO 99/55673, WO 01/17972, WO 01/74770 and WO 03/062244.

Certain 5-phenyl-1,3-thiazine derivatives which are unsubstituted in the phenyl ring are already known (cf. E. Ziegler and E. Steiner, Monatsh. 95, 147 (1964), R. Ketcham, T. Kappe and E. Ziegler, J. Heterocycl. Chem. 10, 223 (1973)), but a possible use of these compounds as pesticides has not been mentioned. 5-Phenyl-1,3-thiazine derivatives which are substituted in the phenyl ring and have herbicidal, acaricidal and insecticidal action are described in WO 94/14 785, WO 96/02 539, WO 96/35 664, WO 97/01 535, WO 97/02 243, WO 97/02 243, WO 97/36 868, WO 99/05638, WO 99/43649, WO 99/48869, WO 99/55673, WO 01/17972, WO 01/74770 and WO 03/062244.

It is known that certain substituted 2-arylcyclopentanediones have herbicidal and acaricidal properties (cf., for example, U.S. Pat. Nos. 4,283,348; 4,338,122; 4,436,666; 4,526,723; 4,551,547; 4,632,698; WO 96/01 798; WO 96/03 366, WO 97/14 667 and also WO 98/39281, WO 99/43649, WO 99/48869, WO 99/55673, WO 01/17972, WO 01/74770 and WO 03/062244). Moreover, compounds having similar substitutions are known; 3-hydroxy-5,5-dimethyl-2-phenylcyclopent-2-en-1-one from the publication Micklefield et al., Tetrahedron, (1992), 7519-26, and the natural product involutin (−)-cis-5-(3,4-dihydroxyphenyl)-3,4-dihydroxy-2-(4-hydroxyphenyl)cyclopent-2-enone from the publication Edwards et al., J. Chem. Soc. S, (1967), 405-9. An insecticidal or acaricidal action is not described. Moreover, 2-(2,4,6-trimethylphenyl)-1,3-indanedione is known from the publication J. Economic Entomology, 66, (1973), 584 and the Offenlegungsschrift (German Published Specification) DE-A 2 361 084, with herbicidal and acaricidal actions being mentioned.

It is known that certain substituted 2-arylcyclohexanediones have herbicidal and acaricidal properties (U.S. Pat. Nos. 4,175,135, 4,209,432, 4,256,657, 4,256,658, 4,256,659, 4,257,858, 4,283,348, 4,303,669, 4,351,666, 4,409,153, 4,436,666, 4,526,723, 4,613,617, 4,659,372, DE-A 2 813 341, and also Wheeler, T. N., J. Org. Chem. 44, 4906 (1979)), WO 99/43649, WO 99/48869, WO 99/55673, WO 01/17972, WO 01/74770 and WO 03/062244).

It is known that certain substituted 4-arylpyrazolidine-3,5-diones have acaricidal, insecticidal and herbicidal properties (cf., for example, WO 92/16 510, EP-A-508 126, WO 96/11 574, WO 96/21 652, WO 99/43649, WO 99/47525, WO 99/48869, WO 99/55673, WO 01/17 351, WO01/17 352, WO 01/17 353, WO 01/17 972, WO 01/17 973, WO 03/028446 and WO 03/062244).

However, the activity and/or activity spectrum of these compounds is, in particular at low application rates and concentrations, not always entirely satisfactory. Furthermore, these compounds are not always sufficiently well tolerated by plants.

We have now found novel compounds of the formula (I)

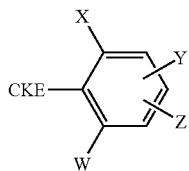
(I)

in which

X represents halogen, alkyl, alkenyl, alkynyl, alkoxy, alkenyloxy, alkylthio, alkylsulphinyl, alkylsulphonyl, haloalkyl, haloalkoxy, haloalkenyloxy, nitro, cyano or in each case optionally substituted phenyl, phenoxy, phenylthio, phenylalkoxy or phenylalkylthio, W and Y independently of one another represent hydrogen, halogen, alkyl, alkenyl, alkynyl, alkoxy, alkenyloxy, haloalkyl, haloalkoxy, haloalkenyloxy, nitro or cyano, Z represents an in each case optionally saturated or unsaturated, optionally substituted heterocycle which is attached to the phenyl ring via a nitrogen atom and which may be interrupted by one or two carbonyl groups, CKE represents one of the groups

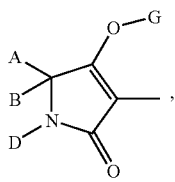
(1)

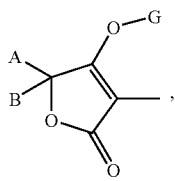
(2)

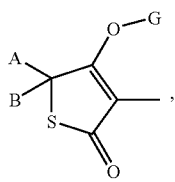
(3)

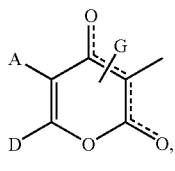
(4)

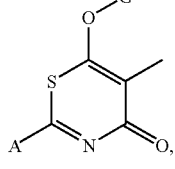
(5)

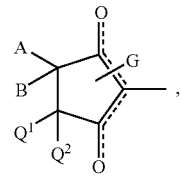
(6)

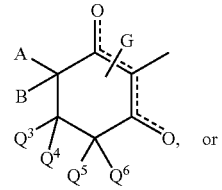
(7)

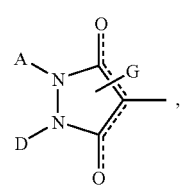
(8)

in which

A represents hydrogen, represents in each case optionally halogen-substituted alkyl, alkenyl, alkoxyalkyl, alkylthioalkyl, saturated or unsaturated, optionally substituted cycloalkyl in which optionally at least one ring atom is replaced by a heteroatom, or in each case optionally halogen-, alkyl-, haloalkyl-, alkoxy-, halo-alkoxy-, cyano- or nitro-substituted aryl, arylalkyl or hetaryl, B represents hydrogen, alkyl or alkoxyalkyl, or A and B together with the carbon atom to which they are attached represent a saturated or unsaturated, unsubstituted or substituted cycle which optionally contains at least one heteroatom, D represents hydrogen or represents an optionally substituted radical from the group consisting of alkyl, alkenyl, alkynyl, alkoxyalkyl, saturated or unsaturated cycloalkyl, in which optionally one or more ring members are replaced by heteroatoms, arylalkyl, aryl, hetarylalkyl or hetaryl or A and D together with the atoms to which they are attached represent a saturated or unsaturated cycle which optionally contains at least one (in the case of CKE=8 further) heteroatom and which is unsubstituted or substituted in the A,D moiety, or A and $Q^1$ together represent optionally halogen- or hydroxy-substituted alkenediyl or alkanediyl or alkenediyl substituted by in each case optionally substituted alkyl, alkoxy, alkylthio, cycloalkyl, benzyloxy or aryl or $Q^1$ represents hydrogen or alkyl, $Q^2$, $Q^4$, $Q^5$ and $Q^6$ independently of one another represent hydrogen or alkyl, $Q^3$ represents hydrogen, in each case optionally substituted alkyl, alkoxyalkyl, alkylthioalkyl, optionally substituted cycloalkyl (in which optionally one methylene group is replaced by oxygen or sulphur) or optionally substituted phenyl, or $Q^3$ and $Q^4$ together with the carbon atom to which they are attached represent a saturated or unsaturated, unsubstituted or substituted cycle which optionally contains a heteroatom, G represents hydrogen (a) or represents one of the groups

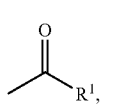
(b)

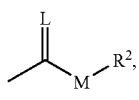
(c)

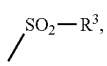
(d)

(e)

E or (f)

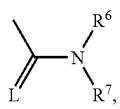
(g)

in which

E represents a metal ion equivalent or an ammonium ion,

L represents oxygen or sulphur,

M represents oxygen or sulphur, $R^1$ represents in each case optionally halogen-substituted alkyl, alkenyl, alkoxyalkyl, alkylthioalkyl, polyalkoxyalkyl or optionally halogen-, alkyl- or alkoxy-substituted cycloalkyl which may be interrupted by at least one heteroatom, in each case optionally substituted phenyl, phenylalkyl, hetaryl, phenoxyalkyl or hetaryloxyalkyl, $R^2$ represents in each case optionally halogen-substituted alkyl, alkenyl, alkoxyalkyl, polyalkoxyalkyl or represents in each case optionally substituted cycloalkyl, phenyl or benzyl, $R^3$, $R^4$ and $R^5$ independently of one another represent in each case optionally halogen-substituted alkyl, alkoxy, alkylamino, dialkylamino, alkylthio, alkenylthio, cycloalkylthio and represent in each case optionally substituted phenyl, benzyl, phenoxy or phenylthio, $R^6$ and $R^7$ independently of one another represent hydrogen, in each case optionally halogen-substituted alkyl, cycloalkyl, alkenyl, alkoxy, alkoxyalkyl, represent optionally substituted phenyl, represent optionally substituted benzyl, or together with the N atom to which they are attached represent a cycle which is optionally interrupted by oxygen or sulphur.

Depending inter alia on the nature of the substituents, the compounds of the formula (I) can be present as geometrical and/or optical isomers or isomer mixtures of varying composition which, if appropriate, can be separated in a customary manner. The present invention provides both the pure isomers and the isomer mixtures, their preparation and use and compositions comprising them. However, for the sake of simplicity, hereinbelow only compounds of the formula (I) are referred to, although what is meant is both the pure compounds and, if appropriate, mixtures having various proportions of isomeric compounds.

Taking into consideration the meanings (1) to (8) of the group CKE, the following principle structures (I-1) to (I-8) result:

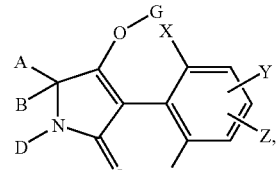
(I-1)

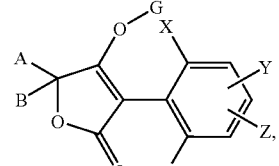
(I-2)

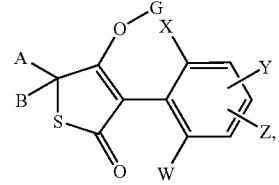
(I-3)

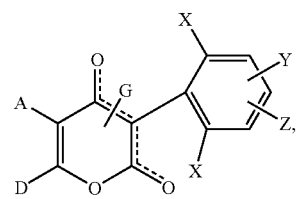
(I-4)

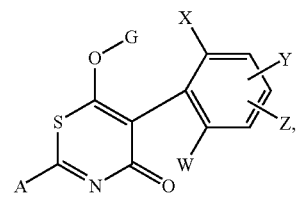
(I-5)

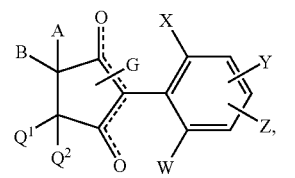
(I-6)

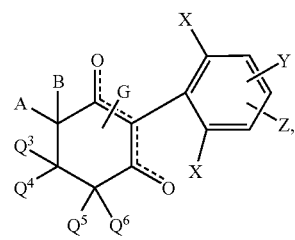
(I-7)

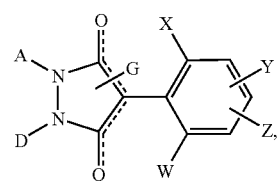
(I-8)

in which

A, B, D, G, $Q^1$, $Q^2$, $Q^3$, $Q^4$, $Q^5$, $Q^6$, W, X, Y and Z are as defined above.

Taking into consideration the different meanings (a), (b), (c), (d), (e), (f) and (g) of the group G, the following principle structures (I-1-a) to (I-1-g) result if CKE represents the group (1)

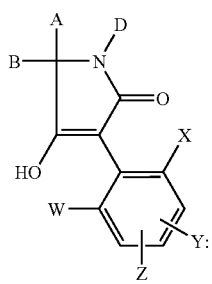
(I-1-a)

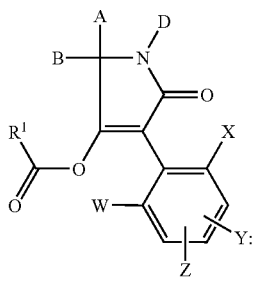
(I-1-b)

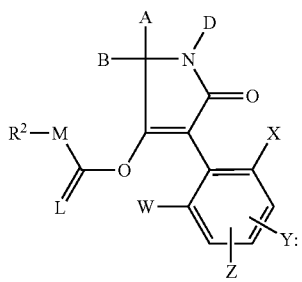
(I-1-c)

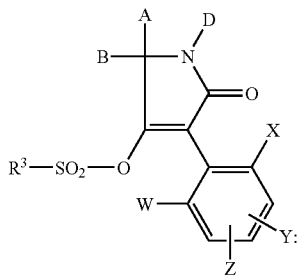
(I-1-d)

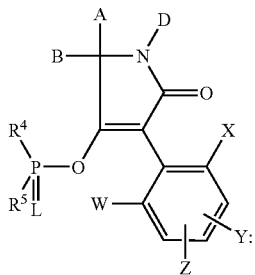
(I-1-e)

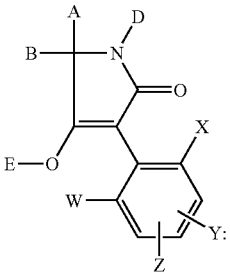
(I-1-f)

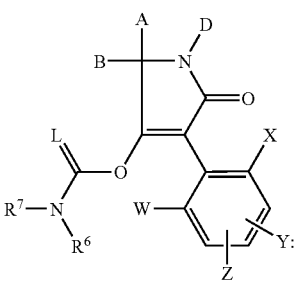
(I-1-g)

in which

A, B, D, E, L, M, W, X, Y, Z, $R^1$, $R^2$, $R^3$, $R^4$, $R^5$, $R^6$ and $R^7$ are as defined above.

Taking into consideration the different meanings (a), (b), (c), (d), (e), (f) and (g) of the group G, the following principle structures (I-2-a) to (I-2-g) result if CKE represents the group (2)

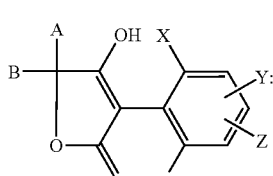
(I-2-a)

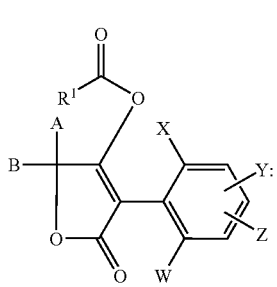
(I-2-b)

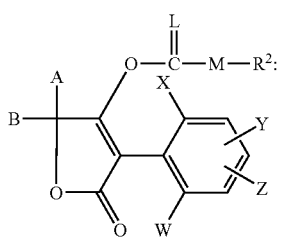
(I-2-c)

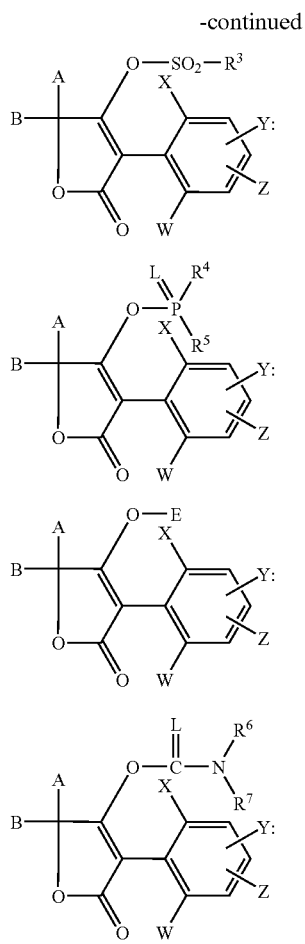

in which

A, B, E, L, M, W, X, Y, Z, R¹, R², R³, R⁴, R⁵, R⁶ and R⁷ are as defined above.

Taking into consideration the different meanings (a), (b), (c), (d), (e), (f) and (g) of the group G, the following principle structures (I-3-a) to (I-3-g) result if CKE represents the group (3)

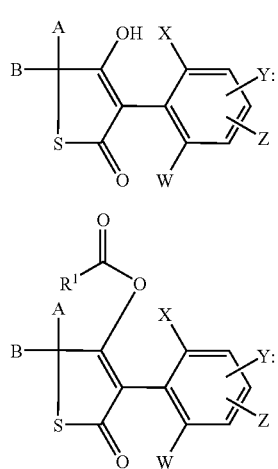

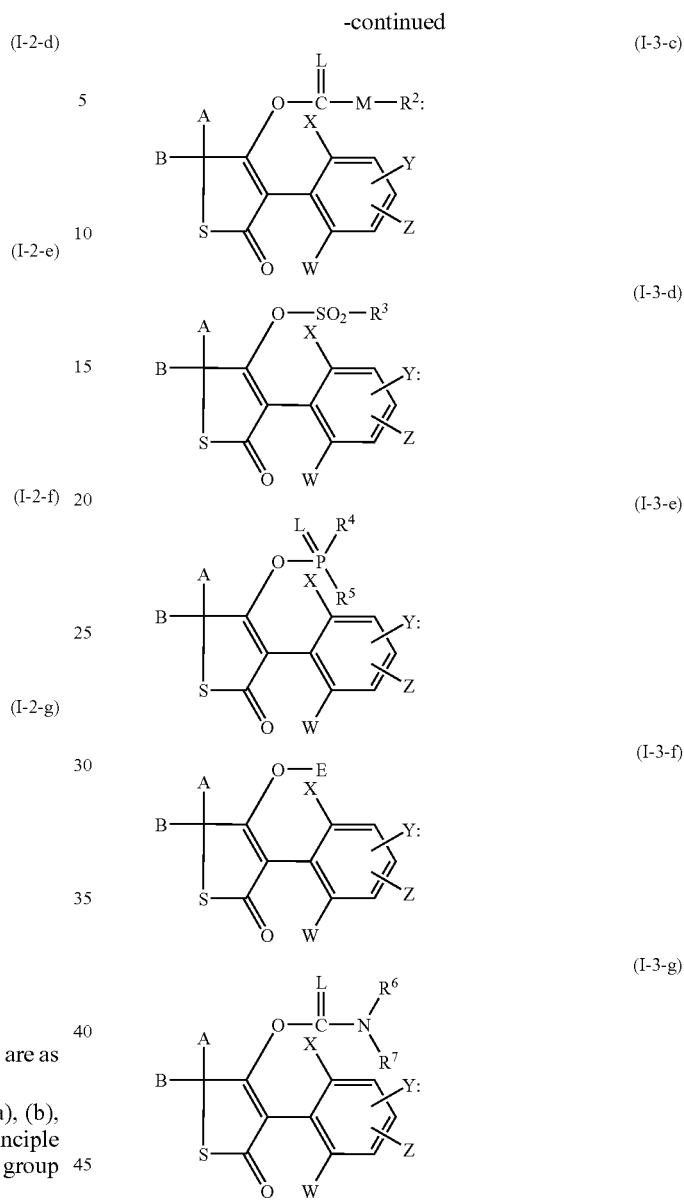

in which

A, B, E, L, M, W, X, Y, Z, R¹, R², R³, R⁴, R⁵, R⁶ and R⁷ are as defined above.

Depending on the position of the substituent G, the compounds of the formula (I-4) can be present in the two isomeric forms of the formulae (I-4-A) and (I-4-B)

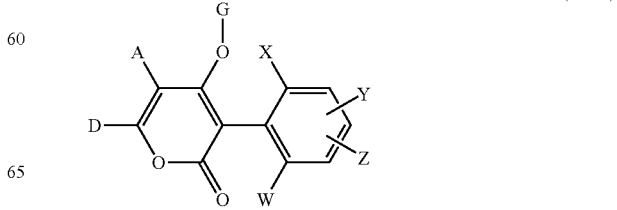

-continued

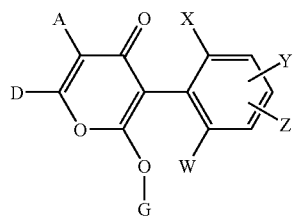
(I-4-B)

which is meant to be indicated by the broken line in formula (I-4).

The compounds of the formulae (I-4-A) and (I-4-B) can be present both as mixtures and in the form of their pure isomers. Mixtures of the compounds of the formulae (I-4-A) and (I-4-B) can, if appropriate, be separated in a manner known per se by physical methods, for example by chromatographic methods.

For reasons of clarity, hereinbelow only one of the possible isomers is shown in each case. This does not exclude that the compounds may, if appropriate, be present in the form of the isomer mixtures or in the respective other isomeric form.

Taking into consideration the different meanings (a), (b), (c), (d), (e), (f) and (g) of the group G, the following principle structures (I-4-a) to (I-4-g) result if CKE represents the group (4)

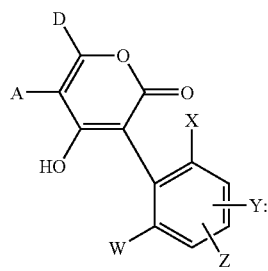
(I-4-a)

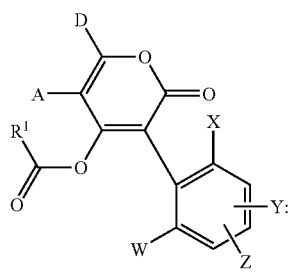
(I-4-b)

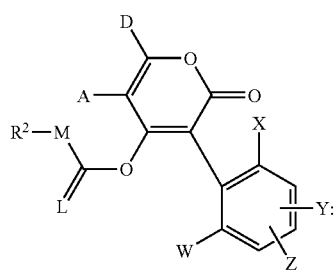
(I-4-c)

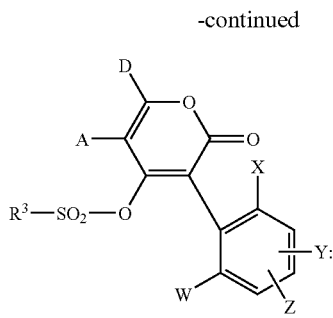
(I-4-d)

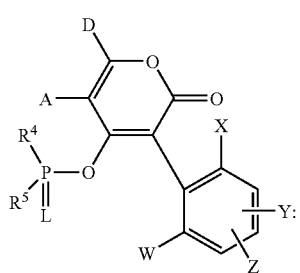
(I-4-e)

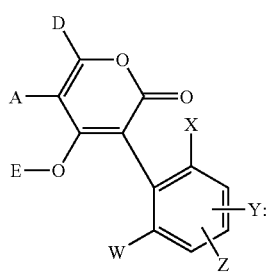
(I-4-f)

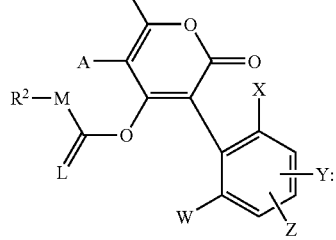
(I-4-g)

in which

A, D, E, L, M, W, X, Y, Z, $R^1$, $R^2$, $R^3$, $R^4$, $R^5$, $R^6$ and $R^7$ are as defined above.

Taking into consideration the different meanings (a), (b), (c), (d), (e), (f) and (g) of the group G, the following principle structures (I-5-a) to (I-5-g) result if CKE represents the group (5)

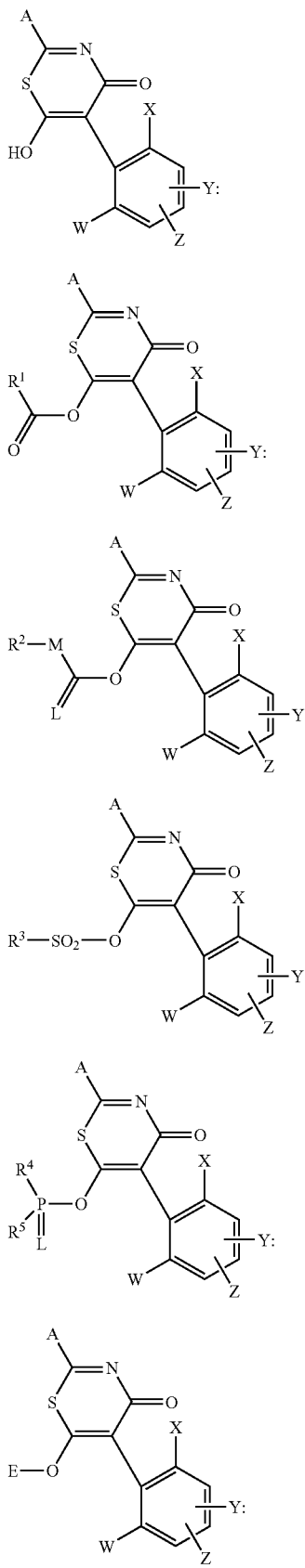

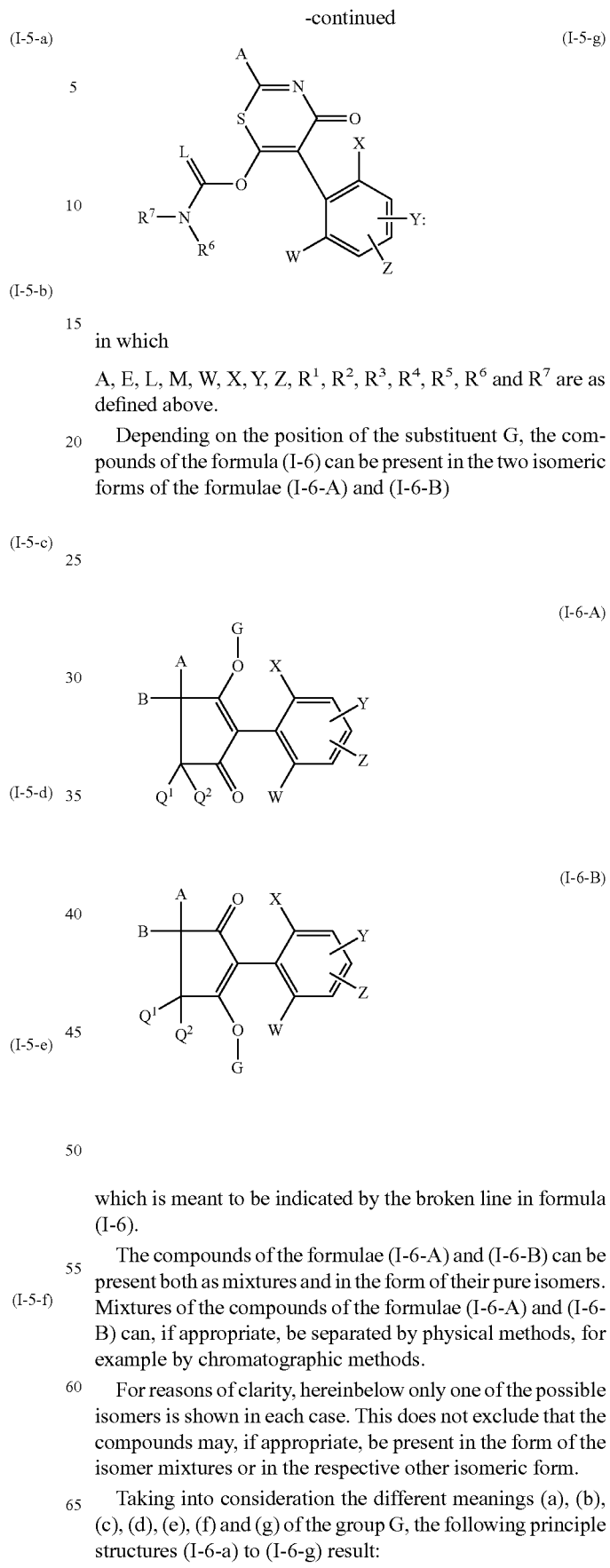

in which

A, E, L, M, W, X, Y, Z, $R^1$, $R^2$, $R^3$, $R^4$, $R^5$, $R^6$ and $R^7$ are as defined above.

Depending on the position of the substituent G, the compounds of the formula (I-6) can be present in the two isomeric forms of the formulae (I-6-A) and (I-6-B)

which is meant to be indicated by the broken line in formula (I-6).

The compounds of the formulae (I-6-A) and (I-6-B) can be present both as mixtures and in the form of their pure isomers. Mixtures of the compounds of the formulae (I-6-A) and (I-6-B) can, if appropriate, be separated by physical methods, for example by chromatographic methods.

For reasons of clarity, hereinbelow only one of the possible isomers is shown in each case. This does not exclude that the compounds may, if appropriate, be present in the form of the isomer mixtures or in the respective other isomeric form.

Taking into consideration the different meanings (a), (b), (c), (d), (e), (f) and (g) of the group G, the following principle structures (I-6-a) to (I-6-g) result:

(I-6-a)
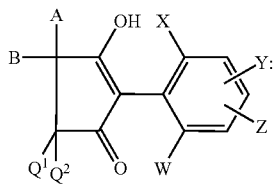

(I-6-b)
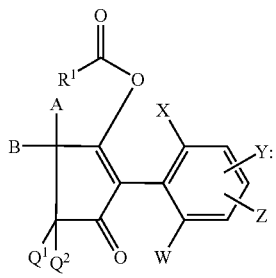

(I-6-c)
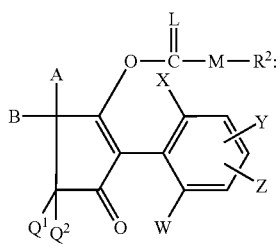

(I-6-d)
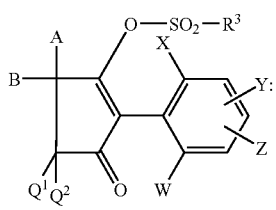

(I-6-e)
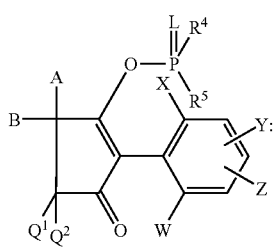

(I-6-f)
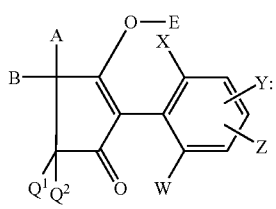

-continued (I-6-g)
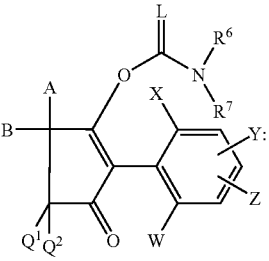

in which

A, B, $Q^1$, $Q^2$, E, L, M, W, X, Y, Z, $R^1$, $R^2$, $R^3$, $R^4$, $R^5$, $R^6$ and $R^7$ are as defined above.

Depending on the position of the substituent G, the compounds of the formula (I-7) can be present in the two isomeric forms of the formulae (I-7-A) and (I-7-B), which is meant to be indicated by the broken line in formula (I-7).

(I-7-A)
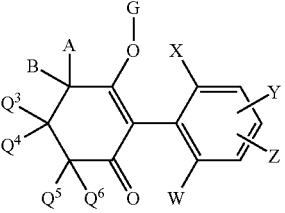

(I-7-B)
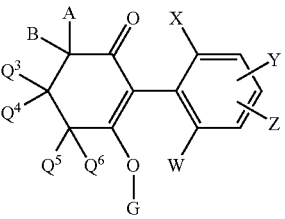

The compounds of the formulae (I-7-A) and (I-7-B) can be present both as mixtures and in the form of their pure isomers. Mixtures of the compounds of the formulae (I-7-A) and (I-7-B) can, if appropriate, be separated by physical methods, for example by chromatographic methods.

For reasons of clarity, hereinbelow only one of the possible isomers is shown in each case. This includes that the relevant compound may, if appropriate, be present in the form of the isomer mixture or in the respective other isomeric form.

Taking into consideration the different meanings (a), (b), (c), (d), (e), (f) and (g) of the group G, the following principle structures (I-7-a) to (I-7-g) result:

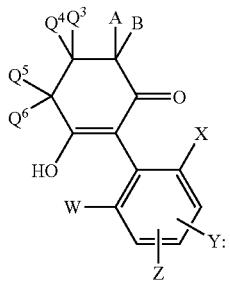
(I-7-a)

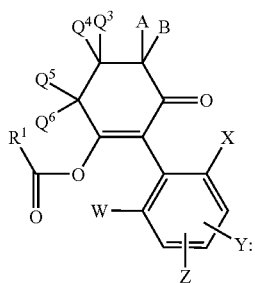
(I-7-b)

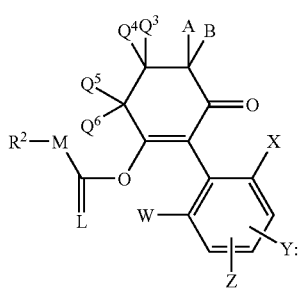
(I-7-c)

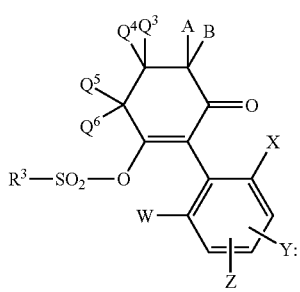
(I-7-d)

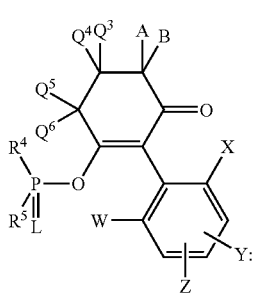
(I-7-e)

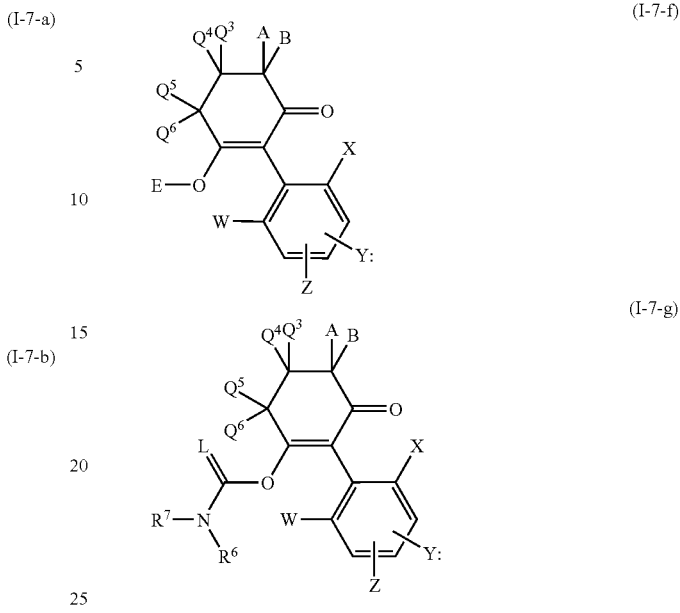
(I-7-f), (I-7-g)

in which

A, B, E, L, M, $Q^3$, $Q^4$, $Q^5$, $Q^6$, W, X, Y, Z, $R^1$, $R^2$, $R^3$, $R^4$, $R^5$, $R^6$ and $R^7$ are as defined above.

Depending on the position of the substituent G, the compounds of the formula (I-8) can be present in the two isomeric formulae (I-8-A) and (I-8-B)

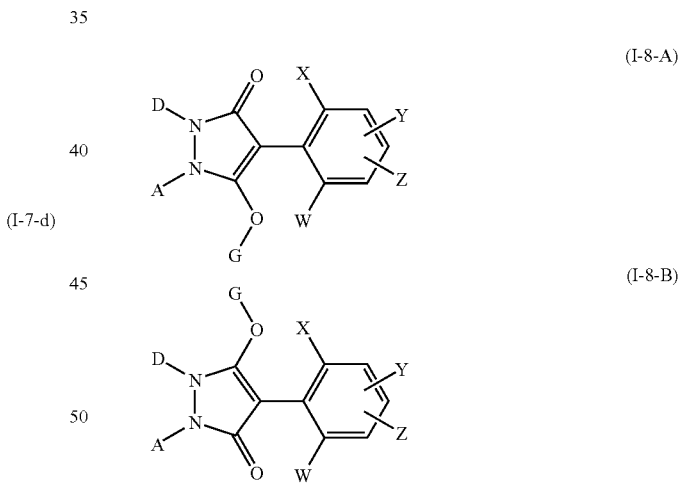
(I-8-A), (I-8-B)

which is meant to be indicated by the broken line in formula (I-8).

The compounds of the formulae (I-8-A) and (I-8-B) can be present both as mixtures and in the form of their pure isomers. Mixtures of the compounds of the formulae (I-8-A) and (I-8-B) can, if appropriate, be separated in a manner known per se by physical methods, for example by chromatographic methods.

For reasons of clarity, hereinbelow only one of the possible isomers is shown in each case. This does not exclude that the compounds may, if appropriate, be present in the form of the isomer mixtures or in the respective other isomeric form.

Taking into consideration the different meanings (a), (b), (c), (d), (e), (f) and (g) of the group G, the following principle structures (I-8-a) to (I-8-g) result if Het represents the group (8):

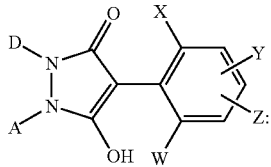
(I-8-a)

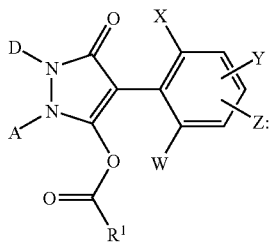
(I-8-b)

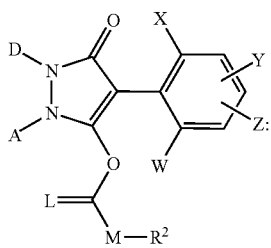
(I-8-c)

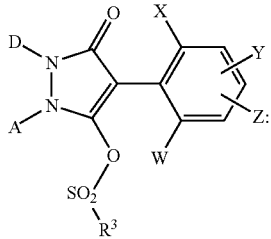
(I-8-d)

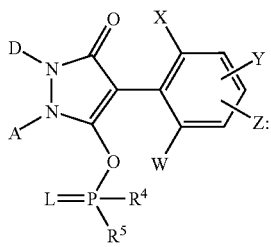
(I-8-e)

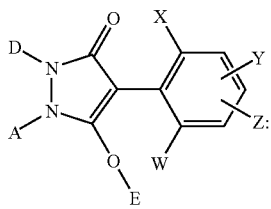
(I-8-f)

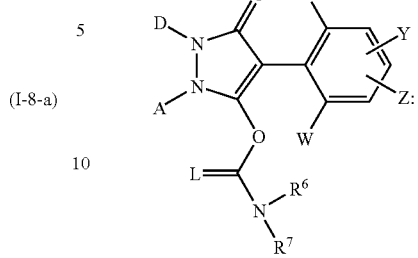
(I-8-g)

in which

A, D, E, L, M, W, X, Y, Z, $R^1$, $R^2$, $R^3$, $R^4$, $R^5$, $R^6$ and $R^7$ are as defined above.

Furthermore, it has been found that the novel compounds of the formula (I) are obtained by one of the processes described below:

(A) Substituted 3-(N-heterocyclyl)phenylpyrrolidine-2,4-diones or enols thereof of the formula (I-1-a)

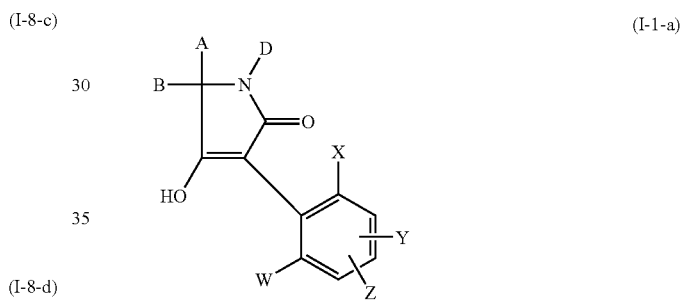
(I-1-a)

in which

A, B, D, W, X, Y and Z are as defined above are obtained when

N-acylamino acid esters of the formula (II)

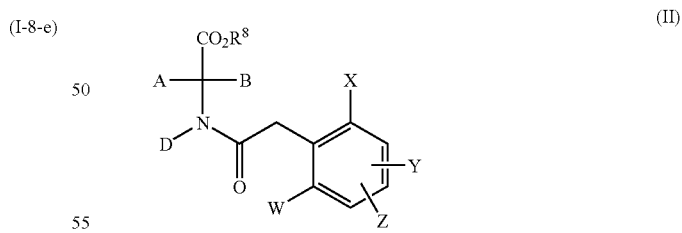
(II)

in which

A, B, D, W, X, Y and Z are as defined above and $R^8$ represents alkyl (preferably $C_1$-$C_6$-alkyl)

are condensed intramolecularly in the presence of a diluent and in the presence of a base.

(B) Moreover, it has been found that substituted 3-(N-heterocyclyl)phenyl-4-hydroxy-$\Delta^3$-di-hydrofuranone derivatives of the formula (I-2-a)

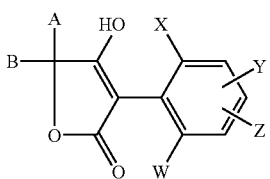

(I-2-a)

in which
A, B, W, X, Y and Z are as defined above
are obtained when
carboxylic esters of the formula (III)

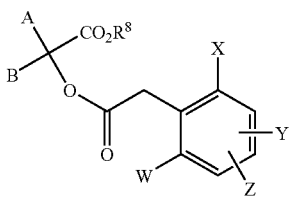

(III)

in which
A, B, W, X, Y, Z and $R^8$ are as defined above
are condensed intramolecularly in the presence of a diluent and in the presence of a base.

(C) Furthermore, it has been found that substituted 3-(N-heterocyclyl)phenyl-4-hydroxy-$\Delta^3$-di-hydrothiophenone derivatives of the formula (I-3-a)

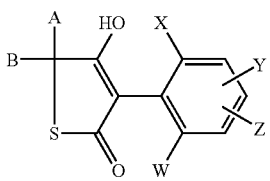

(I-3-a)

in which
A, B, W, X, Y and Z are as defined above
are obtained when
β-ketocarboxylic esters of the formula (IV)

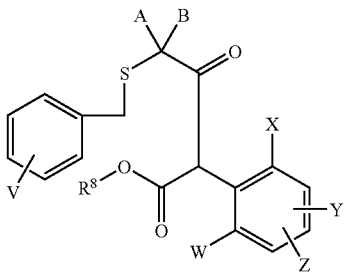

(IV)

in which
A, B, W, X, Y, Z and $R^8$ are as defined above and
V represents hydrogen, halogen, alkyl (preferably $C_1$-$C_6$-alkyl) or alkoxy (preferably $C_1$-$C_8$-alkoxy)

are cyclized intramolecularly, if appropriate in the presence of a diluent and in the presence of an acid.

(D) Furthermore, it has been found that the novel substituted 3-(N-heterocyclyl)phenylpyrone derivatives of the formula (I-4-a)

(I-4-a)

in which
A, D, W, X, Y and Z are as defined above
are obtained when
carbonyl compounds of the formula (V)

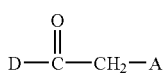

(V)

in which
A and D are as defined above
or silylenol ethers thereof of the formula (Va)

(Va)

in which
A, D and $R^8$ are as defined above
are reacted with ketene acid halides of the formula (VI)

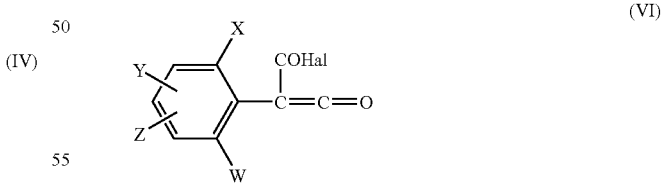

(VI)

in which
W, X, Y and Z are as defined above and
Hal represents halogen (preferably chlorine or bromine),
if appropriate in the presence of a diluent and if appropriate in the presence of an acid acceptor.

Furthermore, it has been found (E) that the novel substituted 2-(N-heterocyclyl)phenyl-1,3-thiazine derivatives of the formula (I-5-a)

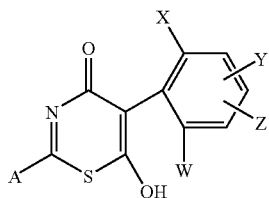

(I-5-a)

in which
A, W, X, Y and Z are as defined above
are obtained when thioamides of the formula (VII)

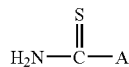

(VII)

in which
A⁻ is as defined above
are reacted with ketene acid halides of the formula (VI)

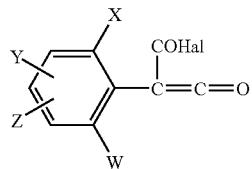

(VI)

in which
Hal, W, X, Y and Z are as defined above,
if appropriate in the presence of a diluent and if appropriate in the presence of an acid acceptor.

Furthermore, it has been found
(F) that compounds of the formula (I-6-a)

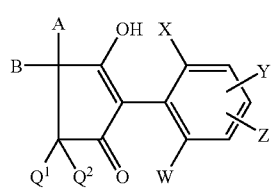

(I-6-a)

in which
A, B, $Q^1$, $Q^2$, W, X, Y and Z are as defined above
are obtained when
ketocarboxylic acid esters of the formula (VII)

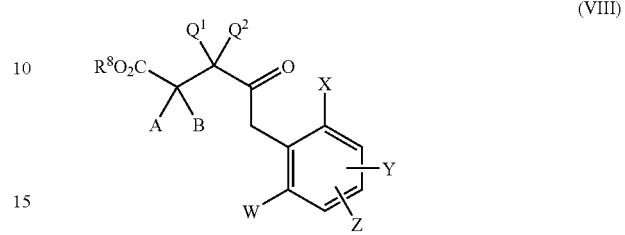

(VIII)

in which
A, B, $Q^1$, $Q^2$, W, X, Y and Z are as defined above and
$R^8$ represents alkyl (in particular $C_1$-$C_8$-alkyl)
are cyclized intramolecularly, if appropriate in the presence of a diluent and if appropriate in the presence of a base.

Moreover, it has been found
(G) that compounds of the formula (I-7-a)

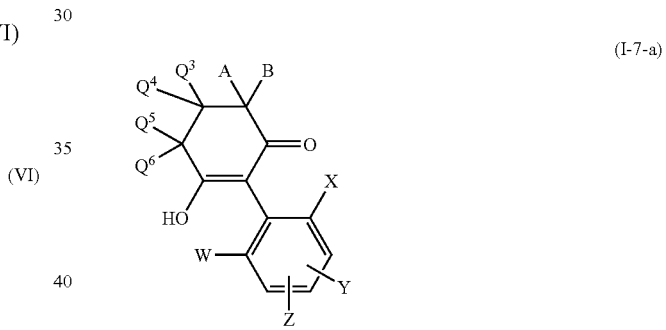

(I-7-a)

in which
A, B, $Q^3$, $Q^4$, $Q^5$, $Q^6$, W, X, Y and Z are as defined above
are obtained when
6-aryl-5-ketohexanoic esters of the formula (IX)

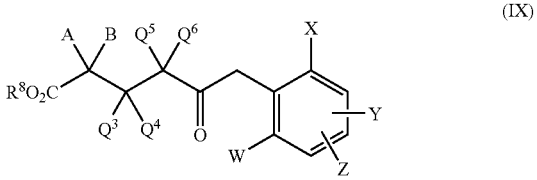

(IX)

in which
A, B, $Q^3$, $Q^4$, $Q^5$, $Q^6$, W, X, Y and Z are as defined above
and
$R^8$ represents alkyl (preferably $C_1$-$C_6$-alkyl)
are condensed intramolecularly in the presence of a diluent and in the presence of a base.

(H) Furthermore, it has been found that the compounds of the formula (I-8-a)

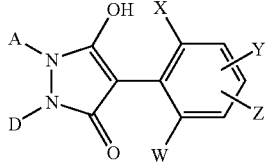
(I-8-a)

in which
A, D, W, X, Y and Z are as defined above
are obtained when
compounds of the formula (X)

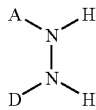
(X)

in which
A and D are as defined above
α) are reacted with compounds of the formula (VI)

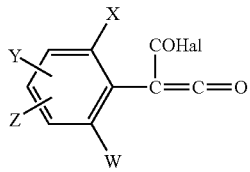
(VI)

in which
Hal, W, X, Y and Z are as defined above,
if appropriate in the presence of a diluent and if appropriate in the presence of an acid acceptor, or
β) are reacted with compounds of the formula (XI)

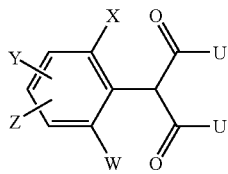
(XI)

in which
W, X, Y and Z are as defined above
and U represents $NH_2$ or $O-R^8$,
where $R^8$ is as defined above,
if appropriate in the presence of a diluent and if appropriate in the presence of a base, or γ) are reacted with compounds of the formula (XII)

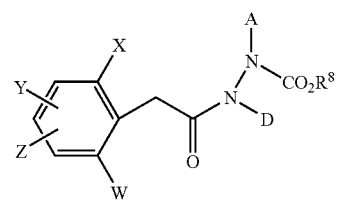
(XII)

in which
A, D, W, X, Y, Z and $R^8$ are as defined above,
if appropriate in the presence of a diluent and if appropriate in the presence of a base.

Moreover, it has been found
(I) that the compounds of the formulae (I-1-b) to (I-8-b) shown above in which A, B, D, $Q^1$, $Q^2$, $Q^3$, $Q^4$, $Q^5$, $Q^6$, $R^1$, W, X, Y and Z are as defined above are obtained when compounds of the formulae (I-1-a) to (I-8-a) shown above in which A, B, D, $Q^1$, $Q^2$, $Q^3$, $Q^4$, $Q^5$, $Q^6$, W, X, Y and Z are as defined above are in each case
(α) reacted with acid halides of the formula (XIII)

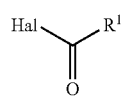
(XIII)

in which
$R^1$ is as defined above and
Hal represents halogen (in particular chlorine or bromine) or
(β) reacted with carboxylic anhydrides of the formula (XIV)

$$R^1-CO-O-CO-R^1 \quad (XIV)$$

in which
$R^1$ is as defined above,
if appropriate in the presence of a diluent and if appropriate in the presence of an acid binder;
(J) that the compounds of the formulae (I-1-c) to (I-8-c) shown above in which A, B, D, $Q^1$, $Q^2$, $Q^3$, $Q^4$, $Q^5$, $Q^6$, $R^2$, M, W, X, Y and Z are as defined above and L represents oxygen are obtained when compounds of the formulae (I-1-a) to (I-8-a) shown above in which A, B, D, $Q^1$, $Q^2$, $Q^3$, $Q^4$, $Q^5$, $Q^6$, W, X, Y and Z are as defined above are in each case
reacted with chloroformic esters or chloroformic thioesters of the formula (XV)

$$R^2\text{-M-CO-Cl} \quad (XV)$$

in which
$R^2$ and M are as defined above
if appropriate in the presence of a diluent and if appropriate in the presence of an acid binder;
(K) that compounds of the formulae (I-1-c) to (I-8-c) shown above in which A, B, D, $Q^1$, $Q^2$, $Q^3$, $Q^4$, $Q^5$, $Q^6$, $R^2$, M, W, X, Y and Z are as defined above and L represents sulphur are obtained when compounds of the formulae (I-1-a) to (I-8-a) shown above in which A, B, D, $Q^1$, $Q^2$, $Q^3$, $Q^4$, $Q^5$, $Q^6$, W, X, Y and Z are as defined above are in each case reacted with chloromonothioformic esters or chlorodithioformic esters of the formula (XVI)

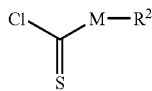

(XVI)

in which

M and $R^2$ are as defined above, if appropriate in the presence of a diluent and if appropriate in the presence of an acid binder and (L) that compounds of the formulae (I-1-d) to (I-8-d) shown above in which A, B, D, $Q^1$, $Q^2$, $Q^3$, $Q^4$, $Q^5$, $Q^6$, $R^3$, W, X, Y and Z are as defined above are obtained when compounds of the formulae (I-1-a) to (I-8-a) shown above in which A, B, D, $Q^1$, $Q^2$, $Q^3$, $Q^4$, $Q^5$, $Q^6$, W, X, Y and Z are as defined above are in each case reacted with sulphonyl chlorides of the formula (XVII)

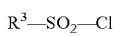

(XVII)

in which $R^3$ is as defined above, if appropriate in the presence of a diluent and if appropriate in the presence of an acid binder, (M) that compounds of the formulae (I-1-e) to (I-8-e) shown above in which A, B, D, L, $Q^1$, $Q^2$, $Q^3$, $Q^4$, $Q^5$, $Q^6$, $R^4$, $R^5$, W, X, Y and Z are as defined above are obtained when compounds of the formulae (I-1-a) to (I-8-a) shown above in which A, B, D, $Q^1$, $Q^2$, $Q^3$, $Q^4$, $Q^5$, $Q^6$, W, X, Y and Z are as defined above are in each case reacted with phosphorus compounds of the formula (XVIII)

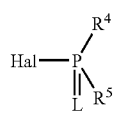

(XVIII)

in which

L, $R^4$ and $R^5$ are as defined above and

Hal represents halogen (in particular chlorine or bromine), if appropriate in the presence of a diluent and if appropriate in the presence of an acid binder, (N) that compounds of the formulae (I-1-f) to (I-8-f) shown above in which A, B, D, E, $Q^1$, $Q^2$, $Q^3$, $Q^4$, $Q^5$, $Q^6$, W, X, Y and Z are as defined above are obtained when compounds of the formulae (I-1-a) to (I-8-a) shown above in which A, B, D, $Q^1$, $Q^2$, $Q^3$, $Q^4$, $Q^5$, $Q^6$, W, X, Y and Z are as defined above are in each case reacted with metal compounds or amines of the formulae (XIX) and (XX), respectively,

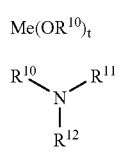

(XIX)

(XX)

in which

Me represents a mono- or divalent metal (preferably an alkali metal or alkaline earth metal, such as lithium, sodium, potassium, magnesium or calcium), t represents the number 1 or 2 and $R^{10}$, $R^{11}$, $R^{12}$ independently of one another represent hydrogen or alkyl (preferably $C_1$-$C_8$-alkyl), if appropriate in the presence of a diluent, (O) that compounds of the formulae (I-1-g) to (I-8-g) shown above in which A, B, D, L, $Q^1$, $Q^2$, $Q^3$, $Q^4$, $Q^5$, $Q^6$, $R^6$, $R^7$, W, X, Y and Z are as defined above are obtained when compounds of the formulae (I-1-a) to (I-8-a) shown above in which A, B, D, $Q^1$, $Q^2$, $Q^3$, $Q^4$, $Q^5$, $Q^6$, W, X, Y and Z are as defined above are in each case (α) reacted with isocyanates or isothiocyanates of the formula (XXI)

(XXI)

in which $R^6$ and L are as defined above, if appropriate in the presence of a diluent and if appropriate in the presence of a catalyst, or (β) reacted with carbamoyl chlorides or thiocarbamoyl chlorides of the formula (XXII)

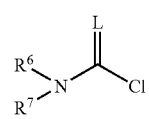

(XXII)

in which

L, $R^6$ and $R^7$ are as defined above, if appropriate in the presence of a diluent and if appropriate in the presence of an acid binder, (P) that compounds of the formulae (I-1) to (I-8) shown above in which A, B, D, $Q^1$, $Q^2$, $Q^3$, $Q^4$, $Q^5$, $Q^6$, W, X, Y and Z are as defined above are obtained when compounds of the formulae (I-1') to (I-8')

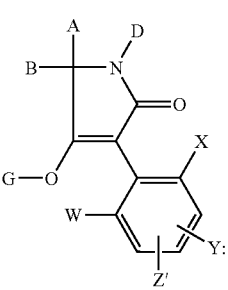

(I-1')

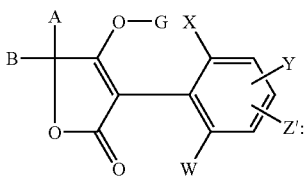

(I-2')

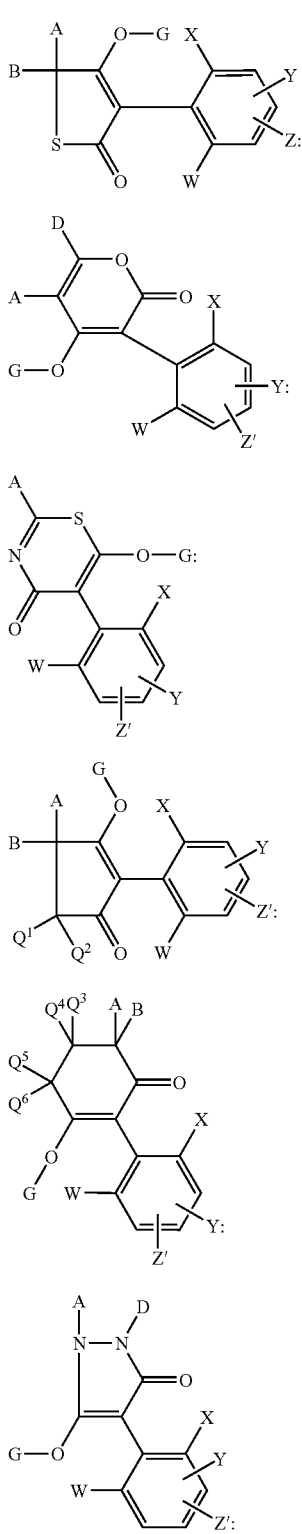

in which

A, B, D, G, Q¹, Q², Q³, Q⁴, Q⁵, Q⁶, W, X and Y are as defined above and

Z' represents chlorine, bromine, iodine, preferably bromine, are reacted with NH-heterocycles of the formula (XXIII)

H—Z (XXIII)

in which

Z is as defined above in the presence of a solvent, a base and a catalyst, suitable catalysts being in particular copper(I) salts.

Furthermore, it has been found that the novel compounds of the formula (I) are highly active as pesticides, preferably as insecticides and/or acaricides and/or herbicides and/or fungicides.

Surprisingly, it has now also been found that certain substituted cyclic ketoenols, when used jointly with the compounds which improve crop plant tolerance (safeners/antidotes) described hereinbelow, are extremely effective in preventing damage of the crop plants and can be used especially advantageously as combination products with a broad range of activity for the selective control of undesired plants in crops of useful plants, such as, for example, in cereals, but also in maize, soybeans and rice.

The invention also relates to selectively herbicidal compositions with an effective content of an active compound combination comprising, as components, (a') at least one substituted cyclic ketoenol of the formula (I) in which CKE, W, X, Y and Z have the abovementioned meanings and (b') at least one compound which improves crop plant tolerance and which is selected from the following group of compounds:

4-dichloroacetyl-1-oxa-4-aza-spiro[4.5]-decane (AD-67, MON-4660), 1-dichloroacetyl-hexahydro-3,3,8a-trimethylpyrrolo[1,2-a]-pyrimidin-6(2H)-one (dicyclonon, BAS-145138), 4-dichloroacetyl-3,4-dihydro-3-methyl-2H-1,4-benzoxazine (benoxacor), 1-methyl-hexyl 5-chloroquinolin-8-oxy-acetate (cloquintocet-mexyl—cf. also related compounds in EP-A-86750, EP-A-94349, EP-A-191736, EP-A-492366), 3-(2-chloro-benzyl)-1-(1-methyl-1-phenyl-ethyl)-urea (cumyluron), α-(cyanomethoximino)-phenylacetonitrile (cyometrinil), 2,4-dichloro-phenoxyacetic acid (2,4-D), 4-(2,4-dichloro-phenoxy)-butyric acid (2,4-DB), 1-(1-methyl-1-phenyl-ethyl)-3-(4-methyl-phenyl)-urea (daimuron, dymron), 3,6-dichloro-2-methoxy-benzoic acid (dicamba), S-1-methyl-1-phlenyl-ethyl piperidine-1-thiocarboxylate (dimepiperate), 2,2-dichloro-N-(2-oxo-2-(2-propenylamino)-ethyl)-N-(2-propenyl)-acetamide (DKA-24), 2,2-dichloro-N,N-di-2-propenyl acetamide (dichlormid), 4,6-dichloro-2-phenyl-pyrimidine (fenclorim), ethyl 1-(2,4-dichloro-phenyl)-5-trichloro-methyl-1H-1,2,4-triazole-3-carboxylate (fenchlorazole-ethyl—cf. also related compounds in EP-A-174562 and EP-A-346620), phenyl-methyl 2-chloro-4-trifluoromethyl-thiazole-5-carboxylate (flurazole), 4-chloro-N-(1,3-dioxolan-2-yl-methoxy)-α-trifluoro-acetophenone oxime (fluxofenim), 3-dichloroacetyl-5-(2-furanyl)-2,2-dimethyl-oxazolidine (furilazole, MON-13900), ethyl 4,5-dihydro-5,5-diphenyl-3-isoxazolecarboxylate (isoxadifen-ethyl—cf. also related compounds in WO-A-95/07897), 1-(ethoxycarbonyl)-ethyl-3,6-dichloro-2-methoxybenzoate (lactidichlor), (4-chloro-o-tolyloxy)-acetic acid (MCPA), 2-(4-chloro-o-tolyloxy)-propionic acid (mecoprop), diethyl 1-(2,4-dichloro-phenyl)-4,5-dihydro-5-methyl-1H-pyrazole-3,5-dicarboxylate (mefenpyr-diethyl-cf. also related compounds in WO-A-91/07874), 2-dichloromethyl-2-methyl-1,3-dioxolane (MG-191), 2-propenyl-1-oxa-4-azaspiro [4.5]decane 4-carbodithioate (MG-838), 1,8-naphthalic anhydride, α-(1,3-dioxolan-2-yl-methoximino)-phenylacetonitrile (oxabetrinil), 2,2-dichloro-N-(1,3-dioxolan-2-yl-methyl)-N-(2-propenyl)-acetamide (PPG-1292), 3-dichloroacetyl-2,2-dimethyl-oxazolidine (R-28725), 3-dichloroacetyl-2,2,5-trimethyl-oxazolidine (R-29148), 4-(4-chloro-o-tolyl)-butyric acid, 4-(4-chloro-phenoxy)-butyric acid, diphenylmethoxyacetic acid, methyl diphenylmethoxyacetate, ethyl diphenylmethoxyacetate, methyl 1-(2-chloro-phenyl)-5-phenyl-1H-pyrazole-3-carboxylate, ethyl 1-(2,4-dichloro-phenyl)-5-methyl-1H-pyrazole-3-carboxylate, ethyl 1-(2,4-dichloro-phenyl)-5-isopropyl-1H-pyrazole-3-carboxylate, ethyl 1-(2,4-dichloro-phenyl)-5-(1,1-dimethyl-ethyl)-1H-pyrazole-3-carboxylate, ethyl 1-(2,4-dichloro-phenyl)-5-phenyl-1H-pyrazole-3-carboxylate (cf. also related compounds in EP-A-269806 and EP-A-333131), ethyl 5-(2,4-dichloro-benzyl)-2-isoxazoline-3-carboxylate, ethyl 5-phenyl-2-isoxazoline-3-carboxylate, ethyl 5-(4-fluoro-phenyl)-5-phenyl-2-isoxazoline-3-carboxylate (cf. also related compounds in WO-A-91/08202), 1,3-dimethyl-but-1-yl 5-chloro-quinolin-8-oxy-acetate, 4-allyloxy-butyl 5-chloro-quinolin-8-oxy-acetate, 1-allyloxy-prop-2-yl 5-chloro-quinolin-8-oxy-acetate, methyl 5-chloro-quinoxalin-8-oxy-acetate, ethyl 5-chloro-quinolin-8-oxy-acetate, allyl 5-chloro-quinoxalin-8-oxy-acetate, 2-oxo-prop-1-yl 5-chloro-quinolin-8-oxy-acetate, diethyl 5-chloro-quinolin-8-oxy-malonate, diallyl 5-chloro-quinoxalin-8-oxy-malonate, diethyl 5-chloro-quinolin-8-oxy-malonate (cf. also related compounds in EP-A-582198), 4-carboxy-chroman-4-yl-acetic acid (AC-304415, cf. EP-A-613618), 4-chloro-phenoxy-acetic acid, 3,3'-dimethyl-4-methoxy-benzophenone, 1-bromo-4-chloromethylsulphonyl-benzene, 1-[4-(N-2-methoxybenzoyl-sulphamoyl)-phenyl]-3-methyl-urea (alias N-(2-methoxy-benzoyl)-4-[(methylamino-carbonyl)-amino]-benzenesulphonamide), 1-[4-(N-2-methoxybenzoyl-sulphamoyl)-phenyl]-3,3-dimethyl-urea, 1-[4-(N-4,5-dimethylbenzoylsulphamoyl)-phenyl]-3-methyl-urea, 1-[4-(N-naphthylsulphamoyl)-phenyl]-3,3-dimethyl-urea, N-(2-methoxy-5-methyl-benzoyl)-4-(cyclopropylaminocarbonyl)-benzenesulphonamide, and/or one of the following compounds (defined by general formulae)

of the general formula (IIa)

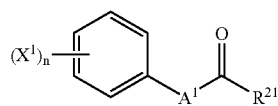

(IIa)

or of the general formula (IIb)

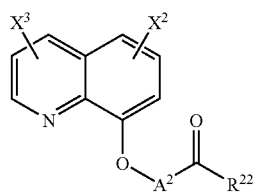

(IIb)

or of the formula (IIc)

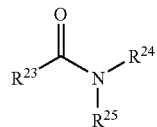

(IIc)

where n represents a number of between 0 and 5, $A^1$ represents one of the divalent heterocyclic groups outlined hereinbelow,

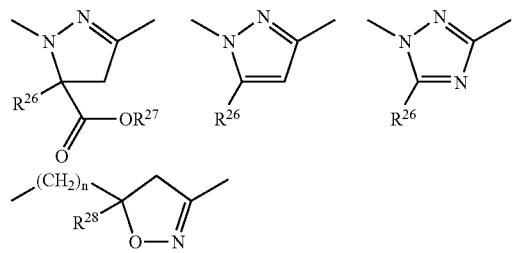

n represents a number of between 0 and 5, $A^2$ represents alkanediyl having 1 or 2 carbon atoms which is optionally substituted by $C_1$-$C_4$-alkyl and/or $C_1$-$C_4$-alkoxy-carbonyl, $R^{21}$ represents hydroxyl, mercapto, amino, $C_1$-$C_6$-alkoxy, $C_1$-$C_6$-alkylthio, $C_1$-$C_6$-alkylamino or di-($C_1$-$C_4$-alkyl)amino, $R^{22}$ represents hydroxyl, mercapto, amino, $C_1$-$C_6$-alkoxy, $C_1$-$C_6$-alkylthio, $C_1$-$C_6$-alkylamino or di-($C_1$-$C_4$-alkyl)amino, $R^{23}$ represents $C_1$-$C_4$-alkyl which is optionally substituted in each case by fluorine, chlorine and/or bromine, $R^{24}$ represents hydrogen, or represents $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, each of which is optionally substituted by fluorine, chlorine and/or bromine, or represents phenyl which is optionally substituted by fluorine, chlorine and/or bromine or $C_1$-$C_4$-alkyl, $R^{25}$ represents hydrogen, or represents $C_1$-$C_6$-alkyl, $C_2$-$C_6$-alkenyl or $C_2$-$C_6$-alkynyl, $C_1$-$C_4$-alkoxy-$C_1$-$C_4$-alkyl, dioxolanyl-$C_1$-$C_4$-alkyl, furyl, furyl-$C_1$-$C_4$-alkyl, thienyl, thiazolyl, piperidinyl, each of which is optionally substituted by fluorine, chlorine and/or bromine, or represents phenyl which is optionally substituted by fluorine, chlorine and/or bromine or $C_1$-$C_4$-alkyl, or together with $R^{24}$ represents $C_3$-$C_6$-alkanediyl or $C_2$-$C_5$-oxaalkanediyl, each of which is optionally substituted by $C_1$-$C_4$-alkyl, phenyl, furyl, a fused benzene ring or by two substituents which, together with the C atom to which they are bonded, form a 5- or 6-membered carbocycle, $R^{26}$ represents hydrogen, cyano, halogen, or represents $C_1$-$C_4$-alkyl, $C_3$-$C_6$-cycloalkyl or phenyl, each of which is optionally substituted by fluorine, chlorine and/or bromine, $R^{27}$ represents hydrogen, or represents $C_1$-$C_6$-alkyl, $C_3$-$C_6$-cycloalkyl or tri($C_1$-$C_4$-alkyl)silyl, optionally substituted by hydroxyl, cyano, halogen or $C_1$-$C_4$-alkoxy, $R^{28}$ represents hydrogen, cyano, halogen, or represents $C_1$-$C_4$-alkyl, $C_3$-$C_6$-cycloalkyl or phenyl, each of which is optionally substituted by fluorine, chlorine and/or bromine, $X^1$ represents nitro, cyano, halogen, $C_1$-$C_4$-alkyl, $C_1$-$C_4$-haloalkyl, $C_1$-$C_4$-alkoxy or $C_1$-$C_4$-haloalkoxy, $X^2$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, $X^3$ represents hydrogen, cyano, nitro, halogen, $C_1$-$C_4$-alkyl, $C_1$-$C_4$-haloalkyl, $C_1$-$C_4$-alkoxy or $C_1$-$C_4$-haloalkoxy, and/or the following compounds (defined by general formulae)

of the general formula (IId)

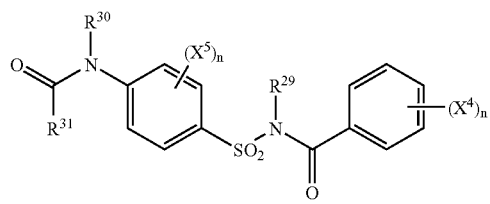

or of the general formula (IIe)

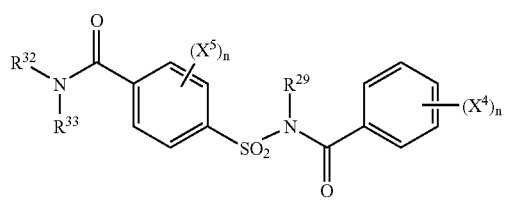

where n represents a number of between 0 and 5, $R^{29}$ represents hydrogen or $C_1$-$C_4$-alkyl, $R^{30}$ represents hydrogen or $C_1$-$C_4$-alkyl, $R^{31}$ represents hydrogen, or represents $C_1$-$C_6$-alkyl, $C_1$-$C_6$-alkoxy, $C_1$-$C_6$-alkylthio, $C_1$-$C_6$-alkylamino or di-($C_1$-$C_4$-alkyl)amino, each of which is optionally substituted by cyano, halogen or $C_1$-$C_4$-alkoxy, or represents $C_3$-$C_6$-cycloalkyl, $C_3$-$C_6$-cycloalkyloxy, $C_3$-$C_6$-cycloalkylthio or $C_3$-$C_6$-cycloalkylamino, each of which is optionally substituted by cyano, halogen or $C_1$-$C_4$-alkyl, $R^{32}$ represents hydrogen, or represents $C_1$-$C_6$-alkyl which is optionally substituted by cyano, hydroxyl, halogen or $C_1$-$C_4$-alkoxy, or represents $C_3$-$C_6$-alkenyl or $C_3$-$C_6$-alkynyl, each of which is optionally substituted by cyano or halogen, or represents $C_3$-$C_6$-cycloalkyl which is optionally substituted by cyano, halogen or $C_1$-$C_4$-alkyl, $R^{33}$ represents hydrogen, or represents $C_1$-$C_6$-alkyl which is optionally substituted by cyano, hydroxyl, halogen or $C_1$-$C_4$-alkoxy, or represents $C_3$-$C_6$-alkenyl or $C_3$-$C_6$-alkynyl, each of which is optionally substituted by cyano or halogen, or represents $C_3$-$C_6$-cycloalkyl which is optionally substituted by cyano, halogen or $C_1$-$C_4$-alkyl, or represents phenyl which is optionally substituted by nitro, cyano, halogen, $C_1$-$C_4$-alkyl, $C_1$-$C_4$-haloalkyl, $C_1$-$C_4$-alkoxy or $C_1$-$C_4$-haloalkoxy, or together with $R^{32}$ represents $C_2$-$C_6$-alkanediyl or $C_2$-$C_5$-oxaalkanediyl, each of which is optionally substituted by $C_1$-$C_4$-alkyl, $X^4$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy, and $X^5$ represents nitro, cyano, carboxyl, carbamoyl, formyl, sulphamoyl, hydroxyl, amino, halogen, $C_1$-$C_4$-alkyl, $C_1$-$C_4$-haloalkyl, $C_1$-$C_4$-alkoxy or $C_1$-$C_4$-haloalkoxy.

Formula (I) provides a general definition of the compounds according to the invention. Preferred substituents or ranges of the radicals given in the formulae mentioned hereinabove and hereinbelow are illustrated in the following text:

X preferably represents halogen, $C_1$-$C_6$-alkyl, $C_1$-$C_6$-alkenyl, $C_1$-$C_6$-alkynyl, $C_1$-$C_6$-haloalkyl, $C_1$-$C_6$-alkoxy, $C_3$-$C_6$-alkenyloxy, $C_1$-$C_6$-alkylthio, $C_1$-$C_6$-alkylsulphinyl, $C_1$-$C_6$-alkylsulphonyl, $C_1$-$C_6$-haloalkoxy, $C_3$-$C_6$-haloalkenyloxy, nitro, cyano or represents phenyl, phenoxy, phenylthio, benzyloxy or benzylthio, each of which is optionally mono- or disubstituted by halogen, $C_1$-$C_6$-alkyl, $C_1$-$C_6$-alkoxy, $C_1$-$C_4$-haloalkyl, $C_1$-$C_4$-haloalkoxy, nitro or cyano, W and Y independently of one another preferably represent hydrogen, halogen, $C_1$-$C_6$-alkyl, $C_1$-$C_6$-alkenyl, $C_1$-$C_6$-alkynyl, $C_1$-$C_6$-haloalkyl, $C_1$-$C_6$-alkoxy, $C_1$-$C_6$-haloalkoxy, nitro or cyano, Z preferably represents optionally substituted pyrazolyl, triazolyl, tetrazolyl, pyrrolyl, indolyl, benzimidazolyl, benzpyrazolyl, benztriazolyl, pyrrolidinyl, piperidinyl, piperazidinyl, morpholinyl or thiomorpholinyl which is attached via a nitrogen atom to the phenyl ring, CKE preferably represents one of the groups

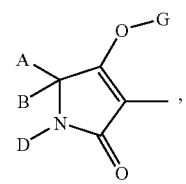

(1)

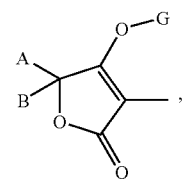

(2)

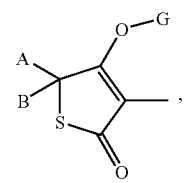

(3)

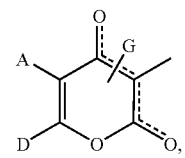

(4)

-continued

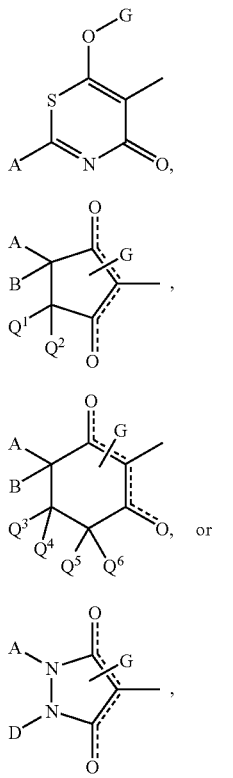

(5)

(6)

(7)

(8)

A preferably represents hydrogen or represents $C_1$-$C_{12}$-alkyl, $C_3$-$C_8$-alkenyl, $C_1$-$C_{10}$-alkoxy-$C_1$-$C_8$-alkyl, $C_1$-$C_{10}$-alkylthio-$C_1$-$C_6$-alkyl, each of which is optionally mono- to pentasubstituted by halogen, represents $C_3$-$C_8$-cycloalkyl which is optionally mono- to trisubstituted by halogen, $C_1$-$C_6$-alkyl, $C_1$-$C_2$-haloalkyl or $C_1$-$C_6$-alkoxy and in which optionally one or two not directly adjacent ring members are replaced by oxygen and/or sulphur or represents phenyl, naphthyl, hetaryl having 5 or 6 ring atoms (for example furanyl, pyridyl, imidazolyl, triazolyl, pyrazolyl, pyrimidyl, thiazolyl or thienyl), phenyl-$C_1$-$C_6$-alkyl or naphthyl-$C_1$-$C_6$-alkyl, each of which is optionally mono- to trisubstituted by halogen, $C_1$-$C_6$-alkyl, $C_1$-$C_6$-haloalkyl, $C_1$-$C_6$-alkoxy, $C_1$-$C_6$-haloalkoxy, cyano or nitro, B preferably represents hydrogen, $C_1$-$C_{12}$-alkyl or $C_1$-$C_8$-alkoxy-$C_1$-$C_6$-alkyl, or A, B and the carbon atom to which they are attached preferably represent saturated $C_3$-$C_{10}$-cycloalkyl or unsaturated $C_5$-$C_{10}$-cycloalkyl in which optionally one ring member is replaced by oxygen or sulphur and which are optionally mono- or disubstituted by $C_1$-$C_8$-alkyl, $C_3$-$C_{10}$-cycloalkyl, $C_1$-$C_8$-haloalkyl, $C_1$-$C_8$-alkoxy, $C_1$-$C_8$-alkylthio, halogen or phenyl or A, B and the carbon atom to which they are attached preferably represent $C_3$-$C_6$-cycloalkyl which is substituted by an alkylenediyl group which optionally contains one or two not directly adjacent oxygen and/or sulphur atoms and which is optionally mono- to tetrasubstituted by $C_1$-$C_4$-alkyl or by an alkylenedioxyl or by an alkylenedithioyl group which, together with the carbon atom to which it is attached, forms a further five- to eight-member ring or A, B and the carbon atom to which they are attached preferably represent $C_3$-$C_8$-cycloalkyl or $C_5$-$C_8$-cycloalkenyl in which two substituents together with the carbon atoms to which they are attached represent $C_2$-$C_6$-alkanediyl, $C_2$-$C_6$-alkenediyl or $C_4$-$C_6$-alkanediendiyl, each of which is optionally mono- to disubstituted by $C_1$-$C_6$-alkyl, $C_1$-$C_6$-alkoxy or halogen and in which optionally one methylene group is replaced by oxygen or sulphur, D preferably represents hydrogen, represents $C_1$-$C_{12}$-alkyl, $C_3$-$C_8$-alkenyl, $C_3$-$C_8$-alkynyl, $C_1$-$C_{10}$-alkoxy-$C_1$-$C_8$-alkyl, each of which is optionally mono- to pentasubstituted by halogen, represents $C_3$-$C_8$-cycloalkyl which is optionally mono- to trisubstituted by halogen, $C_1$-$C_4$-alkyl, $C_1$-$C_4$-alkoxy or $C_1$-$C_4$-haloalkyl and in which optionally one ring member is replaced by oxygen or sulphur or represents phenyl, hetaryl having 5 or 6 ring atoms (for example furanyl, imidazolyl, pyridyl, thiazolyl, pyrazolyl, pyrimidyl, pyrrolyl, thienyl or triazolyl), phenyl-$C_1$-$C_6$-alkyl or hetaryl-$C_1$-$C_6$-alkyl having 5 or 6 ring atoms (for example furanyl, imidazolyl, pyridyl, thiazolyl, pyrazolyl, pyrimidyl, pyrrolyl, thienyl or triazolyl), each of which radicals is optionally mono- to trisubstituted by halogen, $C_1$-$C_6$-alkyl, $C_1$-$C_6$-haloalkyl, $C_1$-$C_6$-alkoxy, $C_1$-$C_6$-haloalkoxy, cyano or nitro, or A and D together preferably represent in each case optionally mono- or disubstituted $C_3$-$C_6$-alkanediyl or $C_3$-$C_6$-alkenediyl in which optionally one methylene group is replaced by a carbonyl group, oxygen or sulphur, possible substituents being in each case:

halogen, hydroxyl, mercapto or $C_1$-$C_{10}$-alkyl, $C_1$-$C_6$-alkoxy, $C_1$-$C_6$-alkylthio, $C_3$-$C_7$-cycloalkyl, phenyl or benzyloxy, each of which is optionally mono- to trisubstituted by halogen, or a further $C_3$-$C_6$-alkanediyl grouping, $C_3$-$C_6$-alkenediyl grouping or butadienyl grouping which is optionally substituted by $C_1$-$C_6$-alkyl or in which optionally two adjacent substituents together with the carbon atoms to which they are attached form a further saturated or unsaturated cycle having 5 or 6 ring atoms (in the case of the compound of the formula (I-1), A and D together with the atoms to which they are attached then represent, for example, the groups mentioned further below (AD-1 to AD-10)) which can contain oxygen or sulphur, or which optionally contains one of the following groups

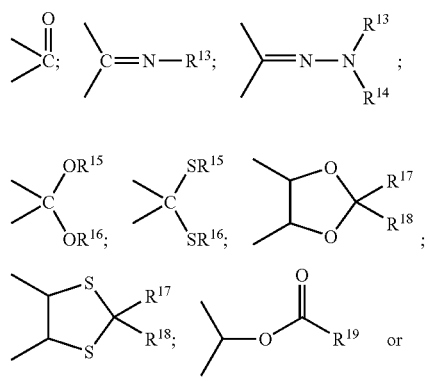

-continued

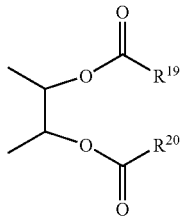

or

A and Q¹ together preferably represent $C_3$-$C_6$-alkanediyl or $C_4$-$C_6$-alkenediyl, each of which is optionally mono- or disubstituted by identical or different substituents from the group consisting of halogen, hydroxyl, of $C_1$-$C_{10}$-alkyl, $C_1$-$C_6$-alkoxy, $C_1$-$C_6$-alkylthio, $C_3$-$C_7$-cycloalkyl, each of which is optionally mono- to trisubstituted by identical or different halogen, and of benzyloxy and phenyl, each of which is optionally mono- to trisubstituted by identical or different substituents from the group consisting of halogen, $C_1$-$C_6$-alkyl and $C_1$-$C_6$-alkoxy, which $C_3$-$C_6$-alkanediyl or $C_4$-$C_6$-alkenediyl moreover optionally contains one of the groups below

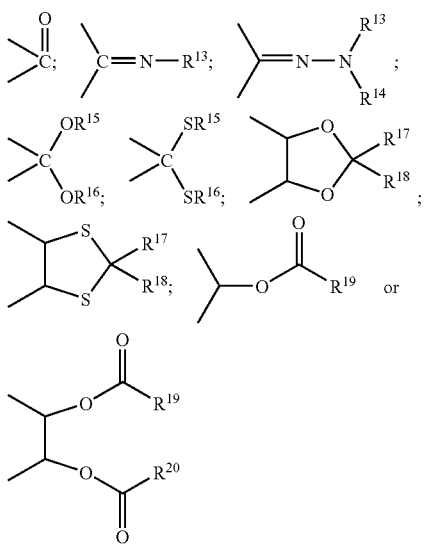

or is bridged by a $C_1$-$C_2$-alkanediyl group or by an oxygen atom or

Q¹ preferably represents hydrogen or $C_1$-$C_4$-alkyl, $Q^2$, $Q^4$, $Q^5$ and $Q^6$ independently of one another preferably represent hydrogen or $C_1$-$C_4$-alkyl, Q³ preferably represents hydrogen, represents $C_1$-$C_6$-alkyl, $C_1$-$C_6$-alkoxy-$C_1$-$C_2$-alkyl, $C_1$-$C_6$-alkylthio-$C_1$-$C_2$-alkyl, each of which is optionally mono- to pentasubstituted by halogen, represents $C_3$-$C_8$-cycloalkyl which is optionally substituted by $C_1$-$C_4$-alkyl or $C_1$-$C_4$-alkoxy and in which optionally one methylene group is replaced by oxygen or sulphur or represents phenyl which is optionally mono- or disubstituted by halogen, $C_1$-$C_4$-alkyl, $C_1$-$C_4$-alkoxy, $C_1$-$C_2$-haloalkyl, $C_1$-$C_2$-haloalkoxy, cyano or nitro, or Q³ and Q⁴ together with the carbon atom to which they are attached preferably represent a $C_3$-$C_7$-ring which is optionally mono- to trisubstituted by $C_1$-$C_4$-alkyl, $C_1$-$C_4$-alkoxy or $C_1$-$C_2$-haloalkyl and in which optionally one ring member is replaced by oxygen or sulphur, G preferably represents hydrogen (a) or represents one of the groups

 (b)

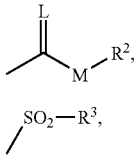 (c)

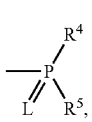 (d)

(e)

E  or (f)

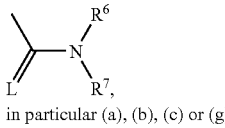 (g)

in particular (a), (b), (c) or (g)

in which

E represents a metal ion equivalent or an ammonium ion,

L represents oxygen or sulphur and

M represents oxygen or sulphur,

R¹ preferably represents $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl, poly-$C_1$-$C_8$-alkoxy-$C_1$-$C_8$-alkyl, each of which is optionally mono- to pentasubstituted by halogen, or represents $C_3$-$C_8$-cycloalkyl which is optionally mono- to trisubstituted by halogen, $C_1$-$C_6$-alkyl or $C_1$-$C_6$-alkoxy and in which optionally one or more (preferably not more than two) not directly adjacent ring members are replaced by oxygen and/or sulphur, preferably represents phenyl which is optionally mono- to trisubstituted by halogen, cyano, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylthio or $C_1$-$C_6$-alkylsulphonyl, preferably represents phenyl-$C_1$-$C_6$-alkyl which is optionally mono- to trisubstituted by halogen, nitro, cyano, $C_1$-$C_6$-alkyl, $C_1$-$C_6$-alkoxy, $C_1$-$C_6$-haloalkyl or $C_1$-$C_6$-haloalkoxy, preferably represents 5- or 6-membered hetaryl which is optionally mono- or disubstituted by halogen or $C_1$-$C_6$-alkyl (for example pyrazolyl, thiazolyl, pyridyl, pyrimidyl, furanyl or thienyl), preferably represents phenoxy $C_1$-$C_6$-alkyl which is optionally mono- or disubstituted by halogen or $C_1$-$C_6$-alkyl or preferably represents 5- or 6-membered hetaryloxy $C_1$-$C_6$-alkyl which is optionally mono- or disubstituted by halogen, amino or $C_1$-$C_6$-alkyl (for example pyridyloxy-$C_1$-$C_6$-alkyl, pyrimidyloxy-$C_1$-$C_6$-alkyl or thiazolyloxy-$C_1$-$C_6$-alkyl), $R^2$ preferably represents $C_1$-$C_{20}$-alkyl, $C_2$-$C_{20}$-alkenyl, $C_1$-$C_8$-alkoxy-$C_2$-$C_8$-alkyl, poly-$C_1$-$C_8$-alkoxy-$C_2$-$C_8$-alkyl, each of which is optionally mono- to pentasubstituted by halogen, preferably represents $C_3$-$C_8$-cycloalkyl which is optionally mono- or disubstituted by halogen, $C_1$-$C_6$-alkyl or $C_1$-$C_6$-alkoxy or preferably represents phenyl or benzyl, each of which is optionally mono- to trisubstituted by halogen, cyano, nitro, $C_1$-$C_6$-alkyl, $C_1$-$C_6$-alkoxy, $C_1$-$C_6$-haloalkyl or $C_1$-$C_6$-halo-alkoxy, $R^3$ preferably represents $C_1$-$C_8$-alkyl which is optionally mono- to nonasubstituted by halogen or represents phenyl or benzyl, each of which is optionally mono- to trisubstituted by halogen, $C_1$-$C_6$-alkyl, $C_1$-$C_6$-alkoxy, $C_1$-$C_4$-haldalkyl, $C_1$-$C_4$-haloalkoxy, cyano or nitro, $R^4$ and $R^5$ independently of one another preferably represent $C_1$-$C_8$-alkyl, $C_1$-$C_8$-alkoxy, $C_1$-$C_8$-alkylamino, di-($C_1$-$C_8$-alkyl)amino, $C_1$-$C_8$-alkylthio, $C_2$-$C_8$-alkenylthio, $C_3$-$C_7$-cyclo-alkylthio, each of which is optionally mono- to pentasubstituted by halogen, or represent phenyl, phenoxy or phenylthio, each of which is optionally mono- to trisubstituted by halogen, nitro, cyano, $C_1$-$C_4$-alkoxy, $C_1$-$C_4$-haloalkoxy, $C_1$-$C_4$-alkylthio, $C_1$-$C_4$-halo-alkylthio, $C_1$-$C_4$-alkyl or $C_1$-$C_4$-haloalkyl, $R^6$ and $R^7$ independently of one another preferably represent hydrogen, represent $C_1$-$C_8$-alkyl, $C_3$-$C_8$-cycloalkyl, $C_1$-$C_8$-alkoxy, $C_3$-$C_8$-alkenyl, $C_1$-$C_8$-alkoxy-$C_1$-$C_8$-alkyl, each of which is optionally mono- to pentasubstituted by halogen, represent phenyl which is optionally mono- to trisubstituted by halogen, $C_1$-$C_8$-haloalkyl, $C_1$-$C_8$-alkyl or $C_1$-$C_8$-alkoxy, represent benzyl which is optionally mono- to trisubstituted by halogen, $C_1$-$C_8$-alkyl, $C_1$-$C_8$-haloalkyl or $C_1$-$C_8$-alkoxy or together represent a $C_3$-$C_6$-alkylene radical which is optionally mono- or disubstituted by $C_1$-$C_4$-alkyl and in which optionally one carbon atom is replaced by oxygen or sulphur, $R^{13}$ preferably represents hydrogen, preferably represents $C_1$-$C_8$-alkyl or $C_1$-$C_8$-alkoxy, each of which is optionally mono- to trisubstituted by halogen, represents $C_3$-$C_8$-cycloalkyl which is optionally mono- to trisubstituted by halogen, $C_1$-$C_4$-alkyl or $C_1$-$C_4$-alkoxy and in which optionally one methylene group is replaced by oxygen or sulphur, or represents phenyl, phenyl-$C_1$-$C_4$-alkyl or phenyl-$C_1$-$C_4$-alkoxy, each of which is optionally mono- or disubstituted by halogen, $C_1$-$C_6$-alkyl, $C_1$-$C_6$-alkoxy, $C_1$-$C_4$-haloalkyl, $C_1$-$C_4$-haloalkoxy, nitro or cyano, $R^{14}$ preferably represents hydrogen or $C_1$-$C_8$-alkyl or $R^{13}$ and $R^{14}$ together preferably represent $C_4$-$C_6$-alkanediyl, $R^{15}$ and $R^{16}$ are identical or different and preferably represent $C_1$-$C_6$-alkyl or $R^{15}$ and $R^{16}$ together preferably represent a $C_2$-$C_4$-alkanediyl radical which is optionally mono- or disubstituted by $C_1$-$C_6$-alkyl, $C_1$-$C_6$-haloalkyl or by phenyl which is optionally mono- or disubstituted by halogen, $C_1$-$C_6$-alkyl, $C_1$-$C_4$-haloalkyl, $C_1$-$C_6$-alkoxy, $C_1$-$C_4$-haloalkoxy, nitro or cyano, $R^{17}$ and $R^{18}$ independently of one another preferably represent hydrogen, represent optionally halogen-substituted $C_1$-$C_8$-alkyl or represent phenyl which is optionally mono- or disubstituted by halogen, $C_1$-$C_6$-alkyl, $C_1$-$C_6$-alkoxy, $C_1$-$C_4$-haloalkyl, $C_1$-$C_4$-haloalkoxy, nitro or cyano or $R^{17}$ and $R^{18}$ together with the carbon atom to which they are attached preferably represent a carbonyl group or represent $C_5$-$C_7$-cycloalkyl which is optionally mono- or disubstituted by halogen, $C_1$-$C_4$-alkyl or $C_1$-$C_4$-alkoxy and in which optionally one methylene group is replaced by oxygen or sulphur, $R^{19}$ and $R^{20}$ independently of one another preferably represent $C_1$-$C_{10}$-alkyl, $C_2$-$C_{10}$-alkenyl, $C_1$-$C_{10}$-alkoxy, $C_1$-$C_{10}$-alkylamino, $C_3$-$C_{10}$-alkenylamino, di-($C_1$-$C_{10}$-alkyl)amino or di-($C_3$-$C_{10}$-alkenyl)amino.

In the radical definitions mentioned as being preferred, halogen represents fluorine, chlorine, bromine and iodine, in particular fluorine, chlorine and bromine.

X particularly preferably represents fluorine, chlorine, bromine, $C_1$-$C_4$-alkyl, $C_1$-$C_4$-alkoxy, $C_1$-$C_4$-haloalkyl, $C_1$-$C_4$-haloalkoxy, nitro or cyano, W and Y independently of one another particularly preferably represent hydrogen, fluorine, chlorine, bromine, $C_1$-$C_4$-alkyl, $C_1$-$C_4$-haloalkyl, $C_1$-$C_4$-alkoxy, $C_1$-$C_4$-haloalkoxy, Z particularly preferably represents one of the radicals

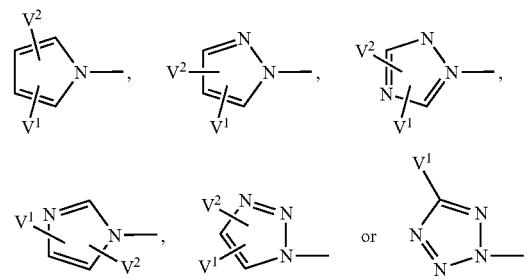

$V^1$ particularly preferably represents hydrogen, fluorine, chlorine, bromine, iodine, $C_1$-$C_6$-alkyl, $C_1$-$C_4$-alkoxy, $C_1$-$C_4$-haloalkyl, $C_1$-$C_4$-haloalkoxy, cyano or nitro, $V^2$ particularly preferably represents hydrogen, fluorine, chlorine, bromine, $C_1$-$C_4$-alkyl or $C_1$-$C_2$-haloalkyl, $V^1$ and $V^2$ together particularly preferably represent $C_3$-$C_4$-alkanediyl which is optionally mono- to tetrasubstituted by fluorine and which may optionally be interrupted once or twice by oxygen or represent butadienyl which is optionally mono- or disubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, cyano or nitro, CKE particularly preferably represents one of the groups

-continued

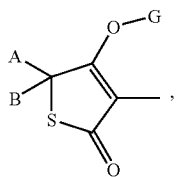
(3)

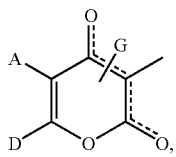
(4)

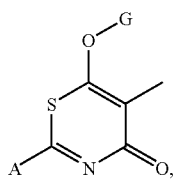
(5)

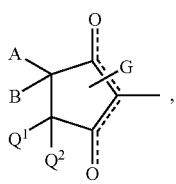
(6)

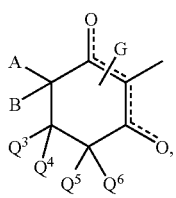
(7)

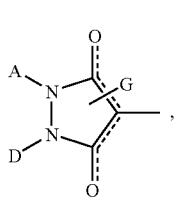
(8)

A particularly preferably represents hydrogen, represents $C_1$-$C_6$-alkyl, $C_1$-$C_4$-alkoxy-$C_1$-$C_2$-alkyl, each of which is optionally mono- to trisubstituted by fluorine or chlorine, represents $C_3$-$C_6$-cycloalkyl which is optionally mono- or disubstituted by fluorine, chlorine, $C_1$-$C_2$-alkyl, trifluoromethyl or $C_1$-$C_2$-alkoxy or (but not in the case of the compounds of the formulae (I-3), (I-4), (I-6) and (I-7)) represents phenyl or benzyl, each of which is optionally mono- or disubstituted by fluorine, chlorine, bromine, $C_1$-$C_4$-alkyl, $C_1$-$C_2$-haloalkyl, $C_1$-$C_4$-alkoxy, $C_1$-$C_2$-haloalkoxy, cyano or nitro, B particularly preferably represents hydrogen, $C_1$-$C_4$-alkyl or $C_1$-$C_2$-alkoxyl-$C_1$-$C_2$-alkyl or A, B and the carbon atom to which they are attached particularly preferably represent saturated $C_3$-$C_7$-cycloalkyl or unsaturated $C_5$-$C_7$-cycloalkyl in which optionally one ring member is replaced by oxygen or sulphur and which is optionally mono- or disubstituted by $C_1$-$C_6$-alkyl, trifluoromethyl or $C_1$-$C_6$-alkoxy, with the proviso that in this case $Q^3$ particularly preferably represents hydrogen or methyl, or A, B and the carbon atom to which they are attached particularly preferably represent $C_5$-$C_6$-cycloalkyl which is substituted by an alkylenediyl group which optionally contains one or two not directly adjacent oxygen or sulphur atoms and which is optionally mono- or disubstituted by methyl or ethyl, or by an alkylenedioxyl or by an alkylenedithiol group which, together with the carbon atom to which it is attached, forms a further five- or six-membered ring, with the proviso that in this case $Q^3$ particularly preferably represents hydrogen or methyl, A, B and the carbon atom to which they are attached particularly preferably represent $C_3$-$C_6$-cycloalkyl or $C_5$-$C_6$-cycloalkenyl in which two substituents together with the carbon atoms to which they are attached represent $C_2$-$C_4$-alkanediyl, $C_2$-$C_4$-alkenediyl or buta-dienediyl, each of which is optionally substituted by $C_1$-$C_2$-alkyl or $C_1$-$C_2$-alkoxy, with the proviso that in this case $Q^3$ particularly preferably represents hydrogen or methyl, D particularly preferably represents hydrogen, represents $C_1$-$C_6$-alkyl, $C_3$-$C_6$-alkenyl, $C_1$-$C_4$-alkoxy-$C_2$-$C_3$-alkyl, each of which is optionally mono- to trisubstituted by fluorine, represents $C_3$-$C_6$-cycloalkyl which is optionally mono- or disubstituted by $C_1$-$C_4$-alkyl, $C_1$-$C_4$-alkoxy or $C_1$-$C_2$-haloalkyl and in which optionally one methylene group is replaced by oxygen or (but not in the case of the compounds of the formula (I-1)) represents phenyl or pyridyl, each of which is optionally mono- or disubstituted by fluorine, chlorine, bromine, $C_1$-$C_4$-alkyl, $C_1$-$C_4$-haloalkyl, $C_1$-$C_4$-alkoxy or $C_1$-$C_4$-halo-alkoxy, or A and D together particularly preferably represent $C_3$-$C_5$-alkanediyl which is optionally mono- or disubstituted and in which one methylene group may be replaced by a carbonyl group, oxygen or sulphur, possible substituents being $C_1$-$C_2$-alkyl or $C_1$-$C_2$-alkoxy, or A and D (in the case of the compounds of the formula (I-1)) together with the atoms to which they are attached represent one of the groups AD-1 to AD-10:

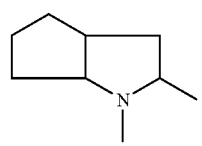
AD-1

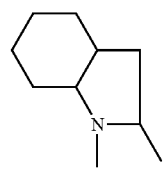
AD-2

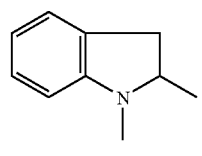
AD-3

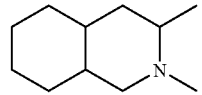
AD-4

-continued

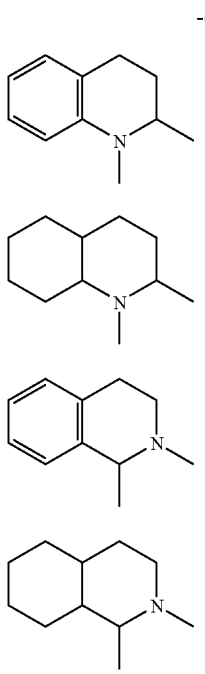

AD-5
AD-6
AD-7
AD-8
AD-9

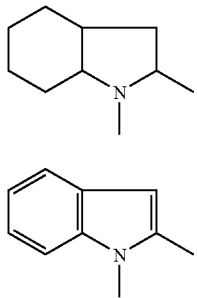

AD-10 or

A and $Q^1$ together particularly preferably represent $C_3$-$C_4$-alkanediyl or $C_4$-alkenediyl, each of which is optionally mono- or disubstituted by identical or different substituents from the group consisting of fluorine, chlorine, hydroxyl and $C_1$-$C_8$-alkyl and $C_1$-$C_4$-alkoxy, each of which is optionally mono- to trisubstituted by fluorine, or $Q^1$ particularly preferably represents hydrogen, $Q^2$ particularly preferably represents hydrogen, $Q^4$, $Q^5$ and $Q^6$ independently of one another particularly preferably represent hydrogen or $C_1$-$C_3$-alkyl, $Q^3$ particularly preferably represents hydrogen, $C_1$-$C_4$-alkyl, trifluoromethyl or represents $C_3$-$C_6$-cycloalkyl which is optionally mono- or disubstituted by methyl or methoxy, or $Q^3$ and $Q^4$ together with the carbon to which they are attached particularly preferably represent a saturated $C_5$-$C_6$-ring which is optionally mono- or disubstituted by $C_1$-$C_2$-alkyl or $C_1$-$C_2$-alkoxy and in which optionally one ring member is replaced by oxygen or sulphur, with the proviso that in this case A particularly preferably represents hydrogen or methyl, or G particularly preferably represents hydrogen (a) or represents one of the groups

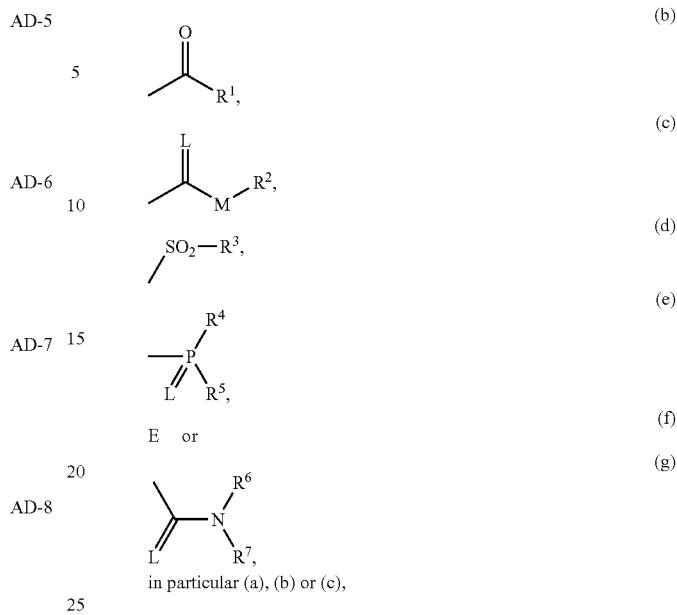

in particular (a), (b) or (c), in which

E represents a metal ion equivalent or an ammonium ion,

L represents oxygen or sulphur and

M represents oxygen or sulphur, $R^1$ particularly preferably represents $C_1$-$C_8$-alkyl, $C_2$-$C_8$-alkenyl, $C_1$-$C_4$-alkoxy-$C_1$-$C_2$-alkyl, $C_1$-$C_4$-alkylthio-$C_1$-$C_2$-alkyl, each of which is optionally mono- to trisubstituted by fluorine or chlorine, or represents $C_3$-$C_6$-cycloalkyl which is optionally mono- or disubstituted by fluorine, chlorine, $C_1$-$C_2$-alkyl or $C_1$-$C_2$-alkoxy and in which optionally one or two not directly adjacent ring members are replaced by oxygen, particularly preferably represents phenyl which is optionally mono- or disubstituted by fluorine, chlorine, bromine, cyano, nitro, $C_1$-$C_4$-alkyl, $C_1$-$C_4$-alkoxy, $C_1$-$C_2$-haloalkyl or $C_1$-$C_2$-haloalkoxy, $R^2$ particularly preferably represents $C_1$-$C_8$-alkyl, $C_2$-$C_8$-alkenyl or $C_1$-$C_4$-alkoxy-$C_2$-$C_4$-alkyl, each of which is optionally mono- to trisubstituted by fluorine, particularly preferably represents $C_3$-$C_6$-cycloalkyl which is optionally monosubstituted by $C_1$-$C_2$-alkyl or $C_1$-$C_2$-alkoxy or particularly preferably represents phenyl or benzyl, each of which is optionally mono- or disubstituted by fluorine, chlorine, bromine, cyano, nitro, $C_1$-$C_4$-alkyl, $C_1$-$C_3$-alkoxy, trifluoromethyl or trifluoromethoxy, $R^3$ particularly preferably represents $C_1$-$C_6$-alkyl which is optionally mono- to trisubstituted by fluorine or represents phenyl or benzyl, each of which is optionally monosubstituted by fluorine, chlorine, bromine, $C_1$-$C_4$-alkyl, $C_1$-$C_4$-alkoxy, trifluoromethyl, trifluoro-methoxy, cyano or nitro, $R^4$ particularly preferably represents $C_1$-$C_6$-alkyl, $C_1$-$C_6$-alkoxy, $C_1$-$C_6$-alkylamino, di-($C_1$-$C_6$-alkyl)amino, $C_1$-$C_6$-alkylthio, $C_3$-$C_4$-alkenylthio, $C_3$-$C_6$-cycloalkylthio, each of which is optionally mono- to trisubstituted by fluorine, or represents phenyl, phenoxy or phenylthio, each of which is optionally mono- or disubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-halo-alkylthio, $C_1$-$C_3$-alkyl or trifluoromethyl, $R^5$ particularly preferably represents $C_1$-$C_6$-alkoxy or $C_1$-$C_6$-alkylthio, $R^6$ particularly preferably represents hydrogen, represents $C_1$-$C_6$-alkyl, $C_3$-$C_6$-cycloalkyl, $C_1$-$C_6$-alkoxy, $C_3$-$C_6$-alkenyl, $C_1$-$C_6$-alkoxy-$C_1$-$C_4$-alkyl, each of which is optionally mono- to trisubstituted by fluorine, represents phenyl which is optionally mono- or disubstituted by fluorine, chlorine, bromine, trifluoromethyl, $C_1$-$C_4$-alkyl or $C_1$-$C_4$-alkoxy, represents benzyl which is optionally monosubstituted by fluorine, chlorine, bromine, $C_1$-$C_4$-alkyl, trifluoromethyl or $C_1$-$C_4$-alkoxy, $R^7$ particularly preferably represents $C_1$-$C_6$-alkyl, $C_3$-$C_6$-alkenyl or $C_1$-$C_6$-alkoxy-$C_1$-$C_4$-alkyl, $R^6$ and $R^7$ together particularly preferably represent a $C_4$-$C_5$-alkylene radical which is optionally mono- or disubstituted by methyl or ethyl and in which optionally a methylene group is replaced by oxygen or sulphur.

In the radical definitions mentioned as being particularly preferred, halogen represents fluorine, chlorine, bromine and iodine, in particular fluorine, chlorine and bromine.

W very particularly preferably represents hydrogen, methyl, ethyl or chlorine,

X very particularly preferably represents chlorine, methyl, ethyl, propyl, methoxy, ethoxy, propoxy, trifluoromethyl, difluoromethoxy or trifluoromethoxy, Y very particularly preferably represents hydrogen or methyl, Z very particularly preferably represents one of the radicals

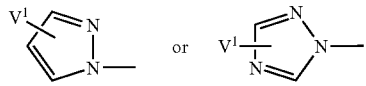

$V^1$ very particularly preferably represents hydrogen, fluorine, chlorine, bromine, methyl, ethyl, methoxy, ethoxy, trifluoromethyl or cyano, CKE very particularly preferably represents one of the groups

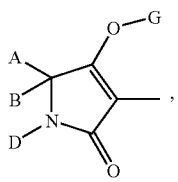 (1)

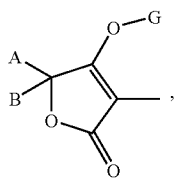 (2)

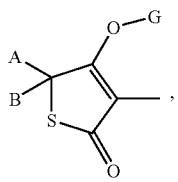 (3)

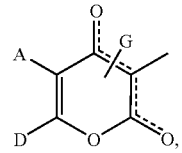 (4)

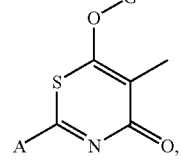 (5)

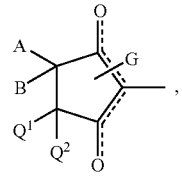 (6)

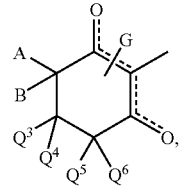 (7)

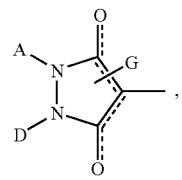 (8)

A very particularly preferably represents hydrogen, represents $C_1$-$C_4$-alkyl or $C_1$-$C_2$-alkoxy-$C_1$-$C_2$-alkyl, each of which is optionally mono- to trisubstituted by fluorine, represents cyclopropyl, cyclopentyl or cyclohexyl and, only in the case of the compounds of the formula (I-5), represents phenyl which is optionally mono- or disubstituted by fluorine, chlorine, bromine, methyl, ethyl, n-propyl, isopropyl, methoxy, ethoxy, trifluoromethyl, trifluoromethoxy, cyano or nitro, B very particularly preferably represents hydrogen, methyl or ethyl or A, B and the carbon atom to which they are attached very particularly preferably represent saturated $C_5$-$C_6$-cycloalkyl in which optionally one ring member is replaced by oxygen or sulphur and which is optionally monosubstituted by methyl, ethyl, propyl, isopropyl, trifluoromethyl, methoxy, ethoxy, propoxy, butoxy or isobutoxy, with the proviso that in this case $Q^3$ very particularly preferably represents hydrogen, or A, B and the carbon atom to which they are attached very particularly preferably represent $C_6$-cycloalkyl which is substituted by an alkylenedioxyl group containing two not directly adjacent oxygen atoms, with the proviso that in this case $Q^3$ very particularly preferably represents hydrogen, or A, B and the carbon atom to which they are attached very particularly preferably represent $C_5$-$C_6$-cycloalkyl or $C_5$-$C_6$-cycloalkenyl in which two substituents together with the carbon atoms to which they are attached represent $C_2$-$C_4$-alkanediyl or $C_2$-$C_4$-alkenediyl or butadienediyl, with the proviso that in this case $Q^3$ very particularly preferably represents hydrogen, D very particularly preferably represents hydrogen, represents $C_1$-$C_4$-alkyl, $C_3$-$C_4$-alkenyl, $C_1$-$C_4$-alkoxy-$C_1$-$C_3$-alkyl, each of which is optionally mono- to trisubstituted by fluorine, represents cyclopropyl, cyclopentyl or cyclohexyl or (but not in the case of the compounds of the formula (I-1)) represents pyridyl or phenyl which is optionally monosubstituted by fluorine, chlorine, methyl, ethyl, n-propyl, isopropyl, methoxy, ethoxy or trifluoromethyl, or A and D together very particularly preferably represent $C_3$-$C_5$-alkanediyl which is optionally mono- or disubstituted by methyl or methoxy and in which optionally one carbon atom is replaced by oxygen or sulphur or represent the group AD-1

A and $Q^1$ together very particularly preferably represent $C_3$-$C_4$-alkanediyl which is optionally mono- or disubstituted by methyl or methoxy, or $Q^1$ very particularly preferably represents hydrogen, $Q^2$ very particularly preferably represents hydrogen, $Q^4$, $Q^5$ and $Q^6$ independently of one another very particularly preferably represent hydrogen or methyl, $Q^3$ very particularly preferably represents hydrogen, methyl, ethyl, propyl or isopropyl, or $Q^3$ and $Q^4$ together with the carbon to which they are attached very particularly preferably represent a saturated $C_5$-$C_6$-ring which is optionally monosubstituted by methyl or methoxy, with the proviso that in this case A very particularly preferably represents hydrogen, G very particularly preferably represents hydrogen (a) or represents one of the groups (b)

(c)

—SO$_2$—R$^3$, (d)

(e)

(f)

E or

-continued (g)

in particular (a), (b) or (c)

in which

E represents a metal ion equivalent or an ammonium ion,

L represents oxygen or sulphur and

M represents oxygen or sulphur, $R^1$ very particularly preferably represents $C_1$-$C_6$-alkyl, $C_2$-$C_6$-alkenyl, $C_1$-$C_2$-alkoxy-$C_1$-alkyl, $C_1$-$C_2$-alkylthio-$C_1$-alkyl, each of which is optionally mono- to trisubstituted by fluorine, or represents cyclopropyl or cyclohexyl, each of which is optionally monosubstituted by fluorine, chlorine, methyl or methoxy, very particularly preferably represents phenyl which is optionally monosubstituted by fluorine, chlorine, bromine, cyano, nitro, methyl, methoxy, trifluoromethyl or tri-fluoromethoxy, $R^2$ very particularly preferably represents $C_1$-$C_8$-alkyl, $C_2$-$C_6$-alkenyl or $C_1$-$C_4$-alkoxy-$C_2$-$C_3$-alkyl, each of which is optionally monosubstituted by fluorine, or very particularly preferably represents phenyl or benzyl, each of which is optionally monosubstituted by fluorine, chlorine, cyano, nitro, methyl, ethyl, n-propyl, i-propyl, methoxy, ethoxy, trifluoromethyl or trifluoromethoxy, $R^3$ very particularly preferably represents methyl, ethyl, n-propyl, isopropyl, each of which is optionally mono- to trisubstituted by fluorine, or represents phenyl or benzyl, each of which is optionally monosubstituted by fluorine, chlorine, bromine, methyl, tert-butyl, methoxy, trifluoromethyl, trifluoromethoxy, cyano or nitro, $R^4$ very particularly preferably represents $C_1$-$C_4$-alkyl, $C_1$-$C_4$-alkoxy, $C_1$-$C_4$-alkylamino, di-($C_1$-$C_4$-alkyl)amino, $C_1$-$C_4$-alkylthio, each of which is optionally mono- to trisubstituted by fluorine, or represents phenyl, phenoxy or phenylthio, each of which is optionally monosubstituted by fluorine, chlorine, bromine, nitro, cyano, $C_1$-$C_2$-alkoxy, $C_1$-$C_2$-fluoroalkoxy, $C_1$-$C_2$-alkylthio, $C_1$-$C_2$-fluoroalkylthio or $C_1$-$C_3$-alkyl, $R^5$ very particularly preferably represents methoxy, ethoxy, propoxy, butoxy, methylthio, ethylthio, propylthio or butylthio, $R^6$ very particularly preferably represents hydrogen, represents $C_1$-$C_4$-alkyl, $C_3$-$C_6$-cycloalkyl, $C_1$-$C_4$-alkoxy, $C_3$-$C_4$-alkenyl, $C_1$-$C_4$-alkoxy-$C_1$-$C_4$-alkyl, each of which is optionally mono- to trisubstituted by fluorine, represents phenyl which is optionally monosubstituted by fluorine, chlorine, bromine, trifluoromethyl, methyl or methoxy, represents benzyl which is optionally monosubstituted by fluorine, chlorine, bromine, methyl, trifluoromethyl or methoxy, $R^7$ very particularly preferably represents methyl, ethyl, propyl, isopropyl, butyl, isobutyl or allyl, $R^6$ and $R^7$ very particularly preferably represent a $C_4$-$C_5$-alkylene radical in which optionally one methylene group is replaced by oxygen or sulphur.

W most preferably represents hydrogen, methyl or ethyl,

X most preferably represents chlorine, methyl or ethyl,

Y most preferably represents hydrogen,

Z most preferably represents, in the 4- or 5-position, the radical

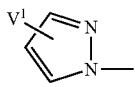

$V^1$ most preferably represents chlorine or methoxy,
CKE most preferably represents one of the groups

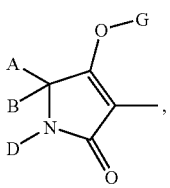 (1)

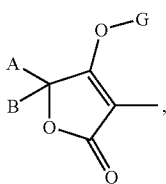 (2)

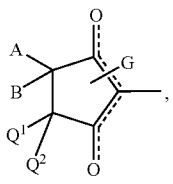 (6)

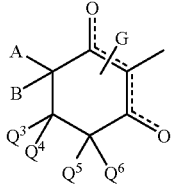 (7)

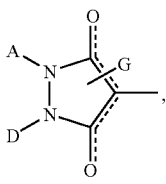 (8)

A most preferably represents hydrogen, $C_1$-$C_4$-alkyl or cyclopropyl,
B most preferably represents hydrogen or methyl, or
A, B and the carbon atom to which they are attached most preferably represent saturated $C_5$-$C_6$-cycloalkyl in which optionally one ring member is replaced by oxygen and which is optionally monosubstituted by methyl or methoxy, with the proviso that in this case $Q^3$ most preferably represents hydrogen,
D most preferably represents hydrogen,
or
A and D together most preferably represent $C_3$-$C_5$-alkanediyl in which optionally one carbon atom is replaced by oxygen, $Q^1$ most preferably represents hydrogen,
$Q^2$ most preferably represents hydrogen,
$Q^3$ most preferably represents methyl,
$Q^4$ most preferably represents methyl, or
$Q^3$ and $Q^4$ together with the carbon to which they are attached most preferably represent a saturated $C_5$-$C_6$-ring, with the proviso that in this case A most preferably represents hydrogen,
$Q^5$ most preferably represents hydrogen,
$Q^6$ most preferably represents hydrogen,
G most preferably represents hydrogen (a) or represents one of the groups (b)
$$\underset{R^1}{\overset{O}{\underset{\|}{\text{—C—}}}}$$

(c)
$$\underset{M-R^2}{\overset{L}{\underset{\|}{\text{—C—}}}}$$

in which
L represents oxygen and
M represents oxygen or sulphur,
$R^1$ most preferably represents $C_1$-$C_6$-alkyl or $C_1$-$C_2$-alkoxy-$C_1$-alkyl,
$R^2$ most preferably represents $C_1$-$C_8$-alkyl or benzyl.

The general or preferred radical definitions or illustrations given above can be combined with one another as desired, i.e. including combinations between the respective ranges and preferred ranges. They apply both to the end product and, correspondingly, to precursors and intermediates.

Preference according to the invention is given to the compounds of the formula (I) which contain a combination of the meanings given above as being preferred (preferable).

Particular preference according to the invention is given to the compounds of the formula (I) which contain a combination of the meanings given above as being particularly preferred.

Very particular preference according to the invention is given to the compounds of the formula (I) which contain a combination of the meanings given above as being very particularly preferred.

Most preference according to the invention is given to the compounds of the formula (I) which contain a combination of the meanings given above as being most preferred.

Saturated or unsaturated hydrocarbon radicals, such as alkyl or alkenyl, can in each case be straight-chain or branched as far as this is possible, including in combination with heteroatoms, such as, for example, in alkoxy.

Optionally substituted radicals can, unless stated otherwise, be mono- or polysubstituted, where in the case of polysubstitution the substituents can be identical or different.

In addition to the compounds mentioned in the Preparation Examples, the following compounds of the formula (I-1-a) may be specifically mentioned:

TABLE 1

Structure: Pyrrolinone with OH, A, B substituents on ring; N-D; connected to phenyl with positions 1-6, X at 2, Y at 3, Z at 4/5, W at 6.

W = CH$_3$, X = CH$_3$, Y = H, Z = 4-(4-chloro-1H-pyrazol-1-yl)

| A | B | D |
|---|---|---|
| CH$_3$ | H | H |
| C$_2$H$_5$ | H | H |
| C$_3$H$_7$ | H | H |
| i-C$_3$H$_7$ | H | H |
| C$_4$H$_9$ | H | H |
| i-C$_4$H$_9$ | H | H |
| s-C$_4$H$_9$ | H | H |
| t-C$_4$H$_9$ | H | H |
| CH$_3$ | CH$_3$ | H |
| C$_2$H$_5$ | CH$_3$ | H |
| C$_3$H$_7$ | CH$_3$ | H |
| i-C$_3$H$_7$ | CH$_3$ | H |
| C$_4$H$_9$ | CH$_3$ | H |
| i-C$_4$H$_9$ | CH$_3$ | H |
| s-C$_4$H$_9$ | CH$_3$ | H |
| t-C$_4$H$_9$ | CH$_3$ | H |
| C$_2$H$_5$ | C$_2$H$_5$ | H |
| C$_3$H$_7$ | C$_3$H$_7$ | H |
| cyclopropyl | CH$_3$ | H |
| cyclopentyl | CH$_3$ | H |
| cyclohexyl | CH$_3$ | H |
| —(CH$_2$)$_2$— | | H |
| —(CH$_2$)$_4$— | | H |
| —(CH$_2$)$_5$— | | H |
| —(CH$_2$)$_6$— | | H |
| —(CH$_2$)$_7$— | | H |
| —(CH$_2$)$_2$—O—(CH$_2$)$_2$— | | H |
| —CH$_2$—O—(CH$_2$)$_3$— | | H |
| —(CH$_2$)$_2$—S—(CH$_2$)$_2$— | | H |
| —CH$_2$—CHCH$_3$—(CH$_2$)$_3$— | | H |
| —(CH$_2$)$_2$—CHCH$_3$—(CH$_2$)$_2$— | | H |
| —(CH$_2$)$_2$—CHC$_2$H$_5$—(CH$_2$)$_2$— | | H |
| —(CH$_2$)$_2$—CHC$_3$H$_7$—(CH$_2$)$_2$— | | H |
| —(CH$_2$)$_2$—CHi-C$_3$H$_7$—(CH$_2$)$_2$— | | H |
| —(CH$_2$)$_2$—CHOCH$_3$—(CH$_2$)$_2$— | | H |
| —(CH$_2$)$_2$—CHOC$_2$H$_5$—(CH$_2$)$_2$— | | H |
| —(CH$_2$)$_2$—CHOC$_3$H$_7$—(CH$_2$)$_2$— | | H |
| —(CH$_2$)$_2$—CHOC$_4$H$_9$—(CH$_2$)$_2$— | | H |
| —(CH$_2$)$_2$—C(CH$_3$)$_2$—(CH$_2$)$_2$— | | H |
| —CH$_2$—(CHCH$_3$)$_2$—(CH$_2$)$_2$— | | H |
| —CH$_2$—CH—(CH$_2$)$_2$—CH— with —CH$_2$— bridge | | H |
| —CH$_2$—CH—CH—CH$_2$— with —(CH$_2$)$_4$— bridge | | H |
| —CH$_2$—CH—CH—(CH$_2$)$_2$— with —(CH$_2$)$_3$— bridge | | H |
| indanyl (benzo-fused cyclopentane-1,2-diyl) | | H |
| tetrahydronaphthyl (benzo-fused cyclohexane-1,2-diyl) | | H |
| —(CH$_2$)$_3$— | | H |
| —(CH$_2$)$_4$— | | H |
| —CH$_2$—CHCH$_3$—CH$_2$— | | H |
| —CH$_2$—CH$_2$—CHCH$_3$— | | H |
| —CH$_2$—CHCH$_3$—CHCH$_3$— | | H |
| —CH$_2$—S—CH$_2$— | | H |
| —CH$_2$—S—(CH$_2$)$_2$— | | H |
| —(CH$_2$)$_2$—S—CH$_2$— | | H |
| —CH$_2$—CH—CH— with —(CH$_2$)$_3$— bridge | | H |
| H | CH$_3$ | H |
| H | C$_2$H$_5$ | H |
| H | C$_3$H$_7$ | H |
| H | i-C$_3$H$_7$ | H |
| H | cyclopropyl | H |
| H | cyclopentyl | H |
| H | cyclohexyl | H |
| CH$_3$ | CH$_3$ | H |
| CH$_3$ | C$_2$H$_5$ | H |
| CH$_3$ | C$_3$H$_7$ | H |
| CH$_3$ | i-C$_3$H$_7$ | H |
| CH$_3$ | cyclopropyl | H |
| CH$_3$ | cyclopentyl | H |

TABLE 1-continued

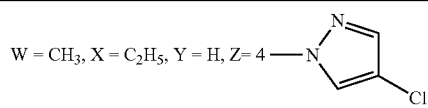

| A | B | D |
|---|---|---|
| CH₃ | (cyclohexyl) | H |
| C₂H₅ | CH₃ | H |
| C₂H₅ | C₂H₅ | H |

TABLE 2

A, B and D are as shown in Table 1

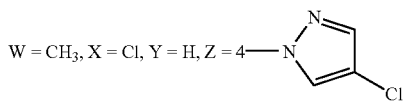

TABLE 3

A, B and D are as shown in Table 1

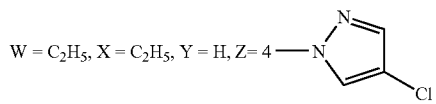

TABLE 4

A, B and D are as shown in Table 1

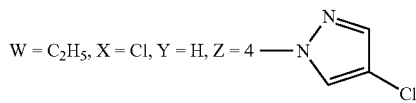

TABLE 5

A, B and D are as shown in Table 1

W = C₂H₅, X = Cl, Y = H, Z = 4—(4-Cl-pyrazol-1-yl)

TABLE 6

A, B and D are as shown in Table 1

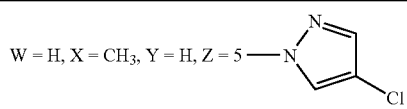

TABLE 7

A, B and D are as shown in Table 1

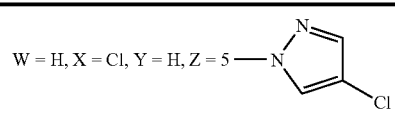

In addition to the compounds mentioned in the Preparation Examples, the following compounds of the formula (I-2-a) may be specifically mentioned:

TABLE 8

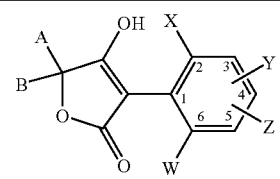

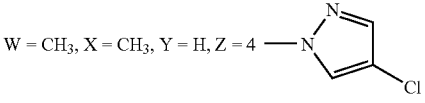

| A | B |
|---|---|
| CH₃ | H |
| C₂H₅ | H |
| C₃H₇ | H |
| i-C₃H₇ | H |
| C₄H₉ | H |
| i-C₄H₉ | H |
| s-C₄H₉ | H |
| t-C₄H₉ | H |
| CH₃ | CH₃ |
| C₂H₅ | CH₃ |
| C₃H₇ | CH₃ |
| i-C₃H₇ | CH₃ |
| C₄H₉ | CH₃ |
| i-C₄H₉ | CH₃ |
| s-C₄H₉ | CH₃ |
| t-C₄H₉ | CH₃ |
| C₂H₅ | C₂H₅ |
| C₃H₇ | C₃H₇ |
| (cyclopropyl) | CH₃ |
| (cyclopentyl) | CH₃ |
| (cyclohexyl) | CH₃ |
| —(CH₂)₂— | |
| —(CH₂)₄— | |
| —(CH₂)₅— | |

TABLE 8-continued

Structure: furanone core with OH, A, B substituents attached to phenyl ring with positions 1-6 and substituents W, X, Y, Z.

W = CH$_3$, X = CH$_3$, Y = H, Z = 4 — (4-chloropyrazol-1-yl)

| A | B |
|---|---|
| —(CH$_2$)$_6$— | |
| —(CH$_2$)$_7$— | |
| —(CH$_2$)$_2$—O—(CH$_2$)$_2$— | |
| —CH$_2$—O—(CH$_2$)$_3$— | |
| —(CH$_2$)$_2$—S—(CH$_2$)$_2$— | |
| —CH$_2$—CHCH$_3$—(CH$_2$)$_3$— | |
| —(CH$_2$)$_2$—CHCH$_3$—(CH$_2$)$_2$— | |
| —(CH$_2$)$_2$—CHC$_2$H$_5$—(CH$_2$)$_2$— | |
| —(CH$_2$)$_2$—CHC$_3$H$_7$—(CH$_2$)$_2$— | |
| —(CH$_2$)$_2$—CHi—C$_3$H$_7$—(CH$_2$)$_2$— | |
| —(CH$_2$)$_2$—CHOCH$_3$—(CH$_2$)$_2$— | |
| —(CH$_2$)$_2$—CHOC$_2$H$_5$—(CH$_2$)$_2$— | |
| —(CH$_2$)$_2$—CHOC$_3$H$_7$—(CH$_2$)$_2$— | |
| —(CH$_2$)$_2$—CHOC$_4$H$_9$—(CH$_2$)$_2$— | |
| —(CH$_2$)$_2$—C(CH$_3$)$_2$—(CH$_2$)$_2$— | |
| —CH$_2$—(CHCH$_3$)$_2$—(CH$_2$)$_2$— | |

—CH$_2$—CH—(CH$_2$)$_2$—CH— bridged by —CH$_2$—

—CH$_2$—CH————CH—CH$_2$— bridged by —(CH$_2$)$_4$—

—CH$_2$—CH————CH—(CH$_2$)$_2$— bridged by —(CH$_2$)$_3$—

(indane-type fused bicyclic structure)

(tetralin-type fused bicyclic structure)

TABLE 9

A and B are as shown in Table 8

W = CH$_3$, X = C$_2$H$_5$, Y = H, Z = 4 — (4-chloropyrazol-1-yl)

TABLE 10

A and B are as shown in Table 8

W = CH$_3$, X = Cl, Y = H, Z = 4 — (4-chloropyrazol-1-yl)

TABLE 11

A and B are as shown in Table 8

W = CH$_3$, X = C$_2$H$_5$, Y = H, Z = 4 — (4-chloropyrazol-1-yl)

TABLE 12

A and B are as shown in Table 8

W = C$_2$H$_5$, X = Cl, Y = H, Z = 4 — (4-chloropyrazol-1-yl)

TABLE 13

A and B are as shown in Table 8

W = H, X = CH$_3$, Y = H, Z = 5 — (4-chloropyrazol-1-yl)

TABLE 14

A and B are as shown in Table 8

W = H, X = Cl, Y = H, Z = 5 — (4-chloropyrazol-1-yl)

In addition to the compounds mentioned in the Preparation Examples, the following compounds of the formula (I-8-a) may be specifically mentioned:

TABLE 15

W, X, Y and Z are as shown in Table 1

Structure: pyrazolidine-3,5-dione with A-N and D-N substituents attached to phenyl ring with W, X, Y, Z substituents.

| A | D |
|---|---|
| CH$_3$ | CH$_3$ |
| CH$_3$ | —(CH$_2$)$_2$OH— |

TABLE 15-continued

W, X, Y and Z are as shown in Table 1

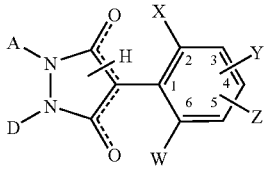

| A | D |
|---|---|
| CH$_3$ | —(CH$_2$)$_2$OCH$_3$— |
| CH$_3$ | —(CH$_2$)$_2$—O—(CH$_2$)$_2$—OCH$_3$— |
| —(CH$_2$)$_2$—O—CH$_3$— | —(CH$_2$)$_2$—O—CH$_3$— |
| —(CH$_2$)$_2$—O—(CH$_2$)$_2$—OCH$_3$— | —(CH$_2$)$_2$—O—(CH$_2$)$_2$—OCH$_3$— |
| | —(CH$_2$)$_3$— |
| | —(CH$_2$)$_4$— |
| | —(CH2)$_2$—O—(CH$_2$)$_2$— |

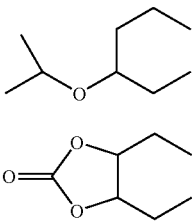

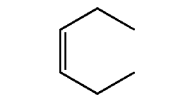

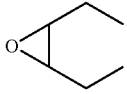

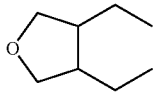

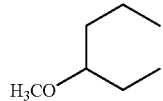

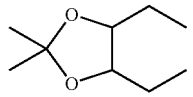

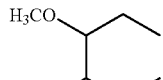

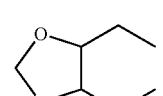

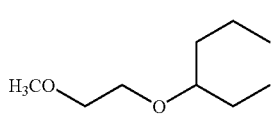

Table 16: A and D are as shown in Table 15
W, X, Y and Z are as shown in Table 2.

Table 17: A and D are as shown in Table 15
W, X, Y and Z are as shown in Table 3.

Table 18: A and D are as shown in Table 15
W, X, Y and Z are as shown in Table 4.

Table 19: A and D are as shown in Table 15
W, X, Y and Z are as shown in Table 5.

Table 20: A and D are as shown in Table 15
W, X, Y and Z are as shown in Table 6.

Table 21: A and D are as shown in Table 15
W, X, Y and Z are as shown in Table 7.

Preferred meanings of the groups mentioned above in connection with the compounds improving crop plant tolerance ("herbicide safeners") of the formulae (IIa), (IIb), (IIc), (IId) and (IIe) are defined hereinbelow.

n preferably represents the numbers 0, 1, 2, 3 or 4.

$A^1$ preferably represents one of the divalent heterocyclic groups outlined hereinbelow

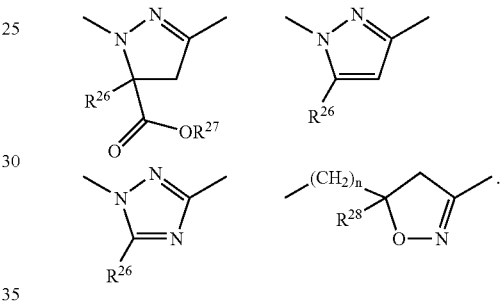

$A^2$ preferably represents methylene or ethylene, each of which is optionally substituted by methyl, ethyl, methoxycarbonyl or ethoxycarbonyl.

$R^{21}$ preferably represents hydroxyl, mercapto, amino, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^{22}$ preferably represents hydroxyl, mercapto, amino, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino.

$R^{23}$ preferably represents methyl, ethyl, n- or i-propyl, each of which is optionally substituted by fluorine, chlorine and/or bromine.

$R^{24}$ preferably represents hydrogen, or represents methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furylmethyl, thienyl, thiazolyl, piperidinyl, each of which is optionally substituted by fluorine and/or chlorine, or represents phenyl which is optionally substituted by fluorine, chlorine, methyl, ethyl, n- or i-propyl, n-, i-, s- or t-butyl.

$R^{25}$ preferably represents hydrogen, or represents methyl, ethyl, n- or i-propyl, n-, i-, s- or t-butyl, propenyl, butenyl, propynyl or butynyl, methoxymethyl, ethoxymethyl, methoxyethyl, ethoxyethyl, dioxolanylmethyl, furyl, furylmethyl, thienyl, thiazolyl, piperidinyl, each of which is optionally substituted by fluorine and/or chlorine, or represents phenyl which is optionally substituted by fluorine, chlorine, methyl, ethyl, n- or i-propyl, n-, i-, s- or t-butyl or together with $R^{24}$ represents one of the radicals —$CH_2$—O—$CH_2$—$CH_2$— and —$CH_2$—$CH_2$—O—$CH_2$—$CH_2$— which are optionally substituted by methyl, ethyl, furyl, phenyl, a fused benzene ring or by two substituents which, together with the carbon atom to which they are bonded, form a 5- or 6-membered carbocycle.

$R^{26}$ preferably represents hydrogen, cyano, fluorine, chlorine, bromine, or represents methyl, ethyl, n- or i-propyl, cyclopropyl, cyclobutyl, cyclopentyl, cyclohexyl or phenyl, each of which is optionally substituted by fluorine, chlorine and/or bromine.

$R^{27}$ preferably represents hydrogen, or represents methyl, ethyl, n- or i-propyl, n-, i-, s- or t-butyl, optionally substituted by hydroxyl, cyano, fluorine, chlorine, methoxy, ethoxy, n- or i-propoxy.

$R^{28}$ preferably represents hydrogen, cyano, fluorine, chlorine, bromine, or represents methyl, ethyl, n- or i-propyl, n-, i-, s- or t-butyl, cyclopropyl, cyclobutyl, cyclopentyl, cyclohexyl or phenyl, each of which is optionally substituted by fluorine, chlorine and/or bromine.

$X^1$ preferably represents nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$X^2$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$X^3$ preferably represents hydrogen, nitro, cyano, fluorine, chlorine, bromine, methyl, ethyl, n- or i-propyl, n-, i-, s- or t-butyl, difluoromethyl, dichloromethyl, trifluoromethyl, trichloromethyl, chlorodifluoromethyl, fluorodichloromethyl, methoxy, ethoxy, n- or i-propoxy, difluoromethoxy or trifluoromethoxy.

$R^{29}$ preferably represents hydrogen, methyl, ethyl, n- or i-propyl.

$R^{30}$ preferably represents hydrogen, methyl, ethyl, n- or i-propyl.

$R^{31}$ preferably represents hydrogen, or represents methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylamino, ethylamino, n- or i-propylamino, n-, i-, s- or t-butylamino, dimethylamino or diethylamino, each of which is optionally substituted by cyano, fluorine, chlorine, methoxy, ethoxy, n- or i-propoxy, or represents cyclopropyl, cyclobutyl, cyclopentyl, cyclohexyl, cyclopropyloxy, cyclobutyloxy, cyclopentyloxy, cyclohexyloxy, cyclopropylthio, cyclobutylthio, cyclopentylthio, cyclohexylthio, cyclopropylamino, cyclobutylamino, cyclopentylamino or cyclohexylamino, each of which is optionally substituted by cyano, fluorine, chlorine, bromine, methyl, ethyl, n- or i-propyl.

$R^{32}$ preferably represents hydrogen, or represents methyl, ethyl, n- or i-propyl, n-, i- or s-butyl, each of which is optionally substituted by cyano, hydroxyl, fluorine, chlorine, methoxy, ethoxy, n- or i-propoxy, or represents propenyl, butenyl, propynyl or butynyl, each of which is optionally substituted by cyano, fluorine, chlorine or bromine, or represents cyclopropyl, cyclobutyl, cyclopentyl or cyclohexyl, each of which is optionally substituted by cyano, fluorine, chlorine, bromine, methyl, ethyl, n- or i-propyl.

$R^{33}$ preferably represents hydrogen, or represents methyl, ethyl, n- or i-propyl, n-, i- or s-butyl, each of which is optionally substituted by cyano, hydroxyl, fluorine, chlorine, methoxy, ethoxy, n- or i-propoxy, or represents propenyl, butenyl, propynyl or butynyl, each of which is optionally substituted by cyano, fluorine, chlorine or bromine, or represents cyclopropyl, cyclobutyl, cyclopentyl or cyclohexyl, each of which is optionally substituted by cyano, fluorine, chlorine, bromine, methyl, ethyl, n- or i-propyl, or represents phenyl which is optionally substituted by nitro, cyano, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy, or together with $R^{32}$ represents butane-1,4-diyl(trimethylene), pentane-1,5-diyl, 1-oxabutane-1,4-diyl or 3-oxapentane-1,5-diyl, each of which is optionally substituted by methyl or ethyl.

$X^4$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

$X^5$ preferably represents nitro, cyano, carboxyl, carbamoyl, formyl, sulphamoyl, hydroxyl, amino, fluorine, chlorine, bromine, methyl, ethyl, n- or i-propyl, n-, i-, s- or t-butyl, trifluoromethyl, methoxy, ethoxy, n- or i-propoxy, difluoromethoxy or trifluoromethoxy.

Examples of the compounds of the formula (IIa) which are very particularly preferred as herbicide safeners according to the invention are listed in the table which follows.

TABLE

Examples of the compounds of the formula (IIa)

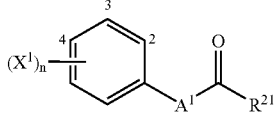

(IIa)

| Example No. | (Positions) $(X^1)_n$ | $A^1$ | $R^{21}$ |
|---|---|---|---|
| IIa-1 | (2) Cl, (4) Cl | (structure) | $OCH_3$ |
| IIa-2 | (2) Cl, (4) Cl | (structure) | $OC_2H_5$ |
| IIa-3 | (2) Cl, (4) Cl | (structure) | $OC_2H_5$ |

TABLE-continued

Examples of the compounds of the formula (IIa)

(IIa)

$(X^1)_n$ — phenyl(4,3,2) — $A^1$ — C(=O) — $R^{21}$

| Example No. | (Positions) $(X^1)_n$ | $A^1$ | $R^{21}$ |
|---|---|---|---|
| IIa-4 | (2) Cl, (4) Cl | 1,3-dimethyl-pyrazoline with H₃C and CO-OC₂H₅ substituents | OC₂H₅ |
| IIa-5 | (2) Cl | 1,3-dimethyl-5-phenylpyrazole | OCH₃ |
| IIa-6 | (2) Cl, (4) Cl | 1,3-dimethyl-5-phenylpyrazole | OCH₃ |
| IIa-7 | (2) F | 1,3-dimethyl-5-phenylpyrazole | OCH₃ |
| IIa-8 | (2) F | 1,3-dimethyl-5-(2-chlorophenyl)pyrazole | OCH₃ |
| IIa-9 | (2) Cl, (4) Cl | 1-methyl-3-trichloromethyl-1,2,4-triazole | OC₂H₅ |
| IIa-10 | (2) Cl, (4) CF₃ | 1-methyl-5-(2-fluorophenyl)-1,2,4-triazole | OCH₃ |
| IIa-11 | (2) Cl | 1,3-dimethyl-5-(2-fluorophenyl)pyrazole | OCH₃ |
| IIa-12 | — | 3-methyl-5-phenyl-isoxazoline | OC₂H₅ |
| IIa-13 | (2) Cl, (4) Cl | 1,3-dimethyl-5-methylpyrazole | OC₂H₅ |
| IIa-14 | (2) Cl, (4) Cl | 1,3-dimethyl-5-isopropylpyrazole | OC₂H₅ |
| IIa-15 | (2) Cl, (4) Cl | 1,3-dimethyl-5-tert-butylpyrazole | OC₂H₅ |
| IIa-16 | (2) Cl, (4) Cl | 3,5-dimethyl-isoxazoline-CH₂ | OC₂H₅ |
| IIa-17 | (2) Cl, (4) Cl | 3,5-dimethyl-isoxazoline | OC₂H₅ |
| IIa-18 | — | 3-methyl-5-phenyl-isoxazoline | OH |

Examples of the compounds of the formula (IIb) which are very particularly preferred as herbicide safeners according to the invention are listed in the table which follows.

TABLE

Examples of the compounds of the formula (IIb)

(IIb)

| Example No. | (Position) X² | (Position) X³ | A² | R²² |
|---|---|---|---|---|
| IIb-1 | (5) Cl | — | CH₂ | OH |
| IIb-2 | (5) Cl | — | CH₂ | OCH₃ |
| IIb-3 | (5) Cl | — | CH₂ | OC₂H₅ |
| IIb-4 | (5) Cl | — | CH₂ | OC₃H₇-n |
| IIb-5 | (5) Cl | — | CH₂ | OC₃H₇-i |
| IIb-6 | (5) Cl | — | CH₂ | OC₄H₉-n |
| IIb-7 | (5) Cl | — | CH₂ | OCH(CH₃)C₅H₁₁-n |
| IIb-8 | (5) Cl | (2) F | CH₂ | OH |
| IIb-9 | (5) Cl | (2) Cl | CH₂ | OH |
| IIb-10 | (5) Cl | — | CH₂ | OCH₂CH=CH₂ |
| IIb-11 | (5) Cl | — | CH₂ | OC₄H₉-i |
| IIb-12 | (5) Cl | — | CH₂ | (structure with OCH₂CH(CH₃)OCH₂CH=CH₂, Cl) |
| IIb-13 | (5) Cl | — | (isobutyrate with allyloxymethyl group) | CH₂OCH₂CH=CH₂ |
| IIb-14 | (5) Cl | — | (2-ethyl-propanoate) C₂H₅ | OC₂H₅ |
| IIb-15 | (5) Cl | — | (isobutyrate) CH₃ | OCH₃ |

Examples of the compounds of the formula (IIc) which are very particularly preferred as herbicide safeners according to the invention are listed in the table which follows.

TABLE

Examples of the compounds of the formula (IIc)

(IIc)

| Example No. | R²³ | N(R²⁴, R²⁵) |
|---|---|---|
| IIc-1 | CHCl₂ | N(CH₂CH=CH₂)₂ |
| IIc-2 | CHCl₂ | 2,2-dimethyl-oxazolidin-3-yl |
| IIc-3 | CHCl₂ | 2,2-dimethyl-5-methyl-oxazolidin-3-yl |
| IIc-4 | CHCl₂ | 1-oxa-4-azaspiro[4.5]decan-4-yl |
| IIc-5 | CHCl₂ | 2,2-dimethyl-5-phenyl-oxazolidin-3-yl |
| IIc-6 | CHCl₂ | 3-methyl-3,4-dihydro-2H-benzo[1,4]oxazin-4-yl |
| IIc-7 | CHCl₂ | 2,2-dimethyl-5-(furan-2-yl)-oxazolidin-3-yl |

Examples of the compounds of the formula (IId) which are very particularly preferred as herbicide safeners according to the invention are listed in the table which follows.

TABLE

Examples of the compounds of the formula (IId)

(IId)

| Example No. | $R^{29}$ | $R^{30}$ | $R^{31}$ | (Positions) $(X^4)_n$ | (Positions) $(X^5)_n$ |
|---|---|---|---|---|---|
| IId-1 | H | H | $CH_3$ | (2) $OCH_3$ | — |
| IId-2 | H | H | $C_2H_5$ | (2) $OCH_3$ | — |
| IId-3 | H | H | $C_3H_7$-n | (2) $OCH_3$ | — |
| IId-4 | H | H | $C_3H_7$-i | (2) $OCH_3$ | — |
| IId-5 | H | H | cyclopropyl | (2) $OCH_3$ | — |
| IId-6 | H | H | $CH_3$ | (2) $OCH_3$ | (5) $CH_3$ |
| IId-7 | H | H | $C_2H_5$ | (2) $OCH_3$ | (5) $CH_3$ |
| IId-8 | H | H | $C_3H_7$-n | (2) $OCH_3$ | (5) $CH_3$ |
| IId-9 | H | H | $C_3H_7$-i | (2) $OCH_3$ | (5) $CH_3$ |
| IId-10 | H | H | cyclopropyl | (2) $OCH_3$ | (5) $CH_3$ |
| IId-11 | H | H | $OCH_3$ | (2) $OCH_3$ | (5) $CH_3$ |
| IId-12 | H | H | $OC_2H_5$ | (2) $OCH_3$ | (5) $CH_3$ |
| IId-13 | H | H | $OC_3H_7$-i | (2) $OCH_3$ | (5) $CH_3$ |
| IId-14 | H | H | $SCH_3$ | (2) $OCH_3$ | (5) $CH_3$ |
| IId-15 | H | H | $SC_2H_5$ | (2) $OCH_3$ | (5) $CH_3$ |
| IId-16 | H | H | $SC_3H_7$-i | (2) $OCH_3$ | (5) $CH_3$ |
| IId-17 | H | H | $NHCH_3$ | (2) $OCH_3$ | (5) $CH_3$ |
| IId-18 | H | H | $NHC_2H_5$ | (2) $OCH_3$ | (5) $CH_3$ |
| IId-19 | H | H | $NHC_3H_7$-i | (2) $OCH_3$ | (5) $CH_3$ |
| IId-20 | H | H | NH-cyclopropyl | (2) $OCH_3$ | (5) $CH_3$ |
| IId-21 | H | H | $NHCH_3$ | (2) $OCH_3$ | — |
| IId-22 | H | H | $NHC_3H_7$-i | (2) $OCH_3$ | — |
| IId-23 | H | H | $N(CH_3)_2$ | (2) $OCH_3$ | — |
| IId-24 | H | H | $N(CH_3)_2$ | (3) $CH_3$ (4) $CH_3$ | — |
| IId-25 | H | H | $CH_2$—O—$CH_3$ | (2) $OCH_3$ | — |

Examples of the compounds of the formula (IIe) which are very particularly preferred as herbicide safeners according to the invention are listed in the table which follows.

TABLE

Examples of the compounds of the formula (IIe)

(IIe)

| Example No. | $R^{29}$ | $R^{32}$ | $R^{33}$ | (Positions) $(X^4)_n$ | (Positions) $(X^5)_n$ |
|---|---|---|---|---|---|
| IIe-1 | H | H | $CH_3$ | (2) $OCH_3$ | — |
| IIe-2 | H | H | $C_2H_5$ | (2) $OCH_3$ | — |
| IIe-3 | H | H | $C_3H_7$-n | (2) $OCH_3$ | — |
| IIe-4 | H | H | $C_3H_7$-i | (2) $OCH_3$ | — |
| IIe-5 | H | H | cyclopropyl | (2) $OCH_3$ | — |
| IIe-6 | H | $CH_3$ | $CH_3$ | (2) $OCH_3$ | — |
| IIe-7 | H | H | $CH_3$ | (2) $OCH_3$ | (5) $CH_3$ |
| IIe-8 | H | H | $C_2H_5$ | (2) $OCH_3$ | (5) $CH_3$ |
| IIe-9 | H | H | $C_3H_7$-n | (2) $OCH_3$ | (5) $CH_3$ |
| IIe-10 | H | H | $C_3H_7$-i | (2) $OCH_3$ | (5) $CH_3$ |
| IIe-11 | H | H | cyclopropyl | (2) $OCH_3$ | (5) $CH_3$ |
| IIe-12 | H | $CH_3$ | $CH_3$ | (2) $OCH_3$ | (5) $CH_3$ |

Cloquintocet-mexyl, fenchlorazol-ethyl, isoxadifen-ethyl, mefenpyr-diethyl, furilazole, fenclorim, cumyluron, dymron, dimepiperate and the compounds IIe-5 and IIe-11 are most preferred as the compound which improves crop plant tolerance [component (b')], with cloquintocet-mexyl and mefenpyr-diethyl being especially preferred.

The compounds of the general formula (IIa) to be used in accordance with the invention as safeners are known and/or can be prepared by methods known per se (cf. WO-A-91/07874, WO-A-95/07897).

The compounds of the general formula (IIb) to be used in accordance with the invention as safeners are known and/or can be prepared by methods known per se (cf. EP-A-191736).

The compounds of the general formula (IIc) to be used in accordance with the invention as safeners are known and/or can be prepared by methods known per se (cf. DE-A-2218097, DE-A-2350547).

The compounds of the general formula (IId) to be used in accordance with the invention as safeners are known and/or can be prepared by methods known per se (cf. DE-A-19621522/U.S. Pat. No. 6,235,680).

The compounds of the general formula (IIe) to be used in accordance with the invention as safeners are known and can be prepared by methods known per se (cf. WO-A-99/66795/U.S. Pat. No. 6,251,827).

Examples of the selectively herbicidal combinations according to the invention of in each case one active compound of the formula (I) and in each case one of the above-defined safeners are listed in the table which follows.

TABLE

Examples of the combinations according to the invention

| Active compounds of the formula (I) | Safener |
|---|---|
| I-1 | cloquintocet-mexyl |
| I-1 | fenchlorazole-ethyl |
| I-1 | isoxadifen-ethyl |
| I-1 | mefenpyr-diethyl |
| I-1 | furilazole |
| I-1 | fenclorim |
| I-1 | cumyluron |
| I-1 | daimuron/dymron |
| I-1 | dimepiperate |
| I-1 | IIe-11 |
| I-1 | IIe-5 |
| I-2 | cloquintocet-mexyl |
| I-2 | fenchlorazole-ethyl |
| I-2 | isoxadifen-ethyl |
| I-2 | mefenpyr-diethyl |
| I-2 | furilazole |
| I-2 | fenclorim |
| I-2 | cumyluron |
| I-2 | daimuron/dymron |
| I-2 | dimepiperate |
| I-2 | IIe-11 |
| I-2 | IIe-5 |
| I-3 | cloquintocet-mexyl |
| I-3 | fenchlorazole-ethyl |
| I-3 | isoxadifen-ethyl |
| I-3 | mefenpyr-diethyl |
| I-3 | furilazole |
| I-3 | fenclorim |
| I-3 | cumyluron |
| I-3 | daimuron/dymron |
| I-3 | dimepiperate |
| I-3 | IIe-5 |
| I-3 | IIe-11 |
| I-4 | cloquintocet-mexyl |
| I-4 | fenchlorazole-ethyl |
| I-4 | isoxadifen-ethyl |
| I-4 | mefenpyr-diethyl |
| I-4 | furilazole |
| I-4 | fenclorim |
| I-4 | cumyluron |
| I-4 | daimuron/dymron |
| I-4 | dimepiperate |
| I-4 | IIe-11 |
| I-4 | IIe-5 |
| I-5 | cloquintocet-mexyl |
| I-5 | fenchlorazole-ethyl |
| I-5 | isoxadifen-ethyl |
| I-5 | mefenpyr-diethyl |
| I-5 | furilazole |
| I-5 | fenclorim |
| I-5 | cumyluron |
| I-5 | daimuron/dymron |
| I-5 | dimepiperate |
| I-5 | IIe-5 |
| I-5 | IIe-11 |
| I-6 | cloquintocet-mexyl |
| I-6 | fenchlorazole-ethyl |
| I-6 | isoxadifen-ethyl |
| I-6 | mefenpyr-diethyl |
| I-6 | furilazole |
| I-6 | fenclorim |
| I-6 | cumyluron |
| I-6 | daimuron/dymron |
| I-6 | dimepiperate |
| I-6 | IIe-5 |
| I-6 | IIe-11 |
| I-7 | cloquintocet-mexyl |
| I-7 | fenchlorazole-ethyl |
| I-7 | isoxadifen-ethyl |
| I-7 | mefenpyr-diethyl |
| I-7 | furilazole |
| I-7 | fenclorim |
| I-7 | cumyluron |
| I-7 | daimuron/dymron |
| I-7 | dimepiperate |
| I-7 | IIe-5 |
| I-7 | IIe-11 |
| I-8 | cloquintocet-mexyl |
| I-8 | fenchlorazole-ethyl |
| I-8 | isoxadifen-ethyl |
| I-8 | mefenpyr-diethyl |
| I-8 | furilazole |
| I-8 | fenclorim |
| I-8 | cumyluron |
| I-8 | daimuron/dymron |
| I-8 | dimepiperate |
| I-8 | IIe-5 |
| I-8 | IIe-11 |

Surprisingly, it has now been found that the above-defined active compound combinations of N-heterocyclylphenyl-substituted cyclic ketoenols of the general formula (I) and safeners (antidotes) from the above group (b') are not only very well tolerated by useful plants, but also have a particularly high herbicidal activity and can be used in a variety of crops, in particular in cereals (mainly wheat), but also in soybeans, potatoes, maize and rice, for the selective control of weeds.

It must be considered as surprising that, from a multiplicity of known safeners or antidotes which are capable of antagonizing the damaging effect of a herbicide on the crop plants, it is precisely the abovementioned compounds of group (b') which are capable of virtually completely compensating for the harmful effect of N-heterocyclylphenyl-substituted cyclic ketoenols on the crop plants without adversely affecting the herbicidal activity towards the weeds to a substantial degree.

What must be emphasized in this context is the particularly advantageous activity of the particularly and most preferred components from group (b'), in particular with regard to leaving cereal plants, such as, for example, wheat, barley and rye, but also maize and rice, as crop plants unharmed.

Using, for example, according to process (A) ethyl N-[6-methyl-3-(N-4-chloropyrazolyl)-phenylacetyl]-1-aminocyclohexanecarboxylate as starting material, the course of the process according to the invention can be represented by the following equation:

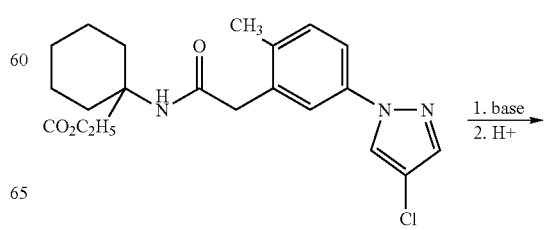

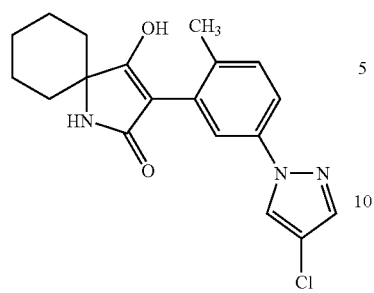

Using, for example, according to process (B) ethyl O-[2-chloro-5-(N-4-chloropyrazolyl)-phenylacetyl]-2-hydroxy-isobutyrate, the course of the process according to the invention can be represented by the following equation:

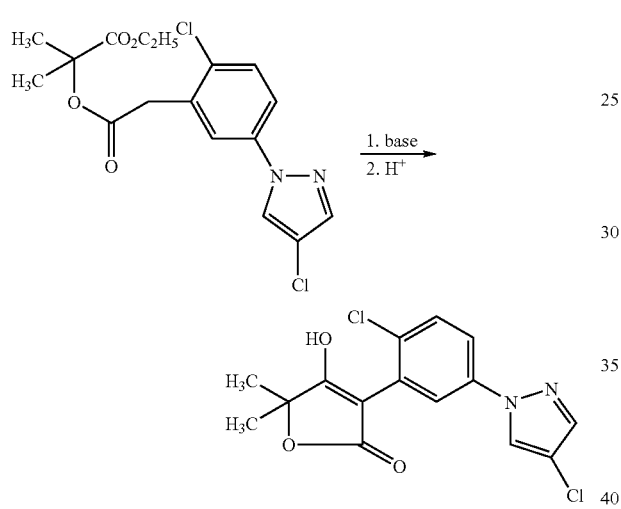

Using, for example, according to process (C) ethyl 2-[6-methyl-3-(N-4-chloropyrazolyl)-phenyl]-4-(4-methoxy)benzylmercapto-4-methyl-3-oxovalerate, the course of the process according to the invention can be represented by the following equation:

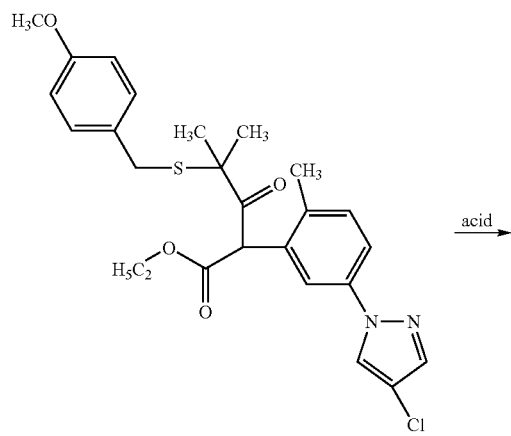

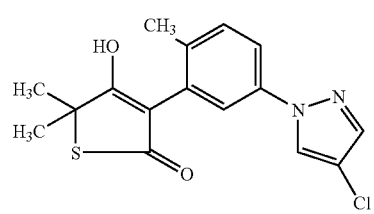

Using, for example, according to process (D) chlorocarbonyl 2-[2,6-dimethyl-4-(N-4-chloropyrazolyl)phenyl]ketene and acetone as starting materials, the course of the process according to the invention can be represented by the following equation:

Using, for example, according to process (E) chlorocarbonyl 2-[2,6-dimethyl-4-(N4-chloropyrazolyl)phenyl]ketene and thiobenzamide as starting materials, the course of the process according to the invention can be represented by the following equation:

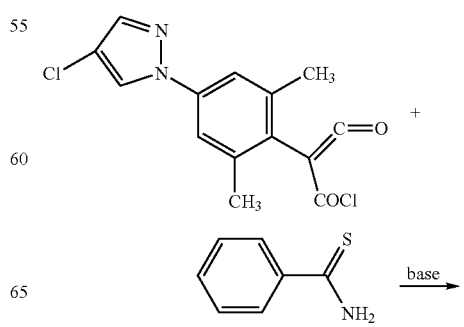

-continued

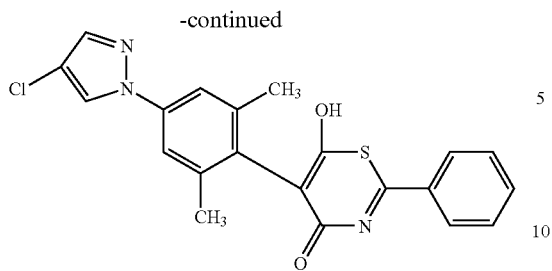

Using, for example, according to process (F) ethyl 5-[2,6-dimethyl-(N-4-chloropyrazolyl-phenyl)]-2,3-tetramethylene-4-oxovalerate, the course of the process according to the invention can be represented by the following equation:

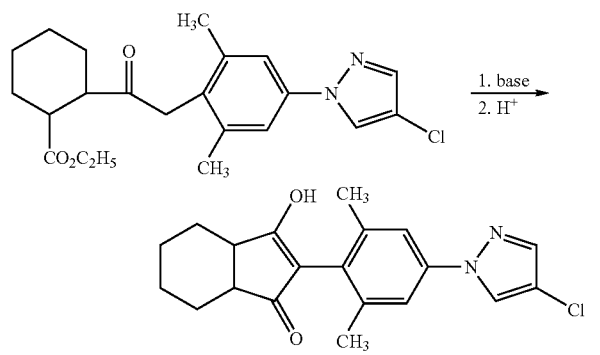

Using, for example, according to process (G) ethyl 5-[2,6-dimethyl-4-(N-4-chloro-pyrazolyl)phenyl]-2,2-dimethyl-5-oxohexanoate, the course of the process according to the invention can be represented by the following equation:

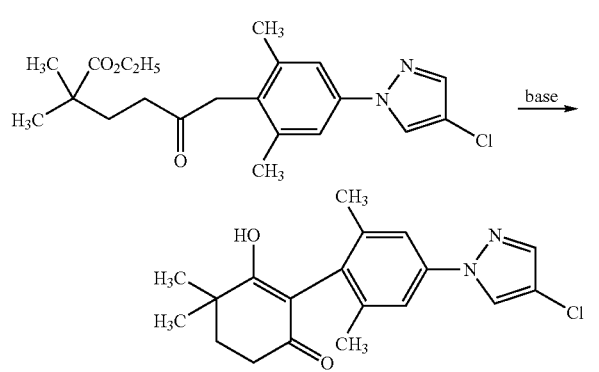

Using, for example, according to process (Hα) hexahydropyridazine and chlorocarbonyl 2-[2,6-dimethyl-4-(N-4-chloropyrazolyl)phenyl]ketene as starting materials, the course of the reaction of the process according to the invention can be represented by the following equation:

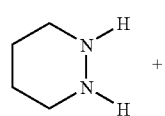
+

-continued

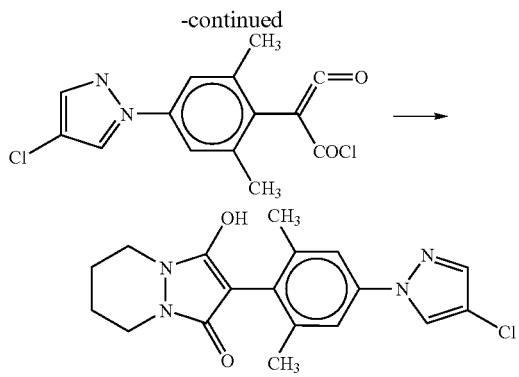

Using, for example, according to process (Hβ) hexahydropyridazine and dimethyl 2,6-dimethyl-4-(N-4-chloropyrazolyl)phenylmalonate as starting materials, the course of the process according to the invention can be represented by the following equation:

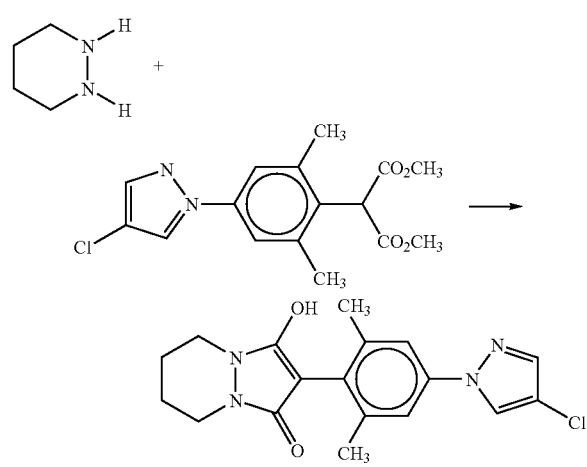

Using, for example, according to process (Hγ) 1-ethoxycarbonyl-2-[2,6-dimethyl-4-(N-4-chloropyrazolyl)phenylacetyl]hexahydropyridazine as starting material, the course of the reaction can be represented by the following equation:

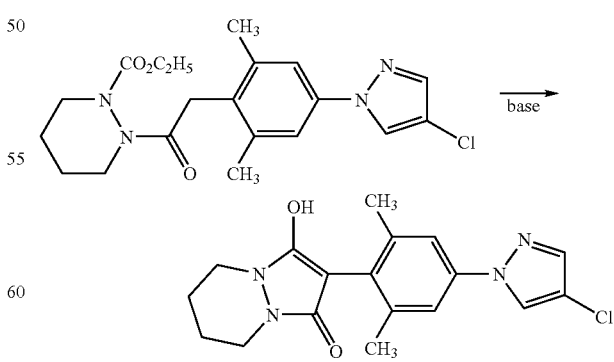

Using, for example, according to process (Iα) 3-[2,6-dimethyl-4-(N-4-chloropyrazolyl)-phenyl]-5,5-dimethylpyrrolidine-2,4-dione and pivaloyl chloride as starting materials, the course of the process according to the invention can be represented by the following equation:

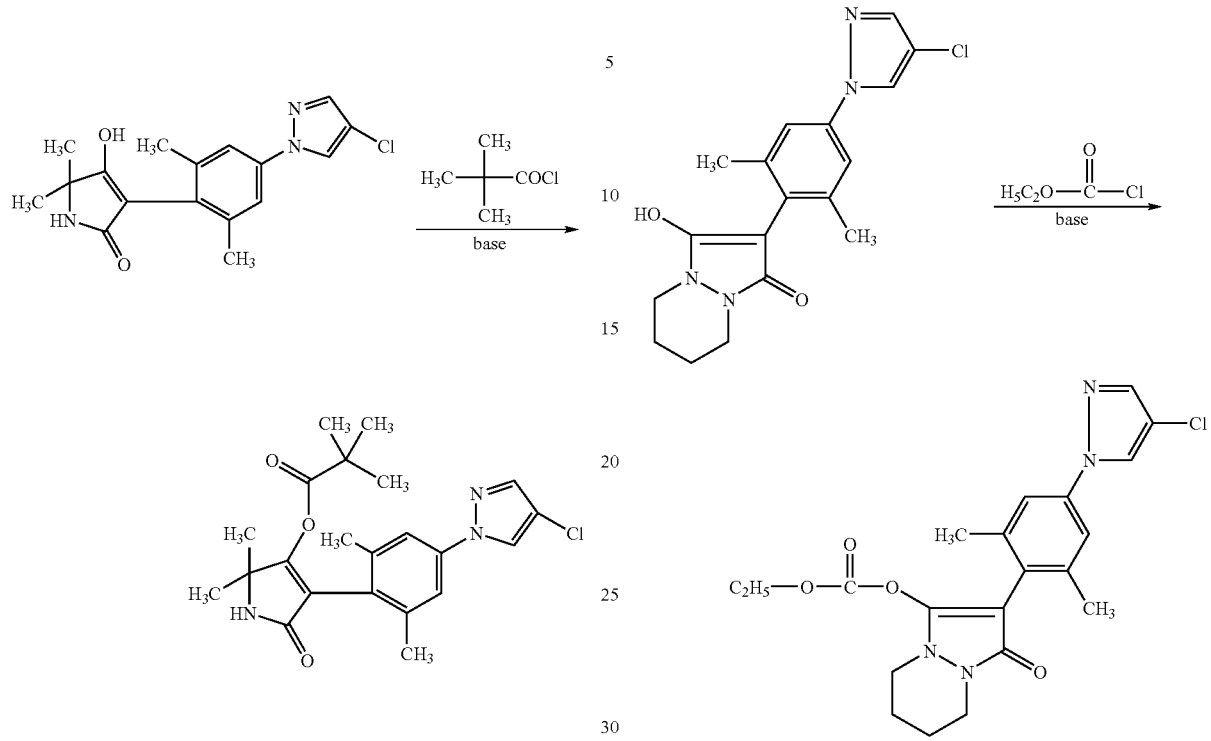

Using, for example, according to process (I) (variant β) 3-[2,6-dimethyl-4-(N4-chloro-pyrazolyl)phenyl]4-hydroxy-5-phenyl-$\Delta^3$-dihydrofuran-2-one and acetic anhydride as starting materials, the course of the process according to the invention can be represented by the following equation:

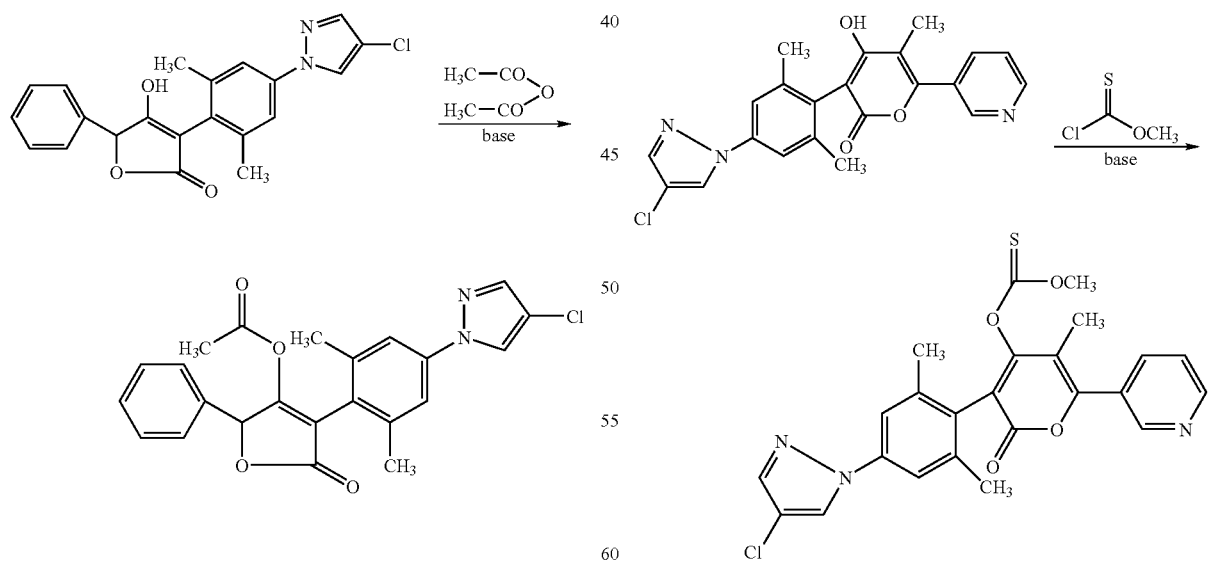

Using, for example, according to process (J) 8-[2,6-dimethyl-4-(N-4-chloropyrazolyl)-phenyl]-1,6-diazabicyclo-(4, 3,0$^{1,6}$)-nonane-7,9-dione and ethoxyethyl chloroformate as starting materials, the course of the process according to the invention can be represented by the following equation:

Using, for example, according to process (K) 3-[2,6-dimethyl-4-(N-4-chloropyrazolyl)-phenyl]-4-hydroxy-5-methyl-6-(3-pyridyl)pyrone and methyl chloromonothioformate as starting materials, the course of the reaction can be represented by the following equation:

Using, for example, according to process (L) 2-[2,6-dimethyl-4-(N-4-chloropyrazolyl)-phenyl]-5,5-pentamethyl-enepyrrolidine-2,4-dione and methanesulphonyl chloride as starting materials, the course of the reaction can be represented by the following equation:

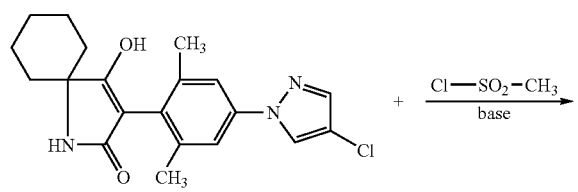

Using, for example, according to process (M) 2-[2,6-dimethyl-4-(N-4-chloropyrazolyl)-phenyl]-4-hydroxy-5,5-dimethyl-Δ³-dihydrofuran-2-one and 2,2,2-trifluoroethyl methane-thiophosphonyl chloride as starting materials, the course of the reaction can be represented by the following equation:

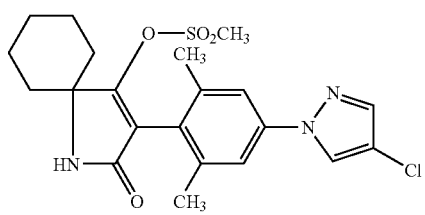

Using, for example, according to process (N) 3-[2-chloro-5-(N-4-chloropyrazolyl)phenyl]-5-cyclopropyl-5-methylpyrrolidine-2,4-dione and NaOH as components, the course of the process according to the invention can be represented by the following equation:

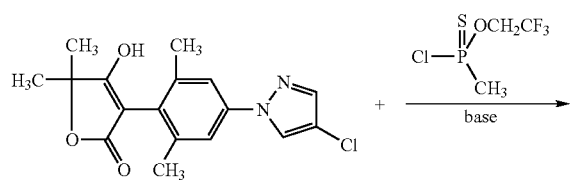

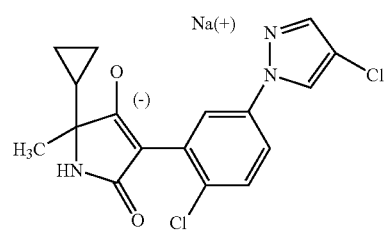

Using, for example, according to process (O) (variant α) 3-[6-methyl-3-(N-4-chloropyrazolyl)phenyl]-4-hydroxy-5-tetramethylene-Δ³-dihydrofuran-2-one and ethyl iso-cyanate as starting materials, the course of the reaction can be represented by the following equation:

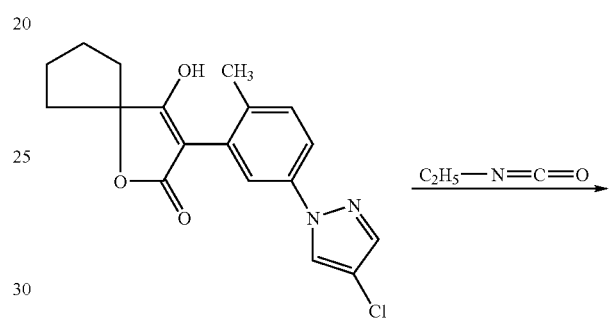

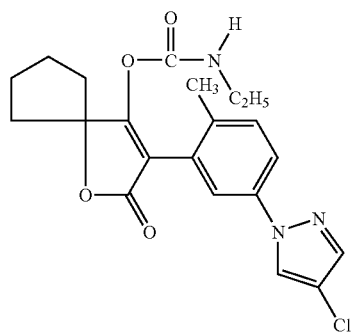

Using, for example, according to process (O) (variant β) 3-[2-chloro-5-(N-4-chloro-pyrazolyl)phenyl]-5-methylpyrrolidine-2,4-dione and dimethylcarbamoyl chloride as starting materials, the course of the reaction can be represented by the following equation:

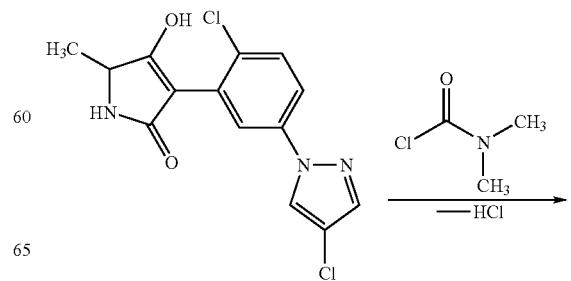

-continued

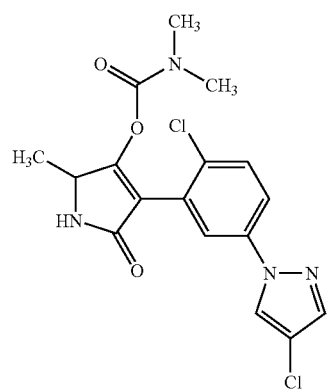

Using, for example, according to process (P) 3-[(2,6-dimethyl-4-bromo)phenyl]-4,4-(penta-methylene)pyrrolidine-2,4-dione and 4-chloropyrazole as starting materials, the course of the reaction can be represented by the following equation:

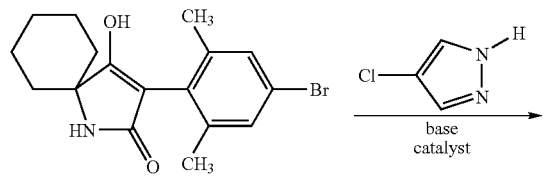

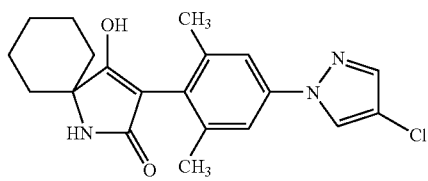

The compounds, required as starting materials in the process (a) according to the invention, of the formula (II)

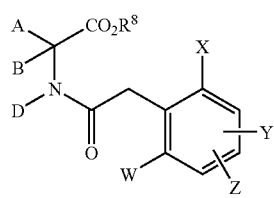
(II)

in which

A, B, D, W, X, Y, Z and $R^8$ are as defined above are novel.

The acylamino acid esters of the formula (II) are obtained, for example, when amino acid derivatives of the formula (XXIV)

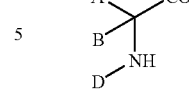
(XXIV)

in which

A, B, $R^8$ and D are as defined above are acylated with substituted phenylacetic acid derivatives of the formula (XXV)

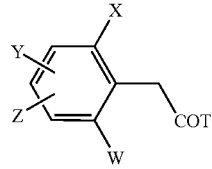
(XXV)

in which

W, X, Y and Z are as defined above and

T represents a leaving group introduced by reagents that activate carboxylic acids, such as carbonyldiimidazole, carbodiimides (such as, for example, dicyclohexylcarbodiimide), phosphorylating reagents (such as, for example, $POCl_3$, BOP-Cl), halogenating agents, for example thionyl chloride, oxalyl chloride, phosgene, sulphonyl chlorides (for example toluenesulphonyl chloride) or chloroformic esters, (Chem. Reviews 52, 237-416 (1953); Bhattacharya, Indian J. Chem. 6, 341-5, 1968) or when acylamino acids of the formula (XXVI)

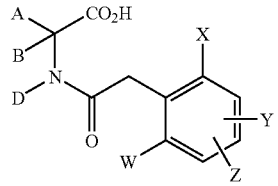
(XXVI)

in which

A, B, D, W, X, Y and Z are as defined above are esterified (Chem. Ind. (London) 1568 (1968)).

The compounds of the formula (XXVI)

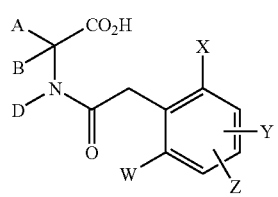
(XXVI)

in which

A, B, D, W, X, Y and Z are as defined above are novel.

The compounds of the formula (XXVI) are obtained when amino acids of the formula (XXVII)

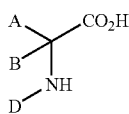
(XXVII)

in which

A, B and D are as defined above are acylated with substituted phenylacetic acid derivatives of the formula (XXV)

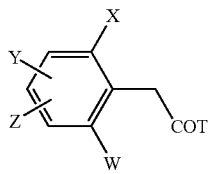
(XXV)

in which

W, X, Y and Z are as defined above and

T is as defined above, for example according to Schotten-Baumann (Organikum, VEB Deutscher Verlag der Wissenschaften, Berlin 1977, p. 505).

The compounds of the formula (XXV) are novel. They can be prepared by processes known in principle and as shown in the Preparation Examples (see, for example, H. Henecka, Houben-Weyl, Methoden der Organischen Chemie [Methods of Organic Chemistry], Vol. 8, pp. 467-469 (1952)).

The compounds of the formula (XXV) are obtained, for example, by reacting substituted phenylacetic acids of the formula (XXVIII)

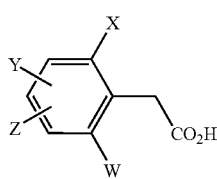
(XXVIII)

in which

W, X, Y and Z are as defined above with halogenating agents (for example thionyl chloride, thionyl bromide, oxalyl chloride, phosgene, phosphorus trichloride, phosphorus tribromide or phosphorus pentachloride), phosphorylating reagents (such as, for example, $POCl_3$, BOP—Cl), carbonyldiimidazole, carbodiimides (for example dicyclohexylcarbodiimide), if appropriate in the presence of a diluent (for example, optionally chlorinated aliphatic or aromatic hydrocarbons, such as toluene or methylene chloride, or ethers, for example tetrahydrofuran, dioxane, methyl tert-butyl ether), at temperatures of from −20° C. to 150° C., preferably from −10° C. to 100° C.

Some of the compounds of the formulae (XXIV) and (XXVII) are known and/or can be prepared by known processes (see, for example, Compagnon, Miocque Ann. Chim. (Paris) [14] 5, p. 11-22, 23-27 (1970)).

The substituted cyclic aminocarboxylic acids of the formula (XXVII) in which A and B form a ring are generally obtained by means of a Bucherer-Bergs synthesis or a Strecker synthesis, where they are obtained in each case in different isomeric forms. Thus, the conditions of the Bucherer-Bergs synthesis give predominantly the isomers (for simplicity reasons referred to as β hereinbelow) in which the radicals R and the carboxyl group are in equatorial positions, while the conditions of the Strecker synthesis give predominantly the isomers (for simplicity reasons referred to as α hereinbelow) where the amino group and the radical R are in equatorial positions.

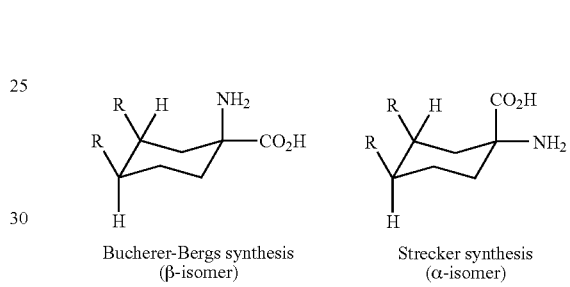

Bucherer-Bergs synthesis (β-isomer)　　Strecker synthesis (α-isomer)

(L. Munday, J. Chem. Soc. 4372 (1961); J. T. Eward, C. Jitrangeri, Can. J. Chem. 53, 3339 (1975)).

Furthermore, the starting materials, used in process (A) above, of the formula (II)

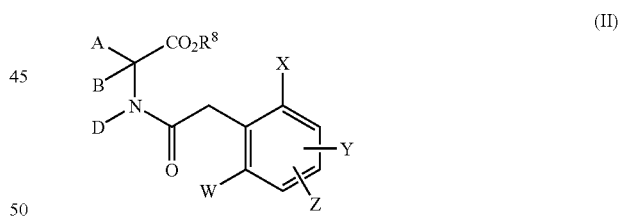
(II)

in which

A, B, D, W, X, Y, Z and $R^8$ are as defined above can be prepared by reacting aminonitriles of the formula (XXIX)

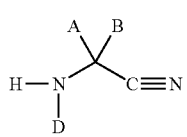
(XXIX)

in which

A, B and D are as defined above with substituted phenylacetic acid derivatives of the formula (XXV)

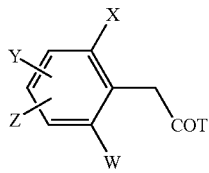
(XXV)

in which

T, W, X, Y and Z are as defined above to give compounds of the formula (XXX)

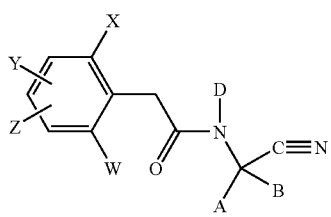
(XXX)

in which

A, B, D, W, X, Y and Z are as defined above which are then subjected to an acidic alcoholysis.

The compounds of the formula (XXX) are also novel.

The compounds, required as starting materials for the process (B) according to the invention, of the formula (III)

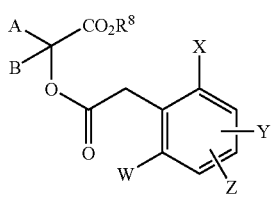
(III)

in which

A, B, W, X, Y, Z and $R^8$ are as defined above are novel.

They can be prepared by methods known in principle.

Thus, the compounds of the formula (III) are obtained, for example, when 2-hydroxycarboxylic esters of the formula (XXXI-A)

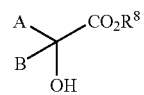
(XXXI-A)

in which

A, B and $R^8$ are as defined above are acylated with substituted phenylacetic acid derivatives of the formula (XXV)

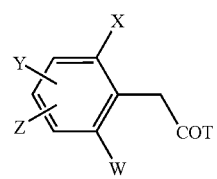
(XXV)

in which

T, W, X, Y and Z are as defined above (Chem. Reviews 52, 237-416 (1953)).

Furthermore, compounds of the formula (III) are obtained when substituted phenylacetic acids of the formula (XXVIII)

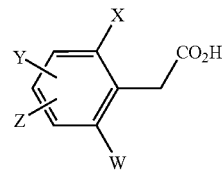
(XXVIII)

in which

W, X, Y and Z are as defined above are alkylated with α-halocarboxylic esters of the formula (XXXI-B)

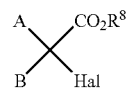
(XXXI-B)

in which

A, B and $R^8$ are as defined above and

Hal represents chlorine or bromine.

The compounds of the formula (XXVIII) are novel.

The compounds of the formula (XXXI-B) are commercially available.

The compounds of the formula (XXVIII)

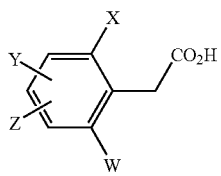

(XXVIII)

in which

W, X, Y and Z are as defined above are obtained, for example, when phenylacetic esters of the formula (XXXII)

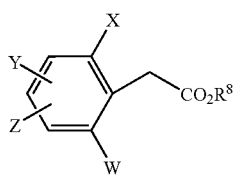

(XXXII)

in which

W, X, Y, Z and $R^8$ are as defined above are hydrolyzed in the presence of acids or bases in the presence of a solvent under generally known standard conditions.

The compounds of the formula (XXXII) are novel.
The compounds of the formula (XXXII)

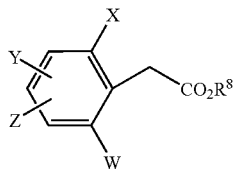

(XXXII)

in which

W, X, Y, Z and $R^8$ are as defined above are obtained, for example, by the process (Q) described in the examples when phenylacetic esters of the formula (XXXII-a)

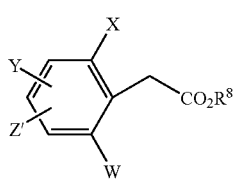

(XXXII-a)

in which $R^8$, W, X and Y are as defined above and

Z' represents halogen (in particular bromine)

are reacted in the presence of an HN-containing heterocycle of the formula (XXIII) in which Z is as defined above in the presence of a base and, if appropriate, in the presence of a catalyst (preferably copper salts, such as, for example, copper (I) iodide) (S. Buchwald et. al. JACS 123, 7727, 2001).

Some of the phenylacetic esters of the formula (XXXII-a) are known from the applications WO 96/35 664 and WO 97/02 243, or they can be prepared by the processes described therein.

The compounds, required as starting materials in the above process (C), of the formula (IV)

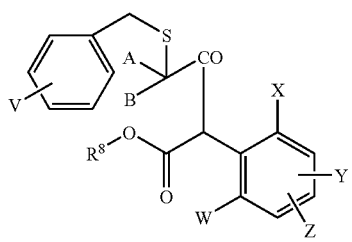

(IV)

in which

A, B, V, W, X, Y, Z and $R^8$ are as defined above are novel.

They can be prepared by methods known in principle.

The compounds of the formula (IV) are obtained, for example, when substituted phenylacetic esters of the formula (XXXII)

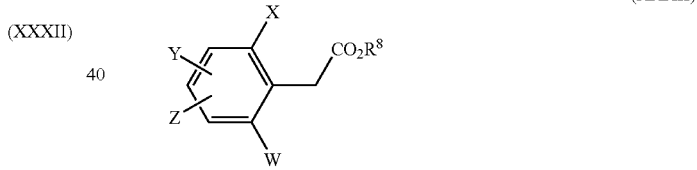

(XXXII)

in which

W, X, Y, Z and $R^8$ are as defined above are acylated with 2-benzylthiocarbonyl halides of the formula (XXXIII)

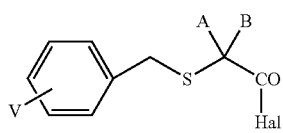

(XXXIII)

in which

A, B and V are as defined above and

Hal represents halogen (in particular chlorine or bromine)

in the presence of strong bases (see, for example, M. S. Chambers, E. J. Thomas, D. J. Williams, J. Chem. Soc. Chem. Commun., (1987), 1228).

Some of the benzylthiocarbonyl halides of the formula (XXXIII) are known, and/or they can be prepared by known processes (J. Antibiotics (1983), 26, 1589).

The halocarbonyl ketenes of the formula (VI) required as starting materials for the above processes (D), (E) and (H-α) are novel. They can be prepared in a simple manner by methods known in principle (cf., for example, Org. Prep. Proced. Int., 7, (4), 155-158, 1975 and DE 1 945 703). Thus, for example, the compounds of the formula (VI)

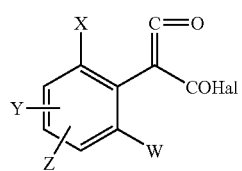
(VI)

in which

W, X, Y and Z are as defined above and

Hal represents chlorine or bromine are obtained when substituted phenylmalonic acids of the formula (XXXIV)

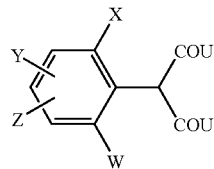
(XXXIV)

in which

W, X, Y and Z are as defined above are reacted with acid halides, such as, for example, thionyl chloride, phosphorus(V) chloride, phosphorus(III) chloride, oxalyl chloride, phosgene or thionyl bromide, if appropriate in the presence of catalysts, such as, for example, diethylformamide, methyl-steryl formamide or triphenylphosphine and, if appropriate, in the presence of bases, such as, for example, pyridine or triethylamine.

The substituted phenylmalonic acids of the formula (XXXIV) are novel. They can be prepared in a simple manner by known processes (cf., for example, Organikum, VEB Deutscher Verlag der Wissenschaften, Berlin 1977, p. 517 ff, EP-A-528 156, WO 96/35 664, WO 97/02 243, WO 97/01535, WO 97/36868 and WO 98/05638).

Thus, phenylmalonic acids of the formula (XXXIV)

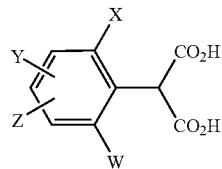
(XXXIV)

in which

W, X, Y and Z are as defined above are obtained when phenylmalonic acid derivatives of the formula (XI) where $U=OR^8$

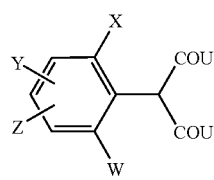
(XI)

in which

U, W, X, Y and Z are as defined above are initially hydrolyzed in the presence of a base and a solvent and then carefully acidified (EP-A-528 156, WO 96/35 664, WO 97/02 243).

The malonic esters of the formula (XI) where $U=OR^8$ (XI)

in which

U, W, X, Y and Z are as defined above are novel.

They can be prepared by generally known methods of organic chemistry (cf., for example, Tetrahedron Lett. 27, 2763 (1986), Organikum VEB Deutscher Verlag der Wissenschaften, Berlin 1977, p. 587 ff., WO 96/35664, WO 97/02243, WO 97/01535, WO 97/36868, WO 98/05638 and WO 99/47525).

The carbonyl compounds, required as starting materials for the process (D) according to the invention, of the formula (V)

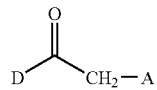
(V)

in which

A and D are as defined above or their silyl enol ethers of the formula (Va)

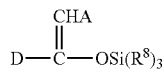
(Va)

in which

A, D and $R^8$ are as defined above are compounds which are commercially available, generally known or obtainable by known processes.

The preparation of the ketene acid chlorides of the formula (VI) required as starting materials for carrying out the process (E) according to the invention has already been described above. The thioamides, required for carrying out the process (E) according to the invention, of the formula (VII)

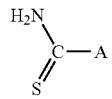
(VII)

in which

A is as defined above are compounds which are generally known in organic chemistry.

The compounds, required as starting materials for the above process (F), of the formula (VIII)

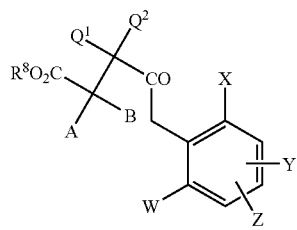
(VIII)

in which

A, B, $Q^1$, $Q^2$, W, X, Y, Z and $R^8$ are as defined above are novel.

They can be prepared by methods known in principle.

The 5-aryl-4-ketocarboxylic esters of the formula (VIII) are obtained, for example, when 5-aryl-4-ketocarboxylic acids of the formula (XXXV)

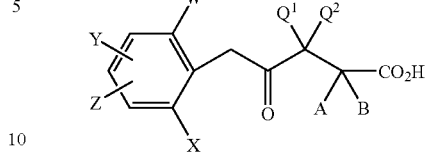
(XXXV)

in which

W, X, Y, Z, A, B, $Q^1$ and $Q^2$ are as defined above are esterified (cf., for example, Organikum, 15th Edition, Berlin, 1977, page 499) or alkylated (see Preparation Example).

The 5-aryl-4-ketocarboxylic acids of the formula (XXXV)

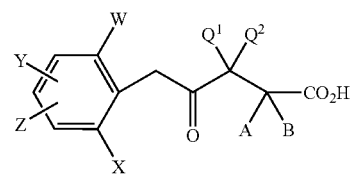
(XXXV)

in which

A, B, $Q^1$, $Q^2$, W, X, Y and Z are as defined above are novel, but can be prepared by methods known in principle (WO 96/01 798, WO 97/14667, WO 98/39281).

The 5-aryl-4-ketocarboxylic acids of the formula (XXXV) are obtained, for example, when 2-phenyl-3-oxoadipic esters of the formula (XXXVI)

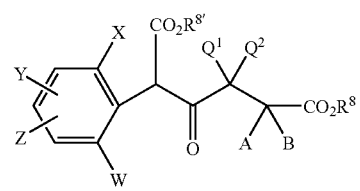
(XXXVI)

in which

A, B, $Q^1$, $Q^2$, W, X, Y and Z are as defined above and $R^8$ and $R^{8'}$ represent alkyl (in particular $C_1$-$C_8$-alkyl) and when the compound of the formula (XXXVIII) is used, $R^8$ represents hydrogen, are decarboxylated, if appropriate in the presence of a diluent and if appropriate in the presence of a base or an acid (cf., for example, Organikum, 15th Edition, Berlin, 1977, pages 519 to 521).

The compounds of the formula (XXXVI)

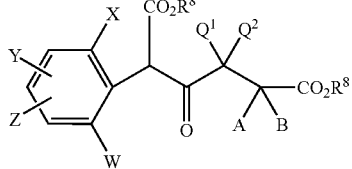

(XXXVI)

in which

A, B, $Q^1$, $Q^2$, W, X, Y, Z, $R^8$, $R^{8'}$ are as defined above and in which if the compound of the formula (XXXVIII) is used, $R^8$ also represents hydrogen, are novel.

The compounds of the formula (XXXVI) are obtained, for example, when dicarboxylic semiester chlorides of the formula (XXXVII),

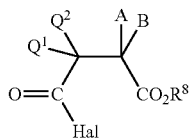

(XXXVII)

in which

A, B, $Q^1$, $Q^2$ and $R^8$ are as defined above and

Hal represents chlorine or bromine or carboxylic anhydrides of the formula (XXXVIII)

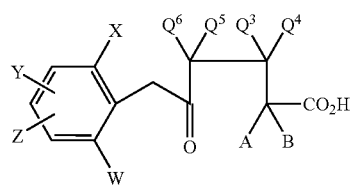

(XXXVIII)

in which

A, B, $Q^1$ and $Q^2$ are as defined above are acylated with a phenylacetic ester of the formula (XXXII)

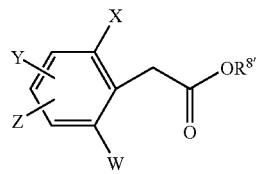

(XXXII)

in which

W, X, Y, Z and $R^{8'}$ are as defined above in the presence of a diluent and in the presence of a base (cf., for example, M. S. Chambers, E. J. Thomas, D. J. Williams, J. Chem. Soc. Chem. Commun., (1987), 1228, cf. also the Preparation Examples).

Some of the compounds of the formulae (XXXVII) and (XXXVIII) are known compounds of organic chemistry, and/or they can be prepared in a simple manner by methods known in principle.

The compounds, required as starting materials for the above process (G), of the formula (IX)

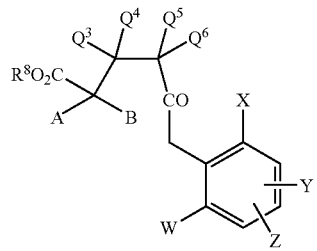

(IX)

in which

A, B, $Q^3$, $Q^4$, $Q^5$, $Q^6$, W, X, Y, Z and $R^8$ are as defined above are novel.

They can be prepared by methods known in principle.

The 6-aryl-5-ketocarboxylic esters of the formula (IX) are obtained, for example, when 6-aryl-5-ketocarboxylic acids of the formula (XXXIX)

(XXXIX)

in which

A, B, $Q^3$, $Q^4$, $Q^5$, $Q^6$, W, X, Y and Z are as defined above are esterified (cf., for example, Organikum, 15th Edition, Berlin, 1977, page 499).

The 6-aryl-5-ketocarboxylic acids of the formula (XXXIX)

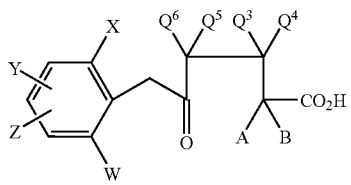
(XXXIX)

in which

A, B, $Q^3$, $Q^4$, $Q^5$, $Q^6$, W, X, Y and Z are as defined above are novel. They can be prepared by methods known in principle (WO 99/43649, WO 99/48869), for example by hydrolyzing and decarboxylating substituted 2-phenyl-3-oxoheptanedioic esters of the formula (XL)

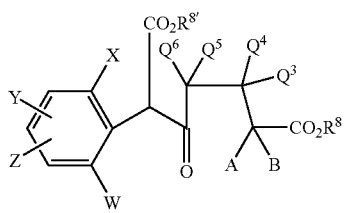
(XL)

in which

A, B, $Q^3$, $Q^4$, $Q^5$, $Q^6$, W, X, Y and Z are as defined above and $R^8$ and $R^{8'}$ represent alkyl (preferably $C_1$-$C_6$-alkyl) and, if the compound of the formula (XLII) is used, $R^8$ represents hydrogen, if appropriate in the presence of a diluent and if appropriate in the presence of a base or an acid (cf., for example, Organikum, 15th Edition, Berlin, 1977, pages 519 to 521).

The compounds of the formula (XL)

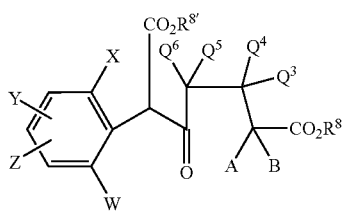
(XL)

in which

A, B, $Q^3$, $Q^4$, $Q^5$, $Q^6$, W, X, Y, Z, $R^8$ and $R^{8'}$ are as defined above are novel and can be obtained by condensing dicarboxylic esters of the formula (XLI),

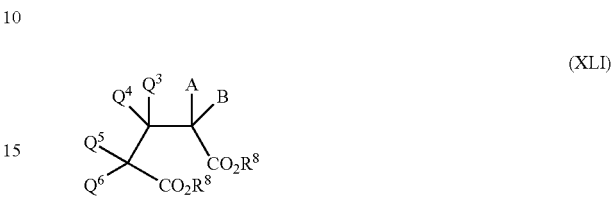
(XLI)

in which

A, B, $Q^3$, $Q^4$, $Q^5$, $Q^6$ and $R^8$ are as defined above or carboxylic anhydrides of the formula (XLII)

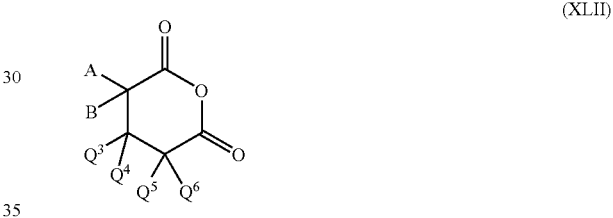
(XLII)

in which

A, B, $Q^3$, $Q^4$, $Q^5$, $Q^6$ are as defined above with a substituted phenylacetic ester of the formula (XXXII)

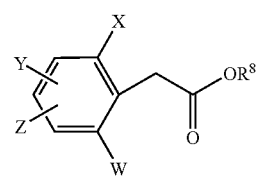
(XXXII)

in which

W, X, Y, Z and $R^8$ are as defined above in the presence of a diluent and in the presence of a base.

Some of the compounds of the formulae (XLI) and (XLII) are known, and/or they can be prepared by known processes.

Some of the hydrazines, required as starting materials for the processes (H-α) and (H-β) according to the invention, of the formula (X)

A-NH—NH-D    (X)

in which

A and D are as defined above are known, and/or they can be prepared by methods known from literature (cf., for example, Liebigs Ann. Chem. 585, 6

(1954); Reaktionen der organischen Synthese [Reaction of organic synthesis], C. Ferri, pages 212, 513; Georg Thieme Verlag Stuttgart, 1978; Liebigs Ann. Chem. 443, 242 (1925); Chem. Ber. 98, 2551 (1965), EP-A-508 126, WO 92/16510, WO 99/47 525, WO 01/17 972).

The compounds, required for the process (H-γ) according to the invention, of the formula (XII)

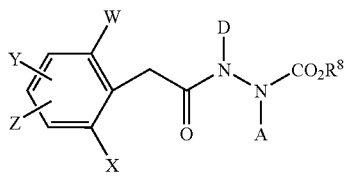
(XII)

in which

A, D, W, X, Y, Z and $R^8$ are as defined above are novel.

The acylcarbazates of the formula (XII) are obtained, for example, when carbazates of the formula (XLIII)

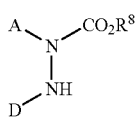
(XLIII)

in which

A, $R^8$ and D are as defined above are acylated with substituted phenylacetic acid derivatives of the formula (XXV)

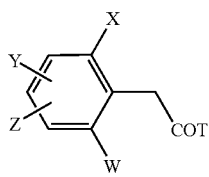
(XXV)

in which

T, W, X, Y and Z are as defined above (Chem. Reviews 52, 237-416 (1953); Bhattacharya, Indian J. Chem. 6, 341-5, 1968).

Some of the carbazates of the formula (XLHI) are commercially available and some are known compounds, or they can be prepared by processes of organic chemistry known in principle.

Some of the compounds, required as starting materials for the above process (P), of the formulae (I-1') to (1-8') in which A, B, D, G, $Q^1$, $Q^2$, $Q^3$, $Q^4$, $Q^5$, $Q^6$, W, X and Y defined above and Z' represents chlorine or bromine, preferably bromine, are known from the patent applications cited at the outset (for example WO 96/35 664, WO 97/02 243), or they can be prepared by the processes described therein.

Some of the compounds of the formula (XXIII)

$$H-Z \quad \text{(XXIII)}$$

in which

Z is as defined above are commercially available, or they can be prepared by general processes known in principle.

The acid halides of the formula (XIII), carboxylic anhydrides of the formula (XIV), chloroformic esters or chloroformic thioesters of the formula (XV), chloromonothioformic esters or chlorodithioformic esters of the formula (XVI), sulphonyl chlorides of the formula (XVII), phosphorus compounds of the formula (XVIII) and metal hydroxides, metal alkoxides or amines of the formulae (XIX) and (XX) and isocyanates of the formula (XXI) and carbamoyl chlorides of the formula (XXII) furthermore required as starting materials for carrying out the processes (I), (J), (K), (L), (M), (N) and (O) according to the invention are generally known compounds of organic or inorganic chemistry.

In addition, the compounds of the formulae (V), (VII), (XIII) to (XXII), (XXIV), (XXVII), (XXIX), (XXXI-A), (XXXI-B), (XXXIII), (XXXVII), (XXXVIII), (XLI) and (XLII) are known from the patent applications cited at the outset, and/or they can be prepared by the methods given therein.

The process (A) is characterized in that compounds of the formula (II) in which A, B, D, W, X, Y, Z and $R^8$ are as defined above are, in the presence of a base, subjected to an intramolecular condensation.

Suitable diluents for the process (A) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide, dimethylacetamide and N-methylpyrrolidone, and also alcohols, such as methanol, ethanol, propanol, isopropanol, butanol, isobutanol and tert-butanol.

Suitable bases (deprotonating agents) for carrying out the process (A) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals such as sodium or potassium. Also suitable are alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (A) according to the invention, the reaction temperatures can be varied within a relatively large range. In general, the process is carried out at temperatures between 0° C. and 250° C., preferably between 50° C. and 150° C.

The process (A) according to the invention is generally carried out under atmospheric pressure.

When carrying out the process (A) according to the invention, the reaction components of the formula (II) and the deprotonating bases are generally employed in approximately doubly equimolar amounts. However, it is also possible to use a relatively large excess (up to 3 mol) of one component or the other.

The process (B) is characterized in that compounds of the formula (III) in which A, B, W, X, Y, Z and $R^8$ are as defined above are, in the presence of a diluent and in the presence of a base, subjected to an intramolecular condensation.

Suitable diluents for the process (B) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone. It is furthermore possible to use alcohols, such as methanol, ethanol, propanol, isopropanol, butanol, isobutanol and tert-butanol.

Suitable bases (deprotonating agents) for carrying out the process (B) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase-transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. Also suitable are alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (B) according to the invention, the reaction temperatures can be varied within a relatively wide range. In general, the process is carried out at temperatures between 0° C. and 250° C., preferably between 50° C. and 150° C.

The process (B) according to the invention is generally carried out under atmospheric pressure.

When carrying out the process (B) according to the invention, the reaction components of the formula (III) and the deprotonating bases are generally employed in approximately equimolar amounts. However, it is also possible to use a relatively large excess (up to 3 mol) of one component or the other.

The process (C) is characterized in that compounds of the formula (IV) in which A, B, V, W, X, Y, Z and $R^8$ are as defined above are, in the presence of an acid and, if appropriate, in the presence of a diluent, subjected to intramolecular cyclization.

Suitable diluents for the process (C) according to the invention are all inert organic solvents. Preference is given to using hydrocarbons, such as toluene and xylene, furthermore halogenated hydrocarbons, such as dichloromethane, chloroform, ethylene chloride, chlorobenzene, dichlorobenzene, moreover polar solvents, such as dimethyl sulphoxide, sulpholane, dimethylformamide and N-methylpyrrolidone. It is furthermore possible to use alcohols, such as methanol, ethanol, propanol, isopropanol, butanol, isobutanol, tert-butanol.

If appropriate, the acid used can also serve as diluent.

Suitable acids for the process (C) according to the invention are all customary inorganic and organic acids, such as, for example, hydrohalic acids, sulphuric acid, alkyl-, aryl- and haloalkylsulphonic acids, in particular halogenated alkylcarboxylic acids, such as, for example, trifluoroacetic acid.

When carrying out the process (C) according to the invention, the reaction temperatures can be varied within a relatively wide range. In general, the process is carried out at temperatures between 0° C. and 250° C., preferably between 50° C. and 150° C.

The process (C) according to the invention is generally carried out under atmospheric pressure.

When carrying out the process (C) according to the invention, the reaction components of the formula (IV) and the acids are employed, for example, in equimolar amounts. However, it is, if appropriate, also possible to use the acid as solvent or as catalyst.

The process (D) according to the invention is characterized in that carbonyl compounds of the formula (V) or enol ethers thereof of the formula (V-a) are reacted with ketene acid halides of the formula (VI) in the presence of a diluent and, if appropriate, in the presence of an acid acceptor.

Suitable diluents for the process (D) according to the invention are all inert organic solvents. Preference is given to using optionally halogenated hydrocarbons, such as toluene, xylene, mesitylene, chlorobenzene and dichlorobenzene, furthermore ethers, such as dibutyl ether, glycol dimethyl ether, diglycol dimethyl ether and diphenyl ether, moreover polar solvents, such as dimethyl sulphoxide, sulpholane, dimethylformamide or N-methylpyrrolidone.

Suitable acid acceptors for carrying out the process variant (D) according to the invention are all customary acid acceptors.

Preference is given to using tertiary amines, such as triethylamine, pyridine, diazabicyclooctane (DABCO), diazabicycloundecane (DBU), diazabicyclononene (DBN), Hünig base and N,N-dimethylaniline.

When carrying out the process variant (D) according to the invention, the reaction temperatures can be varied within a relatively wide range. The process variant is expediently carried out at temperatures between 0° C. and 250° C., preferably between 50° C. and 220° C.

The process (D) according to the invention is expediently carried out under atmospheric pressure.

When carrying out the process (D) according to the invention, the reaction components of the formulae (V) and (VI) in which A, D, W, X, Y and Z are as defined above and Hal represents halogen and, if appropriate, the acid acceptors are generally employed in approximately equimolar amounts. However, it is also possible to use a relatively large excess (up to 5 mol) of one component or the other.

The process (E) according to the invention is characterized in that thioamides of the formula (VII) are reacted with ketene acid halides of the formula (VI) in the presence of a diluent and, if appropriate, in the presence of an acid acceptor.

Suitable diluents for the process variant (E) according to the invention are all inert organic solvents. Preference is given to using hydrocarbons, such as toluene and xylene, furthermore ethers, such as dibutyl ether, glycol dimethyl ether and diglycol dimethyl ether, moreover polar solvents, such as dimethyl sulphoxide, sulpholane, dimethylformamide and N-methylpyrrolidone.

Suitable acid acceptors for carrying out the process (E) according to the invention are all customary acid acceptors.

Preference is given to using tertiary amines, such as triethylamine, pyridine, diazabicyclo-octane (DABCO), diazabicycloundecane (DBU), diazabicyclononene (DBN), Hünig base and N,N-dimethylaniline.

When carrying out the process (E) according to the invention, the reaction temperatures can be varied within a relatively wide range. Expediently, the process is carried out at temperatures between 0° C. and 250° C., preferably between 20° C. and 220° C.

The process (E) according to the invention is expediently carried out under atmospheric pressure.

When carrying out the process (E) according to the invention, the reaction components of the formulae (VII) and (VI) in which A, W, X, Y and Z are as defined above and Hal represents halogen and, if appropriate, the acid acceptors are generally employed in approximately equimolar amounts. However, it is also possible to use a relatively large excess (up to 5 mol) of one component or the other.

The process (F) is characterized in that compounds of the formula (VIII) in which A, B, $Q^1$, $Q^2$, W, X, Y, Z and $R^8$ are as defined above are, in the presence of a base, subjected to an intramolecular condensation.

Suitable diluents for the process (F) according to the invention are all organic solvents which are inert towards the reactants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone. It is furthermore possible to use alcohols, such as methanol, ethanol, propanol, isopropanol, butanol, isobutanol, tert-butanol.

Suitable bases (deprotonating agents) for carrying out the process (F) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase transfer catalysts, such as, for example, triethylbenzylammonium chloride, tetrabutylammonium bromide, Adogen 464 (methyltrialkyl($C_8$-$C_{10}$)ammonium chloride) or TDA 1 (tris(methoxyethoxyethyl)amine). It is furthermore possible to use alkali metals, such as sodium or potassium. Also suitable are alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (F) according to the invention, the reaction temperatures can be varied within a relatively wide range. In general, the process is carried out at temperatures between −75° C. and 250° C., preferably between −50° C. and 150° C.

The process (F) according to the invention is generally carried out under atmospheric pressure.

When carrying out the process (F) according to the invention, the reaction components of the formula (VIII) and the deprotonating bases are generally employed in approximately equimolar amounts. However, it is also possible to use a relatively large excess (up to 3 mol) of one component or the other.

The process (G) is characterized in that compounds of the formula (IX) in which A, B, $Q^3$, $Q^4$, $Q^5$, $Q^6$, W, X, Y, Z and $R^8$ are as defined above are, in the presence of bases, subjected to an intramolecular condensation.

Suitable diluents for the process (G) according to the invention are all organic solvents which are inert towards the reactants. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone. It is furthermore possible to use alcohols, such as methanol, ethanol, propanol, isopropanol, butanol, isobutanol, tert-butanol.

Suitable bases (deprotonating agents) for carrying out the process (G) according to the invention are all customary proton acceptors.

Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be used in the presence of phase transfer catalysts, such as, for example, triethylbenzylammonium chloride, tetrabutylammonium bromide, Adogen 464 (methyltrialkyl($C_8$-$C_{10}$)ammonium chloride) or TDA 1 (tris(methoxyethoxyethyl)amine). It is furthermore possible to use alkali metals, such as sodium or potassium. Also suitable are alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (G) according to the invention, the reaction temperatures can be varied within a relatively wide range. In general, the process is carried out at temperatures between 0° C. and 250° C., preferably between 50° C. and 150° C.

The process (G) according to the invention is generally carried out under atmospheric pressure.

When carrying out the process (G) according to the invention, the reaction components of the formula (IX) and the deprotonating bases are generally employed in approximately equimolar amounts. However, it is also possible to use a relatively large excess (up to 3 mol) of one component or the other.

The process (H-α) according to the invention is characterized in that hydrazines of the formula (X) or salts of these compounds are reacted with ketene acid halides of the formula (VI) in the presence of a diluent and, if appropriate, in the presence of an acid acceptor.

Suitable diluents for the process (H-α) according to the invention are all inert organic solvents. Preference is given to using optionally chlorinated hydrocarbons, such as, for example, mesitylene, chlorobenzene and dichlorobenzene, toluene, xylene, furthermore ethers, such as dibutyl ether, glycol dimethyl ether, diglycol dimethyl ether and diphenyl ether, moreover polar solvents, such as dimethyl sulphoxide, sulpholane, dimethylformamide or N-methylpyrrolidone.

Suitable acid acceptors for carrying out the process variant (H-α) according to the invention are all customary acid acceptors.

Preference is given to using tertiary amines, such as triethylamine, pyridine, diazabicyclooctane (DABCO), diazabicycloundecane (DBU), diazabicyclononene (DBN), Hünig base and N,N-dimethylaniline.

When carrying out the process variant (H-α) according to the invention, the reaction temperatures can be varied within a relatively wide range. The process variant is expediently carried out at temperatures between 0° C. and 250° C., preferably between 50° C. and 220° C.

The process (H-α) according to the invention is expediently carried out under atmospheric pressure.

When carrying out the process (H-α) according to the invention, the reaction components of the formulae (VI) and (X) in which A, D, W, X, Y and Z are as defined above and Hal represents halogen and, if appropriate, the acid acceptors are generally employed in approximately equimolar amounts. However, it is also possible to use a relatively large excess (up to 5 mol) of one component or the other.

The process (H-β) is characterized in that hydrazines of the formula (X) or salts of this compound in which A and D are as defined above are, in the presence of a base, subjected to a condensation with malonic esters or malonamides of the formula (XI) in which U, W, X, Y, Z and $R^8$ are as defined above.

Suitable diluents for the process (H-β) according to the invention are all inert organic solvents. Preference is given to using optionally halogenated hydrocarbons, such as toluene, xylene, mesitylene, chlorobenzene and dichlorobenzene, furthermore ethers, such as dibutyl ether, tetrahydrofuran, dioxane, diphenyl ether, glycol dimethyl ether and diglycol dimethyl ether, moreover polar solvents, such as dimethyl sulphoxide, sulpholane, dimethylformamide, dimethylacetamide and N-methylpyrrolidone, and also alcohols, such as methanol, ethanol, propanol, isopropanol, butanol, isobutanol and tert-butanol.

Suitable bases (deprotonating agents) for carrying out the process (H-β) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, and which can also be used in the presence of phase transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. Also suitable are alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

It is also possible to use tertiary amines, such as triethylamine, pyridine, diazabicyclooctane (DABCO), diazabicycloundecane (DBU), diazabicyclononene (DBN), Hünig base and N,N-dimethylaniline.

When carrying out the process (H-β) according to the invention, the reaction temperatures can be varied within a relatively wide range. In general, the process is carried out at temperatures between 0° C. and 280° C., preferably between 50° C. and 180° C.

The process (H-β) according to the invention is generally carried out under atmospheric pressure.

When carrying out the process (H-β) according to the invention, the reaction components of the formulae (XI) and (X) are generally employed in approximately equimolar amounts. However, it is also possible to use a relatively large excess (up to 3 mol) of one component or the other.

The process (H-γ) is characterized in that compounds of the formula (XII) in which A, D, W, X, Y, Z and $R^8$ are as defined above are, in the presence of a base, subjected to an intramolecular condensation.

Suitable diluents for the process (H-γ) according to the invention are all inert organic solvents. Preference is given to using hydrocarbons, such as toluene and xylene, furthermore ethers such as dibutyl ether, tetrahydrofuran, dioxane, glycol dimethyl ether and diglycol dimethyl ether, moreover polar solvents, such as dimethyl sulphoxide, sulpholane, dimethylformamide and N-methylpyrrolidone, and also alcohols, such as methanol, ethanol, propanol, isopropanol, butanol, isobutanol and tert-butanol.

Suitable bases (deprotonating agents) for carrying out the process (H-γ) according to the invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, and which can also be used in the presence of phase transfer catalysts, such as, for example, triethylbenzylammonium chloride, tetrabutylammonium bromide, Adogen 464 (=methyltrialkyl($C_8$-$C_{10}$)ammonium chloride) or TDA 1 (=tris(methoxyethoxyethyl)amine). It is furthermore possible to use alkali metals, such as sodium or potassium. Also suitable are alkali metal and alkaline earth metal amides and hydrides, such as sodium amide, sodium hydride and calcium hydride, and additionally also alkali metal alkoxides, such as sodium methoxide, sodium ethoxide and potassium tert-butoxide.

When carrying out the process (H-γ) according to the invention, the reaction temperatures can be varied within a relatively wide range. In general, the process is carried out at temperatures between −20° C. and 250° C., preferably between 50° C. and 150° C.

The process (H-γ) according to the invention is generally carried out under atmospheric pressure.

When carrying out the process (H-γ) according to the invention, the reaction components of the formula (XII) and the deprotonating bases are generally employed in approximately doubly equimolar amounts. However, it is also possible to use a relatively large excess (up to 3 mol) of one component or the other.

The process (I-α) is characterized in that compounds of the formulae (I-1-a) to (I-8-a) are in each case reacted with carbonyl halides of the formula (XIII), if appropriate in the presence of a diluent and if appropriate in the presence of an acid binder.

Suitable diluents for the process (I-α) according to the invention are all solvents which are inert towards the acid halides. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane. The hydrolytic stability of the acid halide permitting, the reaction can also be carried out in the presence of water.

Suitable acid binders for the reaction according to the process (I-α) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

In the process (I-α) according to the invention, the reaction temperatures can be varied within a relatively wide range. In general, the process is carried out at temperatures between −20° C. and +150° C., preferably between 0° C. and 100° C.

When carrying out the process (I-α) according to the invention, the starting materials of the formulae (I-1-a) to (I-8-a) and the carbonyl halide of the formula (XIII) are generally each employed in approximately equivalent amounts. However, it is also possible to use a relatively large excess (up to 5 mol) of the carbonyl halide. Work-up is carried out by customary methods.

The process (I-β) is characterized in that compounds of the formulae (I-1-a) to (I-8-a) are reacted with carboxylic anhydrides of the formula (XIV), if appropriate in the presence of a diluent and if appropriate in the presence of an acid binder.

Suitable diluents for the process (I-β) according to the invention are, preferably, those diluents which are also preferred when using acid halides. Besides, it may also be possible for excess carboxylic anhydride to act simultaneously as diluent.

In process (I-β), suitable acid binders, which are added, if appropriate, are preferably those acid binders which are also preferred when using acid halides.

The reaction temperatures in the process (I-β) according to the invention can be varied within a relatively wide range. In general, the process is carried out at temperatures between −20° C. and +150° C., preferably between 0° C. and 100° C.

When carrying out the process (I-β) according to the invention, the starting materials of the formulae (I-1-a) to (I-8-a) and the carboxylic anhydride of the formula (XIV) are generally each employed in approximately equivalent amounts. However, it is also possible to use a relatively large excess (up to 5 mol) of the carboxylic anhydride. Work-up is carried out by customary methods.

In general, diluent and excess carboxylic anhydride and the carboxylic acid formed are removed by distillation or by washing with an organic solvent or with water.

The process (J) is characterized in that compounds of the formulae (I-1-a) to (I-8-a) are in each case reacted with chloroformic esters or chloroformic thioesters of the formula (XV), if appropriate in the presence of a diluent and if appropriate in the presence of an acid binder.

Suitable acid binders for the reaction according to the process (J) according to the invention are all customary acid acceptors. Preference is given to using tertiary amines, such as triethylamine, pyridine, DABCO, DBU, DBA, Hünig base and N,N-dimethylaniline, furthermore alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

Suitable diluents for the process (J) according to the invention are all solvents which are inert towards the chloroformic esters or chloroformic thioesters. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, and also strongly polar solvents, such as dimethyl sulphoxide and sulpholane.

When carrying out the process (J) according to the invention, the reaction temperatures can be varied within a relatively wide range. If the process is carried out in the presence of a diluent and an acid binder, the reaction temperatures are generally between −20° C. and +100° C., preferably between 0° C. and 50° C.

The process (J) according to the invention is generally carried out under atmospheric pressure.

When carrying out the process (J) according to the invention, the starting materials of the formulae (I-1-a) to (I-8-a) and the appropriate chloroformic ester or chloroformic thioester of the formula (XIII) are generally each employed in approximately equivalent amounts. However, it is also possible to use a relatively large excess (up to 2 mol) of one component or the other. Work-up is carried out by customary methods. In general, precipitated salts are removed and the reaction mixture that remains is concentrated by removing the diluent under reduced pressure.

The process (K) according to the invention is characterized in that compounds of the formulae (I-1-a) to (I-8-a) are in each case reacted with compounds of the formula (XVI), in the presence of a diluent and, if appropriate, in the presence of an acid binder.

In Preparation Process (K), about 1 mol of chloromonothioformic ester or chlorodithioformic ester of the formula (XVI) is reacted per mole of starting material of the formulae (I-1-a) to (I-8-a), at from 0 to 120° C., preferably from 20 to 60° C.

Suitable diluents, which are added, if appropriate, are all inert polar organic solvents, such as ethers, amides, sulphones, sulphoxides, and also halogenated alkanes.

Preference is given to using dimethyl sulphoxide, tetrahydrofuran, dimethylformamide or methylene chloride.

If, in a preferred embodiment, the enolate salt of the compounds (I-1-a) to (I-8-a) is prepared by the addition of strong deprotonating agents, such as, for example, sodium hydride or potassium tert-butoxide, the further addition of acid binders can be dispensed with.

If acid binders are used, these are customary inorganic or organic bases, for example sodium hydroxide, sodium carbonate, potassium carbonate, pyridine, triethylamine.

The reaction can be carried out under atmospheric pressure or under elevated pressure and is preferably carried out under atmospheric pressure. Work-up is carried out by customary methods.

The process (L) according to the invention is characterized in that compounds of the formulae (I-1-a) to (I-8-a) are in each case reacted with sulphonyl chlorides of the formula (XVII), if appropriate in the presence of a diluent and if appropriate in the presence of an acid binder.

In the Preparation Process (L), about 1 mol of sulphonyl chloride of the formula (XVII) is reacted per mole of starting material of the formula (I-1-a to I-8-a), at from −20 to 150° C., preferably from 20 to 70° C.

Suitable diluents, which are added, if appropriate, are all inert polar organic solvents, such as ethers, amides, nitrites, sulphones, sulphoxides or halogenated hydrocarbons, such as methylene chloride.

Preference is given to using dimethyl sulphoxide, tetrahydrofuran, dimethylformamide, methylene chloride.

If, in a preferred embodiment, the enolate salt of the compounds (I-1-a) to (I-8-a) is prepared by adding strong deprotonating agents (such as, for example, sodium hydride or potassium tert-butoxide), the further addition of acid binders can be dispensed with.

If acid binders are used, these are customary inorganic or organic bases, for example sodium hydroxide, sodium carbonate, potassium carbonate, pyridine, triethylamine.

The reaction can be carried out under atmospheric pressure or under elevated pressure and is preferably carried out under atmospheric pressure. Work-up is carried out by customary methods.

The process (M) according to the invention is characterized in that compounds of the formulae (I-1-a) to (I-8-a) are in each case reacted with phosphorus compounds of the formula (XVIII), if appropriate in the presence of a diluent and if appropriate in the presence of an acid binder.

In the Preparation Process (M), to obtain compounds of the formulae (I-1-e) to (I-8-e), 1 to 2, preferably 1 to 1.3 mol of the phosphorus compound of the formula (XVIII) are reacted to 1 mol of the compounds (I-1-a) to (I-8-a), at temperatures between −40° C. and 150° C., preferably between −10 and 110° C.

Suitable diluents, which are added, if appropriate, are all inert polar organic solvents, such as ethers, amides, nitriles, alcohols, sulphides, sulphones, sulphoxides, etc.

Preference is given to using acetonitrile, dimethyl sulphoxide, tetrahydrofuran, dimethylformamide, methylene chloride.

Suitable acid binders, which are added, if appropriate, are customary inorganic or organic bases, such as hydroxides, carbonates or amines. Examples are sodium hydroxide, sodium carbonate, potassium carbonate, pyridine, triethylamine.

The reaction can be carried out under atmospheric pressure or under elevated pressure and is preferably carried out under atmospheric pressure. Work-up is carried out by customary methods of organic chemistry. The end products obtained are preferably purified by crystallization, chromatographic purification or by "incipient distillation", i.e. removal of the volatile components under reduced pressure.

The process (N) is characterized in that compounds of the formulae (I-1-a) to (I-8-a) are reacted with metal hydroxides or metal alkoxides of the formula (XIX) or amines of the formula (XX), if appropriate in the presence of a diluent.

Suitable diluents for the process (N) according to the invention are, preferably, ethers, such as tetrahydrofuran, dioxane, diethyl ether, or else alcohols, such as methanol, ethanol, isopropanol, and also water.

The process (N) according to the invention is generally carried out under atmospheric pressure.

The reaction temperatures are generally between −20° C. and 100° C., preferably between 0° C. and 50° C.

The process (O) according to the invention is characterized in that compounds of the formulae (I-1-a) to (I-8-a) are in each case reacted with (O-α) compounds of the formula (XXI), if appropriate in the presence of a diluent and if appropriate in the presence of a catalyst, or with (O-β) compounds of the formula (XXII), if appropriate in the presence of a diluent and if appropriate in the presence of an acid binder.

In Preparation Process (O-α), about 1 mol of isocyanate of the formula (XXI) is reacted per mole of starting material of the formulae (I-1-a) to (I-8-a), at from 0 to 100° C., preferably at from 20 to 50° C.

Suitable diluents, which are added, if appropriate, are all inert organic solvents, such as ethers, amides, nitriles, sulphones, sulphoxides.

If appropriate, catalysts may be added to accelerate the reaction. Suitable catalysts are, very advantageously, organotin compounds, such as, for example, dibutyltin dilaurate. The reaction is preferably carried out under atmospheric pressure.

In the Preparation Process (O-β), about 1 mol of carbamoyl chloride of the formula (XXII) is reacted per mole of starting material of the formulae (I-1-a) to (I-8-a), at from −20 to 150° C., preferably from 0 to 70° C.

Suitable diluents, which are added, if appropriate, are all inert polar organic solvents, such as ethers, amides, sulphones, sulphoxides or halogenated hydrocarbons.

Preference is given to using dimethyl sulphoxide, tetrahydrofuran, dimethylformamide or methylene chloride.

If, in a preferred embodiment, the enolate salt of the compound (I-1-a) to (I-8-a) is prepared by adding strong deprotonating agents (such as, for example, sodium hydride or potassium tert-butoxide), the further addition of acid binders can be dispensed with.

If acid binders are used, these are customary inorganic or organic bases, for example sodium hydroxide, sodium carbonate, potassium carbonate, triethylamine or pyridine.

The reaction can be carried out under atmospheric pressure or under elevated pressure and is preferably carried out under atmospheric pressure. Work-up is carried out by customary methods.

The process (P) is characterized in that compounds of the formula (I-1') to (I-8') in which A, B, D, $Q^1$, $Q^2$, $Q^3$, $Q^4$, $Q^5$, $Q^6$, W, X, Y, $R^1$, $R^2$, $R^3$, $R^4$, $R^5$, $R^6$ and $R^7$ are as defined above and Z' represents halogen, particularly preferably bromine, are, in the presence of a copper salt and in the presence of a base, subjected to a coupling reaction with HN-heterocycles of the formula (XXIII) in which Z is as defined above (J. Am. Chem. Soc. 2001, 123, 7729-29; WO 02-85 838; Synlett 2002, 3, 423-30).

Suitable solvents for the process (P) according to the invention are, for example, optionally halogenated aliphatic, alicyclic or aromatic hydrocarbons, such as, for example, benzine, benzene, toluene, xylene, petroleum ether, hexane, cyclohexane, chlorobenzene, dichlorobenzene, ethers, such as diethyl ether, diisopropyl ether, dioxane, tetrahydrofuran or ethylene glycol dimethyl ether or ethylene glycol diethyl ether; amides, such as, for example, N,N-dimethylformamide, N,N-dimethylacetamide, N-methylformanilide, N-methylpyrrolidone or hexamethylphosphoric triamide; esters, such as methyl acetate or ethyl acetate, or mixtures of such solvents. Preference is given to using N,N-dimethylformamide.

Suitable bases for the process (P) according to the invention are alkali metal and/or alkaline earth metal carbonates, alkoxides, phosphates, fluorides and/or hydroxides, and particular preference is given to potassium carbonate, sodium carbonate, caesium carbonate, caesium bicarbonate, sodium methoxide, potassium tert-butoxide, potassium amylate, caesium fluoride, potassium phosphate and barium hydroxide. Especially preferred are potassium carbonate, sodium carbonate, caesium carbonate and/or caesium bicarbonate. Potassium carbonate is very especially preferred.

The bases can also be employed in the presence of phase transfer catalysts, such as, for example, triethylbenzylammonium chloride, tetrabutylammonium bromide or TDA 1 (=tris (methoxy-ethoxyethyl)amine).

The copper salts used in the process (P) according to the invention are copper(I) salts, such as, for example, CuI.

The process (P) can furthermore also be carried out in the presence of additional auxiliary bases, such as diamines, such as, for example, ethylenediamine, propylenediamine, 1,2-diaminocyclohexane.

When carrying out the process (P), the reaction temperatures can be varied within a relatively wide range. In general, the process is carried out at temperatures of from 0 to 250° C., preferably from 30 to 200° C.; with very particular preference from 50 to 150° C.

The process (P) according to the invention is generally carried out under atmospheric pressure.

When carrying out the process (P) according to the invention, the reaction components of the formulae (I-1') to (I-8') and (XXIII) are generally employed in equimolar amounts. However, it is also possible to use a relatively large excess (up to 3 mol) of one component or the other. The bases are generally employed in a molar ratio of from 1:1 to 10:1, preferably from 2:1 to 5:1. The copper salts are generally employed in a molar ratio of from 0.01:1 to 1:1, preferably from 0.05:1 to 0.5:1.

The process Q is characterized in that compounds of the formula (XXXII-a) in which W, X, Y and $R^8$ are as defined above and Z' represents halogen, particularly preferably bromine, are, in the presence of a base and in the presence of a copper salt, subjected to a coupling reaction with HN-containing heterocycles of the formula (XXIII) in which Z is as defined above (J. Am. Chem. Soc. 2001, 123, 7727-29; WO 02-85 838, Synlett 2002, 3, 427-30).

Suitable solvents for the process (Q) according to the invention are optionally halogenated aliphatic, alicyclic or aromatic hydrocarbons, such as, for example, benzine, benzene, toluene, xylene, petroleum ether, hexane, cyclohexane, chlorobenzene, dichlorobenzene, ethers, such as diethyl ether, diisopropyl ether, dioxane, tetrahydrofuran or ethylene glycol dimethyl ether or ethylene glycol diethyl ether; amides, such as, for example, N,N-dimethylformamide, N,N-dimethylacetamide, N-methylformanilide, N-methylpyrrolidone or hexamethylphosphoric triamide; esters, such as methyl acetate or ethyl acetate, or mixtures of such solvents. Preference is given to using N,N-dimethylformamide.

Suitable bases for the process (Q) according to the invention are alkali metal and/or alkaline earth metal carbonates, alkoxides, phosphates, fluorides and/or hydroxides, and particular preference is given to potassium carbonate, sodium carbonate, caesium carbonate, caesium bicarbonate, sodium methoxide, potassium tert-butoxide, potassium amylate, caesium fluoride, potassium phosphate and barium hydroxide. Especially preferred are potassium carbonate, sodium carbonate, caesium carbonate and/or caesium bicarbonate. Potassium carbonate is very especially preferred.

The bases can also be employed in the presence of phase-transfer catalysts, such as, for example, triethylbenzylammonium chloride, tetrabutylammonium bromide or TDA 1 (=tris(methoxy-ethoxyethyl)amine).

The copper salts in the process (Q) according to the invention are copper(I) salts, such as, for example, CuI.

The process (Q) can furthermore also be carried out in the presence of additional auxiliary bases, such as diamines, such as, for example, ethylenediamine, propylenediamine, 1,2-diaminocyclohexane.

When carrying out the process (Q), the reaction temperatures can be varied within a relatively wide range. In general, the process is carried out at temperatures of from 0 to 250° C., preferably from 30 to 200° C.; very particularly preferably from 50 to 150° C.

The process (Q) according to the invention is generally carried out under atmospheric pressure.

When carrying out the process (Q) according to the invention, the reaction components of the formulae (XXXII-a) and (XXIII) are generally employed in equimolar amounts. However, it is also possible to use a relatively large excess (up to 3 mol) of one component or the other. The bases are generally employed in a molar ratio of from 1:1 to 10:1, preferably from 2:1 to 5:1. The copper salts are generally employed in a molar ratio of from 0.001:1 to 1:1, preferably from 0.05:1 to 0.5:1.

The active compounds are well tolerated by plants and have advantageous toxicity to warm-blooded species; they can be employed for controlling animal pests, in particular insects, arachnids and nematodes encountered in agriculture, forests, in the protection of stored products and materials and in the hygiene sector. They are preferably used as crop protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp. and *Schistocerca gregaria.*

From the order of the Blattaria, for example, *Blatta orientalis, Periplaneta americana, Leucophaea maderae* and *Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp., *Damalinia* spp.

From the order of the Thysanoptera, for example, *Hercinothrips femoralis, Thrips tabaci, Thrips palmi, Frankliniella occidentalis.*

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofinannophila pseudospretella, Cacoecia podana, Capua reticulana, Choristoneura fumiferana, Clysia ambiguella, Homona magnanima, Tortrix viridana, Cnaphalocerus* spp. and *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus.*

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp.,

*Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the order of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. and *Brevipalpus* spp.

The plant-parasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp. and *Bursaphelenchus* spp.

If appropriate, the compounds or active compound combinations according to the invention may also be used in certain concentrations or application rates to act as herbicides. If appropriate, they can also be employed as intermediates or precursors for the synthesis of further active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

The treatment according to the invention of the plants and plant parts with the active compounds or active compound combinations is carried out directly or by allowing the compounds to act on the surroundings, environment or storage space by the customary treatment methods, for example by immersion, spraying, evaporation, fogging, scattering, painting on or injection and, in the case of propagation material, in particular in the case of seeds, also by applying one or more coats.

The active compounds or active compound combinations can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable Solid Carriers are:

for example ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example ligninsulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention, as such or in their formulations, can also be used as a mixture with known fungicides, bactericides, acaricides, nematicides or insecticides, for example in order to widen the spectrum of action or to prevent the development of resistances in this way. In many cases, synergistic effects result, i.e. the activity of the mixture exceeds the activity of the individual components.

Compounds which are suitable as components in the mixtures are, for example, the following:

Fungicides:

2-phenylphenol; 8-hydroxyquinoline sulphate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine; calcium polysulphide; capsimycin; captafol; captan; carbendazim; carboxin; carpropamid; carvone; quinomethionate; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichione; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazol; imazalil; imibenconazole; iminoctadine triacetate; iminoctadine tris(albesilate); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazol; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolnitrin; quinconazole; quinoxyfen; quintozene; simeconazole; spiroxamine; sulphur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; tritconazole; uniconazole; validamycin A; vinclozolin; zineb; ziram; zoxamide; (2S)—N-[2-[4-[[3-(4-chlorophenyl)-2-propynyl]oxy]-3-methoxyphenyl]ethyl]-3-methyl-2-[(methylsulphonyl)amino]-butanamide; 1-(1-naphthalenyl)-1H-pyrrole-2,5-dione; 2,3,5,6-tetrachloro-4-(methylsulphonyl)-pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; Actinovate; cis-1-(4-chlorophenyl)-2-(1H-1,2,4-triazole-1-yl)-cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)-cyclopropanecarboxamide; N-butyl-8-(1,1-dimethylethyl)-1-oxaspiro[4.5]decan-3-amine; sodium tetrathiocarbonate;

and copper salts and preparations such as Bordeaux mixture; copper hydroxide; copper naphthenate; copper oxychloride; copper sulphate; cufraneb; cuprous oxide; mancopper; oxine-copper.

Bactericides:

bronopol, dichlorophen, nitrapyrin, nickel dimethyldithiocarbamate, kasugamycin, octhilinone, firancarboxylic acid, oxytetracyclin, probenazole, streptomycin, tecloftalam, copper sulphate and other copper preparations.

Insecticides/Acaricides/Nematicides:

abamectin, ABG-9008, acephate, acequinocyl, acetamiprid, acetoprole, acrinathrin, AKD-1022, AKD-3059, AKD-3088, alanycarb, aldicarb, aldoxycarb, allethrin, alpha-cypermethrin (alphamethrin), amidoflumet, aminocarb, amitraz, avermectin, AZ-60541, azadirachtin, azamethiphos, azinphos-methyl, azinphos-ethyl, azocyclotin,

*Bacillus popilliae*, *Bacillus sphaericus*, *Bacillus subtilis*, *Bacillus thuringiensis*, *Bacillus thuringiensis* strain EG-2348, *Bacillus thuringiensis* strain GC-91, *Bacillus thuringiensis* strain NCTC-11821, baculoviruses, *Beauveria bassiana*, *Beauveria tenella*, benclothiaz, bendiocarb, benfuracarb, bensultap, benzoximate, beta-cyfluthrin, beta-cypermethrin, bifenazate, bifenthrin, binapacryl, bioallethrin, bioallethrin S-cyclopentyl isomer, bioethanomethrin, biopermethrin, bioresmethrin, bistrifluron, BPMC, brofenprox, bromophos-ethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulfan, cartap, CGA-50439, quinomethionate, chlordane, chlordimeform, chloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (-ethyl), chlovaporthrin, chromafenozide, cis-cypermethrin, cis-resmethrin, cis-permethrin, clocythrin, cloethocarb, clofentezine, clothianidin, clothiazoben, codlemone, coumaphos, cyanofenphos, cyanophos, cycloprene, cycloprothrin, *Cydia pomonella*, cyfluthrin, cyhalothrin, cyhexatin, cypermethrin, cyphenothrin (1R-trans isomer), cyromazine, DDT, deltamethrin, demeton-S-methyl, demeton-S-methyl-sulphone, diafenthiuron, dialifos, diazinon, dichlofenthion, dichlorvos, dicofol, dicrotophos, dicyclanil, diflubenzuron, dimefluthrin, dimethoate, dimethylvinphos, dinobuton, dinocap, dinotefuran, diofenolan, disulfoton, docusate-sodium, dofenapyn, DOWCO-439, eflusilanate, emamectin, emamectin benzoate, empenthrin (1R isomer), endosulfan, *Entomophthora* spp., EPN, esfenvalerate, ethiofencarb, ethiprole, ethion, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-cyhalothrin, gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulfenfos, metaldehyde, metam-sodium, methacrifos, methamidophos, *Metarhizium anisopliae*, *Metarhizium flavoviride*, methidathion, methiocarb, methomyl, methoprene, methoxychlor, methoxyfenozide, metofluthrin, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl,

*Paecilomyces fumosoroseus*, parathion-methyl, parathion (-ethyl), permethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphos-ethyl, potassium oleate, prallethrin, profenofos, profluthrin, promecarb, propaphos, propargite, propetamphos, propoxur, prothiofos, prothoate, protrifenbute, pymetrozine, pyraclofos, pyresmethrin, pyrethrum, pyridaben, pyridalyl, pyridaphenthion, pyridathion, pyrimidifen, pyriproxyfen, quinalphos, resmethrin, RH-5849, ribavirin, RU-12457, RU-15525, S-421, S-1833, salithion, sebufos, SI-0009, silafluofen, spinosad, spirodiclofen, spiromesifen, sulfluramid, sulfotep, sulprofos, SZI-121, tau-fluvalinate, tebufenozide, tebufenpyrad, tebupirimfos, teflubenzuron, tefluthrin, temephos, Temivinphos, Terbam, Terbufos, Tetrachlorvinphos, Tetradifon, Tetramethrin, Tetramethrin (1R isomer), tetrasul, theta-cypermethrin, thiacloprid, thiamethoxam, thiapronil, thiatriphos, thiocyclam hydrogen oxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, *Trichoderma* atroviride, triflumuron, trimethacarb, vamidothion, vaniliprole, verbutin, *Verticillium lecanii*,

WL-108477, WL-40027,

YI-5201, YI-5301, YI-5302,

XMC, xylylcarb,

ZA-3274, zeta-cypermethrin, zolaprofos, ZXI-8901, the compound 3-methylphenyl propylcarbamate (Tsumacide Z), the compound 3-(5-chloro-3-pyridinyl)-8-(2,2,2-trifluoroethyl)-8-azabicyclo[3.2.1]octane-3-carbonitrile (CAS Reg. No. 185982-80-3) and the corresponding 3-endo isomer (CAS Reg. No. 185984-60-5) (cf. WO 96/37494, WO 98/25923), and preparations which contain insecticidally active plant extracts, nematodes, fungi or viruses.

A mixture with other known active compounds, such as herbicides, or with fertilizers and growth regulators is also possible.

When used as insecticides in their commercially available formulations and in the use forms prepared with these formulations, the active compounds according to the invention can furthermore exist in the form of a mixture with synergists. Synergists are compounds by which the activity of the active compounds is increased without it being necessary for the synergist added to be active itself.

The active compound content of the use forms prepared from the commercially available formulations can vary within broad ranges. The active compound concentration of the use forms can be from 0.0000001 up to 95% by weight of active compound, preferably between 0.0001 and 1% by weight.

They are applied in a customary manner adapted to suit the use forms.

When used against hygiene pests and pests of stored products, the active compound or active compound combination is distinguished by excellent residual action on wood and clay as well as good stability to alkali on limed substrates.

As already mentioned above, it is possible to treat all plants or their parts in accordance with the invention. In a preferred embodiment, wild plant species or plant varieties and plant cultivars which have been obtained by traditional biological breeding methods, such as hybridization or protoplast fusion, and the parts of these varieties and cultivars are treated. In a further preferred embodiment, transgenic plants and plant cultivars which have been obtained by recombinant methods, if appropriate in combination with conventional methods (genetically modified organisms), and their parts are treated. The term "parts" or "parts of plants" or "plant parts" has been explained above.

Plants which are treated particularly preferably in accordance with the invention are those of the plant cultivars which are in each case commercially available or in use. Plant cultivars are understood as meaning plants with new traits which have been bred either by conventional breeding, by mutagenesis or by recombinant DNA techniques. They may take the form of cultivars, biotypes and genotypes.

Depending on the plant species or plant cultivars, their location and growth conditions (soils, climate, vegetation period, nutrition), the treatment according to the invention may also result in superadditive ("synergistic") effects. Thus, for example, reduced application rates and/or a widened activity spectrum and/or an increase in the activity of the substances and compositions which can be used in accordance with the invention, better plant growth, increased tolerance to high or low temperatures, increased tolerance to drought or to salinity in the water or soil, increased flowering performance, facilitated harvesting, accelerated maturation, higher yields, higher quality and/or better nutritional value of the harvested products, better storage characteristics and/or processability of the harvested products are possible which exceed the effects which were actually to be expected.

The preferred transgenic plants or plant cultivars (those obtained by recombinant methods) to be treated in accordance with the invention include all those plants which, owing to the process of recombinant modification, were given genetic material which confers particular, advantageous, valuable traits to these plants. Examples of such properties are better plant growth, increased tolerance to high or low temperatures, increased tolerance to drought or to salinity in the water or soil, increased flowering performance, facilitated harvesting, accelerated maturation, higher yields, higher quality and/or higher nutritional value of the harvested products, better storage characteristics and/or better processability of the harvested products. Further examples of such traits, examples which must be mentioned especially, are better defence of the plants against animal and microbial pests, such as against insects, mites, phytopathogenic fungi, bacteria and/or viruses and an increased tolerance of the plants to certain herbicidal active compounds. Examples of transgenic plants which may be mentioned are the important crop plants, such as cereals (wheat, rice), maize, soybeans, potato, cotton, oilseed rape, beet, sugar cane and fruit plants (with the fruits apples, pears, citrus fruits and grapes), with particular emphasis on maize, soybeans, potatoes, cotton and oilseed rape. Traits which are especially emphasized are the increased defence of the plants against insects, owing to toxins being formed in the plants, in particular toxins which are generated in the plants by the genetic material of Bacillus thuringiensis (for example by the genes CryIA(a), CryIA(b), CryIA(c), CryIIA, CryIIIA, CIIIB2, Cry9c Cry2Ab, Cry3Bb and CryIF and their combinations; hereinbelow "Bt plants"). Other traits which are particularly emphasized are the increased defence of plants against fungi, bacteria and viruses by the systemic acquired resistance (SAR), systemin, phytoalexins, elicitors and resistance genes and correspondingly expressed proteins and toxins. Other traits which are especially emphasized are the increased tolerance of the plants to certain herbicidal active compounds, for example imidazolinones, sulphonylureas, glyphosate or phosphinotricin (for example "PAT" gene). The genes which confer the desired traits in each case may also be present in the transgenic plants in combination with one another. Examples of "Bt plants" which may be mentioned are maize cultivars, cotton cultivars, soybean cultivars and potato cultivars which are commercially available under the trade names YIELD GARD® (for example maize, cotton, soybeans), KnockOut® (for example maize), StarLink® (for example maize), Bollgard® (cotton), Nucotn® (cotton) and NewLeaf® (potato). Examples of herbicide-tolerant plants which may be mentioned are maize cultivars, cotton cultivars and soybean cultivars which are commercially available under the trade names Roundup Ready® (tolerance to glyphosate, for example maize, cotton, soybean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include also the varieties commercially available under the name Clearfield® (for example maize). Naturally, these statements also apply to plant cultivars having these genetic traits or genetic traits still to be developed, which plant cultivars will be developed and/or marketed in the future.

The plants listed can be treated particularly advantageously with the compounds according to the invention or the active compound mixtures according to the invention. The preferred ranges stated above for the active compounds and mixtures also apply to the treatment of these plants. Particular emphasis may be given to the treatment of plants with the compounds or mixtures specifically mentioned in the present text.

The active compounds or active compound combinations according to the invention are not only active against plant, hygiene and stored-product pests, but also, in the veterinary medicine sector, against animal parasites (ectoparasites), such as ixodid ticks, argasid ticks, scab mites, trombi-culid mites, flies (stinging and sucking), parasitic fly larvae, lice, hair lice, bird lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the sub-orders Amblycerina and Ischnocerina, for example, *Trimenopon* spp., *Menopon* spp., *Trinoton* spp., *Bovicola* spp., *Wemeckiella* spp., *Lepikentron* spp., *Damalina* spp., *Trichodectes* spp., *Felicola* spp.

From the order of the Diptera and the sub-orders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopyslla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis*, *Periplaneta americana*, *Blattella germanica* and *Supella* spp.

From the sub-class of the Acaria (Acarida) and the orders of the Meta- and Mesostigmata, for example, *Argas* spp., *Ornithodorus* spp., *Otobius* spp.; *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes spp.*

The active compounds or active compound combinations according to the invention are also suitable for controlling arthropods which attack agricultural livestock, such as, for example, cattle, sheep, goats, horses, pigs, donkeys, camels, buffaloes, rabbits, chickens, turkeys, ducks, geese, honeybees, other domestic animals, such as, for example, dogs, cats, cage birds, aquarium fish, and so-called experimental animals, such as, for example, hamsters, guinea-pigs, rats and mice. By combating these arthropods, it is intended to reduce deaths and decreased performances (in meat, milk, wool, hides, eggs, honey and the like), so that more economical and simpler animal keeping is made possible by using the active compounds according to the invention.

In the veterinary sector, the active compounds or active compound combinations according to the invention are used in a known manner by enteral administration, for example in the form of tablets, capsules, drinks, drenches, granules, pastes, boli, the feed-through method, suppositories, by parenteral administration, such as, for example, by means of injections (intramuscular, subcutaneous, intravenous, intraperitoneal and the like), implants, by nasal application, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds or active compound combinations can be used as formulations (for example powders, emulsions, flowables) which comprise the active compounds in an amount of 1 to 80% by weight, either directly or after dilution by a factor of 100 to 10 000, or they may be used in the form of a chemical bath.

Furthermore, it has been found that the compounds or active compound combinations according to the invention have a potent insecticidal action against insects which destroy industrial materials.

The following insects may be mentioned by way of example and as being preferred, but without any limitation:

Beetles, such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus.*

Dermapterans, such as *Sirex juvencus, Urocerus gigas, Urocerus gigas taignus, Urocerus augur.*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccharina.*

Industrial materials are to be understood as meaning, in the present context, non-live materials, such as, preferably, synthetic materials, glues, sizes, paper and board, leather, wood and timber products, and paint. The materials to be very particularly preferably protected against attack by insects are wood and timber products.

Wood and timber products which can be protected by the composition according to the invention or mixtures comprising such a composition are to be understood as meaning, for example:

construction timber, wooden beams, railway sleepers, bridge components, jetties, wooden vehicles, boxes, pallets, containers, telephone poles, wood cladding, windows and doors made of wood, plywood, particle board, joiner's articles, or wood products which, quite generally, are used in the construction of houses or in joinery.

The active compounds or active compound combinations can be used as such, in the form of concentrates or generally customary formnulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and TV stabilizers and, if appropriate, colorants and pigments and other processing auxiliaries. The insecticidal compositions or concentrates used for the protection of wood and wooden materials comprise the active compound according to the invention in a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by a test series. However, in general, it suffices to employ 0.0001 to 20% by weight, preferably 0.001 to 10% by weight, ofthe active compound, based on the material to be protected.

The solvent and/or diluent used is an organochemical solvent or solvent mixture and/or an oily or oil-type organochemical solvent or solvent mixture of low volatility and/or a polar organochemical solvent or solvent mixture and/or water and, if appropriate, an emulsifier and/or wetting agent.

Organochemical solvents which are preferably employed are oily or oil-type solvents having an evaporation number of above 35 and a flashpoint of above 30° C., preferably above 45° C. Substances which are used as such oily and oil-type solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 160 to 280° C., essence of terpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene, are used.

The organic oily or oil-type solvents of low volatility having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic organochemical solvents having hydroxyl and/or ester and/or ether groups, such as, for example, glycol ethers, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/cumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binders. In addition, colorants, pigments, water repellents, odour-masking substances and inhibitors or anticorrosives known per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or relatively high-molecular-weight glycol ethers, glycerol esters and p-toluenesulphonic esters.

Fixatives are chemically based on polyvinyl alkyl ethers, such as, for example, polyvinyl methyl ether, or ketones, such as benzophenone or ethylenebenzophenone.

Particularly suitable as a solvent or diluent is also water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise other insecticides and, if appropriate, additionally one or more fungicides.

Suitable additional components which may be admixed are, preferably, the insecticides and fungicides mentioned in WO 94/29 268. The compounds mentioned in that document are expressly part of the present application.

Very particularly preferred components which may be admixed are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyphenoxid and triflumuron, and fungicides, such as epoxyconazole, hexaconazole, azaconazole, propiconazole, tebuconazole, cyproconazole, metconazole, imazalil, dichlofluanid, tolylfluanid, 3-iodo-2-propynylbutyl carbamate, N-octyl-isothiazolin-3-one and 4,5-dichloro-N-octylisothiazolin-3-one.

The compounds or active compound combinations according to the invention can at the same time be employed for protecting objects which come into contact with salt water or brackish water, in particular hulls, screens, nets, buildings, moorings and signalling systems, against fouling.

Fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trialkyltin) sulphides, tri-n-butyltin laurate, tri-n-butyltin chloride, copper (I) oxide, triethyltin chloride, tri-n-butyl-(2-phenyl-4-chlorophenoxy)tin, tributyltin oxide, molybdenum disulphide, antimony oxide, polymeric butyl titanate, phenyl-(bispyridine)-bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bisdi-methyldithiocarbamoylzinc ethylene-bisthiocarbamate, zinc oxide, copper(I) ethylene-bis-dithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combination with the antifouling compositions according to the invention are:

algicides such as 2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;

fungicides such as benzo[b]thiophenecarboxylic acid cyclohexylamide S,S-dioxide, dichlofluanid, fluorfolpet, 3-iodo-2-propinyl butylcarbamate, tolylfluanid and azoles such as azaconazole, cyproconazole, epoxyconazole, hexaconazole, metconazole, propiconazole and tebuconazole;

molluscicides such as fentin acetate, metaldehyde, methiocarb, niclosamid, thiodicarb and trimethacarb; Fe chelates;

or conventional antifouling active compounds such as 4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, *Chem. Ind.* 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as rosin to allow controlled release of the active compounds. Furthermore, the paints may comprise plasticizers, modifiers which affect the Theological properties and other conventional constituents. The compounds according to the invention or the abovementioned mixtures may also be incorporated into self-polishing antifouling systems.

The active compounds or active compound combinations are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests alone or in combination with other active compounds and auxiliaries. They are active against sensitive and resistant species and against all development stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, Aviculariidae, Araneidae.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalis, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodinus prolixus, Triatoma infestans*.

They are used in the household insecticides sector alone or in combination with other suitable active compounds such as phosphoric esters, carbamates, pyrethroids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The active compounds or active compound combinations according to the invention can also be used as defoliants, desiccants, haulm killers and, in particular, as weed killers. Weeds in the broadest sense are understood as meaning all plants which grow at locations where they are undesired. Whether the substances according to the invention act as nonselective or selective herbicides depends essentially on the application rate.

The active compounds or active compound combinations according to the invention can be used for example in the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium*.

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*.

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum*.

Monocotyledonous crops of the genera: *Allium, Ananas, Asparagus, Avena, Hordeum, Oryza, Panicum, Saccharum, Secale, Sorghum, Triticale, Triticum, Zea*.

However, the use of the active compounds or active compound combinations according to the invention is in no way restricted to these genera, but extends in the same manner to other plants.

Depending on the concentration, the active compounds or active compound combinations according to the invention are suitable for the nonselective weed control on, for example, industrial terrains and railway tracks and on paths and locations with and without trees. Likewise the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds or active compound combinations according to the invention have strong herbicidal activity and a broad activity spectrum when used on the soil and on aerial plant parts. To a certain extent, they are also suitable for the selective control of monocotyledonous and dicotyledonous weeds in monocotyledonous and dicotyledonous crops, both pre- and post-emergence.

At certain concentrations or application rates, the active compounds or active compound combinations according to the invention can also be employed for controlling animal pests and fungal or bacterial plant diseases. If appropriate, they can also be used as intermediates or precursors for the synthesis of other active compounds.

The active compounds or active compound combinations can be converted into the customary formulations, such as solutions, emulsions, wettable powders, suspensions, powders, dusting agents, pastes, soluble powders, granules, suspoemulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If the extender used is water, it is also possible to use, for example, organic solvents as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates, suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention, as such or in their formulations, can also be used for weed control purposes as a mixture with known herbicides and/or with substances which improve crop plant tolerance ("safeners"), ready mixes or tank mixes being possible. Mixtures with herbicide products which contain one or more known herbicides and a safener are hence also possible.

Herbicides which are suitable for the mixtures are known herbicides, for example acetochlor, acifluorfen (-sodium), aclonifen, alachlor, alloxydim (-sodium), ametryne, amicarbazone, amidochlor, amidosulfuron, anilofos, asulam, atrazine, azafenidin, azimsulfuron, beflubutamid, benazolin (-ethyl), benfuresate, bensulfuron (-methyl), bentazone, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (-P), diclofop (-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (-P-ethyl), fentrazamide, flamprop (-isopropyl, -isopropyl-L, -methyl), flazasulfuron, florasulam, fluazifop (-P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, -P-methyl), hexazinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesosulfurone, mesotrione, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, picolinafen, pinoxaden, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridate, pyridatol, pyriftalide, pyriminobac (-methyl), pyrithiobac (-sodium), quinchlorac, quinmerac, quinoclamine, quizalofop (-P-ethyl, -P-tefuryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, triallate, triasulfuron, tribenuron (-methyl), triclopyr, tridiphane, trifluralin, trifloxysulfuron, triflusulfuron (-methyl), tritosulfuron.

A mixture with other known active compounds, such as fungicides, insecticides, acaricides, nematicides, bird repellents, plant nutrients and soil conditioners, is also possible.

The active compounds or active compound combinations can be applied as such, in the form of their formulations or the use forms prepared therefrom by further dilution, such as ready-to-use solutions, suspensions, emulsions, powders, pastes and granules. They are applied in the customary manner, for example by pouring, spraying, atomizing, spreading.

The active compounds or active compound combinations according to the invention can be applied both before and after plant emergence. They can also be incorporated into the soil prior to planting.

The application rate of active compound can vary within a substantial range. Essentially, it depends on the nature of the desired effect. In general, the application rates are between 1 g and 10 kg of active compound per hectare of soil area, preferably between 5 g and 5 kg per ha.

The advantageous effect of the compatibility with crop plants of the active compound combinations according to the invention is particularly pronounced at certain concentration ratios. However, the weight ratios of the active compounds in the active compound combinations can be varied within relatively wide ranges. In general, from 0.001 to 1000 parts by weight, preferably from 0.01 to 100 parts by weight, particularly preferably 0.05 to 20 parts by weight, of one of the compounds which improves crop plant compatibility (antidotes/safeners) mentioned above under (b') are present per part by weight of active compound of the formula (I).

The active compound combinations according to the invention are generally applied in the form of finished formulations. However, the active compounds contained in the active compound combinations can, as individual formulations, also be mixed during use, i.e. be applied in the form of tank mixes.

For certain applications, in particular by the post-emergence method, it may furthermore be advantageous to include, as further additive in the formulations, mineral or vegetable oils which are tolerated by plants (for example commercial preparation "Rako Binol"), or ammonium salts, such as, for example, ammonium sulphate or ammonium thiocyanate.

The novel active compound combinations can be used as such, in the form of their formulations or the use forms prepared therefrom by further dilution, such as ready-to-use solutions, suspensions, emulsions, powders, pastes and granules. Application is in the customary manner, for example by watering, spraying, atomizing, dusting or scattering.

The application rates of the active compound combinations according to the invention can be varied within a certain range; they depend, inter alia, on the weather and on soil factors. In general, the application rates are between 0.001 and 5 kg per ha, preferably between 0.005 and 2 kg per ha, particularly preferably between 0.01 and 0.5 kg per ha.

The active compound combinations according to the invention can be applied before and after emergence of the plants, that is to say by the pre-emergence and post-emergence method.

Depending on their properties, the safeners to be used according to the invention can be used for pretreating the seed of the crop plant (seed dressing) or can be introduced into the seed furrows prior to sowing or be used separately prior to the herbicide or together with the herbicide, before or after emergence of the plants.

Examples of plants which may be mentioned are important crop plants, such as cereals (wheat, rice), maize, soybeans, potatoes, cotton, oil seed rape, beet, sugarcane and also fruit plants (with the fruits apples, pears, citrus fruits and grapevines), greater emphasis being given to maize, soybeans, potatoes, cotton and oil seed rape.

The substances according to the invention have potent microbicidal activity and can be employed for controlling unwanted microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

*Xanthomonas* species, such as, for example, *Xanthomonas campestris* pv. *oryzae*;

*Pseudomonas* species, such as, for example, *Pseudomonas syringae* pv. *lachrymans*;

*Erwinia* species, such as, for example, *Erwinia amylovora*;

*Pythium* species, such as, for example, *Pythium ultimum*;

*Phytophthora* species, such as, for example, *Phytophthora infestans*;

*Pseudoperonospora* species, such as, for example, *Pseudoperonospora humuli* or *Pseudoperonospora cubensis*;

*Plasmopara* species, such as, for example, *Plasmopara viticola*;

*Bremia* species, such as, for example, *Bremia lactucae*;

*Peronospora* species, such as, for example, *Peronospora pisi* or *P. brassicae*;

*Erysiphe* species, such as, for example, *Erysiphe graminis*;

*Sphaerotheca* species, such as, for example, *Sphaerotheca fuliginea*;

*Podosphaera* species, such as, for example, *Podosphaera leucotricha*;

*Venturia* species, such as, for example, *Venturia inaequalis*;

*Pyrenophora* species, such as, for example, *Pyrenophora teres* or *P. graminea* (conidia form: *Drechslera*, syn: *Helminthosporium*);

*Cochliobolus* species, such as, for example, *Cochliobolus sativus* (conidia form: *Drechslera*, syn: *Helminthosporium*);

*Uromyces* species, such as, for example, *Uromyces appendiculatus*;

*Puccinia* species, such as, for example, *Puccinia recondita;*

*Scierotinia* species, such as, for example, *Sclerotinia sclerotiorum;*

*Tilletia* species, such as, for example, *Tilletia caries;*

*Ustilago* species, such as, for example, *Ustilago nuda* or *Ustilago avenae;*

*Pellicularia* species, such as, for example, *Pellicularia sasakii;*

*Pyricularia* species, such as, for example, *Pyricularia oryzae;*

*Fusarium* species, such as, for example, *Fusarium culmorum;*

*Botrytis* species, such as, for example, *Botrytis cinerea;*

*Septoria* species, such as, for example, *Septoria nodorum;*

*Leptosphaeria* species, such as, for example, *Leptosphaeria nodorum;*

*Cercospora* species, such as, for example, *Cercospora canescens;*

*Alternaria* species, such as, for example, *Alternaria brassicae;* and

*Pseudocercosporella* species, such as, for example, *Pseudocercosporella herpotrichoides.*

The active compounds according to the invention also have very good fortifying action in plants. Accordingly, they can be used for mobilizing the defences of the plant against attack by unwanted microorganisms.

In the present context, plant-fortifying (resistance-inducing) substances are to be understood as meaning those substances which are capable of stimulating the defence system of plants such that, when the treated plants are subsequently inoculated with unwanted microorganisms, they show substantial resistance against these microorganisms.

In the present case, undesirable microorganisms are to be understood as meaning phytopathogenic fungi, bacteria and viruses. Accordingly, the substances according to the invention can be used to protect plants for a certain period after the treatment against attack by the pathogens mentioned. The period for which protection is provided generally extends over 1 to 10 days, preferably 1 to 7 days, after the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention are also suitable for increasing the yield of crops. In addition, they show reduced toxicity and are well tolerated by plants.

At certain concentrations and application rates, the active compounds according to the invention can also be used as herbicides, for influencing plant growth and for controlling animal pests. If appropriate, they can also be used as intermediates and precursors for the synthesis of further active compounds.

In the protection of materials, the compounds according to the invention can be employed for protecting industrial materials against infection with, and destruction by, unwanted microorganisms.

Industrial materials in the present context are understood as meaning non-living materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes), and against slime organisms and algae.

Microorganisms of the following genera may be mentioned as examples:

*Alternaria,* such as *Alternaria tenuis,*

*Aspergillus,* such as *Aspergillus niger,*

*Chaetomium,* such as *Chaetomium globosum,*

*Coniophora,* such as *Coniophora puetana,*

*Lentinus,* such as *Lentinus tigrinus,*

*Penicillium,* such as *Penicillium glaucum,*

*Polyporus,* such as *Polyporus versicolor,*

*Aureobasidium,* such as *Aureobasidium pullulans,*

*Sclerophoma,* such as *Sclerophoma pityophila,*

*Trichoderma,* such as *Trichoderma viride,*

*Escherichia,* such as *Escherichia coli,*

*Pseudomonas,* such as *Pseudomonas aeruginosa,* and

*Staphylococcus,* such as *Staphylococcus aureus.*

Depending on their particular physical and/or chemical properties, the active compounds can be converted into the customary formulations, such as solutions, emulsions, suspensions, powders, foams, pastes, granules, aerosols and microencapsulations in polymeric substances and in coating compositions for seeds, and ULV cool and warm fogging formulations, These formulations are produced in a known manner, for example by mixing the active compounds with extenders, that is liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention can be used as such or in their formulations, also in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Examples of suitable mixing components are the following:

Fungicides:

2-phenylphenol; 8-hydroxyquinoline sulphate; acibenzolar-S-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine; calcium polysulphide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazole; imazalil; imibenconazole; iminoctadine triacetate; iminoctadine tris(albesil); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; metconazole; methasulfocarb; methfuroxam; metiram; metominostrobin; metsulfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfuir; pyrrolenitrine; quinconazole; quinoxyfen; quintozene; simeconazole; spiroxamine; sulphur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)—N-[2-[4-[[3-4-chlorophenyl)-2-propynyl]oxy]-3-methoxyphenyl]ethyl]-3-methyl-2-[(methylsulphonyl)amino]butanamide; 1-(1-naphthalenyl)-1H-pyrrole-2,5-dione; 2,3,5,6-tetrachloro-4-(methylsulphonyl)pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; actinovate; cis-1-(4-chlorophenyl)-2-(1H-1,2,4-triazol-1-yl)cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)cyclopropanecarboxamide; N-butyl-8-(1,1-dimethylethyl)-1-oxaspiro[4.5]decane-3-amine; sodium tetrathiocarbonate; and copper salts and preparations, such as Bordeaux mixture; copper hydroxide; copper naphthenate; copper oxychloride; copper sulphate; cufraneb; cuprous oxide; mancopper; oxine-copper.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

abamectin, ABG-9008, acephate, acequinocyl, acetamiprid, acetoprole, acrinathrin, AKD-1022, AKD-3059, AKD-3088, alanycarb, aldicarb, aldoxycarb, allethrin, allethrin 1R-isomers, alpha-cypermethrin (alphamethrin), amidoflumet, aminocarb, amitraz, avermectin, AZ-60541, azadirachtin, azamethiphos, azinphos-methyl, azinphos-ethyl, azocyclotin,

*Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, baculoviruses, *Beauveria bassiana, Beauveria tenella*, benclothiaz, bendiocarb, benfuracarb, bensultap, benzoximate, beta-cyfluthrin, beta-cypermethrin, bifenazate, bifenthrin, binapacryl, bioallethrin, bioallethrin-S-cyclopentyl-isomer, bioethanomethrin, biopermethrin, bioresmethrin, bistrifluron, BPMC, brofenprox, bromophos-ethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulfan, cartap, CGA-50439, chinomethionat, chlordane, chlordimeform, chloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (-ethyl), chlovaporthrin, chromafenozide, cis-cypermethrin, cis-resmethrin, cis-permethrin, clocythrin, cloethocarb, clofentezine, clothianidin, clothiazoben, codlemone, coumaphos, cyanofenphos, cyanophos, cycloprene, cycloprothrin, *Cydia pomonella*, cyfluthrin, cyhalothrin, cyhexatin, cypermethrin, cyphenothrin (1R-trans-isomer), cyromazine, DDT, deltamethrin, demeton-S-methyl, demeton-S-methyl-sulphone, diafenthiuron, dialifos, diazinon, dichlofenthion, dichlorvos, dicofol, dicrotophos, dicyclanil, diflubenzuron, dimeflurhrin, dimethoate, dimethylvinphos, dinobuton, dinocap, dinotefuran, diofenolan, disulfoton, docusat-sodium, dofenapyn, DOWCO-439, eflusilanate, emamectin, emamectin-benzoate, empenthrin (1R-isomer), endosulfan, *Entomopthora* spp., EPN, esfenvalerate, ethiofencarb, ethiprole, ethion, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-cyhalothrin, gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulfenfos, metaldehyde, metam-sodium, methacrifos, methamidophos, *Metharhizium anisopliae, Metharhizium flavoviride*, methidathion, methiocarb, methomyl, methoprene, methoxychlor, methoxyfenozide, metofluthrin, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl,

*Paecilomyces fumosoroseus*, parathion-methyl, parathion (-ethyl), permethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphos-methyl, pirimiphos-ethyl, potassium oleate, prallethrin, profenofos, profluthrin, promecarb, propaphos, propargite, propetamphos, propoxur, prothiofos, prothoate, protrifenbute, pymetrozine, pyraclofos, pyresmethrin, pyrethrum, pyridaben, pyridalyl, pyridaphenthion, pyridathion, pyrimidifen, pyriproxyfen, quinalphos, resmethrin, RH-5849, ribavirin, RU-12457, RU-15525, S-421, S-1833, salithion, sebufos, SI-0009, silafluofen, spinosad, spirodiclofen, spiromesifen, sulfluramid, sulfotep, sulprofos, SZI-121, tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R-isomer), tetrasul, theta-cypermethrin, thiacloprid, thiamethoxam, thiapronil, thiatriphos, thiocyclam hydrogen oxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, trichoderma atroviride, triflumuron, trimethacarb, vamidothion, vaniliprole, verbutin, *Verticillium lecanii*,

WL-108477, WL-40027,

YI-5201, YI-5301, YI-5302,

XMC, xylylcarb,

ZA-3274, zeta-cypermethrin, zolaprofos, ZXI-8901, the compound 3-methylphenyl propylcarbamate (tsumacide Z), the compound 3-(5-chloro-3-pyridinyl)-8-(2,2,2-trifluoroethyl)-8-azabicyclo[3.2.1]octane-3-carbonitrile (CAS-Reg. No. 185982-80-3) and the corresponding 3-endo-isomer (CAS-Reg. No. 185984-60-5) (cf. WO-96/37494, WO-98/25923), and preparations which comprise insecticidally active plant extracts, nematodes, fungi or viruses.

A mixture with other known active compounds, such as herbicides, or with fertilizers and growth regulators, is also possible.

In addition, the compounds of the formula (I) according to the invention also have very good antimycotic activity. They have a very broad antimycotic activity spectrum in particular against dermatophytes and yeasts, moulds and diphasic fungi (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes*,

*Microsporon* species such as *Microsporon canis* and *audouinii*. The list of these fungi by no means limits the mycotic spectrum covered, but is only for illustration.

The active compounds can be used as such, in the form of their formulations or the use forms prepared therefrom, such as ready-to-use solutions, suspensions wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low-volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10,000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10,000 g/ha, preferably between 1 and 5000 g/ha.

The preparation and the use of the active compounds according to the invention is illustrated by the examples below.

PREPARATION EXAMPLES

Example I-1-a-1

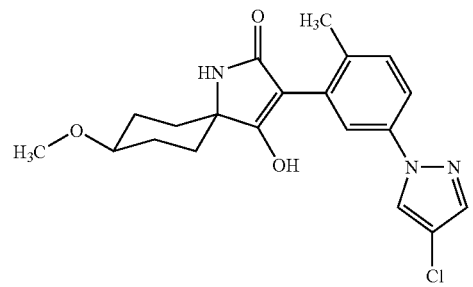

At 40-50° C., 3.15 g of the compound of Example II-1 in 7 ml of anhydrous dimethylformamide (DMF) are added to 1.95 g (0.042 mol) of potassium tert-butoxide in 6 ml of anhydrous DMF, and the mixture is stirred at 60° C. for 1 hour.

The reaction mixture is stirred into ice-water and, at 0-10° C., acidified to pH 4 using concentrated hydrochloric acid. The precipitate is washed with ice-water and dried. This is followed by column-chromatographic purification on silica gel (dichloromethane:methanol, 20:1).

Yield: 190 mg (6% of theory). M.p.: 265° C.

Analogously to Example (I-1-a-1) and in accordance with the general statements on the preparation, the following compounds of the formula (I-1-a) are obtained

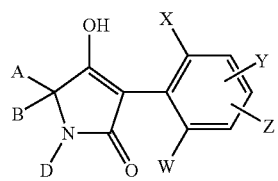

(I-1-a)

| Ex. No. | W | X | Y | Z | D | A | B | m.p. ° C. | isomer |
|---------|-----|-----|---|---|---|---|---|-----------|--------|
| I-1-a-2 | CH₃ | CH₃ | H | 4—N-pyrazole-Cl | H | —(CH₂)₂—CHOCH₃—(CH₂)₂— | | 277 | β |
| I-1-a-3 | H | CH₃ | H | 5—N-pyrazole-Cl | H | —(CH₂)₅— | | 286 | — |
| I-1-a-4 | CH₃ | CH₃ | H | 4—N-pyrazole-Cl | H | CH₃ | CH₃ | 308 | — |
| I-1-a-5 | CH₃ | CH₃ | H | 4—N-pyrazole-OCH₃ | H | —(CH₂)₂—CHOCH₃—(CH₂)₂— | | 291 | β |

-continued

| No. | R1 | R2 | R3 | Het | R4 | R5/bridge | R6 | m.p./NMR | config |
|---|---|---|---|---|---|---|---|---|---|
| I-1-a-6 | CH₃ | C₂H₅ | H | 4-pyrazol-N-yl-OCH₃ | H | —(CH₂)₂—CHOCH₃—(CH₂)₂— | | 284 | β |
| I-1-a-7 | CH₃ | C₂H₅ | H | 4-pyrazol-N-yl-Cl | H | —(CH₂)₂—CHOCH₃—(CH₂)₂— | | 318 | β |
| I-1-a-8 | C₂H₅ | C₂H₅ | H | 4-pyrazol-N-yl-Cl | H | —(CH₂)₂—CHOCH₃—(CH₂)₂— | | 278 | β |
| I-1-a-9 | CH₃ | CH₃ | Cl | 4-pyrazol-N-yl-Cl | H | CH₃ | CH₃ | 305 | — |
| I-1-a-10 | H | C₂H₅ | H | 4-pyrazol-N-yl-Cl | H | —(CH₂)₂—CHOCH₃—(CH₂)₂— | | 167 | β |
| I-1-a-11 | C₂H₅ | Cl | H | 4-pyrazol-N-yl-Cl | H | CH₃ | CH₃ | 294 | — |
| I-1-a-12 | C₂H₅ | Cl | H | 4-pyrazol-N-yl-Cl | H | —(CH₂)₂—CHOCH₃—(CH₂)₂— | | 272 | β |
| I-1-a-13 | CH₃ | C₂H₅ | H | 4-pyrazol-N-yl-Cl | H | —(CH₂)₂—O—(CH₂)₂— | | 269 | — |
| I-1-a-14 | CH₃ | C₂H₅ | H | 4-pyrazol-N-yl-Cl | H | CH₃ | CH₃ | 306 | — |
| I-1-a-15 | H | Cl | H | 5-pyrazol-N-yl-Cl | H | —(CH₂)₂—CHOCH₃—(CH₂)₂— | | *7.57-7.77 (m, 3H, Ar—H), 7.87, 8.18 (2 s, 2H Pyr—H) | β |
| I-1-a-16 | CH₃ | C₂H₅ | H | 4-pyrazol-N-yl-Cl | H | cyclopropyl | CH₃ | 171-172 | — |

*¹H-NMR (400 MHz, d₆-DMSO): Shift δ in ppm.

Example I-1-b-1

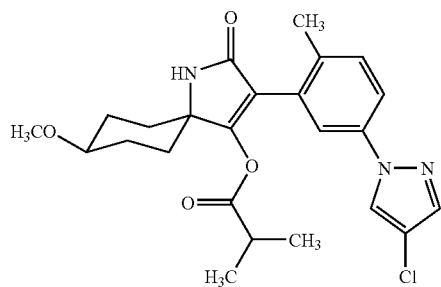

Under argon, 0.6 g of the compound of Example I-1-a-1 is initially charged in 30 ml of anhydrous ethyl acetate and 0.15 g of triethylamine (1.5 mmol)=0.21 ml. The reaction is catalyzed using 10 mg of Steglich base, 0.16 g (0.0015 mol) of isobutyl chloride in 2 ml of anhydrous dichloromethane is added under reflux. The reaction is monitored by thin-layer chromatography. The solvent is evaporated and the residue is chromatographed on silica gel using the mobile phase dichloromethane/ethyl acetate 3:1.

Yield: 0.25 g (34% of theory), m.p. 217° C.

Analogously to Example (I-1-b-1) and in accordance with the general statements on the preparation, the following compounds of the formula (I-1-b) are obtained

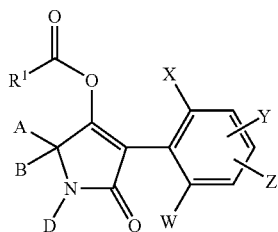

(I-1-b)

| Ex. No. | W | X | Y | Z | D | A | B | R¹ | m.p. °C. | isomer |
|---|---|---|---|---|---|---|---|---|---|---|
| I-1-b-2 | $CH_3$ | $CH_3$ | H | 4—N-pyrazole-Cl | H | —$(CH_2)_2$—$CHOCH_3$—$(CH_2)_2$— | | $i-C_3H_7$ | 247 | β |
| I-1-b-3 | $CH_3$ | $CH_3$ | H | 4—N-pyrazole-$OCH_3$ | H | —$(CH_2)_2$—$CHOCH_3$—$(CH_2)_2$— | | $H_3C$—O—$CH_2$— | 237 | β |
| I-1-b-4 | $CH_3$ | $C_2H_5$ | H | 4—N-pyrazole-Cl | H | —$(CH_2)_2$—$CHOCH_3$—$(CH_2)_2$— | | $i-C_3H_7$ | 221 | β |
| I-1-b-5 | H | $C_2H_5$ | H | 4—N-pyrazole-Cl | H | —$(CH_2)_2$—$CHOCH_3$—$(CH_2)_2$— | | $i-C_3H_7$ | *3.21 (m, 1H, C$\underline{H}$OCH$_3$), 1.05 (d, 6H, CH(CH$_3$)$_2$) | β |
| I-1-b-6 | $CH_3$ | $C_2H_5$ | H | 4—N-pyrazole-Cl | H | $CH_3$ | $CH_3$ | $i-C_3H_7$ | 140-141 | — |

*$^1$H-NMR (400 MHz, CDCl$_3$): Shift δ in ppm.

Example I-1-c-1

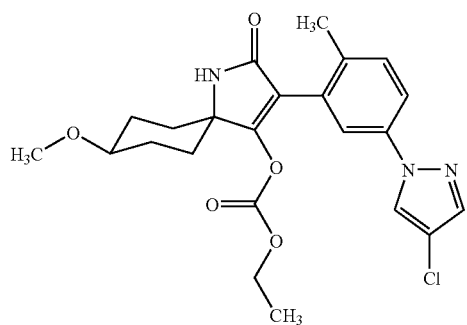

At 10-20° C., 0.14 ml (1 mmol) of triethylamine and 0.1 ml (1 mmol) of ethyl chloroformate in 5 ml of anhydrous dichloromethane are added to 0.48 g of the compound of Example I-1-a-1 in 10 ml of anhydrous dichloromethane.

The mixture is stirred at room temperature and the reaction is monitored by thin-layer chromatography.

The solvent is distilled off and the residue is taken up in dichloromethane, washed twice with 5 ml of 0.5 N NaOH solution and dried. The solvent is distilled off. The product is then purified by column chromatography on silica gel (dichloromethane:ethyl acetate 3:1).

Yield: 0.3 g (65% of theory), m.p. 240° C.

Analogously to Example (I-1-c-1) and in accordance with the general statements on the preparation, the following compounds of the formula (I-1-c) are obtained (I-1-c)

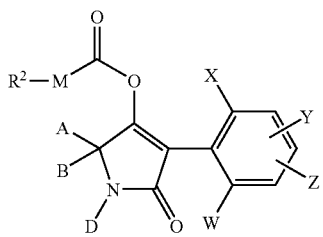

| Ex. No. | W | X | Y | Z | D | A | B | M | R² | m.p. °C. | isomer |
|---|---|---|---|---|---|---|---|---|---|---|---|
| I-1-c-2 | CH₃ | CH₃ | H | 4-N-pyrazolyl-Cl | H | CH₃ | CH₃ | O | C₂H₅ | 159 | — |
| I-1-c-3 | CH₃ | CH₃ | H | 4-N-pyrazolyl-OCH₃ | H | —(CH₂)₂—CHOCH₃—(CH₂)₂— | | O | C₂H₅ | 209-212 | β |
| I-1-c-4 | H | C₂H₅ | H | 4-N-pyrazolyl-Cl | H | —(CH₂)₂—CHOCH₃—(CH₂)₂— | | O | C₂H₅ | 192-197 | β |
| I-1-c-5 | CH₃ | CH₃ | H | 4-N-pyrazolyl-Cl | H | —(CH₂)₂—CHOCH₃—(CH₂)₂— | | O | C₂H₅ | *1.13 (t, 3H, CH₂—$\underline{CH_3}$) 2.28 (s, 6H, Ar—$\underline{CH_3}$) 7.62, 7.88 (2s, 2H, Pyr—$\underline{H}$) | β |
| I-1-c-6 | CH₃ | C₂H₅ | H | 4-N-pyrazolyl-OCH₃ | H | —(CH₂)₂—CHOCH₃—(CH₂)₂— | | O | C₂H₅ | 220 | β |
| I-1-c-7 | CH₃ | C₂H₅ | H | 4-N-pyrazolyl-Cl | H | —(CH₂)₂—CHOCH₃—(CH₂)₂— | | O | C₂H₅ | 197 | β |

| | | | | | | | | | | | |
|---|---|---|---|---|---|---|---|---|---|---|---|
| I-1-c-8 | C$_2$H$_5$ | Cl | H | 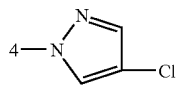 | H | CH$_3$ | | CH$_3$ | O | C$_2$H$_5$ | 178 | — |
| I-1-c-9 | C$_2$H$_5$ | Cl | H | 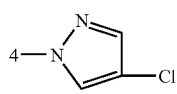 | H | —(CH$_2$)$_2$—CHOCH$_3$—(CH$_2$)$_2$— | | O | C$_2$H$_5$ | 196 | β |
| I-1-c-10 | C$_2$H$_5$ | C$_2$H$_5$ | H | 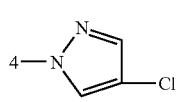 | H | —(CH$_2$)$_2$—CHOCH$_3$—(CH$_2$)$_2$— | | O | C$_2$H$_5$ | 190 | β |
| I-1-c-11 | CH$_3$ | C$_2$H$_5$ | H | 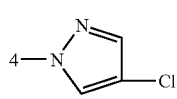 | H | CH$_3$ | | CH$_3$ | O | C$_2$H$_5$ | 149-151 | — |
| I-1-c-12 | CH$_3$ | C$_2$H$_5$ | H | 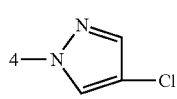 | H | ▷— | | CH$_3$ | O | C$_2$H$_5$ | — | — |

*$^1$H-NMR (400 MHz, CDCl$_3$): Shift δ in ppm.

Example II-16

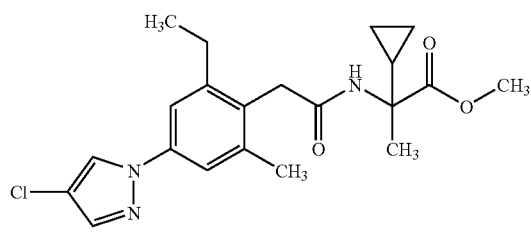

1.29 g of the compound of Example XXX-1 in 10 ml of dichloromethane are added to 1 ml of sulphuric acid. The mixture is stirred at 35° C. for 2 h. 6 ml of methanol are added. The mixture is stirred at 60° C. for 6 h. The mixture is extracted with dichloromethane, the extract is dried over magnesium sulphate and the solvent is distilled off. The product is purified by column chromatography on silica gel (ethyl acetate/n-heptane: 1/4→1/1).

Yield: 1 g (69% of theory), m.p. 136-137° C.

Example II-1

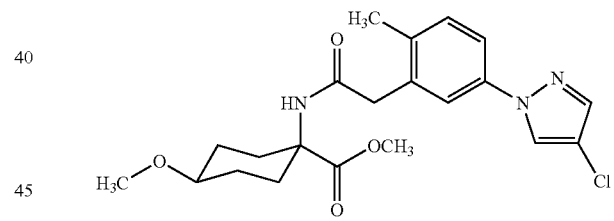

4 ml of triethylamine are added to 3.04 g of methyl 1-amino-4-methoxycyclohexanecarboxylate×HCl in 40 ml of anhydrous tetrahydrofuran (THF), and the mixture is stirred for 5 minutes. 2.51 g of 2-methyl-5-[1-(4-chloro)pyrazolyl]phenylacetic acid are then added, and the mixture is stirred at room temperature for 15 minutes. 2.2 ml of triethylamine are then added, followed immediately by the dropwise addition of 0.56 ml of phosphorus oxychloride such that the solution boils gently. The mixture is stirred under reflux for 30 minutes.

The reaction solution is poured into 200 ml of ice-water, made alkaline using 3.5 ml of triethylamine and extracted with dichloromethane, and the extract is dried. The solvent is then distilled off and the product is purified by column chromatography on silica gel (dichloromethane:ethyl acetate 3:1).

Yield: 3.15 g (75% of theory). m.p.: 153° C.

Analogously to Example (II-1) and in accordance with the general statements on the preparation, the following compounds of the formula (II) are obtained

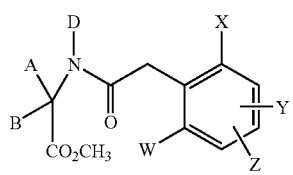

(II)

| Ex. No. | W | X | Y | Z | D | A | B | m.p. °C. | isomer |
|---|---|---|---|---|---|---|---|---|---|
| II-2 | $CH_3$ | $CH_3$ | H | 4-(1H-pyrazol-1-yl)-4-Cl | H | —$(CH_2)_2$—$CHOCH_3$—$(CH_2)_2$— | | 176 | β |
| II-3 | H | $CH_3$ | H | 5-(1H-pyrazol-1-yl)-4-Cl | H | —$(CH_2)_5$— | | 146 | — |
| II-4 | $CH_3$ | $CH_3$ | H | 4-(1H-pyrazol-1-yl)-4-Cl | H | $CH_3$ | $CH_3$ | 194 | — |

| Ex. No. | W | X | Y | Z | D | A | B | $R^8$ | m.p. °C. | isomer |
|---|---|---|---|---|---|---|---|---|---|---|
| II-5 | $CH_3$ | $CH_3$ | H | 4-(1H-pyrazol-1-yl)-4-$OCH_3$ | H | —$(CH_2)_2$—$CHOCH_3$—$(CH_2)_2$— | | $CH_3$ | 314 | β |
| II-6 | $CH_3$ | $C_2H_5$ | H | 4-(1H-pyrazol-1-yl)-4-$OCH_3$ | H | —$(CH_2)_2$—$CHOCH_3$—$(CH_2)_2$— | | $CH_3$ | 128 | β |
| II-7 | $CH_3$ | $C_2H_5$ | H | 4-(1H-pyrazol-1-yl)-4-Cl | H | —$(CH_2)_2$—$CHOCH_3$—$(CH_2)_2$— | | $CH_3$ | 101 | β |
| II-8 | $C_2H_5$ | $C_2H_5$ | H | 4-(1H-pyrazol-1-yl)-4-Cl | H | —$(CH_2)_2$—$CHOCH_3$—$(CH_2)_2$— | | $CH_3$ | 135 | β |
| II-10 | H | $C_2H_5$ | H | 4-(1H-pyrazol-1-yl)-4-Cl | H | —$(CH_2)_2$—$CHOCH_3$—$(CH_2)_2$— | | $CH_3$ | 134 | β |
| II-11 | $C_2H_5$ | Cl | H | 4-(1H-pyrazol-1-yl)-4-Cl | H | $CH_3$ | $CH_3$ | $CH_3$ | 179 | — |

-continued

| | | | | | | | | | | |
|---|---|---|---|---|---|---|---|---|---|---|
| II-12 | C₂H₅ | Cl | H | 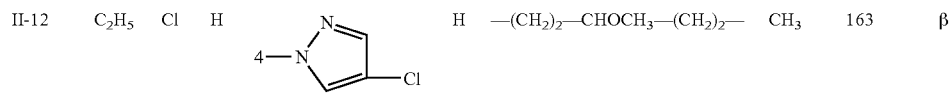 | H | —(CH₂)₂—CHOCH₃—(CH₂)₂— | CH₃ | 163 | β |
| II-13 | CH₃ | C₂H₅ | H | 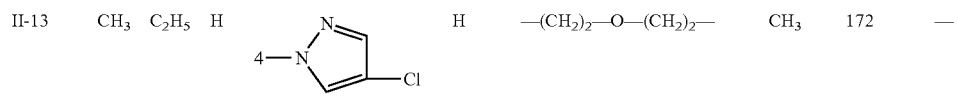 | H | —(CH₂)₂—O—(CH₂)₂— | CH₃ | 172 | — |
| II-14 | CH₃ | C₂H₅ | H | 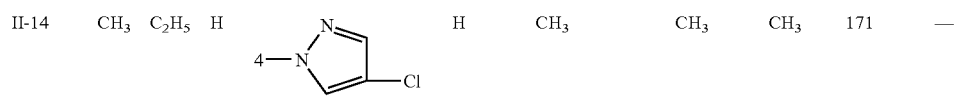 | H | CH₃ | CH₃ | CH₃ | 171 | — |
| II-15 | H | Cl | H | 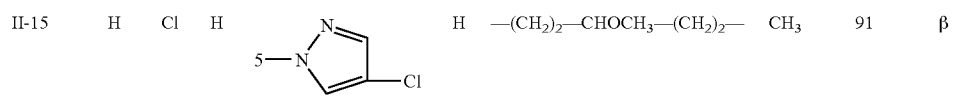 | H | —(CH₂)₂—CHOCH₃—(CH₂)₂— | CH₃ | 91 | β |
| II-9 | CH₃ | C₂H₅ | H | 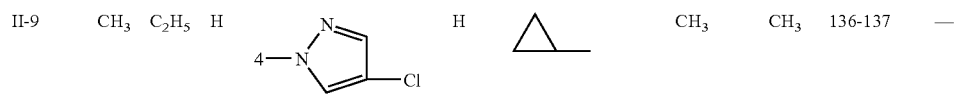 | H | △⎯ | CH₃ | CH₃ | 136-137 | — |

Example XXX-1

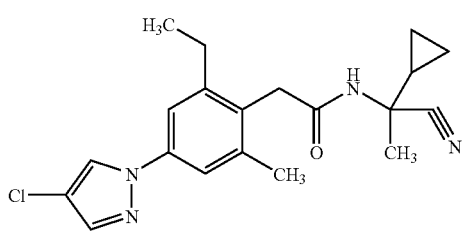

0.38 g of 2-amino-2-cyclopropylpropionitrile and 0.48 ml of triethylamine are initially charged in 20 ml of tetrahydrofuran. At 0° C., 0.97 g of 4-(4-chloro-pyrazolyl)-2-ethyl-6-methylphenylacetyl chloride in 20 ml of tetrahydrofuran is added dropwise over a period of 1 h. The mixture is stirred at room temperature for another 6 h. The reaction solution is filtered off with suction through a frit and washed, and the solvent is distilled off. The product is purified by column chromatography on silica gel (ethyl acetate/n-heptane=1/4→1/1).

Yield: 910 mg (62% of theory) m.p. 65-70° C.

Example I-2-a-1

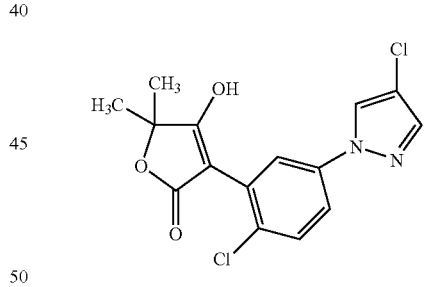

1 g of KOtBu is initially charged in 10 ml of DMF and cooled to 0° C., and 2.1 g of the compound of Example III-1 are dissolved in DMF and added dropwise at 0-10° C. The mixture is stirred at room temperature for 8 h. The solvent is distilled off and the residue is taken up in water. The mixture is extracted with ethyl acetate. The aqueous phase is acidified with HCl, the precipitate is filtered off with suction and the filtrate is dried.

Yield 0.25 g (10% of theory)

$^1$H-NMR (400 MHz, d₆-DMSO): δ=1.50 (s, 6H, C(C$\underline{H}_3$)₂), 7.5-8.9 (m, 5H, Ar—$\underline{H}$, pyrazole-$\underline{H}$) ppm Analogously to Example (I-2-a-1) and in accordance with the general statements on the preparation, the following compounds of the formula (I-2-a) are obtained

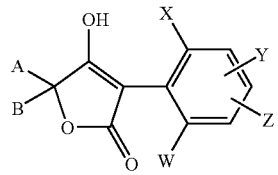

(I-2-a)

| Ex. No. | W | X | Y | Z | A | B | m.p. °C. |
|---|---|---|---|---|---|---|---|
| I-2-a-2 | H | Cl | H | 5-N-pyrazole-4-Cl | —(CH$_2$)$_2$—CHOCH$_3$—(CH$_2$)$_2$— | | *3.3-3.5 (2 m, 1H, CHOCH$_3$) 3.3 (s, 3H, OCH$_3$) 7.73, 7.88 (2s, 2H, Ar—H) 7.90, 8.76 (2 s, 2H, Pyr—H) |
| I-2-a-3 | C$_2$H$_5$ | Cl | H | 4-N-pyrazole-Cl | CH$_3$ | CH$_3$ | *7.72, 7.82 (2 s, 2H, Ar—H) 7.90, 8.87 (2 s, 2H, Pyr—H) |
| I-2-a-4 | C$_2$H$_5$ | Cl | H | 4-N-pyrazole-Cl | —(CH$_2$)$_4$— | | *7.58, 7.67 (2 s, 2H, Ar—H) 7.68, 8.23 (2 s, 2H, Pyr—H) |
| I-2-a-5 | C$_2$H$_5$ | Cl | H | 4-N-pyrazole-Cl | —(CH$_2$)$_2$—CHOCH$_3$—(CH$_2$)$_2$— | | trans-isomer[1] *3.27 (s, 3H, O—CH$_3$) 7.71, 7.82 (2 s, 2H, Ar—H) 7.90, 8.86 (2 s, 2H, Pyr—H) |
| I-2-a-6 | C$_2$H$_5$ | Cl | H | 4-N-pyrazole-Cl | —(CH$_2$)$_2$—CHOCH$_3$—(CH$_2$)$_2$— | | cis-isomer[1] *3.29 (s, 3H, O—CH$_3$) 7.72, 7.82 (2 s, 2H, Ar—H) 7.90, 8.87 (2 s, 2H, Pyr—H) |
| I-2-a-7 | CH$_3$ | C$_2$H$_5$ | H | 4-N-pyrazole-Cl | —(CH$_2$)$_2$—O—(CH$_2$)$_2$— | | *7.48, 7.54 (2 s, 2H, Ar—H) 7.84, 7.95 (2 s, 2H, Pyr—H) |
| I-2-a-8 | CH$_3$ | C$_2$H$_5$ | H | 4-N-pyrazole-Cl | —(CH$_2$)$_2$—CHOCH$_3$—(CH$_2$)$_2$— | | *7.53, 7.55 (2 s, 2H, Ar—H) 7.84, 7.95 (2 s, 2H, Pyr—H) |
| I-2-a-9 | CH$_3$ | C$_2$H$_5$ | H | 4-N-pyrazole-Cl | —(CH$_2$)$_5$— | | *7.53, 7.55 (2 s, 2H, Ar—H) 7.83, 7.95 (2 s, 2H, Pyr—H) |
| I-2-a-10 | CH$_3$ | C$_2$H$_5$ | H | 4-N-pyrazole-Cl | CH$_3$ | CH$_3$ | *7.53, 7.55 (2 s, 2H, Ar—H) 7.84, 7.95 (2 s, 2H, Pyr—H) |

*$^1$H-NMR (400 MHz, d$_6$-DMSO): δ in ppm

[1] separation by column chromatography on silica gel using the mobile phase methylene chloride

Example I-2-b-1

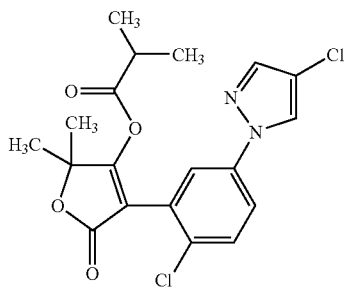

0.12 g of the compound of Example I-2-a-1 is initially charged in 10 ml of dichloromethane and 0.05 ml of triethylamine, and 0.04 g of isobutyl chloride is added with ice-cooling. The mixture is stirred at room temperature for 8 h. The mixture is then washed with 10% strength citric acid, and the phases are separated. The organic phase is dried and the solvent is distilled off.

Yield: 0.04 g (28% of theory), m.p. 150-152° C.

$^1$H-NMR (CD$_3$CN): δ=1.1 (d, 6H), 1.5 (s, 6H), 2.8 (m, 1H), 7.5-8.2 (m, 5H) ppm.

Analogously to Example (I-2-b-1) and in accordance with the general statements on the preparation, the following compounds of the formula (I-2-b) are obtained

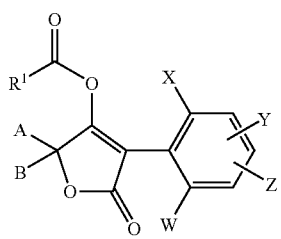

(I-2-b)

| Ex. No. | W | X | Y | Z | A | B | R$^1$ | m.p. ° C. |
|---|---|---|---|---|---|---|---|---|
| I-2-b-2 | C$_2$H$_5$ | Cl | H | 4—N-pyrazole-Cl | CH$_3$ | CH$_3$ | i-C$_3$H$_7$ | *7.64, 7.70 (2 s, 2H, Ar—H)<br>7.71, 8.27 (2 s, 2H, Pyr—H) |
| I-2-b-3 | C$_2$H$_5$ | Cl | H | 4—N-pyrazole-Cl | —(CH$_2$)$_4$— | | i-C$_3$H$_7$ | *7.63, 7.70 (2 s, 2H, Ar—H)<br>7.71, 8.27 (2 s, 2H, Pyr—H) |
| I-2-b-4 | C$_2$H$_5$ | Cl | H | 4—N-pyrazole-Cl | —(CH$_2$)$_2$—CHOCH$_3$—(CH$_2$)$_2$— | | i-C$_3$H$_7$ | trans-isomer[1)]<br>*3.31 (s, 3H, O—CH$_3$)<br>7.63, 7.70 (2 s, 2H, Ar—H)<br>7.71, 8.27 (2 s, 2H, Pyr—H) |
| I-2-b-5 | C$_2$H$_5$ | Cl | H | 4—N-pyrazole-Cl | —(CH$_2$)$_2$—CHOCH$_3$—(CH$_2$)$_2$— | | i-C$_3$H$_7$ | cis-isomer[1)]<br>*3.34 (s, 3H, O—CH$_3$)<br>7.63, 7.70 (2 s, 2H, Ar—H)<br>7.21, 8.27 (2 s, 2H, Pyr—H) |
| I-2-b-6 | CH$_3$ | C$_2$H$_5$ | H | 4—N-pyrazole-Cl | CH$_3$ | CH$_3$ | i-C$_3$H$_7$ | *7.48, 7.49 (2 s, 2H, Ar—H)<br>7.67, 8.23 (2 s, 2H, Pyr—H) |
| I-2-b-7 | CH$_3$ | C$_2$H$_5$ | H | 4—N-pyrazole-Cl | —(CH$_2$)$_2$—O—(CH$_2$)$_2$— | | i-C$_3$H$_7$ | *7.48, 7.50 (2 s, 2H, Ar—H)<br>7.67, 8.23 (2 s, 2H, Pyr—H) |
| I-2-b-8 | CH$_3$ | C$_2$H$_5$ | H | 4—N-pyrazole-Cl | —(CH$_2$)$_5$— | | i-C$_3$H$_7$ | *7.47, 7.48 (2 s, 2H, Ar—H)<br>7.67, 8.22 (2 s, 2H, Pyr—H) |

-continued

| | | | | | | | |
|---|---|---|---|---|---|---|---|
| I-2-b-9 | CH₃ | C₂H₅ | H | 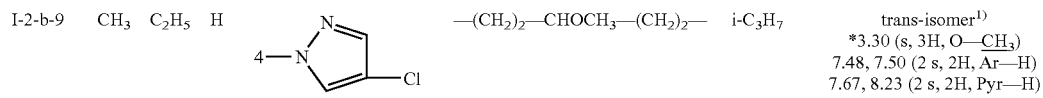 | —(CH₂)₂—CHOCH₃—(CH₂)₂— | i-C₃H₇ | trans-isomer[1])<br>*3.30 (s, 3H, O—CH₃)<br>7.48, 7.50 (2 s, 2H, Ar—H)<br>7.67, 8.23 (2 s, 2H, Pyr—H) |
| I-2-b-10 | CH₃ | C₂H₅ | H | 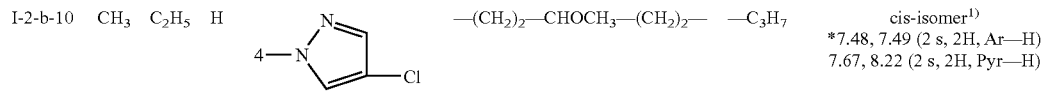 | —(CH₂)₂—CHOCH₃—(CH₂)₂— | —C₃H₇ | cis-isomer[1])<br>*7.48, 7.49 (2 s, 2H, Ar—H)<br>7.67, 8.22 (2 s, 2H, Pyr—H) |

*$^1$H-NMR (400 MHz, d₆-DMSO): δ in ppm
[1]) separation by column chromatography on silica gel using the mobile phase methylene chloride Example III-1

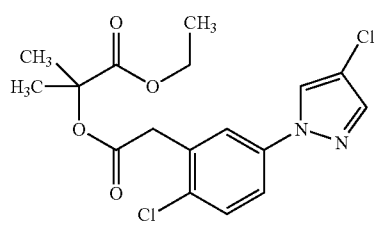

0.9 g of ethyl hydroxyisobutyrate and 2 g of 2-chloro-5-N-(4-chloropyrazolyl)phenylacetyl chloride are stirred in 20 ml of toluene under reflux for 8 h. The solvent is distilled off and the residue is dried.

Yield: 2.2 g (83% of theory)

$^1$H-NMR (400 MHz, d₆ DMSO): δ=1.15 (t, 3H, CH₂—CH₃), 1.50 (s, 6H, C(CH₃)₂), 4.05 (q, 2H, O—CH₂—CH₃), 7.3-8.8 (m, 5H) ppm.

Analogously to Example (III-1) and in accordance with the general statements on the preparation, the following compounds of the formula (III) are obtained

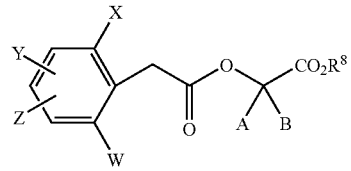

(III)

| Ex. No. | W | X | Y | Z | A | B | R⁸ | m.p. ° C. |
|---|---|---|---|---|---|---|---|---|
| III-2 | H | Cl | H | 5—N-pyrazolyl-Cl | —(CH₂)₂—CHOCH₃—(CH₂)₂— | | C₂H₂ | *7.18, 7.25 (2 s, 2H, Ar—H)<br>7.88, 8.75 (2 s, 2H, Pyr—H) |
| III-3 | C₂H₅ | Cl | H | 4—N-pyrazolyl-Cl | CH₃ | CH₃ | C₂H₅ | *7.57, 7.67 (2 s, 2H, Ar—H)<br>7.69, 8.23 (2 s, 2H, Pyr—H) |
| III-4 | C₂H₅ | Cl | H | 4—N-pyrazolyl-Cl | —(CH₂)₄— | | C₂H₅ | *7.58, 7.67 (2 s, 2H, Ar—H)<br>7.69, 8.24 (2 s, 2H, Pyr—H) |
| III-5 | C₂H₅ | Cl | H | 4—N-pyrazolyl-Cl | —(CH₂)₂—CHOCH₃—(CH₂)₂— | | C₂H₅ | *7.58, 7.67 (2 s, 2H, Ar—H)<br>7.69, 8.24 (2 s, 2H, Pyr—H) |

-continued

| No. | | | | Pyrazolyl | Linker | R | NMR |
|---|---|---|---|---|---|---|---|
| III-6 | $CH_3$ | $C_2H_5$ | H | 4—N-pyrazole-Cl | —$(CH_2)_2$—O—$(CH_2)_2$— | $C_2H_5$ | *7.44, 7.45 (2 s, 2H, Ar—H)<br>7.66, 8.19 (2 s, 2H, Pyr—H) |
| III-7 | $CH_3$ | $C_2H_5$ | H | 4—N-pyrazole-Cl | —$(CH_2)_2$—CHOCH$_3$—$(CH_2)_2$— | $C_2H_5$ | *7.43, 7.44 (2 s, 2H, Ar—H)<br>7.65, 8.19 (2 s, 2H, Pyr—H) |
| III-8 | $CH_3$ | $C_2H_5$ | H | 4—N-pyrazole-Cl | —$(CH_2)_5$— | $C_2H_5$ | *7.43, 7.45 (2 s, 2H, Ar—H)<br>7.65, 8.19 (2 s, 2H, Pyr—H) |
| III-9 | $CH_3$ | $C_2H_5$ | H | 4—N-pyrazole-Cl | $CH_3$   $CH_3$ | $C_2H_5$ | *7.42, 7.43 (2 s, 2H, Ar—H)<br>7.65, 8.19 (2 s, 2H, Pyr—H) |

Example XXV-1

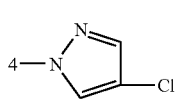

At room temperature, 2.3 g of oxayl chloride are added dropwise to 4 g of 2-chloro-5-N-(4-chloropyrazolyl)phenylacetic acid in 100 ml of dichloromethane. The mixture is stirred at room temperature for 8 h. The mixture is then boiled under reflux until the evolution of gas has ceased. The solvent is distilled off and the residue is degassed.

Yield: 4.25 g (99% of theory), GC/MS: M$^+$ 285 m/e.

Example I-6-a-1

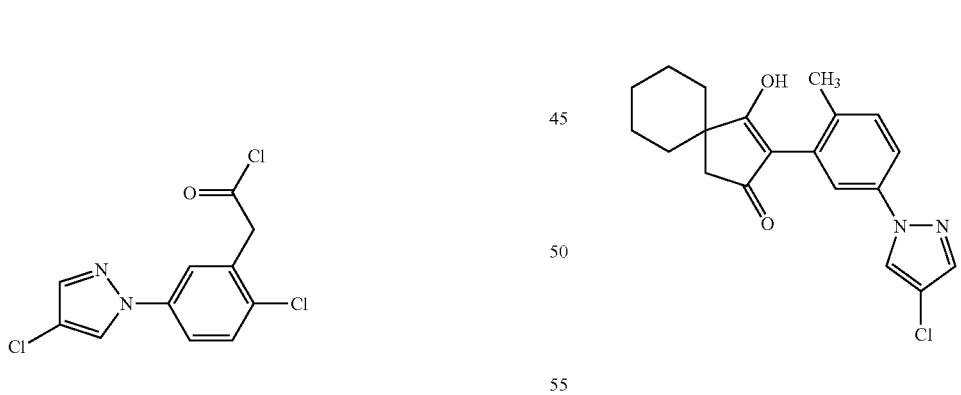

1.73 g (15.4 mmol) of potassium tert-butoxide are initially charged in 20 ml of DMF, and 3.0 g (7.7 mmol) of the compound of Example VIII-1 in 10 ml of DMF are added. The mixture is stirred at 50° C. for 3 hours. The reaction solution is cooled and put into 600 ml of cooled 1 N HCl and the precipitate is filtered off with suction and dried.

Yield: 2.4 g (87% of theory). m.p.: >250° C.

Analogously to Example (I-6-a-1) and in accordance with the general statements on the preparation, the following compound of the formula (I-6-a) is obtained

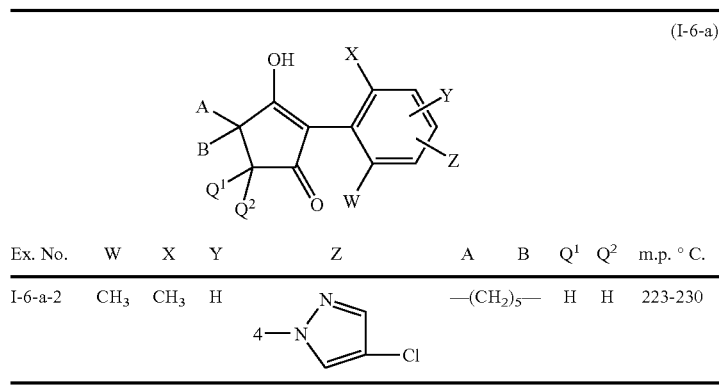

(I-6-a)

| Ex. No. | W | X | Y | Z | A | B | Q¹ | Q² | m.p. ° C. |
|---|---|---|---|---|---|---|---|---|---|
| I-6-a-2 | $CH_3$ | $CH_3$ | H | 4-pyrazol-1-yl-4-Cl | —$(CH_2)_5$— | H | H | | 223-230 |

Example I-6-c-1

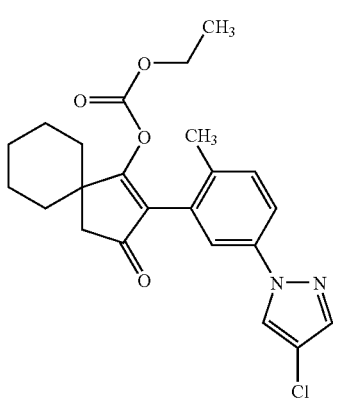

300 mg of the compound of Example I-6-a-1 are initially charged in 5 ml of anhydrous acetone, and 0.174 g of potassium carbonate is added. 0.119 g of ethyl chloroformate is then added. The mixture is stirred at 50° C. for 3 hours.

The reaction solution is concentrated, taken up in 10 ml of $CH_2Cl_2$ and washed with 10 ml of $H_2O$. The organic phase is separated off and the solvent is distilled off.

Yield: 0.36 g (96% of theory). m.p.: 132° C.

Analogously to Example (I-6-c-1) and in accordance with the general statements on the preparation, the following compounds of the formula (I-6-c) are obtained

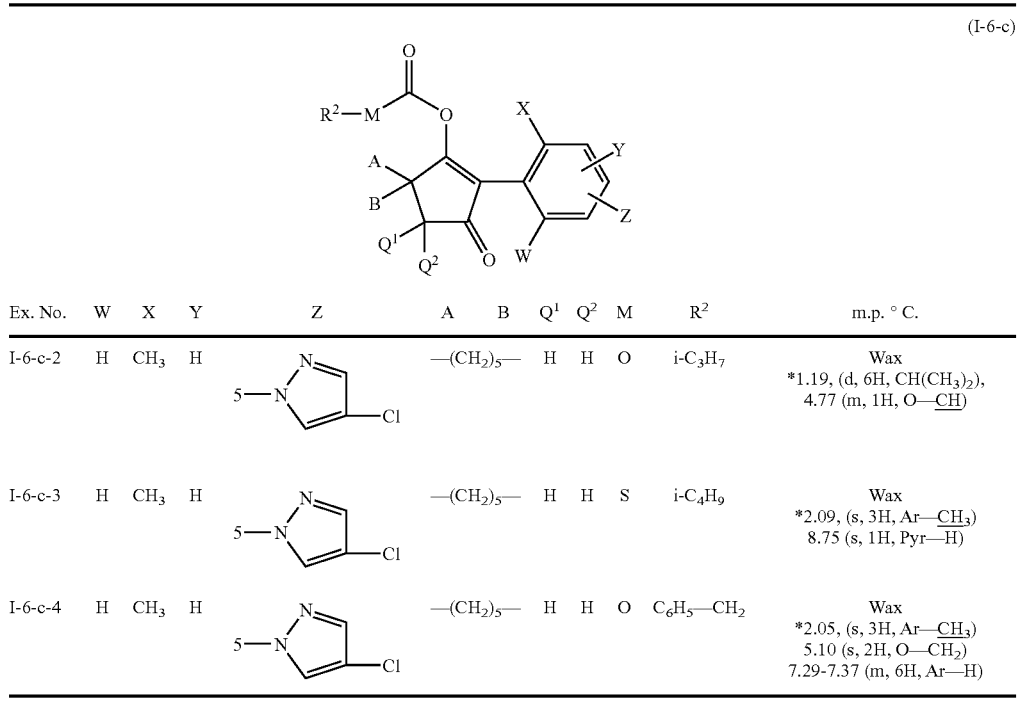

(I-6-c)

| Ex. No. | W | X | Y | Z | A B | Q¹ | Q² | M | R² | m.p. ° C. |
|---|---|---|---|---|---|---|---|---|---|---|
| I-6-c-2 | H | $CH_3$ | H | 5-pyrazol-1-yl-4-Cl | —$(CH_2)_5$— | H | H | O | $i$-$C_3H_7$ | Wax *1.19, (d, 6H, $CH(CH_3)_2$), 4.77 (m, 1H, O—CH) |
| I-6-c-3 | H | $CH_3$ | H | 5-pyrazol-1-yl-4-Cl | —$(CH_2)_5$— | H | H | S | $i$-$C_4H_9$ | Wax *2.09, (s, 3H, Ar—CH₃) 8.75 (s, 1H, Pyr—H) |
| I-6-c-4 | H | $CH_3$ | H | 5-pyrazol-1-yl-4-Cl | —$(CH_2)_5$— | H | H | O | $C_6H_5$—$CH_2$ | Wax *2.05, (s, 3H, Ar—CH₃) 5.10 (s, 2H, O—CH₂) 7.29-7.37 (m, 6H, Ar—H) |

*¹H-NMR (400 MHz, $CDCl_3$): δ in ppm

Example VIII-1

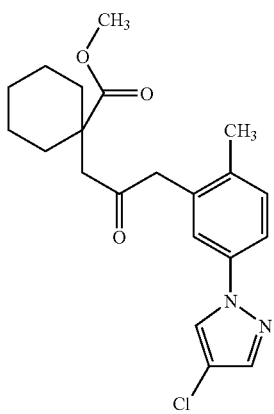

3.2 g (22.9 mmol) of potassium carbonate and 8.1 g (57.3 mmol)=3.6 ml of methyl iodide are added to 8.6 g (22.9 mmol) of crude product of Example XXXV-1 in 100 ml of anhydrous acetone. The mixture is stirred under reflux for 16 hours.

The reaction solution is cooled and the precipitate is filtered off with suction and washed with acetone.

The product is purified by column chromatography on silica gel (dichloromethane:petroleum ether, 2:1→4:1→8:1→dichloromethane).

Yield: 3 g (34% of theory).

1H-NMR (400 MHz, $d_6$-DMSO): δ=1.30-1.78 (m, 10H, cyclohexyl-H), 2.10 (s, 3H, $CH_3$-aryl), 3.51 (s, 3H, $CO_2Me$), 7.28 (d, 1H, aryl-H), 7.54-7.60 (m, 2H, aryl-H), 7.82, 8.72 (2s, 1H each, 2 pyrazolyl-H) ppm Analogously to Example (VIII-1) and in accordance with the general statements on the preparation, the following compound of the formula (VIII) is obtained

Example XXXV-1

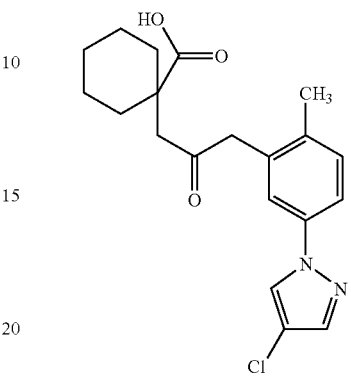

At −15° C., a solution of 5.0 g (18.9 mmol) of methyl 2-methyl-5-[1-(4-chloropyrazolyl)phenyl]acetate in 10 ml of THF is added dropwise to a solution of 9.44 ml of a solution (2 molar) of LDA in 30 ml of anhydrous THF, and the mixture is stirred at 0° C. for 60 minutes.

At −15° C., a solution of 4.13 g (18.9 mmol) of methyl 3,3-pentamethylenesuccinyl chloride in 10 ml of anhydrous THF and simultaneously 14.2 ml of LDA solution (2.0 molar; 1.5 eq) are then added dropwise. The mixture is stirred at room temperature for two hours and then poured into 150 ml of ice-cold 10% strength ammonium chloride solution.

The intermediate is extracted with MTB ether and the solvents are distilled off. The residue is boiled under reflux with 10 g of KOH and 100 ml of water for 3 hours.

The reaction solution is cooled, acidified with concentrated HCl and extracted with 200 ml of $CH_2Cl_2$, the extract is dried and the solvent is distilled off.

Yield: 8.6 g (66.8% of theory).

Analogously to Example (XXXV-1) and in accordance with the general statements on the preparation, the following compound of the formula (XXXV) is obtained

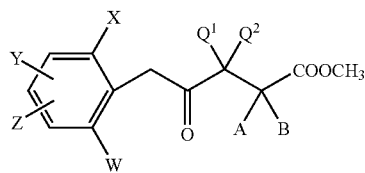

| Ex. No. | W | X | Y | Z | A | B | $Q^1$ | $Q^2$ | m.p. ° C. |
|---|---|---|---|---|---|---|---|---|---|
| VIII-2 | $CH_3$ | $CH_3$ | H | 4—[pyrazolyl-Cl] | —$(CH_2)_5$— | | H | H | |

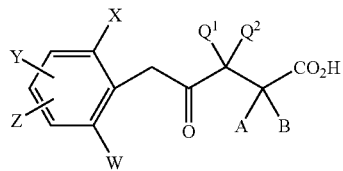

(XXXV)

| Ex. No. | W | X | Y | Z | A | B | Q¹ | Q² | m.p.° C. |
|---|---|---|---|---|---|---|---|---|---|
| XXXV-2 | CH₃ | CH₃ | H | 4-N-pyrazole-Cl | —(CH₂)₅— | | H | H | * |

*Was converted directly, as crude product, into the compound of the formula (VIII-2)

Example I-7-a-1

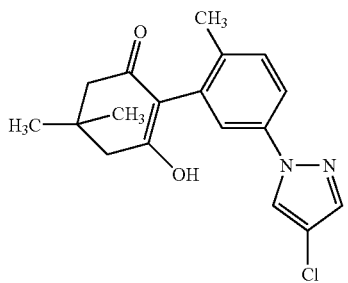

0.80 g (2.2 mmol) of the compound of Example IX-1 in 2 ml of DMF is added to 0.49 g (4.4 mmol, 2.0 eq) of potassium tert-butoxide in 5 ml of DMF.

The mixture is stirred at 50° C. for 3 hours. 20 ml of ice-water are added, cooled 1 N HCl solution is added to make a volume of 250 ml and the mixture is extracted with dichloromethane. The organic phase is dried and concentrated.

The residue is purified by column chromatography on silica gel (petroleum ether:ethyl acetate 2:1).

Yield: 0.15 g (21% of theory). m.p.: 172° C.

Analogously to Example (I-7-a-1) and in accordance with the general statements on the preparation, the following compound of the formula (I-7-a) is obtained Example IX-1

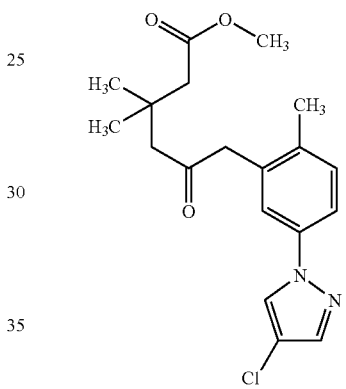

1.58 g of potassium carbonate and 4.07 g (2.5 eq)=1.79 ml of methyl iodide are added to 4.0 g of the crude product of Example XXXIX-1 in 50 ml of anhydrous acetone. The mixture is stirred under reflux for 16 hours. The reaction solution is cooled and the precipitate is filtered off with suction and washed with acetone.

The product is purified by column chromatography on silica gel using a gradient (methylene chloride:ethyl acetate 50:1→5:1).

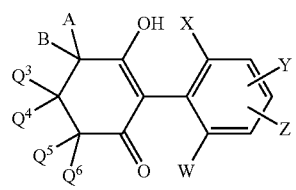

(I-7-a)

| Ex. No. | W | X | Y | Z | A | B | Q³ | Q⁴ | Q⁵ | Q⁶ | m.p.° C. |
|---|---|---|---|---|---|---|---|---|---|---|---|
| I-7-a-2 | H | CH₃ | H | 5-N-pyrazole-Cl | H | H | —(CH₂)₄— | | H | H | 241 |

Yield: 0.8 g (15% of theory).

$^1$H-NMR (400 MHz, d$_6$-DMSO): δ=1.03 (s, 6H, CH$_3$), 2.18 (s, 3H, CH$_3$-aryl), 3.57 (s, 3H, CO$_2$Me), 7.30 (d, 1H, aryl-H), 7.57-7.61 (m, 2H, aryl-H), 7.83, 8.72 (2s, 1H each, 2 pyrazolyl-H) ppm Analogously to Example (IX-1) and in accordance with the general statements on the preparation, the following compound of the formula (IX) is obtained A solution of 3.0 g (11.3 mmol; 1 eq) of methyl 2-methyl-5-[1-(4-chloropyrazolyl)phenyl]acetate in 5 ml of anhydrous THF, is, at −15° C., added dropwise to a solution of 5.7 ml of LDA solution (2 molar; 1.0 eq) in 20 ml of anhydrous THF, and the mixture is stirred at 0° C. for 60 minutes.

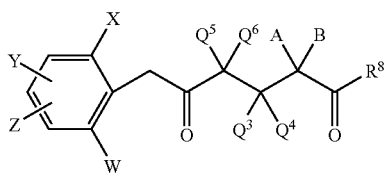

(IX)

| Ex. No. | W | X | Y | Z | A | B | Q$^3$ | Q$^4$ | Q$^5$ | Q$^6$ | R$^8$ | m.p.° C. |
|---|---|---|---|---|---|---|---|---|---|---|---|---|
| IX-2 | H | CH$_3$ | H | 5-N-pyrazolyl-4-Cl | H | H | —(CH$_2$)$_4$— | | H | H | CH$_3$ | * |

*1H-NMR (δ$_6$-400 MHz DMSO): δ = 1.05-1.50 (m, 8H, cyclopentyl-H), 2.13 (s, 3H, CH$_3$-aryl), 3.52 (s, 3H, CO$_2$Me), 7.28 (d, 1H, aryl-H), 7.82, 8.70 (2s, 1H each, 2 pyrazolyl-H) ppm

Example XXXIX-1

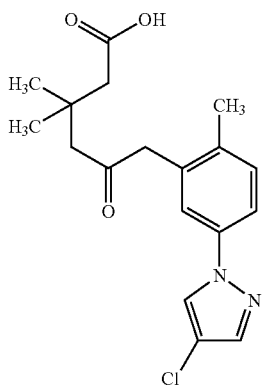

At −15° C., a solution of 1.61 g (11.3 mmol; 1.0 eq) of 3,3-dimethylglutaric anhydride in 10 ml of anhydrous THF and simultaneously 8.52 ml of LDA solution (2.0 molar; 1.5 eq) are then added dropwise. The mixture is stirred at room temperature for 2 hours and then poured into 150 ml of ice-cold 10% strength ammonium chloride solution. The mixture is acidified with concentrated HCl.

The intermediate is extracted with MTBE and the solvents are distilled off. The residue is boiled under reflux with 7 g of KOH and 70 ml of water for 4 hours.

The reaction solution is cooled, acidified with concentrated HCl and extracted with 200 ml of MTBE, and the extract is dried and the solvent is distilled off.

Yield: 4 g.

Analogously to Example (XXXIX-1) and in accordance with the general statements on the preparation, the following compound of the formula (XXXIX) is obtained

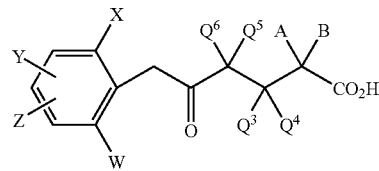

| Ex. No. | W | X | Y | Z | A | B | Q$^3$ | Q$^4$ | Q$^5$ | Q$^6$ | m.p.° C. |
|---|---|---|---|---|---|---|---|---|---|---|---|
| XXXIX-2 | H | CH$_3$ | H | 5-N-pyrazolyl-4-Cl | H | H | —(CH$_2$)$_4$— | | H | H | * |

*The compound was used as crude product for preparing Ex. No. IX-2

Example I-8-a-1

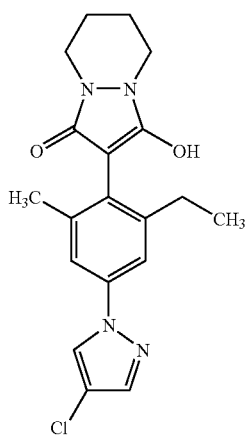

0.85 g of potassium tert-butoxide is initially charged in 36 ml of N,N-dimethylacetamide, 1.6 g of the compound of Example (XII-1) in N,N-dimethylacetamide are slowly added dropwise at 60° C. and the mixture is stirred for 1 hour. After cooling, the solution is added dropwise to ice-cooled hydrochloric acid, and the precipitate is filtered off with suction.

Yield: 1.1 g (81% of theory). m.p. 258° C.

Analogously to Example (I-8-a-1) and in accordance with the general statements on the preparation, the following compound of the formula (I-8-a) is obtained

Example I-8-b-7

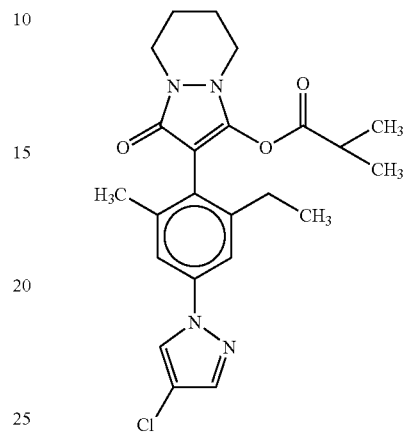

0.2 g of the compound of Example I-8-a-1 is initially charged in 30 ml of dichloromethane, 0.067 g of triethylamine is added, followed by 0.054 g of 2-methylpropionyl chloride, and the mixture is stirred for 3 h.

The mixture is diluted with water and extracted. The organic phase is dried and the solvent is distilled off. n-Heptane and a little dichloromethane are added to the residue. The product crystallizes out and is filtered off with suction.

Yield: 0.19 g (81% of theory), m.p.: 161.4° C.

Analogously to Example (I-8-b-1) and in accordance with the general statements on the preparation, the following compounds of the formula (I-8-b) are obtained (I-8-a)

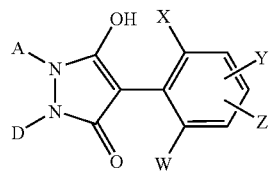

| Ex. No. | W | X | Y | Z | A | D | m.p.° C. |
|---|---|---|---|---|---|---|---|
| I-8-a-2 | CH$_3$ | C$_2$H$_5$ | H | 4-N-pyrazole-Cl | —(CH$_2$)$_2$—O—(CH$_2$)$_2$— | | >300 |

(I-8-b)

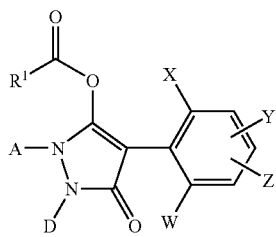

| Ex. No. | W | X | Y | Z | A | D | R¹ | m.p.° C. |
|---|---|---|---|---|---|---|---|---|
| I-8-b-2 | $CH_3$ | $C_2H_5$ | H | 4-N-pyrazole-Cl | —$(CH_2)_2$-O-$(CH_2)_2$— | | $i\text{-}C_3H_7$ | 138.4 |
| I-8-b-3 | $CH_3$ | $C_2H_5$ | H | 4-N-pyrazole-Cl | —$(CH_2)_2$-O-$(CH_2)_2$— | | $CH_2$—$OCH_3$ | 252.6 |
| I-8-b-4 | $CH_3$ | $C_2H_5$ | H | 4-N-pyrazole-Cl | —$(CH_2)_2$-O-$(CH_2)_2$— | | $t\text{-}C_4H_9$ | 119.1 |
| I-8-b-5 | $CH_3$ | $C_2H_5$ | H | 4-N-pyrazole-Cl | —$(CH_2)_4$— | | $CH_2$—$OCH_3$ | 259 |
| I-8-b-6 | $CH_3$ | $C_2H_5$ | H | 4-N-pyrazole-Cl | —$(CH_2)_4$— | | t-Bu | 204.8 |

Example I-8-c-1

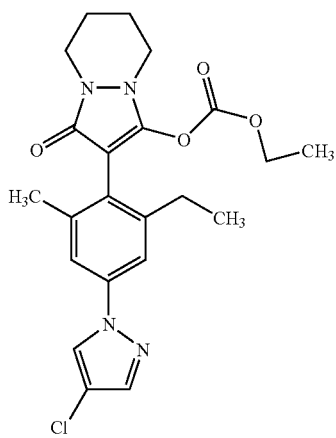

0.25 g of the compound of Example (I-8-a-1) is initially charged in 36 ml of dichloromethane, 0.12 ml of triethylamine is added, 0.06 ml of ethyl chloroformate, dissolved in dichloromethane, is added dropwise at room temperature and the mixture is stirred for 1 hour. The mixture is then diluted with water and extracted. The organic phase is dried and the solvent is distilled off. n-Heptane and a little dichloromethane are added to the residue. The product crystallizes out and is filtered off with suction.

Yield: 0.2 g (71% of theory). m.p. 172° C.

Analogously to Example (I-8-b-1) and in accordance with the general statements on the preparation, the following compound of the formula (I-8-c-1) is obtained

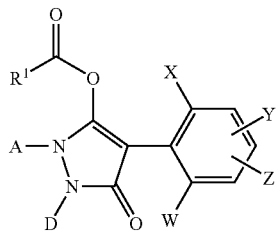

(I-8-c)

| Ex. No. | W | X | Y | Z | A | D | M | R² | m.p. °C |
|---|---|---|---|---|---|---|---|---|---|
| I-8-c-2 | CH₃ | C₂H₅ | H | 4-N-pyrazolyl-Cl | —(CH₂)₂-O-(CH₂)₂— | | O | C₂H₅ | 230 |

Example (XII-1)

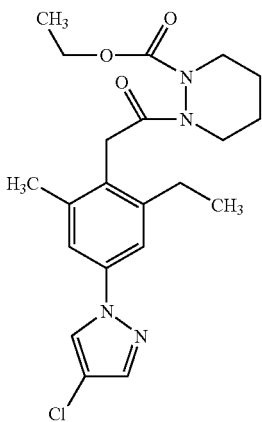

4-([4-Chloropyrazolyl)-2-ethyl-6-methylphenylacetic acid is initially charged in 35 ml of dichloromethane, and 1.28 g of oxalyl chloride is added. The mixture is stirred under reflux, and once the evolution of gas ceases, 1 ml of dimethylformamide is added. The mixture is stirred further under reflux and then cooled under an atmosphere of protective gas. The solvent is distilled off. The residue is taken up in dichloromethane and added dropwise to a solution of 1.2 g of 1-ethoxycarbonylhexahydropyridazine in 35 ml of dichloromethane and 1.6 ml of triethylamine. The mixture is stirred at room temperature for 3 h and then extracted with water and dichloromethane. The organic phase is separated off and dried, and the solvent is distilled off.

Yield: 2 g (63% of theory).

$^1$H-NMR-data (300 MHz, CDCl$_3$): δ=2.6 (q, 2H, Ar—C$\underline{H_2}$CH$_3$), 4.3 (q, 2H, O—C$\underline{H_2}$CH$_3$), 7.3, 7.35 (2s, 2H, ArH), 7.6, 7.9 (2s, 2H, Pyr H) ppm Analogously to Example (XII-1) and in accordance with the general statements on the preparation, the following compound of the formula (XII) is obtained

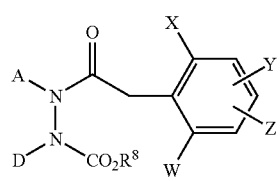

(XII)

| Ex. No. | W | X | Y | Z | A | D | R⁸ | m.p. °C |
|---|---|---|---|---|---|---|---|---|
| XII-2 | CH₃ | C₂H₅ | H | 4-N-pyrazolyl-Cl | —(CH₂)₂-O-(CH₂)₂— | | C₂H₅ | 87 |

Examples According to Process Q

Example XXXII-1

Methyl(4-N-[4-chloropyrazolyl]-2,6-dimethyl)phenylacetate

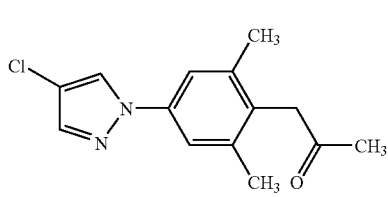

Under an atmosphere of argon, 16.6 g (162 mmol) of 4-chloropyrazole, 10.3 g (54 mmol) of copper(I) iodide and 56 g (405 mmol) of potassium carbonate (dry) are initially charged in 350 ml of absolute DMF, and the mixture is stirred for 5 minutes. 34.7 g (135 mmol) of methyl (4-bromo-2,6-dimethyl)phenylacetate are then slowly added dropwise. The reaction mixture is stirred at 105° C. for four days. During this time, the progress of the reaction is monitored by GC, and in each case after 24 hours (three times in total) 2.6 g (13.5 mmol) of copper(I) iodide and 4.15 g (40.5 mmol) of 4-chloropyrazole are added. The reaction mixture is allowed to cool and the solvent is then removed under reduced pressure and the residue is filtered through a short frit with silica gel and then purified chromatographically.

Yield: 17.2 g (46%).

$^1$H-NMR {400 MHz, CDCl$_3$}: 2.38 (s, 6H, CH$_3$); 3.70 (s, 3H, OCH$_3$); 3.71 (s, 2H, CH$_2$); 7.31 (s, 2H, Ph-H); 7.61 (s, 1H, pyrazolyl-H); 7.88 (s, 1H, pyrazolyl-H).

Analogously to Example (XXXII-1) and in accordance with the general statements on the preparation, the following compounds of the formula (XXXII) are obtained.

Example XXXII-2

Methyl(2-ethyl-4-N-[4-methoxypyrazolyl]-6-methyl)phenylacetate

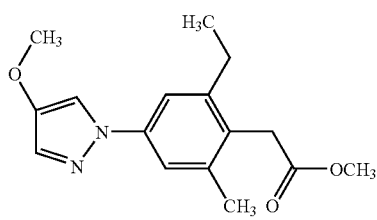

$^1$H-NMR {400 MHz, DMSO-d$_6$}: 1.15 (t, $^3$J$_{HH}$=7 Hz, 3H, CH$_3$); 2.28 (s, 3H, CH$_3$); 2.64 (q, $^3$J$_H$=7 Hz, 2H, CH$_2$); 3.62 (s, 3H, OCH$_3$); 3.73 (s, 2H, CH$_2$); 3.76 (s, 3H, OCH$_3$); 7.46 (m, 2H, Ph-H); 7.50 (s, 1H, pyrazolyl-H); 8.24 (s, 1H, pyrazolyl-H).

MS/CI: 289 (M+1).

Example XXXII-3

Methyl(2,6-dimethyl-4-N-[4-methoxypyrazolyl])phenylacetate

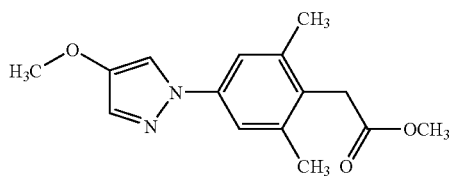

$^1$H-NMR {400 MHz, DMSO-d$_6$}: 2.30 (s, 6H, CH$_3$); 3.62 (s, 3H, OCH$_3$); 3.71 (s, 2H, CH$_2$); 3.76 (s, 3H, OCH$_3$); 7.46 (s, 2H, Ph-H); 7.50 (s, 1H, pyrazolyl-H); 8.22 (s, 1H, pyrazolyl-H).

MS/CI: 275 (M+1).

Example XXXII-4

Methyl(2,6-diethyl-4-N-[4-chloropyrazolyl])phenylacetate

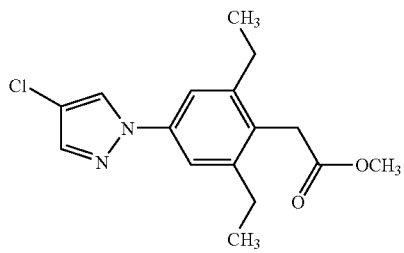

$^1$H-NMR {400 MHz, DMSO-d$_6$}: 1.18 (t, $^3$J$_{HH}$=7 Hz, 6H, CH$_3$); 2.61 (q, $^3$J$_{HH}$=7 Hz, 4H, CH$_2$); 3.57 (s, 3H, OCH$_3$); 3.79 (s, 2H, CH$_2$); 7.50 (m, 2H, Ph-H); 7.84 (s, 1H, pyrazolyl-H); 8.79 (s, 1H, pyrazolyl-H).

MS/CI: 307 (M+1).

Example XXXII-5

Methyl(2,6-dimethyl-4-N-[4-cyanopyrazolyl])phenylacetate

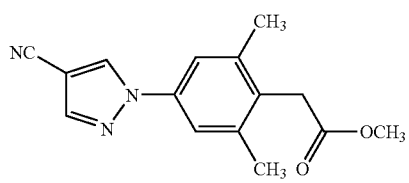

$^1$H-NMR {400 MHz, DMSO-d$_6$}: 2.31 (s, 6H, CH$_3$); 3.62 (s, 2H, CH$_2$); 3.74 (s, 3H, OCH$_3$); 7.52 (s, 2H, Ph-H); 8.05 (s, 1H, pyrazolyl-H); 8.82 (s, 1H, pyrazolyl-H).

MS/CI: 270 (M+1).

Example XXXII-6

Methyl(2,6-dimethyl-4-N-[3-chlorotriazolyl])phenylacetate

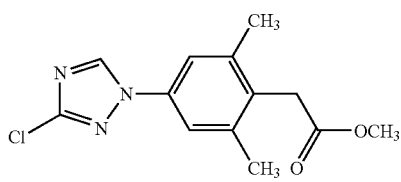

$^1$H-NMR {400 MHz, DMSO-d$_6$}: 2.26 (s, 6H, CH$_3$; 3.55 (s, 2H, CH$_2$); 3.79 (s, 3H, OCH$_3$); 7.44 (s, 2H, Ph-H); 9.22 (s, 1H, triazolyl-H).
MS/CI: 280 (M+1).

Example XXXII-7

Methyl[(3-N-[4-chloropyrazolyl])-6-methyl]phenylacetate

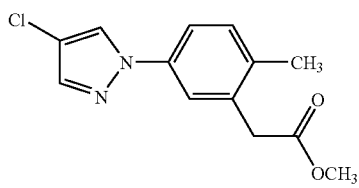

$^1$H-NMR {400 MHz, CDCl$_3$}: 2.32 (s, 3H, CH$_3$); 3.67 (s, 2H, CH$_2$); 3.70 (s, 3H, OCH$_3$); 7.22 (m, 1H, Ph-H); 7.40 (m, 1H, Ph-H); 7.50 (m, 1H, Ph-H); 7.60 (s, 1H, pyrazolyl-H); 7.95 (s, 1H, pyrazolyl-H).
GC-MS/CI: 265 (M+1).

Example XXXII-8

Methyl(2-chloro-6-ethyl-4-[4-chloropyrazolyl])phenylacetate

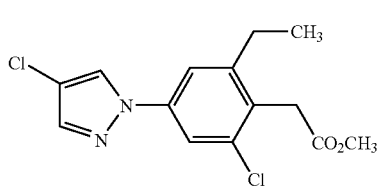

$^1$H-NMR {400 MHz, DMSO-d$_6$}: 1.18 (t, $^3$J$_{HH}$=7 Hz, 3H, CH$_3$); 2.72 (q, $^3$J$_{HH}$=7 Hz, 2H, CH$_2$); 3.64 (s, 3H, OCH$_3$); 3.89 (s, 2H, CH$_2$); 7.69 (m, 1H, Ph-H); 7.81 (m, 1H, Ph-H); 7.89 (s, 1H, pyrazolyl-H); 8.88 (s, 1H, pyrazolyl-H).
MS/CI: 313 (M+1).

Example XXXII-9

Methyl(2-chloro-6-ethyl-4-[4-chloropyrazolyl])phenylacetate

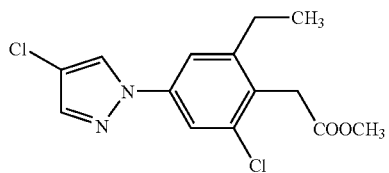

$^1$H-NMR {400 MHz, DMSO-d$_6$}: 1.18 (t, $^3$J$_{HH}$=7 Hz, 3H, CH$_3$); 2.72 (q, $^3$J$_{HH}$=7 Hz, 2H, CH$_2$); 3.64 (s, 3H, OCH$_3$): 3.89 (s, 2H, CH$_2$); 7.69 (m, 1H, Ph-H); 7.81 (m, 1H, Ph-H); 7.89 (s, 1H, pyrazolyl-H); 8.88 (s, 1H, pyrazolyl-H).
MS/CI: 313 (M+1).

Example XXXII-10

Methyl(2-ethyl-6-methyl-4-[4-chloropyrazolyl])phenylacetate

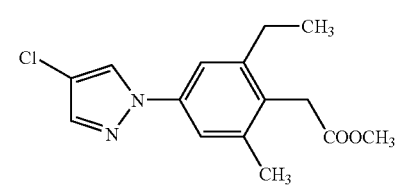

$^1$H-NMR {400 MHz, DMSO-d$_6$}: 1.18 (t, $^3$J$_{HH}$=7 Hz, 3H, CH$_3$): 2.59 (q, $^3$J$_{HH}$=7 Hz, 2H, CH$_2$); 3.59 (s, 3H, OCH$_3$); 3.72 (s, 2H, CH$_2$); 7.51 (m, 2H, Ph-H); 7.89 (s, 1H, pyrazolyl-H); 8.78 (s, 1H, pyrazolyl-H).
MS/CI: 313 (M+1).

Example XXVIII-1

(4-N-[4-Chloropyrazolyl]-2,6-dimethyl)phenylacetic acid

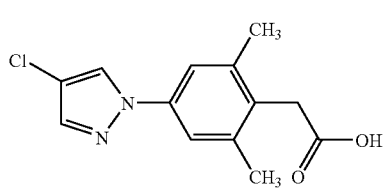

17.2 g (61.7 mmol) of (4-[4-chloropyrazolyl]-2,6-dimethyl)phenylacetic acid are dissolved in 160 ml of methanol and then, with 4.2 g (74 mmol) of potassium hydroxide in 160 ml of water, heated at 80° C. for 12 hours. The methanol is removed using a rotary evaporator, the residue is adjusted to pH 3 and the precipitated product is filtered off and dried.
Yield: 16.2 g (99%)
$^1$H-NMR {400 MHz, CDCl$_3$}: 2.38 (s, 6H, CH$_3$); 3.73 (s, 2H, CH$_2$); 7.32 (s, 2H, Ph-H); 7.61 (s, 1H, pyrazolyl-H); 7.86 (s, 1H, pyrazolyl-H); acid-OH not detected.

Analogously to Example (XXVIII-1), the following compounds of the formula (XXVIII) are obtained.

Example XXVIII-2

(2-Ethyl-4-N-[4-methoxypyrazolyl]-6-methyl)phenylacetic acid

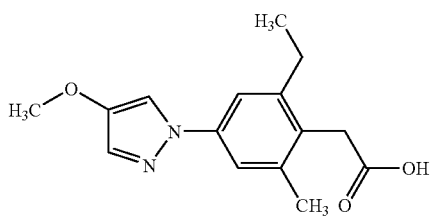

$^1$H-NMR {400 MHz, DMSO-d$_6$}: 1.17 (t, $^3$J$_{HH}$=7 Hz, 3H, CH$_3$); 2.30 (s, 3H, CH$_3$); 2.65 (q, $^3$J$_{HH}$=7 Hz, 2H, CH$_2$); 3.63 (s, 2H, CH$_2$); 3.77 (s, 3H, OCH$_3$); 7.45 (m, 2H, Ph-H); 7.50 (s, 1H, pyrazolyl-H); 8.23 (s, 1H, pyrazolyl-H); 12.5 (s, 1H, OH).

MS/CI: 275 (M+1).

Example XXVIII-3

(2,6-Dimethyl-4-N-[4-methoxypyrazolyl])phenylacetic acid

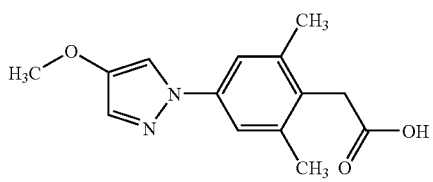

$^1$H-NMR {400 MHz, DMSO-d$_6$}: 2.30 (s, 6H, CH$_3$); 3.61 (s, 2H, CH$_2$); 3.82 (s, 3H, OCH$_3$); 7.44 (s, 2H, Ph-H); 7.50 (s, 1H, pyrazolyl-H); 8.21 (s, 1H, pyrazolyl-H); 12.4 (s, 1H, OH).

MS/CI: 261 (M+1).

Example XXVIII-4

(2,6-Diethyl-4-N-[4-chloropyrazolyl])phenylacetic acid

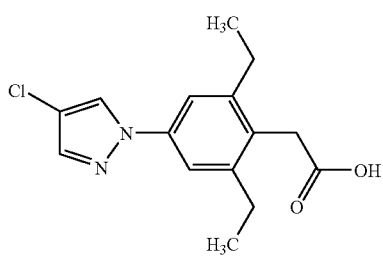

$^1$H-NMR {400 MHz, DMSO-d$_6$}: 1.18 (t, $^3$J$_{HH}$=8 Hz, 6H, CH$_3$); 2.63 (q, $^3$J$_{HH}$=8 Hz, 4H, CH$_2$); 3.67 (s, 2H, CH$_2$); 7.50 (s, 2H, Ph-H); 7.85 (s, 1H, pyrazolyl-H); 8.79 (s, 1H, pyrazoly-H); 12.5 (s, 1H, OH).

MS/CI: 293 (M+1).

Example XXVIII-5

(2,6-Dimethyl-4-N-[4-carboxylatopyrazolyl])phenylacetic acid

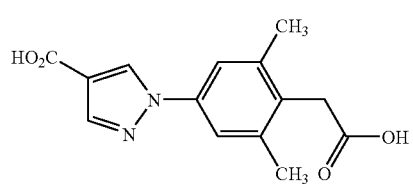

$^1$H-NMR {400 MHz, DMSO-d$_6$}: 2.32 (s, 6H, CH$_3$); 3.64 (s, 2H, CH$_2$); 7.52 (s, 2H, Ph-H); 8.09 (s, 1H, pyrazolyl-H); 8.87 (s, 1H, pyrazolyl-H); 12.3 (s, 2H, OH).

MS/CI: 275 (M+1).

Example XXVIII-6

(2,6-Dimethyl-4-N-[3-chlorotriazolyl])phenylacetic acid

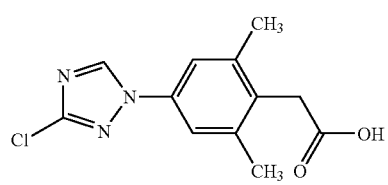

$^1$H-NMR {400 MHz, DMSO-d$_6$}: 2.26 (s, 6H, CH$_3$); 3.56 (s, 2H, CH$_2$); 7.44 (s, 2H, Ph-H); 9.22 (s, 1H, triazolyl-H); 12.2 (s, 1H, OH).

MS/CI: 266 (M+1).

Example XXVIII-7

(3-N-[4-Chloropyrazolyl]-6-methyl)phenylacetic acid

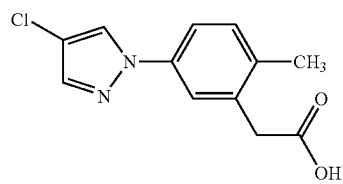

$^1$H-NMR {400 MHz, CDCl$_3$}: 2.34 (s, 3H, CH$_3$); 3.71 (s, 2H, CH$_2$); 7.26 (m, 1H, Ph-H); 7.40 (m, 1H, Ph-H); 7.52 (m, 1H, Ph-H); 7.62 (s, 1H, pyrazolyl-H); 7.85 (s, 1H, pyrazolyl-H); acid-OH not detected.

Example XXVIII-8

(2-Chloro-6-ethyl-4-[4-chloropyrazolyl])phenylacetic acid

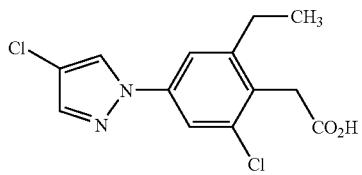

$^1$H-NMR {400 MHz, DMSO-d$_6$}: 1.17 (t, $^3$J$_{HH}$=7 Hz, 3H, CH$_3$); 2.71 (q, $^3$J$_{HH}$=7 Hz, 2H, CH$_2$); 3.79 (s, 2H, CH$_2$); 7.69 (m, 1H, Ph-H); 7.79 (m, 1H, Ph-H); 7.91 (s, 1H, pyrazolyl-H); 8.88 (s, 1H, pyrazolyl-H); 12.6 (s, 1H, OH).

MS/CI: 299 (M+1).

Example XXVIII-9

(2-Chloro-6-ethyl-4-[4-chloropyrazolyl])phenylacetic acid

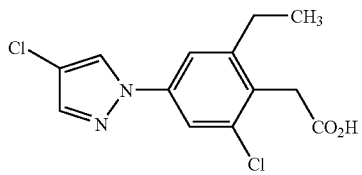

$^1$H-NMR {400 MHz, DMSO-d$_6$}: 1.17 (t, $^3$J$_{HH}$=7 Hz, 3H, CH$_3$); 2.71 (q, $^3$J$_{HH}$=7 Hz, 2H, CH$_2$); 3.79 (s, 2H, CH$_2$); 7.69 (m, 1H, Ph-H); 7.79 (m, 1H, Ph-H); 7.91 (s, 1H, pyrazolyl-H); 8.88 (s, 1H, pyrazolyl-H); 12.6 (s, 1H, OH).

MS/CI: 299 (M+1).

Example XXVIII-10

(2-Ethyl-6-methyl-4-[4-chloropyrazolyl])phenylacetic acid

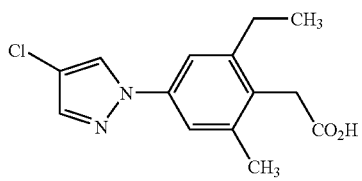

$^1$H-NMR {400 MHz, DMSO-d$_6$}: 1.19 (t, $^3$J$_{HH}$=7 Hz, 3H, CH$_3$); 2.60 (q, $^3$J$_{HH}$=7 Hz, 2H, CH$_2$); 3.81 (s, 2H, CH$_2$); 7.52 (m, 2H, Ph-H); 7.83 (s, 1H, pyrazolyl-H); 8.62 (s, 1H, pyrazolyl-H); OH not detected.

MS/CI: 279 (M+1).

Use Examples

Example A

*Meloidogyne* Test

Solvent: 7 parts by weight of dimethylformamide

Emulsifier: 2 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

Containers are filled with sand, solution of active compound, *Meloidogyne incognita* egg/larvae suspension and lettuce seeds. The lettuce seeds germinate and the plants develop. On the roots, galls are formed.

After the desired period of time, the nematicidal action is determined in % by gall formation. 100% means that no galls are formed; 0% means that the number of galls in the treated plants corresponds to that of the untreated control.

In this test, for example, the following compounds of the Preparation Examples show good activity:

TABLE A

| | Plant-damaging nematodes *Meloidogyne* test | |
|---|---|---|
| Active compounds | Concentration of active compound in ppm | Efficacy in % after 14$^d$ |
| Ex. I-1-a-2 | 20 | 100 |
| Ex. I-6-a-2 | 20 | 100 |

Example B

*Myzus* Test (Spray Treatment)

Solvents: 78 parts by weight of acetone
1.5 parts by weight of dimethylformamide Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Discs of Chinese cabbage (*Brassica pekinensis*) infested by the green peach aphid (*Myzus persicae*) are sprayed with a preparation of active compound of the desired concentration.

After the desired period of time, the kill in % is determined. 100% means that all aphids have been killed; 0% means that none of the aphids have been killed.

In this test, for example, the following compound of the Preparation Examples shows good activity:

TABLE B

| | Plant-damaging insects *Myzus* test | |
|---|---|---|
| Active compounds | Concentration of active compound in g/ha | Kill rate in % after 4$^d$ |
| Ex. I-1-3-a-3 | 100 | 80 |

Example C

Phaedon Larvae Test

Solvent: 7 parts by weight of dimethylformamide

Emulsifier: 2 parts by weight of alkylaryl polyglycol ether

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed.

In this test, for example, the following compounds of the Preparation Examples show good activity:

TABLE C

Plant-damaging insects
*Phaedon* larvae test

| Active compounds | Concentration of active compound in ppm | Kill rate in % after $7^d$ |
|---|---|---|
| Ex. I-6-a-1 | 500 | 90 |
| Ex. I-7-a-1 | 500 | 100 |
| Ex. I-7-a-2 | 500 | 100 |

Example D

Spodoptera Frugiperda Test

Solvent: 7 parts by weight of dimethylformamide

Emulsifier: 2 parts by weight of alkylaryl polyglycol ether

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the army worm (*Spodoptera frugiperda*) while the leaves are still moist.

After the desired period of time, the kill in % is determined. 100% means that all caterpillars have been killed; 0% means that none of the caterpillars have been killed.

In this test, for example, the following compound of the Preparation Examples shows good activity:

TABLE D

Plant-damaging insects
*Spodoptera frugiperda* test

| Active compounds | Concentration of active compound in ppm | Kill rate in % after $7^d$ |
|---|---|---|
| Ex. I-1-a-1 | 100 | 85 |

Example E

Tetranychus Test (OP-Resistant/Spray Treatment)

Solvents: 78 parts by weight of acetone
1.5 parts by weight of dimethylformamide Emulsifier: 0.5 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Discs of bean leaves (*Phaseolus vulgaris*) infested by all stages of the greenhouse red spider mite (*Tetranychus urticae*) are sprayed with a preparation of active compound of the desired concentration.

After the desired period of time, the effect in % is determined. 100% means that all spider mites have been killed; 0% means that none of the spider mites have been killed.

In this test, for example, the following compound of the Preparation Examples shows good activity:

TABLE E

Plant-damaging mites
*Tetranychus* test (OP-resistant/spray treatment)

| Active compounds | Concentration of active compound in ppm | Kill rate in % after $4^d$ |
|---|---|---|
| Ex. I-1-a-2 | 20 | 90 |

Example F

Sphaerotheca Test (Cucumber)/Protective

Solvents: 24.5 parts by weight of acetone
24.5 parts by weight of dimethylacetamide Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, the young plants are sprayed with the preparation of active compound at the stated application rate. After the spray coating has dried on, the plants are inoculated with an aqueous spore suspension of *Sphaerotheca fuliginea*. The plants are then placed in a greenhouse at about 23° C. and a relative atmospheric humidity of about 70%.

Evaluation is carried out 7 days after the inoculation. 0% means an efficacy which corresponds to that of the control, whereas an efficacy of 100% means that no infection is observed.

TABLE F

*Sphaerotheca* test (cucumber)/protective

| Active compound | Application rate of active compound in g/ha | Efficacy in % |
|---|---|---|
| Ex. I-6-a-2 | 100 | 97 |

Example G

In Vitro Test for the $ED_{50}$ Determination in Microorganisms

A methanolic solution of the active compound to be tested, mixed with Emulsifier PS16, is pipetted into the wells of microtitre plates. After the solvent has evaporated, 200 μl of potato/dextrose medium are added to each well.

Beforehand, a suitable concentration of spores or mycelium of the fungus to be tested was added to the medium.

The resulting concentrations of the active compound are 0.1, 1, 10 and 100 ppm. The resulting concentration of the emulsifier is 300 ppm.

The plates are then incubated on a shaker at a temperature of 22° C. for 3-5 days, until sufficient growth can be observed in the untreated control.

Evaluation is carried out photometrically at a wavelength of 620 nm. The dose of active compound which causes 50% inhibition of fungal growth compared to the untreated control ($ED_{50}$) is calculated from the data measured at different concentrations.

TABLE G

In vitro test for the $ED_{50}$ determination in microorganisms

| Active compound | Microorganism | $ED_{50}$ value |
|---|---|---|
| Ex. I-6-a-2 | Botrytis cinerea | <0.1 |
| Ex. I-6-c-1 | Botrytis cinerea | <0.1 |

Example H

Post-Emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants of a height of 5-15 cm are sprayed with the preparation of active compound such that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote:

0%=no effect (like untreated control)

100%=total destruction

Example I

Pre-Emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After about 24 hours, the soil is sprayed with the preparation of active compound such that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote:

0%=no effect (like untreated control)

100%=total destruction

| Pre-emergence Greenhouse | g of a.i./ha | Alopecurus | Avena fatua | Echinochloa | Setaria | Amaranthus | Sinapis |
|---|---|---|---|---|---|---|---|
| Ex. I-1-a-2 | 250 | 100 | 100 | 100 | 100 | 100 | 80 |

J. Herbicidal Pre-Emergence Action

Seeds of monocotyledonous and dicotyledonous weed and crop plants are placed into sandy loam in wood fibre pots and covered with soil. The test compounds, formulated in the form of wettable powders (WP) or emulsifiable concentrates (EC) are then, in various dosages as aqueous suspension or emulsion with a water application rate of 600 l/ha (converted), with 0.2% of wetting agent added, applied to the surface of the covering soil.

After the treatment, the pots are placed in a greenhouse and kept under good growth conditions for the test plants. The visual assessment of the emergence damage on the test plants is carried out after a trial period of 3 weeks by comparison with untreated controls (herbicidal effect in percent (%): 100% effect=the plants have died, 0% effect=like controlled plants).

K. Herbicidal Post-Emergence Action

Seeds of monocotyledonous and dicotyledonous weed and crop plants are placed into sandy loam in wood fibre pots, covered with soil and cultivated in a greenhouse under good growth conditions. 2-3 weeks after sowing, the test plants are treated at the one-leaf stage. The test compounds, formulated as wettable powders (WP) or emulsifiable concentrates (EC), are, in various dosages with a water application rate of 600 l/ha (converted), with 0.2% of wetting agent added, sprayed onto the green parts of the plants. After the test plants were kept in a greenhouse under optimum growth conditions for about 3 weeks, the effect of the preparations is rated visually in comparison to untreated controls (herbicidal effect in percent (%): 100% effect=the plants have died, 0% effect=like controlled plants).

TABLE

|  | Application rate g of a.i./ha | Summer barley observed (%) | Summer wheat observed (%) |
|---|---|---|---|
| I-1-a-7 | 25 | 95 | 60 |
| I-1-a-7 + mefenpyr | 25 + 100 | 50 | 15 |

| Post-emergence | Greenhouse | g of a.i./ha | Sugar beet | Echinochloa | Setaria | Sorghum |
|---|---|---|---|---|---|---|
|  | Ex. I-1-a-1 (EC) | 320 | 0 | 100 | 100 | 90 |

Test Description for Profiling Tests

L. Herbicidal Post-Emergence Action

Seeds of monocotyledonous and dicotyledonous weed and crop plants are placed into sandy loam in wood fibre pots or in plastic pots, covered with soil and cultivated in a greenhouse and during the vegetation period also outdoors, outside the greenhouse, under good growth conditions. 2-3 weeks after sowing, the test plants are treated in the one- to three-leaf stage. The test compounds, formulated as wettable powders (WP) or liquid (EC), are, at various dosages with a water application rate of 300 l/ha (converted), with added wetting agent (0.2 to 0.3%), sprayed onto the plants and the surface of the soil. 3 to 4 weeks after the treatment of the test plants, the effect of the preparations is rated visually in comparison to untreated controls (herbicidal effect in percent (%): 100% effect=the plants have died, 0% effect=like controlled plants).

Use of Safeners

Prior to the application of the test substances, the crop plants are sprayed with the safener using a certain application rate per hectare (usually 1 day before the application of the test substances).

By comparison with the effect of test substances on crop plants treated with and without safener, it is possible to assess the effect of the safener substance.

Container Trials with Cereals in the Greenhouse

TABLE

|  | Application rate g of a.i./ha | Summer wheat observed (%) |
|---|---|---|
| I-1-a-2 | 25 | 50 |
| I-1-a-2 + mefenpyr | 25 + 100 | 10 |

TABLE

|  | Application rate g of a.i./ha | Summer wheat observed (%) |
|---|---|---|
| I-1-a-6 | 100 | 20 |
| I-1-a-6 + mefenpyr | 100 + 100 | 0 | mefenpyr 1 day before the application of herbicide

TABLE

|  | Application rate g of a.i./ha | Summer barley observed (%) | Summer wheat observed (%) |
|---|---|---|---|
| Ex. I-2-a-6 | 100 | 20 | 15 |
|  | 50 | 10 | 15 |
| Ex. I-2-a-6 + mefenpyr | 100 + 100 | 5 | 10 |
|  | 50 + 100 | 0 | 10 |

TABLE

|  | Application rate g of a.i./ha | Summer barley observed (%) | Summer wheat observed (%) |
|---|---|---|---|
| Ex. I-2-a-5 | 100 | 20 | 40 |
|  | 50 | 15 | 20 |
| Ex. I-2-a-5 + mefenpyr | 100 + 100 | 0 | 10 |
|  | 50 + 100 | 0 | 0 |

TABLE

|  | Application rate g of a.i./ha | Summer barley observed (%) | Summer wheat observed (%) |
|---|---|---|---|
| Ex. I-2-b-5 | 100 | 20 | 40 |
|  | 50 | 15 | 40 |
| Ex. I-2-b-5 + mefenpyr | 100 + 100 | 0 | 20 |
|  | 50 + 100 | 0 | 10 | mefenpyr 1 day before the application of herbicide

Example L

Critical Concentration Test/Soil Insects-Treatment of Transgenic Plants

Test insect: *Diabrotica balteata*—Larvae in soil

Solvent: 7 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of active compound in the preparation is virtually immaterial, only the amount by weight of active compound per volume unit of soil, which is stated in ppm (mg/l), matters. The soil is filled in to 0.25 l pots, and these are allowed to stand at 20° C.

Immediately after the preparation, 5 pregerminated maize corns of the cultivar YIELD GUARD (trade mark of Monsanto Domp., USA) are placed into each pot. After 2 days, the appropriate test insects are placed into the treated soil. After a further 7 days, the efficacy of the active compound is determined by counting the maize plants that emerged (1 plant=20% activity).

Example M

Heliothis Virescens Test—Treatment of Transgenic Plants

Solvent: 7 parts by weight of acetone

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Soybean shoots (*Glycine max*) of the cultivar Roundup Ready (trade mark of Monsanto Comp. USA) are treated by being dipped into the preparation of active compound of the desired concentration and are populated with the tobacco budworm *Heliothis virescens* while the leaves are still moist.

After the desired period of time, the kill of the insects is determined.

The invention claimed is:
1. A compound of formula (I)

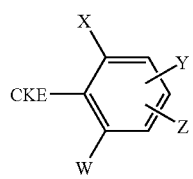

(I)

in which
X represents halogen, $C_1$-$C_6$-alkyl, $C_1$-$C_6$-alkenyl, $C_1$-$C_6$-alkynyl, $C_1$-$C_6$-haloalkyl, $C_1$-$C_6$-alkoxy, $C_3$-$C_6$-alkenyloxy, $C_1$-$C_6$-alkylthio, $C_1$-$C_6$-alkylsulphinyl, $C_1$-$C_6$-alkylsulphonyl, $C_1$-$C_6$-haloalkoxy, $C_3$-$C_6$-haloalkenyloxy, nitro, or cyano; or represents phenyl, phenoxy, phenylthio, benzyloxy, or benzylthio, each of which is optionally mono- or disubstituted by halogen, $C_1$-$C_6$-alkyl, $C_1$-$C_6$-alkoxy, $C_1$-$C_4$-haloalkyl, $C_1$-$C_4$-haloalkoxy, nitro, or cyano, W and Y independently of one another represent hydrogen, halogen, $C_1$-$C_6$-alkyl, $C_1$-$C_6$-alkenyl, $C_1$-$C_6$-alkynyl, $C_1$-$C_6$-haloalkyl, $C_1$-$C_6$-alkoxy, $C_1$-$C_6$-halo-alkoxy, nitro, or cyano, Z represents optionally substituted pyrazolyl or benzpyrazolyl, CKE represents one of the groups

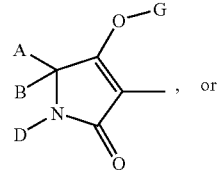

(1)

, or

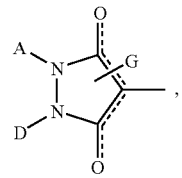

(8)

, in which
A represents hydrogen; represents $C_1$-$C_{12}$-alkyl, $C_3$-$C_8$-alkenyl, $C_1$-$C_{10}$-alkoxy-$C_1$-$C_8$-alkyl, or $C_1$-$C_{10}$-alkylthio-$C_1$-$C_6$-alkyl, each of which is optionally mono- to pentasubstituted by halogen; represents $C_3$-$C_8$-cycloalkyl that is optionally mono- to trisubstituted by halogen, $C_1$-$C_6$-alkyl, $C_1$-$C_2$-haloalkyl, or $C_1$-$C_6$-alkoxy and in which one or two ring members that are not directly adjacent are optionally replaced by oxygen and/or sulphur; or represents phenyl, naphthyl, hetaryl having 5 or 6 ring atoms, phenyl-$C_1$-$C_6$-alkyl, or naphthyl-$C_1$-$C_6$-alkyl, each of which is optionally mono- to trisubstituted by halogen, $C_1$-$C_6$-alkyl, $C_1$-$C_6$-haloalkyl, $C_1$-$C_6$-alkoxy, $C_1$-$C_6$-haloalkoxy, cyano, or nitro, B represents hydrogen, $C_1$-$C_{12}$-alkyl, or $C_1$-$C_8$-alkoxy-$C_1$-$C_6$-alkyl, or A, B and the carbon atom to which they are attached represent saturated $C_3$-$C_{10}$-cycloalkyl or unsaturated $C_5$-$C_{10}$-cycloalkyl in which one ring member is optionally replaced by oxygen or sulphur and that are optionally mono- or disubstituted by $C_1$-$C_8$-alkyl, $C_3$-$C_{10}$-cycloalkyl, $C_1$-$C_8$-haloalkyl, $C_1$-$C_8$-alkoxy, $C_1$-$C_8$-alkylthio, halogen, or phenyl, D represents hydrogen; represents $C_1$-$C_{12}$-alkyl, $C_3$-$C_8$-alkenyl, $C_3$-$C_8$-alkynyl, or $C_1$-$C_{10}$-alkoxy-$C_1$-$C_8$-alkyl, each of which is optionally mono- to pentasubstituted by halogen; represents $C_3$-$C_8$-cycloalkyl that is optionally mono- to trisubstituted by halogen, $C_1$-$C_4$-alkyl, $C_1$-$C_4$-alkoxy, or $C_1$-$C_4$-haloalkyl and in which one ring member is optionally replaced by oxygen or sulphur; or represents phenyl, hetaryl having 5 or 6 ring atoms, phenyl-$C_1$-$C_6$-alkyl, or hetaryl-$C_1$-$C_6$-alkyl having 5 or 6 ring atoms, each of which radicals is optionally mono- to trisubstituted by halogen, $C_1$-$C_6$-alkyl, $C_1$-$C_6$-haloalkyl, $C_1$-$C_6$-alkoxy, $C_1$-$C_6$-haloalkoxy, cyano, or nitro, or A and D together represent $C_3$-$C_6$-alkanediyl in which one methylene group is optionally replaced by oxygen, and G represents hydrogen (a) or represents one of the groups

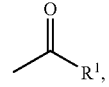

(b)

-continued

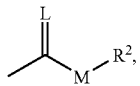
(c)

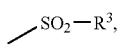
(d)

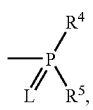
(e)

E or (f)

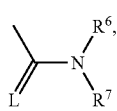
(g)

in which
E represents a metal ion equivalent or an ammonium ion,
L represents oxygen or sulphur, and
M represents oxygen or sulphur, $R^1$ represents $C_1$-$C_{20}$-alkyl, $C_2$-$C_{20}$-alkenyl, $C_1$-$C_8$-alkoxy-$C_1$-$C_8$-alkyl, $C_1$-$C_8$-alkylthio-$C_1$-$C_8$-alkyl, or poly-$C_1$-$C_8$-alkoxy-$C_1$-$C_8$-alkyl, each of which is optionally mono- to pentasubstituted by halogen; represents $C_3$-$C_8$-cycloalkyl that is optionally mono- to trisubstituted by halogen, $C_1$-$C_6$-alkyl, or $C_1$-$C_6$-alkoxy and in which one or more ring members that are not directly adjacent are optionally replaced by oxygen and/or sulphur; represents phenyl that is optionally mono- to trisubstituted by halogen, cyano, nitro, $C_1$-$C_6$-alkyl, $C_1$-$C_6$-alkoxy, $C_1$-$C_6$-haloalkyl, $C_1$-$C_6$-haloalkoxy, $C_1$-$C_6$-alkylthio, or $C_1$-$C_6$-alkylsulphonyl; represents phenyl-$C_1$-$C_6$-alkyl that is optionally mono- to trisubstituted by halogen, nitro, cyano, $C_1$-$C_6$-alkyl, $C_1$-$C_6$-alkoxy, $C_1$-$C_6$-haloalkyl, or $C_1$-$C_6$-haloalkoxy; represents 5- or 6-membered hetaryl that is optionally mono- or disubstituted by halogen or $C_1$-$C_6$-alkyl; represents phenoxy $C_1$-$C_6$-alkyl that is optionally mono- or disubstituted by halogen or $C_1$-$C_6$-alkyl; or represents 5- or 6-membered hetaryloxy $C_1$-$C_6$-alkyl that is optionally mono- or disubstituted by halogen, amino, or $C_1$-$C_6$-alkyl, $R^2$ represents $C_1$-$C_{20}$-alkyl, $C_2$-$C_{20}$-alkenyl, $C_1$-$C_8$-alkoxy-$C_2$-$C_8$-alkyl, or poly-$C_1$-$C_8$-alkoxy-$C_2$-$C_8$-alkyl, each of which is optionally mono- to pentasubstituted by halogen; represents $C_3$-$C_8$-cycloalkyl that is optionally mono- or disubstituted by halogen, $C_1$-$C_6$-alkyl, or $C_1$-$C_6$-alkoxy; or represents phenyl or benzyl, each of which is optionally mono- to trisubstituted by halogen, cyano, nitro, $C_1$-$C_6$-alkyl, $C_1$-$C_6$-alkoxy, $C_1$-$C_6$-haloalkyl, or $C_1$-$C_6$-haloalkoxy, $R^3$ represents $C_1$-$C_8$-alkyl that is optionally mono- to nonasubstituted by halogen; or represents phenyl or benzyl, each of which is optionally mono- to trisubstituted by halogen, $C_1$-$C_6$-alkyl, $C_1$-$C_6$-alkoxy, $C_1$-$C_4$-haloalkyl, $C_1$-$C_4$-haloalkoxy, cyano, or nitro, $R^4$ and $R^5$ independently of one another represent $C_1$-$C_8$-alkyl, $C_1$-$C_8$-alkoxy, $C_1$-$C_8$-alkylamino, di($C_1$-$C_8$-alkyl)amino, $C_1$-$C_8$-alkylthio, $C_2$-$C_8$-alkenylthio, or $C_3$-$C_7$-cycloalkylthio, each of which is optionally mono- to pentasubstituted by halogen; or represent phenyl, phenoxy, or phenylthio, each of which is optionally mono- to trisubstituted by halogen, nitro, cyano, $C_1$-$C_4$-alkoxy, $C_1$-$C_4$-haloalkoxy, $C_1$-$C_4$-alkyl-thio, $C_1$-$C_4$-haloalkylthio, $C_1$-$C_4$-alkyl, or $C_1$-$C_4$-haloalkyl, $R^6$ and $R^7$ independently of one another represent hydrogen; represent $C_1$-$C_8$-alkyl, $C_3$-$C_8$-cycloalkyl, $C_1$-$C_8$-alkoxy, $C_3$-$C_8$-alkenyl, or $C_1$-$C_8$-alkoxy-$C_1$-$C_8$-alkyl, each of which is optionally mono- to pentasubstituted by halogen; represent phenyl that is optionally mono- to trisubstituted by halogen, $C_1$-$C_8$-haloalkyl, $C_1$-$C_8$-alkyl, or $C_1$-$C_8$-alkoxy; or represent benzyl that is optionally mono- to trisubstituted by halogen, $C_1$-$C_8$-alkyl, $C_1$-$C_8$-haloalkyl, or $C_1$-$C_8$-alkoxy; or $R^6$ and $R^7$ together represent a $C_3$-$C_6$-alkylene radical that is optionally mono- or disubstituted by $C_1$-$C_4$-alkyl and in which one carbon atom is optionally replaced by oxygen or sulphur, $R^{13}$ represents hydrogen; represents $C_1$-$C_8$-alkyl or $C_1$-$C_8$-alkoxy, each of which is optionally mono- to trisubstituted by halogen; represents $C_3$-$C_8$-cycloalkyl that is optionally mono- to trisubstituted by halogen, $C_1$-$C_4$-alkyl, or $C_1$-$C_4$-alkoxy and in which one methylene group is optionally replaced by oxygen or sulphur; or represents phenyl, phenyl-$C_1$-$C_4$-alkyl, or phenyl-$C_1$-$C_4$-alkoxy, each of which is optionally mono- or disubstituted by halogen, $C_1$-$C_6$-alkyl, $C_1$-$C_6$-alkoxy, $C_1$-$C_4$-haloalkyl, $C_1$-$C_4$-haloalkoxy, nitro, or cyano, $R^{14}$ represents hydrogen or $C_1$-$C_8$-alkyl, or $R^{13}$ and $R^{14}$ together represent $C_4$-$C_6$-alkanediyl, $R^{15}$ and $R^{16}$ are identical or different and represent $C_1$-$C_6$-alkyl, or $R^{15}$ and $R^{16}$ together represent a $C_2$-$C_4$-alkanediyl radical that is optionally mono- or disubstituted by $C_1$-$C_6$-alkyl or $C_1$-$C_6$-haloalkyl, or by phenyl that is optionally mono- or disubstituted by halogen, $C_1$-$C_6$-alkyl, $C_1$-$C_4$-haloalkyl, $C_1$-$C_6$-alkoxy, $C_1$-$C_4$-haloalkoxy, nitro, or cyano, $R^{17}$ and $R^{18}$ independently of one another represent hydrogen; represent optionally halogen-substituted $C_1$-$C_8$-alkyl; or represent phenyl that is optionally mono- or disubstituted by halogen, $C_1$-$C_6$-alkyl, $C_1$-$C_6$-alkoxy, $C_1$-$C_4$-haloalkyl, $C_1$-$C_4$-haloalkoxy, nitro, or cyano, or $R^{17}$ and $R^{18}$ together with the carbon atom to which they are attached represent a carbonyl group or represent $C_5$-$C_7$-cycloalkyl that is optionally mono- or disubstituted by halogen, $C_1$-$C_4$-alkyl, or $C_1$-$C_4$-alkoxy and in which one methylene group is optionally replaced by oxygen or sulphur, and $R^{19}$ and $R^{20}$ independently of one another represent $C_1$-$C_{10}$-alkyl, $C_2$-$C_{10}$-alkenyl, $C_1$-$C_{10}$-alkoxy, $C_1$-$C_{10}$-alkylamino, $C_3$-$C_{10}$-alkenylamino, di($C_1$-$C_{10}$-alkyl)amino, or di($C_3$-$C_{10}$-alkenyl)amino.

2. A compound of formula (I) according to claim 1 in which
X represents fluorine, chlorine, bromine, $C_1$-$C_4$-alkyl, $C_1$-$C_4$-alkoxy, $C_1$-$C_4$-haloalkyl, $C_1$-$C_4$-haloalkoxy, nitro, or cyano,
W and Y independently of one another represent hydrogen, fluorine, chlorine, bromine, $C_1$-$C_4$-alkyl, $C_1$-$C_4$-haloalkyl, $C_1$-$C_4$-alkoxy, or $C_1$-$C_4$-haloalkoxy, Z represents

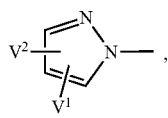

in which
V¹ represents hydrogen, fluorine, chlorine, bromine, iodine, $C_1$-$C_6$-alkyl, $C_1$-$C_4$-alkoxy, $C_1$-$C_4$-haloalkyl, $C_1$-$C_4$-haloalkoxy, cyano, or nitro, and V² represents hydrogen, fluorine, chlorine, bromine, $C_1$-$C_4$-alkyl, or $C_1$-$C_2$-haloalkyl, or V¹ and V² together represent $C_3$-$C_4$-alkanediyl that is optionally mono- to tetrasubstituted by fluorine and that is optionally interrupted once or twice by oxygen; or represent butadienyl that is optionally mono- or disubstituted by fluorine, chlorine, bromine, $C_1$-$C_4$-alkyl, $C_1$-$C_4$-alkoxy, $C_1$-$C_2$-haloalkyl, $C_1$-$C_2$-haloalkoxy, cyano, or nitro, and CKE represents one of the groups

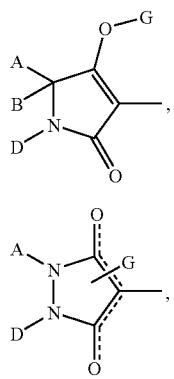

in which

A represents hydrogen, represents $C_1$-$C_6$-alkyl, or $C_1$-$C_4$-alkoxy-$C_1$-$C_2$-alkyl, each of which is optionally mono- to trisubstituted by fluorine or chlorine; represents $C_3$-$C_6$-cycloalkyl that is optionally mono- or disubstituted by fluorine, chlorine, $C_1$-$C_2$-alkyl, trifluoromethyl, or $C_1$-$C_2$-alkoxy; or, except for compounds in which CKE is (3), (4), (6), or (7), represents phenyl or benzyl, each of which is optionally mono- or disubstituted by fluorine, chlorine, bromine, $C_1$-$C_4$-alkyl, $C_1$-$C_2$-haloalkyl, $C_1$-$C_4$-alkoxy, $C_1$-$C_2$-haloalkoxy, cyano, or nitro, B represents hydrogen, $C_1$-$C_4$-alkyl, or $C_1$-$C_2$-alkoxyl-$C_1$-$C_2$-alkyl or A, B, and the carbon atom to which they are attached represent saturated $C_3$-$C_7$-cycloalkyl or unsaturated $C_5$-$C_7$-cycloalkyl in which one ring member is optionally replaced by oxygen or sulphur and that is optionally mono- or disubstituted by $C_1$-$C_6$-alkyl, trifluoromethyl or $C_1$-$C_6$-alkoxy, D represents hydrogen; represents $C_1$-$C_6$-alkyl, $C_3$-$C_6$-alkenyl, or $C_1$-$C_4$-alkoxy-$C_2$-$C_3$-alkyl, each of which is optionally mono- to trisubstituted by fluorine; represents $C_3$-$C_6$-cycloalkyl that is optionally mono- or disubstituted by $C_1$-$C_4$-alkyl, $C_1$-$C_4$-alkoxy, or $C_1$-$C_2$-haloalkyl and in which one methylene group is optionally replaced by oxygen; or, except for compounds in which CKE is (1), represents phenyl or pyridyl, each of which is optionally mono- or disubstituted by fluorine, chlorine, bromine, $C_1$-$C_4$-alkyl, $C_1$-$C_4$-haloalkyl, $C_1$-$C_4$-alkoxy, or $C_1$-$C_4$-haloalkoxy, or A and D together represent $C_3$-$C_5$-alkanediyl in which one methylene group is optionally replaced by oxygen, and G represents hydrogen (a) or represents one of the groups

(b)

(c)

(d)

(e)

E or
(f)

(g)

in which

E represents a metal ion equivalent or an ammonium ion,

L represents oxygen or sulphur

M represents oxygen or sulphur,

R¹ represents $C_1$-$C_8$-alkyl, $C_2$-$C_8$-alkenyl, $C_1$-$C_4$-alkoxy-$C_1$—$O_2$-alkyl, or $C_1$-$C_4$-alkylthio-$C_1$-$C_2$-alkyl, each of which is optionally mono- to trisubstituted by fluorine or chlorine; represents $C_3$-$C_6$-cycloalkyl that is optionally mono- or disubstituted by fluorine, chlorine, $C_1$-$C_2$-alkyl, or $C_1$-$C_2$-alkoxy and in which optionally one or two ring members that are not directly adjacent are replaced by oxygen; or represents phenyl that is optionally mono- or disubstituted by fluorine, chlorine, bromine, cyano, nitro, $C_1$-$C_4$-alkyl, $C_1$-$C_4$-alkoxy, $C_1$-$C_2$-haloalkyl, or $C_1$-$C_2$-haloalkoxy, R² represents $C_1$-$C_8$-alkyl, $C_2$-$C_8$-alkenyl, or $C_1$-$C_4$-alkoxy-$C_2$-$C_4$-alkyl, each of which is optionally mono- to trisubstituted by fluorine; represents $C_3$-$C_6$-cycloalkyl that is optionally mono-substituted by $C_1$-$C_2$-alkyl or $C_1$-$C_2$-alkoxy; or represents phenyl or benzyl, each of which is optionally mono- or disubstituted by fluorine, chlorine, bromine, cyano, nitro, $C_1$-$C_4$-alkyl, $C_1$-$C_3$-alkoxy, trifluoromethyl, or trifluoromethoxy, R³ represents $C_1$-$C_6$-alkyl that is optionally mono- to trisubstituted by fluorine; or represents phenyl or benzyl, each of which is optionally monosubstituted by fluorine, chlorine, bromine, $C_1$-$C_4$-alkyl, $C_1$-$C_4$-alkoxy, trifluoromethyl, trifluoromethoxy, cyano, or nitro, $R^4$ represents $C_1$-$C_6$-alkyl, $C_1$-$C_6$-alkoxy, $C_1$-$C_6$-alkylamino, di($C_1$-$C_6$-alkyl)amino, $C_1$-$C_6$-alkylthio, $C_3$-$C_4$-alkenylthio, or $C_3$-$C_6$-cycloalkylthio, each of which is optionally mono- to trisubstituted by fluorine; or represents phenyl, phenoxy, or phenylthio, each of which is optionally mono- or disubstituted by fluorine, chlorine, bromine, nitro, cyano, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkyl, or trifluoromethyl, $R^5$ represents $C_1$-$C_6$-alkoxy or $C_1$-$C_6$-alkylthio, $R^6$ represents hydrogen; represents $C_1$-$C_6$-alkyl, $C_3$-$C_6$-cycloalkyl, $C_1$-$C_6$-alkoxy, $C_3$-$C_6$-alkenyl, or $C_1$-$C_6$-alkoxy-$C_1$-$C_4$-alkyl, each of which is optionally mono- to trisubstituted by fluorine; represents phenyl that is optionally mono- or disubstituted by fluorine, chlorine, bromine, trifluoromethyl, $C_1$-$C_4$-alkyl, or $C_1$-$C_4$-alkoxy; represents benzyl that is optionally monosubstituted by fluorine, chlorine, bromine, $C_1$-$C_4$-alkyl, trifluoromethyl, or $C_1$-$C_4$-alkoxy, and $R^7$ represents $C_1$-$C_6$-alkyl, $C_3$-$C_6$-alkenyl, or $C_1$-$C_6$-alkoxy-$C_1$-$C_4$-alkyl, or $R^6$ and $R^7$ together represent a $C_4$-$C_5$-alkylene radical that is optionally mono- or disubstituted by methyl or ethyl and in which a methylene group is optionally replaced by oxygen or sulphur.

3. A compound of formula (I) according to claim 1 in which

W represents hydrogen, methyl, ethyl, or chlorine,

X represents chlorine, methyl, ethyl, propyl, methoxy, ethoxy, propoxy, trifluoromethyl, difluoromethoxy, or trifluoromethoxy, Y represents hydrogen or methyl, Z represents

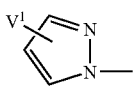

in which $V^1$ represents hydrogen, fluorine, chlorine, bromine, methyl, ethyl, methoxy, ethoxy, trifluoromethyl, or cyano, and CKE represents one of the groups (1)

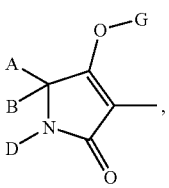

(8)

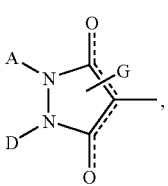

in which

A represents hydrogen; represents $C_1$-$C_4$-alkyl or $C_1$-$C_2$-alkoxy-$C_1$-$C_2$-alkyl, each of which is optionally mono- to trisubstituted by fluorine; represents cyclopropyl, cyclopentyl, or cyclohexyl; or, when CKE is (5), represents phenyl that is optionally mono- or disubstituted by fluorine, chlorine, bromine, methyl, ethyl, n-propyl, isopropyl, methoxy, ethoxy, trifluoromethyl, trifluoromethoxy, cyano, or nitro, B represents hydrogen, methyl, or ethyl, or A, B, and the carbon atom to which they are attached represent saturated $C_5$-$C_6$-cycloalkyl in which one ring member is optionally replaced by oxygen or sulphur and that is optionally monosubstituted by methyl, ethyl, propyl, isopropyl, trifluoromethyl, methoxy, ethoxy, propoxy, butoxy, or isobutoxy, D represents hydrogen; represents $C_1$-$C_4$-alkyl, $C_3$-$C_4$-alkenyl, or $C_1$-$C_4$-alkoxy-$C_1$-$C_3$-alkyl, each of which is optionally mono- to trisubstituted by fluorine; represents cyclopropyl, cyclopentyl, or cyclohexyl; or, except when CKE is (1), represents pyridyl or phenyl that is optionally monosubstituted by fluorine, chlorine, methyl, ethyl, n-propyl, isopropyl, methoxy, ethoxy, or trifluoromethyl, or A and D together represent $C_3$-$C_5$-alkanediyl that is optionally mono- or disubstituted by methyl or methoxy, and G represents hydrogen (a) or represents one of the groups (b)

(c)

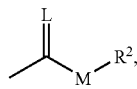

(d)

—$SO_2$—$R^3$, (e)

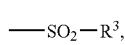

(f)

E or (g)

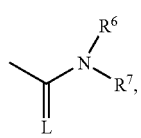

in which

E represents a metal ion equivalent or an ammonium ion,

L represents oxygen or sulphur

M represents oxygen or sulphur, $R^1$ represents $C_1$-$C_6$-alkyl, $C_2$-$C_6$-alkenyl, $C_1$-$C_2$-alkoxy-$C_1$-alkyl, or $C_1$-$C_2$-alkylthio-$C_1$-alkyl, each of which is optionally mono- to trisubstituted by fluorine; represents cyclopropyl or cyclohexyl, each of which is optionally monosubstituted by fluorine, chlorine, methyl, or methoxy; represents phenyl that is optionally mono-substituted by fluorine, chlorine, bromine, cyano, nitro, methyl, methoxy, trifluoromethyl, or trifluoromethoxy, $R^2$ represents $C_1$-$C_8$-alkyl, $C_2$-$C_6$-alkenyl, or $C_1$-$C_4$-alkoxy-$C_2$-$C_3$-alkyl, each of which is optionally monosubstituted by fluorine; or represents phenyl or benzyl, each of which is optionally mono-substituted by fluorine, chlorine, cyano, nitro, methyl, ethyl, n-propyl, i-propyl, methoxy, ethoxy, trifluoromethyl, or trifluoro-methoxy, $R^3$ represents methyl, ethyl, n-propyl, or isopropyl, each of which is optionally mono- to trisubstituted by fluorine; or represents phenyl or benzyl, each of which is optionally monosubstituted by fluorine, chlorine, bromine, methyl, tert-butyl, methoxy, trifluoro-methyl, trifluoromethoxy, cyano, or nitro, $R^4$ represents $C_1$-$C_4$-alkyl, $C_1$-$C_4$-alkoxy, $C_1$-$C_4$-alkylamino, di($C_1$-$C_4$-alkyl)amino, or $C_1$-$C_4$-alkylthio, each of which is optionally mono- to trisubstituted by fluorine; or represents phenyl, phenoxy, or phenylthio, each of which is optionally monosubstituted by fluorine, chlorine, bromine, nitro, cyano, $C_1$-$C_2$-alkoxy, $C_1$-$C_2$-fluoroalkoxy, $C_1$-$C_2$-alkylthio, $C_1$-$C_2$-fluoroalkylthio, or $C_1$-$C_3$-alkyl, $R^5$ represents methoxy, ethoxy, propoxy, butoxy, methylthio, ethylthio, propylthio, or butylthio, $R^6$ represents hydrogen; represents $C_1$-$C_4$-alkyl, $C_3$-$C_6$-cycloalkyl, $C_1$-$C_4$-alkoxy, $C_3$-$C_4$-alkenyl, or $C_1$-$C_4$-alkoxy-$C_1$-$C_4$-alkyl, each of which is optionally mono- to trisubstituted by fluorine; represents phenyl that is optionally monosubstituted by fluorine, chlorine, bromine, trifluoromethyl, methyl, or methoxy; or represents benzyl that is optionally monosubstituted by fluorine, chlorine, bromine, methyl, trifluoromethyl, or methoxy, and $R^7$ represents methyl, ethyl, propyl, isopropyl, butyl, isobutyl, or allyl, or $R^6$ and $R^7$ represent a $C_4$-$C_5$-alkylene radical in which one methylene group is optionally replaced by oxygen or sulphur.

4. A compound of formula (I) according to claim 1 in which

W represents hydrogen, methyl, or ethyl,

X represents chlorine, methyl, or ethyl,

Y represents hydrogen,

Z represents, in the 4- or 5-position, the group

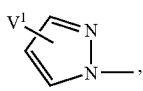

in which $V^1$ represents chlorine or methoxy, and
CKE represents one of the groups

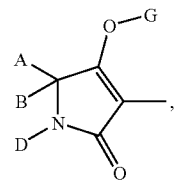

(1)

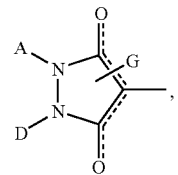

(8)

in which

A represents hydrogen, $C_1$-$C_4$-alkyl, or cyclopropyl,

B represents hydrogen or methyl, or

A, B, and the carbon atom to which they are attached represent saturated $C_5$-$C_6$-cycloalkyl in which one ring member is optionally replaced by oxygen and that is optionally monosubstituted by methyl or methoxy, D represents hydrogen, or A and D together represent $C_3$-$C_5$-alkanediyl in which one carbon atom is optionally replaced by oxygen, and G represents hydrogen (a) or represents one of the groups

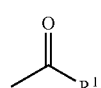

(b)

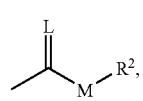

(c)

in which

L represents oxygen,

M represents oxygen or sulphur, $R^1$ represents $C_1$-$C_6$-alkyl or $C_1$-$C_2$-alkoxy-$C_1$-alkyl, and $R^2$ represents $C_1$-$C_8$-alkyl or benzyl.

5. A composition comprising one or more compounds of formula (I) according to claim 1 and one or more extenders and/or surfactants.

* * * * *